(12) United States Patent
Abrahmsén et al.

(10) Patent No.: US 8,937,153 B2
(45) Date of Patent: Jan. 20, 2015

(54) COMPOSITIONS, METHODS AND USES

(75) Inventors: Lars Abrahmsén, Bromma (SE); Andreas Jonsson, Bromma (SE); Jakob Dogan, Spånga (SE); Per-Åke Nygren, Ekerö (SE)

(73) Assignee: Affibody AB, Solna (SE)

( * ) Notice: Subject to any disclaimer, the term of this patent is extended or adjusted under 35 U.S.C. 154(b) by 982 days.

(21) Appl. No.: 12/452,731

(22) PCT Filed: Jul. 17, 2008

(86) PCT No.: PCT/EP2008/059389
§ 371 (c)(1),
(2), (4) Date: Feb. 24, 2010

(87) PCT Pub. No.: WO2009/016043
PCT Pub. Date: Feb. 5, 2009

(65) Prior Publication Data
US 2010/0273979 A1 Oct. 28, 2010

Related U.S. Application Data
(60) Provisional application No. 60/962,618, filed on Jul. 31, 2007.

(30) Foreign Application Priority Data
Jul. 31, 2007 (EP) .................................... 07113533

(51) Int. Cl.
*C07K 14/31* (2006.01)
*C07K 14/315* (2006.01)

(52) U.S. Cl.
CPC ............ *C07K 14/31* (2013.01); *C07K 2319/70* (2013.01); *C07K 14/315* (2013.01)
USPC .......................................... 530/324; 530/350

(58) Field of Classification Search
None
See application file for complete search history.

(56) References Cited

U.S. PATENT DOCUMENTS
2012/0270801 A1 * 10/2012 Frejd et al. ................... 514/19.4

FOREIGN PATENT DOCUMENTS
WO WO 2005/097202 A2 10/2005
WO WO 2006/056464 A2 6/2006

OTHER PUBLICATIONS

He, Yanan et al., "*An artificially evolved albumin binding module facilitates chemical shift epitope mapping of GA domain interactions with phylogenetically diverse albumins*", Protein Science, vol. 16, pp. 1490-1494 (2007).
Rozak, David A. et al., "*Using Offset Recombinant Polymerase Chain Reaction to Identify Functional Determinants in a Common Family of Bacterial Albumin Binding Domains*", American Chemical Society, Biochemistry, vol. 45, pp. 3263-3271 (2006).

* cited by examiner

*Primary Examiner* — Karlheinz R Skowronek
*Assistant Examiner* — Roy Teller
(74) *Attorney, Agent, or Firm* — Cantor Colburn LLP

(57) ABSTRACT

The present invention relates to a class of engineered polypeptides having a binding affinity for albumin. It also relates to new methods and uses that exploit binding by these and other compounds to albumin in different contexts, some of which have significance for the treatment of disease in mammals including humans.

49 Claims, 37 Drawing Sheets

| Polypeptide | Amino acid sequence | SEQ ID NO: |
|---|---|---|
| ABM00001 | GVSDFYKNLI NRAKTVEGVH ALICHI | 1 |
| ABM00002 | GVSDFYKNVI NRAKTVEGVH ALIDHI | 2 |
| ABM00003 | GVSDFYKNLI NRAKTVEGVR ALKLHI | 3 |
| ABM00004 | GVSDFYKNVI NRAKTVEGVS ALIHEI | 4 |
| ABM00005 | GVSDFYKRLI NRAKTVEGVN TLIADI | 5 |
| ABM00006 | GVSDFYKMLI NRAKTVEGVN TLIADI | 6 |
| ABM00007 | GVSDFYKNLI NRAKTVEGVN SLISHI | 7 |
| ABM00008 | GVSDFYKRLI NRAKTVEGVQ SLISEI | 8 |
| ABM00009 | GVSDFYKNLI NRAKTVEGVS SLKGHI | 9 |
| ABM00010 | GVSDFYKNVI NRAKTVEGVD SLTAEI | 10 |
| ABM00011 | GVSDFYKNLI NRAKTVEGVQ TLISDI | 11 |
| ABM00012 | GVSDFYKKFT NRAKTVEGVE TLTSEI | 12 |
| ABM00013 | GVSDFYKSLI NRAKTVEGVS SLTDEI | 13 |
| ABM00014 | GVSDFYKNVI NRAKTVEGVS SLTAEI | 14 |
| ABM00015 | GVSDFYKSLI NRAKTVEGVD ALISHI | 15 |
| ABM00016 | GVSDFYKRLI NRAKTVEGVS SLIHDI | 16 |
| ABM00017 | GVSDFYKNLI NRAKTVEGVD TLIHDI | 17 |
| ABM00018 | GVSDFYKNLI NRAKTVEGVQ ALISEI | 18 |
| ABM00019 | GVSDFYKSLI NRAKTVEGVD SLIVHI | 19 |
| ABM00020 | GVSDFYKNLI NRAKTVEGVQ SLITEI | 20 |
| ABM00021 | GVSDFYKNLI NRAKTVEGVD ALITHI | 21 |
| ABM00022 | GVSDFYKSMI NRAKTVEGVD SLITHI | 22 |
| ABM00023 | GVSDFYKNLI NRAKTVEGVI TLITDI | 23 |
| ABM00024 | GVSDFYKNLI NRAKTVEGVE SLIDHI | 24 |
| ABM00025 | GVSDFYKSYI NRAKTVEGVH TLIGHI | 25 |
| ABM00026 | GVSDFYKNLI NRAKTVEGVQ TLISDI | 26 |
| ABM00027 | GVSDFYKNLI NRAKTVEGVN SETSHI | 27 |
| ABM00028 | GVSDFYKSLI NRAKTVEGVN TLIHDI | 28 |
| ABM00029 | GVSDFYKNLI NRAKTVEGVE SLIGEI | 29 |
| ABM00030 | GVSDFYKRLI NRAKTVEGVH TLIHDI | 30 |
| ABM00031 | GVSDYYKNLI NRAKTVEGVS ALKMHI | 31 |

FIG. 1A

| Polypeptide | Amino acid sequence | SEQ ID NO: |
|---|---|---|
| ABM00032 | GVSDFYKNLI NKAKTVEGVD ALIVHI | 32 |
| ABM00033 | GVSDYYKRLI NRAKTVEGVH ALIAEI | 33 |
| ABM00034 | GVSDFYKNLI NRAKTVEGVD TLIHDI | 34 |
| ABM00035 | GVSDFYKRVI NRAKTVEGVQ ALIADI | 35 |
| ABM00036 | GVSDFYKNLI NRAKVEGVE SLIADI | 36 |
| ABM00037 | GVSDYYKNLI NKAKTVEGVD ALIAHI | 37 |
| ABM00038 | GVSDFYKRLI NRAKTVEGVE SLITHI | 38 |
| ABM00039 | GVSDFYKNLT NRAKTVEGVD SLIVEI | 39 |
| ABM00040 | GVSDFYKNVI NRAKTVEGVS ALIHEI | 40 |
| ABM00041 | GVSDFYKNLI NRAKTVEGVN ALISDI | 41 |
| ABM00042 | GVSDFYKNLI NRAKTVEGVS ALIQEI | 42 |
| ABM00043 | GVSDFYKNLI NRAKTVEGVQ SLIDHI | 43 |
| ABM00044 | GVSDFYKRVI NRAKTVEGVD ALICHI | 44 |
| ABM00045 | GVSDFYKRLI NKAKTVEGVD ALITHI | 45 |
| ABM00046 | GVSDFYKRVI NKAKTVEGVE ALIADI | 46 |
| ABM00047 | GVSDFYKRLI NKAKTVEGVE TLIRDI | 47 |
| ABM00048 | GVSDFYKNLI NRAKTVEGVQ TLITDI | 48 |
| ABM00049 | GVSDFYKNLI NRAKTVEGVN ALTHHI | 49 |
| ABM00050 | GVSDFYKRLI NRAKTVEGVQ ALIANI | 50 |
| ABM00051 | GVSDFYKRVI NRAKTVEGVQ SLINHI | 51 |
| ABM00052 | GVSDFYKSLI NRAKTVEGVD SLIRHI | 52 |
| ABM00053 | GVSDFYKNVI NRAKTVEGVE ALTLHI | 53 |
| ABM00054 | GVSDFYKNLI NRAKTVEGVD ALIAHI | 54 |
| ABM00055 | GVSDFYKNLI NRAKTVEGVQ ALIAHI | 55 |
| ABM00056 | GVSDFYKRLI NRAKTVEGVH ALIADI | 56 |
| ABM00057 | GVSDFYKRVI NRAKTVRGVH ALIDHI | 57 |
| ABM00058 | GVSDFYKRLI NRAKTVEGVR ALKLHI | 58 |
| ABM00059 | GVSDFYKRVI NRAKTVEGVS ALIHEI | 59 |
| ABM00060 | GVSDFYKRLI NRAKTVEGVN TLIADI | 60 |
| ABM00061 | GVSDYYKRLI NRAKTVEGVN SLISHI | 61 |
| ABM00062 | GVSDFYKRLI NRAKTVEGVS SLKGHI | 62 |

FIG. 1B

| Polypeptide | Amino acid sequence | SEQ ID NO: |
|---|---|---|
| ABM00063 | GVSDFYKRVI NRAKTVEGVD SLIAEI | 63 |
| ABM00064 | GVSDFYKRLI NRAKTVEGVQ TLISDI | 64 |
| ABM00065 | GVSDFYKRFI NRAKTVEGVE TLISEI | 65 |
| ABM00066 | GVSDFYKRLI NRAKTVEGVH SLTDEI | 66 |
| ABM00067 | GVSDYYKKVS NRAKTVEGVS SHIAEI | 67 |
| ABM00068 | GVSDFYKRLI NRAKTVEGVD ALISHI | 68 |
| ABM00069 | GVSDFYKRLI NRAKTVEGVS TLIHDI | 69 |
| ABM00070 | GVSDFYKRLI NRAKTVEGVS TLIHDI | 70 |
| ABM00071 | GVSDFYKRLI NRAKTVEGVQ ALISEI | 71 |
| ABM00072 | GVSDYYKRLI NRAKTVEGVS SLIVHI | 72 |
| ABM00073 | GVSDFYKRLI NRAKTVEGVS SLITEI | 73 |
| ABM00074 | GVSDYYKRLI NRAKTVEGVD ALITHI | 74 |
| ABM00075 | GVSDFYKRMI NRAKTVEGVS SLITHI | 75 |
| ABM00076 | GVSDFYKRLI NRAKTVEGVT ILTTDI | 76 |
| ABM00077 | GVSDFYKRLI NRAKTVEGVS SLIDHI | 77 |
| ABM00078 | GVSDFYKRVI NRAKTVEGVH TLIGHI | 78 |
| ABM00079 | GVSDFYKRLI NRAKTVEGVQ TLISDI | 79 |
| ABM00080 | GVSDFYKRLI NRAKTVEGVN SLISHI | 80 |
| ABM00081 | GVSDFYKRLI NRAKTVEGVN TLIHDI | 81 |
| ABM00082 | GVSDFYKRLI NRAKTVEGVE SLIGEI | 82 |
| ABM00083 | GVSDFYKRLI NRAKTVEGVH TLIHDI | 83 |
| ABM00084 | GVSDYYKRLI NRAKTVEGVS ALKMHI | 84 |
| ABM00085 | GVSDFYKRLI NRAKTVEGVS ALIVHI | 85 |
| ABM00086 | GVSDFYKRLI NRAKTVEGVD TLIHDI | 86 |
| ABM00087 | GVSDFYKRLI NRAKTVEGVD ALIADI | 87 |
| ABM00088 | GVSDFYKRLI NRAKTVEGVE SLIADI | 88 |
| ABM00089 | GVSDFYKRLI NRAKTVEGVD ALIAHI | 89 |
| ABM00090 | GVSDFYKRLI NRAKTVEGVE SLITHI | 90 |
| ABM00091 | GVSDFYKRLI NRAKTVEGVE SLIVEI | 91 |
| ABM00092 | GVSDFYKRVI NRAKTVEGVS ALIREI | 92 |
| ABM00093 | GVSDFYKRLI NRAKTVEGVN ALISDI | 93 |

FIG. 1C

| Polypeptide | Amino acid sequence | SEQ ID NO: |
|---|---|---|
| ABM00094 | GVSDFYKRLI NRAKTVEGVS ALIQEI | 94 |
| ABM00095 | GVSDFYKRLI NRAKTVEGVQ SLIDHI | 95 |
| ABM00096 | GVSDFYKRLI NRAKTVEGVD ALICHI | 96 |
| ABM00097 | GVSDFYKRVI NRAKTVEGVE ALIADI | 97 |
| ABM00098 | GVSDFYKRLI NRAKTVEGVE ILIRDI | 98 |
| ABM00099 | GVSDFYKRLI NRARTVEGVQ TLITDI | 99 |
| ABM00100 | GVSDFYKRLI NRAKTVEGVQ ALIAHI | 100 |
| ABM00101 | GVSDFYKRVI NRAKTVEGVN SLINHI | 101 |
| ABM00102 | GVSDFYKRLI NRAKTVEGVD SLIRHI | 102 |
| ABM00103 | GVSDYYKRLI NRAKTVEGVE ALTLHI | 103 |
| ABM00104 | GVSDFYKRLI NRAKTVEGVD ALIAHI | 104 |
| ABM00105 | GVSDYYKRLI NRAKTVEGVQ ALIAHI | 105 |
| ABM00106 | GVSDFYKMLI NRAKTVEGVH ALKGHI | 106 |
| ABM00107 | GVSDFYKNVI NRAKTVEGVH ALKDHI | 107 |
| ABM00108 | GVSDFYKMVI NRAKTVEGVS ALKHEI | 108 |
| ABM00109 | GVSDFYKNLI NRAKTVEGVN TLKADI | 109 |
| ABM00110 | GVSDFYKNLI NRAKTVEGVN TLKADI | 110 |
| ABM00111 | GVSDFYKNLI NRAKTVEGVN SLKSHI | 111 |
| ABM00112 | GVSDFYKNLI NRAKTVEGVQ SLKSEI | 112 |
| ABM00113 | GVSDFYKNVI NRAKTVEGVD SLKAEI | 113 |
| ABM00114 | GVSDFYKNLI NRAKTVEGVD TLKSDI | 114 |
| ABM00115 | GVSDFYKKTI NRAKTVEGVE TLKSEI | 115 |
| ABM00116 | GVSDFYKSLI NRAKTVEGVH SLKDEI | 116 |
| ABM00117 | GVSDFYKNVI NRAKTVEGVS SLKAEI | 117 |
| ABM00118 | GVSDFYKSLI NRAKTVEGVD ALKSHI | 118 |
| ABM00119 | GVSDFYKNLI NRAKTVEGVS TLKDDI | 119 |
| ABM00120 | GVSDFYKNLI NRAKTVEGVQ TLKHDI | 120 |
| ABM00121 | GVSDFYKNLI NRAKTVEGVQ ALKSEI | 121 |
| ABM00122 | GVSDFYKSLI NRAKTVEGVD SLKVHI | 122 |
| ABM00123 | GVSDYYKNLI NRAKTVEGVQ SLKTEI | 123 |
| ABM00124 | GVSDYYKNLI NRAKTVEGVD ALKTHI | 124 |

FIG. 1D

| Polypeptide | Amino acid sequence | SEQ ID NO: |
|---|---|---|
| ABM00125 | GVSDFYKSMI NRAKTYEGVD SLKTHI | 125 |
| ABM00126 | GVSDFYKNLI NRAKTYEGVZ TLKTDI | 126 |
| ABM00127 | GVSDFYKNLI NRAKTVEGVE SLKDHI | 127 |
| ABM00128 | GVSDFYKSYI NRAKTVEGVH TLKGHI | 128 |
| ABM00129 | GVSDFYKNLI NRAKTVEGVQ TLKSDI | 129 |
| ABM00130 | GVSDFYKNLI NRAKTVBGVN SLKSHI | 130 |
| ABM00131 | GVSDFYKNLI NRAKTVEGVN TLKHDI | 131 |
| ABM00132 | GVSDFYRNLI NRAKTVBGVE SLKGEI | 132 |
| ABM00133 | GVSDFYKNLI NKAKTVEGVH TLKADI | 133 |
| ABM00134 | GVSDFYKNLI NRAKTVEGVQ ALKVHI | 134 |
| ABM00135 | GVSDYYKRLI NRAKTVEGVB ALKAEI | 135 |
| ABM00136 | GVSDYYKNLI NRAKTVEGVE TLKDHI | 136 |
| ABM00137 | GVSDFYKKVI NRAKTVEGVQ ALKADI | 137 |
| ABM00138 | GVSDFYKNLI NRAKTVEGVE SLKADI | 138 |
| ABM00139 | GVSDYYKNLI NRAKTVBGVD ALKAHI | 139 |
| ABM00140 | GVSDFYKNLI NRAKTVBGVE SLKTHI | 140 |
| ABM00141 | GVSDFYKNLI NRARTVBGVS SLKVEI | 141 |
| ABM00142 | GVSDFYKRLI NRAKTVEGVS ALKREI | 142 |
| ABM00143 | GVSDFYRNLI NKAKTVEGVN ALKSDI | 143 |
| ABM00144 | GVSDFYKNLI NRAKTVEGVS ALKQEI | 144 |
| ABM00145 | GVSDFYKNLI NRAKTVEGVD SLKDHI | 145 |
| ABM00146 | GVSDFYRNLI NRAKTVBGVD ALKCHI | 146 |
| ABM00147 | GVSDFYKRLI NRAKTVEGVN ALKTHI | 147 |
| ABM00148 | GVSDFYKNVI NKAKTVEGVE ALKADI | 148 |
| ABM00149 | GVSDFYKNLI NRAKTVBGVE TLKRDI | 149 |
| ABM00150 | GVSDFYKNLI NRAKTVBGVQ TLKIDI | 150 |
| ABM00151 | GVSDFYKRLI NKAKTVEGVN ALKHHI | 151 |
| ABM00152 | GVSDFYRNLI NRAKTVBGVQ ALKAHI | 152 |
| ABM00153 | GVSDFYRNLI NRAKTVEGVN SLKNHI | 153 |
| ABM00154 | GVSDFYKSLI NRAKTVEGVD SLKRHI | 154 |
| ABM00155 | GVSDYYKNLI NRAKTVEGVE ALKLHI | 155 |

FIG. 1E

| Polypeptide | Amino acid sequence | SEQ ID NO: |
|---|---|---|
| ABM00156 | GVSDFYKRLI NRAKTVEGVD ALKAHI | 156 |
| ABM00157 | GVSDYYKNLI NRAKTVEGVQ ALKAHI | 157 |
| ABM00158 | GVSDFYKRLI NRAKTVEGVH ALKGHI | 158 |
| ABM00159 | GVSDFYKRVI NRAKTVEGVH ALRDHI | 159 |
| ABM00160 | GVSDYYKRII NRAKTVEGVR ALKLHI | 160 |
| ABM00161 | GVSDFYKRVI NRAKTVEGVS ALKHEI | 161 |
| ABM00162 | GVSIFYKRLI NRAKTVEGVN SLKSHI | 162 |
| ABM00163 | GVSIFYKRLI NRAKTVGGVQ SLKSEI | 163 |
| ABM00164 | GVSDFYKRLI NRAKTVEGVS SLKGHI | 164 |
| ABM00165 | GVSDFYKRVI NRAKTVEGVD SLKAEI | 165 |
| ABM00166 | GVSDFYKRLI NRAKTVEGVQ TLKSDI | 166 |
| ABM00167 | GVSOFYKRFI NRAKTVEGVE TLKSEI | 167 |
| ABM00168 | GVSDFYKRLI NRAKTVEGVH SLKDEI | 168 |
| ABM00169 | GVSDFYKRVI NRAKTVEGVS SLKAEI | 169 |
| ABM00170 | GVSIFYKRLI NRAKTVEGVD ALKSHI | 170 |
| ABM00171 | GVSIFYKRLI NRAKTVEGVS TLKHDI | 171 |
| ABM00172 | GVSIFYKRLI NRAKTVEGVS TLKHDI | 172 |
| ABM00173 | GVSIFYKRLI NRAKTVEGVQ ALKSEI | 173 |
| ABM00174 | GVSDFYKRLI NRAKTVEGVD SLKVHI | 174 |
| ABM00175 | GVSIFYKRLI NRAKTVEGVQ SLKTEI | 175 |
| ABM00176 | GVSDFYKRLI NRAKTVEGVD ALKTHI | 176 |
| ABM00177 | GVSDFYKRMI NRAKTVEGVH SLKTHI | 177 |
| ABM00178 | GVSDYYKRLI NRAKTVEGVQ TLKTDI | 178 |
| ABM00179 | GVSDFYKRLI NRAKTVEGVE SLKDHI | 179 |
| ABM00180 | GVSDYYKRYI NRAKTVEGVH TLKGHI | 180 |
| ABM00181 | GVSDFYKRLI NRAKTVEGVQ TLKSDI | 181 |
| ABM00182 | GVSIFYKRLI NRAKTVEGVN SLKSHI | 182 |
| ABM00183 | GVSIFYKRLI NRAKTVEGVN TLKHDI | 183 |
| ABM00184 | GVSDFYKRLI NRAKTVEGVE SLKGEI | 184 |
| ABM00185 | GVSDFYKRLI NRAKTVEGVH TLKHDI | 185 |
| ABM00186 | GVSDYYKRLI NRAKTVEGVS ALKMHI | 186 |

FIG. 1F

| Polypeptide | Amino acid sequence | SEQ ID NO: |
|---|---|---|
| ABM00187 | GVSDFYKRLI NKAKTVEGVD ALKHHI | 187 |
| ABM00188 | GVSDYYKRLI NRAKTVEGVH ALKAHI | 188 |
| ABM00189 | GVSDFYKRLI NRAKTVEGVD TLKHDI | 189 |
| ABM00190 | GVSDFYKRVI NRAKTVEGVD ALKADI | 190 |
| ABM00191 | GVSDFYKRLI NRAKTVEGVE SLKADI | 191 |
| ABM00192 | GVSDYYKRLI NRAKTVEGVD ALKAHI | 192 |
| ABM00193 | GVSDYYKRLI NRAKTVEGVE SLKTHI | 193 |
| ABM00194 | GVSDYYKRLI NRAKTVEGVD SLKVEI | 194 |
| ABM00195 | GVSDFYKRVI NRAKTVEGVS ALKHEI | 195 |
| ABM00196 | GVSDFYKRLI NRAKTVEGVN ALKSDI | 196 |
| ABM00197 | GVSDFYKRLI NRAKTVEGVS ALKQEI | 197 |
| ABM00198 | GVSDYYKRLI NRAKTVEGVQ SLKDHI | 198 |
| ABM00199 | GVSDFYKRLI NRAKTVEGVD ALKCHI | 199 |
| ABM00200 | GVSDFYKRLI NRAKTVEGVD ALKTHI | 200 |
| ABM00201 | GVSDFYKRLI NRAKTVEGVE ALKADI | 201 |
| ABM00202 | GVSDFYKRLI NRAKTVEGVE TLKRDI | 202 |
| ABM00203 | GVSDFYKRLI NRAKTVEGVQ TLKTDI | 203 |
| ABM00204 | GVSDFYKRLI NRAKTVEGVN ALKHHI | 204 |
| ABM00205 | GVSDFYKRLI NRAKTVEGVQ ALKAHI | 205 |
| ABM00206 | GVSDFYKRVI NRAKTVEGVN SLKNHI | 206 |
| ABM00207 | GVSDFYKRLI NRAKTVEGVD SLKRHI | 207 |
| ABM00208 | GVSDFYKRLI NRAKTVEGVE ALKLHI | 208 |
| ABM00209 | GVSDYYKRLI NRAKTVEGVS ALKAHI | 209 |
| ABM00210 | GVSDFYKRLI NKAKTVEGVS ALKHHI | 210 |
| ABM00211 | GVSDFYKRVI NRAKTVEGVN TLKHHI | 211 |
| ABM00212 | GVSDFYKRLI NRAKTVEGVN TLKABI | 212 |
| ABM00213 | GVSDFYKRLI NRAKTVEGVD SLKSHI | 213 |
| ABM00214 | GVSDFYKRLI NRARTVEGVD SLKAHI | 214 |
| ABM00215 | GVSDFYKRFI NRAKTVEGVQ SLKAHI | 215 |
| ABM00216 | GVSDFYKRFI NRAKTVEGVE TLKSHI | 216 |
| ABM00217 | GVSDFYKRLI NRAKTVEGVH SLKDHI | 217 |

FIG. 1G

| Polypeptide | Amino acid sequence | SEQ ID NO: |
| --- | --- | --- |
| ABM00218 | GVSDYYKRVI NRAKTVEGVS SLKAHI | 218 |
| ABM00219 | GVSDFYKRVI NRAKVEGVS TLKHHI | 219 |
| ABM00220 | GVSDFYKRLI NRAKVEGVS TLKHHI | 220 |
| ABM00221 | GVSDFYKRLI NRAKVEGVQ ALKSHI | 221 |
| ABM00222 | GVSDFYKRLI NRAKVEGVQ SLKTHI | 222 |
| ABM00223 | GVSDFYKRLI NRAKVEGVT TLKTHI | 223 |
| ABM00224 | GVSDFYKRLI NRAKVEGVQ TLKSHI | 224 |
| ABM00225 | GVSDFYKRLI NRAKVEGVN TLKHHI | 225 |
| ABM00226 | GVSDFYKRLI NRAKVEGVE SLKGHI | 226 |
| ABM00227 | GVSDFYKRLT NRAKVEGVH TLKHHI | 227 |
| ABM00228 | GVSDFYKRLI NRAKVEGVH ALKAHI | 228 |
| ABM00229 | GVSDYYKRLI NRAKVEGVD TLKHHI | 229 |
| ABM00230 | GVSDFYKRLI NRAKVEGVQ ALKAHI | 230 |
| ABM00231 | GVSDFYKRVI NRAKVEGVE SLKAHI | 231 |
| ABM00232 | GVSLFYKRLI NRAKVEGVD SLKVHI | 232 |
| ABM00233 | GVSDFYKRVI NRAKTVEGVS ALKRHI | 233 |
| ABM00234 | GVSDFYKRLI NRAKTVEGVN ALKSHI | 234 |
| ABM00235 | GVSDFYKRLI NRAKTVEGVE ALKQHI | 235 |
| ABM00236 | GVSDFYKRLI NRAKTVEGVE ALKAHI | 236 |
| ABM00237 | GVSDFYKRLI NRAKTVEGVE TLKRHI | 237 |
| ABM00238 | GVSDFYKRLI NRAKVEGVQ TLKTHI | 238 |
| ABM00239 | GVSDFYKRLI NRAKVEGVE ALKLHI | 239 |
| ABM00240 | GVSDYYKNLI NRAKVEGVE ALKLHI | 240 |
| ABM00241 | GVSDYYKMLI NRAKVEGVE ALKLHI | 241 |
| ABM00242 | GVSDFYKMLI NRAKVEGVE ALKLHI | 242 |
| ABM00243 | GVSDFYKNVI NRAKVEGVE ALKLHI | 243 |
| ABM00244 | GVSDFYKNLI NRAKVEGVH ALIDHI | 244 |
| ABM00245 | GVSDYYKMLI NRAKVEGVH ALIDHI | 245 |
| ABM00246 | GVSDFYKRLI NRAKVEGVE ALKLHI | 246 |
| ABM00247 | GVSDFYKRLI SRAKVEGVK ALISEI | 247 |
| ABM00248 | GVSDFYKRLI NRAKVEGVE ALKLHI | 248 |

FIG. 1H

| Polypeptide | Amino acid sequence | SEQ ID NO: |
|---|---|---|
| ABM00249 | GVSDYYKRLI SKAKTVEGVK ALISEI | 249 |
| ABM00250 | GVSDYYKRLI SKAKTVEGVK ALISEI | 250 |
| ABM00251 | GVSDYYKRLI SKAKTVEGVK ALISEI | 251 |
| ABM00252 | GVSDYYKRLI SKAKTVEGVK ALISEI | 252 |
| ABM00253 | GVSDYYKRLI SKAKTVEGVK ALISEI | 253 |
| ABM00254 | GVSDYYKRLI SKAKTVEGVK ALISEI | 254 |
| ABM00255 | GVSDYYKRLI SKAKTVEGVK ALISEI | 255 |
| ABM00256 | GVSDYYKRLI SKAKTVEGVK ALISEI | 256 |
| ABM00257 | GVSDYYKRLI SKAKTVEGVK ALISEI | 257 |
| ABD00001 | LAEAKVLANR ELDKYGVSDF YKNLINRAKT VEGVHALIGH ILAALP | 258 |
| ABD00002 | LAEAKVLANR ELDKYGVSDF YKNVINRAKT VEGVHALIDE ILAALP | 259 |
| ABD00003 | LAEAKVLANR ELDKYGVSDF YKNIINRAKT VEGVRALKLH ILAALP | 260 |
| ABD00004 | LAEAKVLANR ELDKYGVSDF YKNVINRAKT VEGVSALIHE ILAALP | 261 |
| ABD00005 | LAEAKVLANR ELDKYGVSDF YKNLINRAKT VEGVNTLIAD ILAALP | 262 |
| ABD00006 | LAEAKVLANR ELDKYGVSDF YKNLINRAKT VEGVNTLIAD ILAALP | 263 |
| ABD00007 | LAEAKVLANR ELDKYGVSDF YKRLINRAKT VEGVNSLISH ILAALP | 264 |
| ABD00008 | LAEAKVLANR ELDKYGVSDF YKNLINRAKT VGGVQSLISE ILAALP | 265 |
| ABD00009 | LAEAKVLANR ELDKYGVSDF YRNLINRAKT VEGVESIKGH ILAALP | 266 |
| ABD00010 | LAEAKVLANR ELDKYGVSDF YKNVINRAKT VEGVSLIAE ILAALP | 267 |
| ABD00011 | LAEAKVLANR ELDKYGVSDF YKNLINRAKT VEGVDSLIAE ILAALP | 268 |
| ABD00012 | LAEAKVLANR ELDKYGVSDF YKKFINKAKT VEGVQTLIDD ILAALP | 269 |
| ABD00013 | LAEAKVLANR ELDKMQVSDF YKSLINKAKT VEGVTLISE ILAALP | 270 |
| ABD00014 | LAEAKVLANR ELDKYGVSDY YKNVINKAKT VEGVSSLIAE ILAALP | 271 |
| ABD00015 | LAEAKVLANR ELDKYGVSDF YKSLINRAKT VEGVDALTSH ILAALP | 272 |
| ABD00016 | LAEAKVLANR ELDKYGVSDF YKMLINRAKT VEGVSTLIED ILAALP | 273 |
| ABD00017 | LAEAKVLANR ELDKYGVSDF YKMLINRAKT VEGVSTLIED ILAALP | 274 |
| ABD00018 | LAEAKVLANR ELDKYGVSDF YKMLINRAKT VEGVQALISE ILAALP | 275 |
| ABD00019 | LAEAKVLANR ELDKYGVSDY YKSLINKAKT VEGVSLIVE ILAALP | 276 |
| ABD00020 | LAEAKVLANR ELDKYGVSDF YKMLINRAKT VEGVSLITE ILAALP | 277 |
| ABD00021 | LAEAKVLANR ELDKYGVSDY YRNLINRAKT VEGVQSLITE ILAALP | 278 |
| ABD00022 | LAEAKVLANR ELDKYGVSDF YKSMINRAKT VEGVDSLITE ILAALP | 279 |

FIG. 11

| Polypeptide | Amino acid sequence | | | | SEQ ID NO: |
|---|---|---|---|---|---|
| ABD00023 | LAEAKVLANR ELDKYGVSDF YKNLINRAKT VEGVTTLTTD ILAALP | | | | 280 |
| ABD00024 | LAEAKVLANR ELDKYGVSDF YKNLINRAKT VEGVESLIDH ILAALP | | | | 281 |
| ABD00025 | LAEAKVLANR ELDKYGVSDF YKSYINRAKT VEGVHTLIGH ILAALP | | | | 282 |
| ABD00026 | LAEAKVLANR ELDKYGVSDF YKNLINRAKT VEGVQTLISD ILAALP | | | | 283 |
| ABD00027 | LAEAKVLANR ELDKYGVSDF YKMLINRAKT VEGVNSLISH ILAALP | | | | 284 |
| ABD00028 | LAEAKVLANR ELDKYGVSDF YKNLINRAKT VEGVNTLIHD ILAALP | | | | 285 |
| ABD00029 | LAEAKVLANR ELDKYGVSDF YKNLINRAKT VEGVESLIGE ILAALP | | | | 286 |
| ABD00030 | LAEAKVLANR ELDKYGVSDY YKNLINRAKT VEGVTLIHD ILAALP | | | | 287 |
| ABD00031 | LAEAKVLANR ELDKYGVSDF YKNLINKAKT VEGVSALKMH ILAALP | | | | 288 |
| ABD00032 | LAEAKVLANR ELDKYGVSDF YKNLTNRAKT VEGVDALIVH ILAALP | | | | 289 |
| ABD00033 | LAEAKVLANR ELDKYGVSDF YKRLINRAKT VEGVSALIAE ILAALP | | | | 290 |
| ABD00034 | LAEAKVLANR ELDKYGVSDF YKNLINRAKT VEGVDTLIHD ILAALP | | | | 291 |
| ABD00035 | LAEAKVLANR ELDKYGVSDF YKKVINRAKT VEGVQALIAD ILAALP | | | | 292 |
| ABD00036 | LAEAKVLANR ELDKYGVSDF YKNLINRAKT VEGVESLIAD ILAALP | | | | 293 |
| ABD00037 | LAEAKVLANR ELDKYGVSDZ YKNLINRAKT VEGVDALIAH ILAALP | | | | 294 |
| ABD00038 | LAEAKVLANR ELDKYGVSDF YKNLINRAKT VEGVESLIRE ILAALP | | | | 295 |
| ABD00039 | LAEAKVLANR ELDKYGVSDF YKNLINRAKT VEGVDSLIVE ILAALP | | | | 296 |
| ABD00040 | LAEAKVLANR ELDKYGVSDF YKNLINRAKT VEGVSALIRE ILAALP | | | | 297 |
| ABD00041 | LAEAKVLANR ELDKYGVSDF YKNLINRAKT VEGVNALISD ILAALP | | | | 298 |
| ABD00042 | LAEAKVLANR ELDKYGVSDF YKNLINRAKT VEGVSALIQE ILAALP | | | | 299 |
| ABD00043 | LAEAKVLANR ELDKYGVSDF YKNLINRAKT VEGVQSLIDH ILAALP | | | | 300 |
| ABD00044 | LAEAKVLANR ELDKYGVSDF YKNLINRAKT VEGVDALICH ILAALP | | | | 301 |
| ABD00045 | LAEAKVLANR ELDKYGVSDY YKRLINRAKT VEGVNBLITH ILAALP | | | | 302 |
| ABD00046 | LAEAKVLANR ELDKYGVSDF YKNVINRAKT VEGVEALIAD ILAALP | | | | 303 |
| ABD00047 | LAEAKVLANR ELDKYGVSDF YKNLINRAKT VEGVETLIRD ILAALP | | | | 304 |
| ABD00048 | LAEAKVLANR ELDKYGVSDF YKRLINRAKT VEGVQTLITD ILAALP | | | | 305 |
| ABD00049 | LAEAKVLANR ELDKYGVSDF YKNLINRAKT VEGVNALITHE ILAALP | | | | 306 |
| ABD00050 | LAEAKVLANR ELDKYGVSDF YKNLINRAKT VEGVQALIAH ILAALP | | | | 307 |
| ABD00051 | LAEAKVLANR ELDKYGVSDY YKNLINRAKT VEGVNSLINE ILAALP | | | | 308 |
| ABD00052 | LAEAKVLANR ELDKYGVSDY YKSLINRAKT VEGVDSLIRH ILAALP | | | | 309 |
| ABD00053 | LAEAKVLANR ELDKYGVSDY YKNLINRAKT VEGVALTLIH ILAALP | | | | 310 |

FIG. 1J

| Polypeptide | Amino acid sequence | SEQ ID NO: |
|---|---|---|
| ABD00054 | LAEAKVLANR ELDKYGVSDF YKRLINRAKT VEGVDALIAH ILAALP | 311 |
| ABD00055 | LAEAKVLANR ELDKYGVSDY YKKLINRAKT VEGVQALIAH ILAALP | 312 |
| ABD00056 | LAEAKVLANR ELDKYGVSDF YKRVINRAKT VEGVHALICH ILAALP | 313 |
| ABD00057 | LAEAKVLANR ELDKYGVSDY YKRLINRAKT VEGVHALIDH ILAALP | 314 |
| ABD00058 | LAEAKVLANR ELDKYGVSDY YKRVINRAKT VEGVRALKLH ILAALP | 315 |
| ABD00059 | LAEAKVLANR ELDKYGVSDF YKKVINRAKT VEGVSALIHE ILAALP | 316 |
| ABD00060 | LAEAKVLANR ELDKYGVSDY YKRLINRAKT VEGVNTLIAQ ILAALP | 317 |
| ABD00061 | LAEAKVLANR ELDKYGVSDY YKRLINRAKT VEGVNSLISE ILAALP | 318 |
| ABD00062 | LAEAKVLANR ELDKYGVSDF YKRLINRAKT VEGVSSLKGH ILAALP | 319 |
| ABD00063 | LAEAKVLANR ELDKYGVSDF YKRVINRAKT VEGVDSLIAF ILAALP | 320 |
| ABD00064 | LAEAKVLANR ELDKYGVSDF YKRLINRAKT VEGVQTLISD ILAALP | 321 |
| ABD00065 | LAEAKVLANR ELDKYGVSDF YKRFINRAKT VEGVETLISE ILAALP | 322 |
| ABD00066 | LAEAKVLANR ELDKYGVSDF YKKLINRAKT VEGVESITQE ILAALP | 323 |
| ABD00067 | LAEAKVLANR ELDKYGVSDY YKKVINRAKT VEGVSSITAE ILAALP | 324 |
| ABD00068 | LAEAKVLANR ELDKYGVSDY YKRLINRAKT VEGVDALTSH ILAALP | 325 |
| ABD00069 | LAEAKVLANR ELDKYGVSDF YKRLINRAKT VEGVSTLIHD ILAALP | 326 |
| ABD00070 | LAEAKVLANR ELDKYGVSDE YKRLINRAKT VEGVSTLIHD ILAALP | 327 |
| ABD00071 | LAEAKVLANR ELDKYGVSDY YKRLINRAKT VEGVQALISE ILAALP | 328 |
| ABD00072 | LAEAKVLANR ELDKYGVSDY YKRLINKAKT VEGVDSLIVR ILAALP | 329 |
| ABD00073 | LAEAKVLANR ELDKYGVQDF YKRLINRAKT VEGVQSLITE ILAALP | 330 |
| ABD00074 | LAEAKVLANR ELDKYGVSDF YKRLINRAKT VEGVDALITH ILAALP | 331 |
| ABD00075 | LAEAKVLANR ELDKMYGVSDF YKRMINRAKT VEGVDSLITH ILAALP | 332 |
| ABD00076 | LAEAKVLANR ELDKYGVSDF YKRLINRAKT VEGVTLITD ILAALP | 333 |
| ABD00077 | LAEAKVLANR ELDKYGVSDF YKRLINPAKT VEGVESLIDH ILAALP | 334 |
| ABD00078 | LAEAKVLANR ELDKYGVSDF YKRYINRAKT VEGVHTLIGH ILAALP | 335 |
| ABD00079 | LAEAKVLANR ELDKYGVSDF YKKLINRAKT VEGVQTLISD ILAALP | 336 |
| ABD00080 | LAEAKVLANR ELDKYGVSDF YKRLINRAKT VEGVNSLTSH ILAALP | 337 |
| ABD00081 | LAEAKVLANR ELDKYGVSDF YKRLINRAKT VEGVNTLIHD ILAALP | 338 |
| ABD00082 | LAEAKVLANR ELDKYGVSDF YKRLINRAKT VEGVESLIGE ILAALP | 339 |
| ABD00083 | LAEAKVLANR ELDKYGVSDF YKRLINRAKT VEGVHTLIHD ILAALP | 340 |
| ABD00084 | LAEAKVLANR ELDKYGVSDF YKRLINKAKT VEGVSALKMH ILAALP | 341 |

FIG. 1K

| Polypeptide | Amino acid sequence | | | | SEQ ID NO: |
|---|---|---|---|---|---|
| ABD00085 | LAEAKVLANR | ELDKYGVSDF | YKRLINKAKT | VEGVDALIVE ILAALP | 342 |
| ABD00086 | LAEAKVLANR | ELDKYGVSDY | YKRLINKAKT | VEGVDTLIHD ILAALP | 343 |
| ABD00087 | LAEAKVLANR | ELDKYGVSDF | YKRVINRAKT | VEGVQALIAD ILAALP | 344 |
| ABD00088 | LAEAKVLANR | ELDKYGVSDF | YKRLINRAKT | VEGVSLIAD ILAALP | 345 |
| ABD00089 | LAEAKVLANR | ELDKYGVSDY | YKRLINRAKT | VEGVDALIAH ILAALP | 346 |
| ABD00090 | LAEAKVLANR | ELDKYGVSDF | YKRLINRAKT | VEGVESLIIH ILAALP | 347 |
| ABD00091 | LAEAKVLANR | ELDKYGVSDF | YKRLINKAKT | VEGVDSLIVE ILAALP | 348 |
| ABD00092 | LAEAKVLANR | ELDKYGVSDF | YKRVINRAKT | VEGVSALIRE ILAALP | 349 |
| ABD00093 | LAEAKVLANR | ELDKYGVSDF | YKRLINRAKT | VEGVNALISD ILAALP | 350 |
| ABD00094 | LAEAKVLANR | ELDKYGVSDF | YKRLINRAKT | VEGVSALIQE ILAALP | 351 |
| ABD00095 | LAEAKVLANR | ELDKYGVSDF | YKRLINRAKT | VEGVSLIDH ILAALP | 352 |
| ABD00096 | LAEAKVLANR | ELDKYGVSDF | YKRLINRAKT | VEGVDALICH ILAALP | 353 |
| ABD00097 | LAEAKVLANR | ELDKYGVSDF | YKRVINRAKT | VEGVEALIAD ILAALP | 354 |
| ABD00098 | LAEAKVLANR | ELDKYGVSDF | YKRLINRAKT | VEGVETLIRO ILAALP | 355 |
| ABD00099 | LAEAKVLANR | ELDKYGVSDF | YKRLINRAKT | VEGVTQLITD ILAALP | 356 |
| ABD00100 | LAEAKVLANR | ELDKYGVSDF | YKRLINRAKT | VEGVQALIAH ILAALP | 357 |
| ABD00101 | LAEAKVLANR | ELDKYGVSDF | YKRVINRAKT | VEGVNSLINE ILAALP | 358 |
| ABD00102 | LAEAKVLANR | ELDKYGVSDF | YKRVINRAKT | VEGVDSLIRH ILAALP | 359 |
| ABD00103 | LAEAKVLANR | ELDKYGVSDF | YKRLINRAKT | VEGVTALTIR ILAALP | 360 |
| ABD00104 | LAEAKVLANR | ELDKYGVSDF | YKNVINRAKT | VEGVDALIAH ILAALP | 361 |
| ABD00105 | LAEAKVLANR | ELDKYGVSDF | YKRLINRAKT | VEGVQALIAH ILAALP | 362 |
| ABD00106 | LAEAKVLANR | ELDKYGVSDF | YKRLINRAKT | VEGVALKGH ILAALP | 363 |
| ABD00107 | LAEAKVLANR | ELDKIGVSDF | YKRLINRAKT | VEGVALKOH ILAALP | 364 |
| ABD00108 | LAEAKVLANR | ELDKYGVSDF | YKRLINKAKT | VEGVSALKHE ILAALP | 365 |
| ABD00109 | LAEAKVLANR | ELDKYGVSDF | YKRLINKAKT | VEGVNTLKAD ILAALP | 366 |
| ABD00110 | LAEAKVLANR | ELDKYGVSDF | YKRLINRAKT | VEGVNTLKAD ILAALP | 367 |
| ABD00111 | LAEAKVLANR | ELDKYGVSDY | YKRLINRAKT | VEGVNSIKSH ILAALP | 368 |
| ABD00112 | LAEAKVLANR | ELDKYGVSDF | YKRLINRAKT | VGGVQSIKSE ILAALP | 369 |
| ABD00113 | LAEAKVLANR | ELDKYGVSDF | YKNVINRAKT | VEGVDSLKAE ILAALP | 370 |
| ABD00114 | LAEAKVLANR | ELDKYGVSDF | YKRLINKAKT | VEGVQILKSD ILAALP | 371 |
| ABD00115 | LAEAKVLANR | ELDKYGVSDF | YKRFINKAKT | VEGVETLKSE ILAALP | 372 |

FIG. 1L

| Polypeptide | Amino acid sequence | | | | SEQ ID NO: |
|---|---|---|---|---|---|
| ABD00116 | LAEAKVLANR | ELDKYGVSDF | YKSLINRAKT | VEGVESLKDE ILAALP | 373 |
| ABD00117 | LAEAKVLANR | ELDKYGVSDY | YKNVINKAKT | VEGVSSLKAE ILAALP | 374 |
| ABD00118 | LAEAKVLANR | ELDKYGVSDF | YKSLINRAKT | VEGVDALKSH ILAALP | 375 |
| ABD00119 | LAEAKVLANR | ELDKYGVSDF | YKNLINRAKT | VEGVSTLKHD ILAALP | 376 |
| ABD00120 | LAEAKVLANR | ELDKYGVSDF | YKNLINRAKT | VEGVQALKSE ILAALP | 377 |
| ABD00121 | LAEAKVLANR | ELDKYGVSDF | YKSLINRAKT | VEGVDSLKVH ILAALP | 378 |
| ABD00122 | LAEAKVLANR | ELDKYGVSDY | YKNLINKAKT | VEGVSLKRH ILAALP | 379 |
| ABD00123 | LAEAKVLANR | ELDKYGVSDF | YKNLINRAKT | VEGVQSLKTE ILAALP | 380 |
| ABD00124 | LAEAKVLANR | ELDKYGVSDY | YKNLINRAKT | VEGVDALKTH ILAALP | 381 |
| ABD00125 | LAEAKVLANR | ELDKYGVSDF | YKSMINRAKT | VEGVDSLKTH ILAALP | 382 |
| ABD00126 | LAEAKVLANR | ELDKYGVSDF | YKNLINRAKT | VEGVTLKTD ILAALP | 383 |
| ABD00127 | LAEAKVLANR | ELDKYGVSDF | YKNLINRAKT | VEGVESLKDH ILAALP | 384 |
| ABD00128 | LAEAKVLANR | ELDKYGVSDF | YKSYINRAKT | VEGVHTLKGH ILAALP | 385 |
| ABD00129 | LAEAKVLANR | ELDKYGVSDF | YKNLINRAKT | VEGVQTLKSD ILAALP | 386 |
| ABD00130 | LAEAKVLANR | ELDKYGVSDF | YKNRSLKSH | VEGVSLKSH ILAALP | 387 |
| ABD00131 | LAEAKVLANR | ELDKYGVSDF | YKNLINRAKT | VEGVNTLKHD ILAALP | 388 |
| ABD00132 | LAEAKVLANR | ELDKYGVSDF | YKNLINRAKT | VEGVESLKGE ILAALP | 389 |
| ABD00133 | LAEAKVLANR | ELDKYGVSDF | YKNLINRAKT | VEGVHTLKHD ILAALP | 390 |
| ABD00134 | LAEAKVLANR | ELDKYGVSDF | YKNLINRAKT | VEGVDALKVH ILAALP | 391 |
| ABD00135 | LAEAKVLANR | ELDKYGVSDF | YKRLINRART | VEGVHALKAE ILAALP | 392 |
| ABD00136 | LAEAKVLANR | ELDKYGVSDY | YKNLINRAKT | VEGVDTLKHD ILAALP | 393 |
| ABD00137 | LAEAKVLANR | ELDKYGVSDF | YKKVTNRAKT | VEGVQALKAD ILAALP | 394 |
| ABD00138 | LAEAKVLANR | ELDKYGVSDF | YKNLINRAKT | VEGVESLKAD ILAALP | 395 |
| ABD00139 | LAEAKVLANR | ELDKYGVSDY | YKNLINRAKT | VEGVDALKRH ILAALP | 396 |
| ABD00140 | LAEAKVLANR | ELDKYGVSDF | YKNLINRAKT | VEGVESLKTH ILAALP | 397 |
| ABD00141 | LAEAKVLANR | ELDKYGVSDY | YKNLINRANT | VEGVDSLKVE ILAALP | 398 |
| ABD00142 | LAEAKVLANR | ELDKYGVSDF | YKNVINRAKT | VEGVSALKRE ILAALP | 399 |
| ABD00143 | LAEAKVLANR | ELDKYGVSDF | YKNLINRAKT | VEGVNALKSQ ILAALP | 400 |
| ABD00144 | LAEAKVLANR | ELDKYGVSDF | YKNLINRAKT | VEGVSALKQE ILAALP | 401 |
| ABD00145 | LAEAKVLANR | ELDKYGVSDF | YKNLINRAKT | VEGVQSLKDR ILAALP | 402 |
| ABD00146 | LAEAKVLANR | ELDKYGVSDF | YKNLINRAKT | VEGVDALKCH ILAALP | 403 |

FIG. 1M

| Polypeptide | Amino acid sequence | SEQ ID NO: |
|---|---|---|
| ABD00147 | LAEAKVLANR ELDKYGVSDY YKRLINKAKT VEGVNALKTH ILAALP | 404 |
| ABD00148 | LAEAKVLANR ELDKYGVSDF YKRVINKAKT VEGVEALKAD ILAALP | 405 |
| ABD00149 | LAEAKVLANR ELDKYGVSDF YKNLINKAKT VEGVETLKRD ILAALP | 406 |
| ABD00150 | LAEAKVLANR ELDKYGVSDF YKRLINKAKT VEGVQTLKTD ILAALP | 407 |
| ABD00151 | LAEAKVLANR ELDKYGVSDF YKRLINKAKT VEGVNALKHH ILAALP | 408 |
| ABD00152 | LAEAKVLANR ELDKYGVSDF YKRLINKAKT VEGVQALKAH ILAALP | 409 |
| ABD00153 | LAEAKVLANR ELDKYGVSDF YKRVINKAKT VEGVNSLKNH ILAALP | 410 |
| ABD00154 | LAEAKVLANR ELDKYGVSDF YKSLINRAKT VEGVDSIKRH ILAALP | 411 |
| ABD00155 | LAEAKVLANR ELDKYGVSDF YKNLINKAKT VEGVEALKLH ILAALP | 412 |
| ABD00156 | LAEAKVLANR ELDKYGVSDF YKNLINRAKT VEGVDAIKAH ILAALP | 413 |
| ABD00157 | LAEAKVLANR ELDKYGVSDY YKNLINKAKT VEGVQALKAH ILAALP | 414 |
| ABD00158 | LAFAKVLANR ELDKYGVSDF YKRLINRAKT VEGVHAIKGH ILAALP | 415 |
| ABD00159 | LAEAKVLANR ELDKYGVSDF YKRVTNRAKT VEGVRALKQH ILAALP | 416 |
| ABD00160 | LAEAKVLANR ELDKYGVSDF YKRINRAKT VEGVRAIKLH ILAALP | 417 |
| ABD00161 | LAEAKVLANR ELDKYGVSDF YKRVINRAKT VEGVSALKHE ILAALP | 418 |
| ABD00162 | LAEAKVLANR ELDKYGVSDY YKNLINRAKT VEGVNSLKSH ILAALP | 419 |
| ABD00163 | LAEAKVLANR ELDKYGVSDF YKRLINKAKT VGGVQSLKSE ILAALP | 420 |
| ABD00164 | LAEAKVLANR ELDKYGVSDF YKRLINRAKT VEGVSLKGH ILAALP | 421 |
| ABD00165 | LAEAKVLANR ELDKYGVSDF YKRVINRAKT VEGVDSLKAE ILAALP | 422 |
| ABD00166 | LAEAKVLANR ELDKYGVSDF YKRLINRAKT VEGVQTLKSD ILAALP | 423 |
| ABD00167 | LAEAKVLANR ELDKYGVSDF YKRFINKAKT VEGVETLKSE ILAALP | 424 |
| ABD00168 | LAEAKVLANR ELDKYGVSDY YKRLINRAKT VEGVNSLKDE ILAALP | 425 |
| ABD00169 | LAEAKVLANR ELDKYGVSDY YKRVINKAKT VEGVSSLKAE ILAALP | 426 |
| ABD00170 | LAEAKVLANR ELDKYGVSDF YKRLINRAKT VEGVDALKSH ILAALP | 427 |
| ABD00171 | LAEAKVLANR ELDKYGVSDF YKRLINRAKT VEGVSTLKRD ILAALP | 428 |
| ABD00172 | LAEAKVLANR ELDKYGVSDF YKRLINRAKT VEGVQALKSE ILAALP | 429 |
| ABD00173 | LAEAKVLANR ELDKYGVSDF YKRLINRAKT VEGVQALKSE ILAALP | 430 |
| ABD00174 | LAEAKVLANR ELDKYGVSDF YKRLINRAKT VEGVDSIKVH ILAALP | 431 |
| ABD00175 | LAEAKVLANR ELDKYGVSDF YKRLINRAKT VEGVQSLKTE ILAALP | 432 |
| ABD00176 | LAEAKVLANR ELDKYGVSDF YKRLINRAKT VEGVDAIKTH ILAALP | 433 |
| ABD00177 | LAEAKVLANR ELDKYGVSDF YKRMINRAKT VEGVDSLKTH ILAALP | 434 |

FIG. 1N

| Polypeptide | Amino acid sequence | SEQ ID NO: |
|---|---|---|
| ABD00178 | LAEAKVLANR ELDKYGVSDF YKRLINRAKT VEGVTLKTD ILAALP | 435 |
| ABD00179 | LAEAKVLANR ELDKYGVSDF YKRLINRAKT VEGVESLKDH ILAALP | 436 |
| ABD00180 | LAEAKVLANR ELDKYGVSDF YKRYINRAKT VEGVHTLKGH ILAALP | 437 |
| ABD00181 | LAEAKVLANR ELDKYGVSDF YKRLINRAKT VEGVQTLKSD ILAALP | 438 |
| ABD00182 | LAEAKVLANR ELDKYGVSDF YKRLINRAKT VEGVNSLKSE ILAALP | 439 |
| ABD00183 | LAEAKVLANR ELDKYGVSDF YKRLINRAKT VEGVNTLKHD ILAALP | 440 |
| ABD00184 | LAEAKVLANR ELDKYGVSDF YKRLINRAKT VEGVESLKGE ILAALP | 441 |
| ABD00185 | LAEAKVLANR ELDKYGVSDF YKRLINRAKT VEGVNTLKHD ILAALP | 442 |
| ABD00186 | LAEAKVLANR ELDKYGVSDY YKRLINRAKT VEGVSALKME ILAALP | 443 |
| ABD00187 | LAEAKVLANR ELDKYGVSDF YKRLINRAKT VEGMDAIKVE ILAALP | 444 |
| ABD00188 | LAEAKVLANR ELDKYGVSDF YKRLINRAKT VEGVHALKAE ILAALP | 445 |
| ABD00189 | LAEAKVLANR ELDKYGVSDF YKRLINRART VEGVDTLKHD ILAALP | 446 |
| ABD00190 | LAEAKVLANR ELDKYGVSDF YKRVINRAKT VEGVQALKAD ILAALP | 447 |
| ABD00191 | LAEAKVLANR ELDKYGVSDF YKRLINRAKT VEGVESIKAD ILAALP | 448 |
| ABD00192 | LAEAKVLANR ELDKYGVSDV YKRLINRAKT VEGVESIKTH ILAALP | 449 |
| ABD00193 | LAEAKVLANR ELDKYGVSDV YKRLINRAKT VEGVESLKTH ILAALP | 450 |
| ABD00194 | LAEAKVLANR ELDKYGVSDF YKRLINRAKT VEGVDSIKVE ILAALP | 451 |
| ABD00195 | LAEAKVLANR ELDKYGVSDF YKRVINRAKT VEGVSAIKRE ILAALP | 452 |
| ABD00196 | LAEAKVLANR ELDKYGVSDF YKRLINRAKT VEGVNAIKSD ILAALP | 453 |
| ABD00197 | LAEAKVLANR ELDKYGVSDF YKRLINRAKT VEGVSAINQE ILAALP | 454 |
| ABD00198 | LAEAKVLANR ELDKYGVSDF YKRLINRAKT VEGVQSIKDH ILAALP | 455 |
| ABD00199 | LAEAKVLANR ELDKYGVSDF YKRLINRAKT VEGVDAIKCH ILAALP | 456 |
| ABD00200 | LAEAKVLANR ELDKYGVSDY YKRLINKAKT VEGVNAIKTH ILAALP | 457 |
| ABD00201 | LAEAKVLANR ELDKYGVSDF YKRLINKAKT VEGVEAIKAD ILAALP | 458 |
| ABD00202 | LAEAKVLANR ELDKYGVSDF YKRLINRAKT VEGVETIKRD ILAALP | 459 |
| ABD00203 | LAEAKVLANR ELDKYGVSDF YKRLINRART VEGVQTLKTD ILAALP | 460 |
| ABD00204 | LAEAKVLANR ELDKYGVSDF YKRLINKAKT VEGVNAIKRE ILAALP | 461 |
| ABD00205 | LAEAKVLANR ELDKYGVSDF YKRLINKAKT VEGVQAIKAE ILAALP | 462 |
| ABD00206 | LAEAKVLANR ELDKYGVSDY YKRVINRAKT VEGVNSIKNE ILAALP | 463 |
| ABD00207 | LAEAKVLANR ELDKYGVSDF YKRLINRART VEGVDSIKRE ILAALP | 464 |
| ABD00208 | LAEAKVLANR ELDKYGVSDY YKRLINKAKT VEGVEAIKIH ILAALP | 465 |

FIG. 10

| Polypeptide | Amino acid sequence | SEQ ID NO: |
|---|---|---|
| ABD00209 | LAEAKVLANR ELDKYGVSDF YKRLINRAKT VEGVDALKAH ILAALP | 466 |
| ABD00210 | LAEAKVLANR ELDKYGVSDY YKRLINKAKT VEGVQALKAH ILAALP | 467 |
| ABD00211 | LAEAKVLANR ELDKYGVSDF YKRVINRAKT VEGVSALKHH ILAALP | 468 |
| ABD00212 | LAEAKVLANR ELDKYGVSDF YKRLINRAKT VEGVNTLKAH ILAALP | 469 |
| ABD00213 | LAEAKVLANR ELDKYGVSDF YKRLINRAKT VCGVQSLKSH ILAALP | 470 |
| ABD00214 | LAEAKVLANR ELDKYGVSDY YKRVINRAKT VEGVDSLKAH ILAALP | 471 |
| ABD00215 | LAEAKVLANR ELDKYGVSDF YKRLINRAKT VEGVQILKSH ILAALP | 472 |
| ABD00216 | LAEAKVLANR ELDKYGVSDF YKRFINRAKT VEGVETIKSH ILAALP | 473 |
| ABD00217 | LAEAKVLANR ELDKYGVSDF YKRVINKAKT VEGVSSLKDH ILAALP | 474 |
| ABD00218 | LAEAKVLANR ELDKYGVSDY YKRVINKAKT VEGVSSLKAH ILAALP | 475 |
| ABD00219 | LAEAKVLANR ELDKYGVSDF YKRLINKAKT VEGVSTLKHH ILAALP | 476 |
| ABD00220 | LAEAKVLANR ELDKYGVSDF YKRLINRAKT VEGVSTLKHH ILAALP | 477 |
| ABD00221 | LAEAKVLANR ELDKYGVSDF YKRLINRAKT VEGVQSLKGH ILAALP | 478 |
| ABD00222 | LAEAKVLANR ELDKYGVSDF YKRLINKAKT VEGVQSLKTH ILAALP | 479 |
| ABD00223 | LAEAKVLANR ELDKYGVSDF YKRLINKAKT VEGVTTLKIH ILAALP | 480 |
| ABD00224 | LAEAKVLANR ELDKYGVSDF YKRLINKAKT VEGVSTLKSH ILAALP | 481 |
| ABD00225 | LAEAKVLANR ELDKYGVSDF YKRLINRAKT VEGVNTIKHH ILAALP | 482 |
| ABD00226 | LAEAKVLANR ELDKYGVSDF YKRLINRAKT VEGVESLKGH ILAALP | 483 |
| ABD00227 | LAEAKVLANR ELDKYGVSDF YKRLINRAKT VEGVFTLKHH ILAALP | 484 |
| ABD00228 | LAEAKVLANR ELDKYGVSDY YKRLINRART VEGVHALKAH ILAALP | 485 |
| ABD00229 | LAEAKVLANR ELDKYGVSDF YKRVINRAKT VEGVQALKAH ILAALP | 486 |
| ABD00230 | LAEAKVLANR ELDKYGVSDF YKRLINRAKT VEGVDTLKHH ILAALP | 487 |
| ABD00231 | LAEAKVLANR ELDKYGVSDF YKRLINRAKT VEGVESLKAH ILAALP | 488 |
| ABD00232 | LAEAKVLANR ELDKYGVSDF YKRLINRAKT VEGVDSLKVH ILAALP | 489 |
| ABD00233 | LAEAKVLANR ELDKYGVSDF YKRVINKAKT VEGVNALKSH ILAALP | 490 |
| ABD00234 | LAEAKVLANR ELDKYGVSDF YKRLINRAKT VEGVSALKQH ILAALP | 491 |
| ABD00235 | LAEAKVLANR ELDKYGVSDF YKRVINKAKT VEGVEALKRH ILAALP | 492 |
| ABD00236 | LAEAKVLANR ELDKYGVSDF YKRLINRAKT VEGVEALKRH ILAALP | 493 |
| ABD00237 | LAEAKVLANR ELDKYGVSDF YKRLINRAKT VEGVETLKRH ILAALP | 494 |
| ABD00238 | LAEAKVLANR ELDKYGVSDF YKRLINKTH VEGVQTLKTH ILAALP | 495 |
| ABD00239 | LAEAKVLANR ELDKYGVSDF YKRLINKAKT VEGVSALKIH ILAALP | 496 |

FIG. 1P

| Polypeptide | Amino acid sequence | SEQ ID NO: |
|---|---|---|
| ABD00240 | LAEAKVLANR ELDKYGVSDY YKNLINRART VEGVEALKLH ILAALP | 497 |
| ABD00241 | LAEAKVLANR ELDKYGVSDY YKNLINRAKT VEGVEALKLH ILAALP | 498 |
| ABD00242 | LAEAKVLANR ELDKYGVSDF YKNLINRAKT VEGVEALKLH ILAALP | 499 |
| ABD00243 | LAEAKVLANR ELDKYGVSDF YKNVINKAKT VEGVEALKLH ILAALP | 500 |
| ABD00244 | LAEAKVLANR ELDKYGVSDY YKNLINKAKT VEGVEALKLH ILAALP | 501 |
| ABD00245 | LAEAKVLANR ELDKYGVSDY YKNLINRART VEGVKALIDF ILAALP | 502 |
| ABD00246 | LAEAKVLALR ELDKYGVSDF YKRLINKAKT VEGVEALKLH ILAALP | 503 |
| ABD00247 | LAEAKVLAIR ELDKYGVSDY YKRLISKAKT VEGVEALKLH ILAALP | 504 |
| ABD00248 | LAEAKVLAIR ELDKYGVSDF YKRLISKAKT VEGVKALISE ILAALP | 505 |
| ABD00249 | LAEAKVLATR ELDKYGVSDY YKRLISKAKT VEGVKALISE ILAALP | 506 |
| ABD00250 | LAEAKVLAIK ELDKYGVSDY YKNLINKAKT VEGVKALISE ILAALP | 507 |
| ABD00251 | LAEAKELANR ELDKYGVSDY YKRLISKAKT VEGVKALISE ILAALP | 508 |
| ABD00252 | LAEAKVLANR ELDKYGVSDY YKRLISKAKT VEGVKALISE ILAALP | 509 |
| ABD00253 | LAEAKEDANR ELDKYGVSDY YKPLISKAKT VEGVKALISE ILAALP | 510 |
| ABD00254 | LAEAKEDAIK ELDKYGVSDY YKRLISKAKT VEGVKALISE ILAALP | 511 |
| ABD00255 | LAEAKVLALN ELDKYGVSDY YKRLISKAKT VEGVKALISE ILAALP | 512 |
| ABD00256 | LAEAKELAIK ELDKYGVSDY YKRLISKAKT VEGVKALISE ILAALP | 513 |
| ABD00257 | LAEAKVDATK ELDKYGVSDY YKRLISKAKT VEGVKALISE ILAALP | 514 |
| ABDwt | LAEAKVLANR ELDKYGVSDY YKNLINNAKT VEGVKALIDE ILAALP | 515 |

FIG. 1Q

| | Pos18 | Pos18 | Pos20 | Pos20 | Pos23 | Pos23 | Pos24 | Pos24 | Pos27 | Pos27 | Pos29 | Pos29 | Pos30 | Pos30 | Pos32 | Pos32 | Pos33 | Pos33 | Pos35 | Pos35 | Pos36 | Pos36 | Pos37 | Pos37 | Pos39 | Pos39 | Pos40 | Pos40 | Pos41 | Pos41 |
|---|---|---|---|---|---|---|---|---|---|---|---|---|---|---|---|---|---|---|---|---|---|---|---|---|---|---|---|---|---|---|
| Ala (A) | | | | | | | | | | | | | | | 5,53 | 1,33 | 8,5 | 8 | 6,25 | 10,7 | 34 | 26,7 | | | 6,25 | 5,3 | | | | |
| Arg (R) | 10 | 6,67 | | | 25 | 21 | | | 25 | 17 | 10 | 11 | | | 0,93 | 2,67 | 12,38 | 11 | 9,38 | 4 | | | | | 9,38 | 11 | | | | |
| Asn (N) | | | | | 25 | 37 | | | 25 | 39 | | | 10 | 12 | 0,55 | 0 | 4,125 | 1,3 | 3,13 | 2,67 | | | | | 3,13 | 2,7 | 25 | 27 | | |
| Asp (D) | | | | | | | | | | | | | | | 6,24 | 2,67 | 4,25 | 1,3 | 3,13 | 5,33 | | | | | 3,13 | 2,7 | | | | |
| Cys (C) | | | | | | | | | | | | | | | 0,05 | 0 | | | 3,13 | 1,33 | | | | | 3,13 | 2,7 | 25 | 23 | | |
| Gln (Q) | | | | | | | | | | | | | | | 5 | 8 | 4,125 | 1,3 | 3,13 | 0 | | | | | 3,13 | 0 | 25 | 16 | | |
| Glu (E) | | | | | 25 | 20 | 5 | 8 | 25 | 15 | | | | | 56,17 | 52 | 4,24 | 2,7 | 3,13 | 2,67 | | | | | 3,13 | 0 | | | | |
| Gly (G) | | | | | | | 75 | 76 | | | | | | | 5,53 | 5,33 | 8,5 | 6,7 | 6,25 | 2,67 | | | | | 6,25 | 2,7 | | | | |
| His (H) | | | | | | | 5 | 2,7 | | | | | | | 0,55 | 4 | 4,125 | 4 | 3,13 | 1,33 | | | 5 | 9,3 | 3,13 | 1,3 | | | 79 | 77 |
| Ile (I) | | | | | | | 5 | 0 | | | 90 | 89 | 10 | 10 | 0,05 | 0 | 4,125 | 8 | 3,13 | 2,67 | | | 75 | 76 | 3,13 | 1,3 | | | 4,4 | 6,7 |
| Leu (L) | | | | | 25 | | | | 25 | 29 | | | 80 | 79 | 0,93 | 1,33 | 8,25 | 12 | 9,38 | 18,7 | | | | | 9,38 | 17 | 35 | | | |
| Lys (K) | | | | | | | | | | | | | | | 5 | 9,33 | 4,125 | 0 | 3,13 | 0 | | | | | 3,13 | 0 | | | 8,8 | 9,3 |
| Met (M) | | | | | | | | | | | | | | | 0,44 | 1,33 | 4,125 | 4 | 3,13 | 2,67 | | | 5 | 2,7 | 3,13 | 2,7 | | | 3,6 | 0 |
| Phe (F) | | | 50 | 54,7 | | | | | | | | | | | 0,05 | 0 | | | 3,13 | 6,67 | | | 5 | 4 | 3,13 | 2,7 | | | | |
| Pro (P) | | | | | | 21 | | | 25 | | | | | | 0,49 | 0 | 8,25 | 23 | 6,25 | 5,33 | | | | | 6,25 | 16 | | | | |
| Ser (S) | 80 | 88 | | | | | | | | | | | | | 0,54 | 0 | 4,125 | 2,7 | 9,38 | 9,33 | 33 | 52 | | | 9,38 | 16 | | | | |
| Thr (T) | 10 | 5,33 | | | | | | | | | | | | | 0,49 | 0 | 8,25 | 6,7 | 6,25 | 2,67 | 33 | 20 | | | 6,25 | 2,7 | | | | |
| Trp (w) | | | | | | | | | | | | | | | 0,44 | 0 | 4,125 | | 3,13 | 5,33 | | | | | 3,13 | 4 | | | | |
| Tyr (Y) | | | 50 | 45,3 | | | 10 | 13 | | | | | | | 0,55 | 4 | | | 3,13 | 6,67 | | | 10 | 11 | 3,13 | 2,7 | | | 4 | 6,7 |
| Val (V) | | | | | | | | | | | | | | | 5,53 | 8 | 8,5 | 8 | 6,25 | 5,33 | | | | | 6,25 | 6,7 | | | | |
| Stop (.) | | | | | | | | | | | | | | | 5 | | | | 3,13 | 4 | | | | | 3,13 | 0 | | | | |

| | Ala (A) | Arg (R) | Asn (N) | Asp (D) | Cys (C) | Gln (Q) | Glu (E) | Gly (G) | His (H) | Ile (I) | Leu (L) | Lys (K) | Met (M) | Phe (F) | Pro (P) | Ser (S) | Thr (T) | Trp (W) | Tyr (Y) | Val (V) | Stop (.) |
|---|---|---|---|---|---|---|---|---|---|---|---|---|---|---|---|---|---|---|---|---|---|
| "Pos18" | | | | | | | | | | | | | | | | 50 | 50 | | | | |
| "Pos18" | | | | | | | | | | | | | | | | 45 | 55 | | | | |
| Pos18 | | 10 | | | | | | | | | | | | | | 80 | 10 | | | | |
| Pos18 | | 11,7 | | | | | | | | | | | | | | 72,7 | 15,6 | | | | |
| Pos20 | | | | | | | | | | | | | 50 | | | | | | 50 | | |
| Pos20 | | | | | | | | | | | | | 58,4 | | | | | | 41,6 | | |
| Pos23 | | 25 | 25 | | | | | | | | 25 | | | | 25 | | | | | | |
| Pos23 | | 12 | 42 | | | | | | | | 16 | | | | 31 | | | | | | |
| Pos24 | | | | | | 5 | 75 | | | | 5 | 5 | | | | | | | 10 | | |
| Pos24 | | | | | | 9,1 | 78 | | | | 3,9 | 5,2 | | | | | | | 3,9 | | |
| Pos27 | | 25 | 25 | | | | | | | | 25 | | | | | 25 | | | | | |
| Pos27 | | 16 | 39 | | | | | | | | 7,8 | | | | | 38 | | | | | |
| Pos29 | | 10 | | | | | | | | | 90 | | | | | | | | | | |
| Pos29 | | 14 | | | | | | | | | 86 | | | | | | | | | | |
| Pos30 | | | 10 | | | | | | | | | | | | | 10 | 80 | | | | |
| Pos30 | | | 10 | | | | | | | | | | | | | 7,8 | 82 | | | | |
| Pos32 | 5,53 | 0,93 | 0,55 | 6,24 | 0,05 | 5 | 56,17 | 5,53 | 0,55 | 0,05 | 0,93 | 5 | 0,44 | 0,05 | 0,49 | 0,54 | 0,49 | 0,44 | 0,55 | 5,53 | 5 |
| Pos32 | 3,9 | 0 | 1,3 | 7,79 | 0 | 5,19 | 57,1 | 6,49 | 0 | 0 | 0 | 5,19 | 1,3 | 0 | 0 | 0 | 1,3 | 0 | 0 | 5,19 | 5,19 |
| Pos33 | 8,5 | 12,38 | 4,125 | 4,25 | | 4,125 | 4,24 | 8,5 | 4,125 | | 8,25 | 4,125 | 4,125 | | 8,25 | 4,125 | 8,25 | | | 8,5 | |
| Pos33 | 7,8 | 10 | 1,3 | 1,3 | | 1,3 | 2,6 | 6,5 | 3,9 | 7,8 | 12 | 0 | 3,9 | | 22 | 2,6 | 6,5 | | | 7,8 | |
| Pos35 | 6,25 | 9,38 | 3,13 | 3,13 | 3,13 | 3,13 | 3,13 | 6,25 | 3,13 | 3,13 | 9,38 | 3,13 | 3,13 | 6,25 | 9,38 | 6,25 | 3,13 | 3,13 | 6,25 | 3,13 | 3,13 |
| Pos35 | 11,7 | 11,7 | 0 | 3,9 | 0 | 3,9 | 1,3 | 1,3 | 2,6 | 0 | 23,4 | 1,3 | 1,3 | 6,49 | 13 | 6,49 | 2,6 | 1,3 | 0 | 6,49 | 1,3 |
| Pos36 | 34 | | | | | | | | | | | | | | | 33 | 33 | | | | |
| Pos36 | 32,5 | | | | | | | | | | | | | | | 40,3 | 27,3 | | | | |
| Pos37 | | | | | | | | | | 5 | 75 | | 5 | 5 | | | | | 10 | | |
| Pos37 | | | | | | | | | | 1,3 | 71 | | 3,9 | 6,5 | | | | | 17 | | |
| Pos39 | 6,25 | 9,38 | 3,13 | 3,13 | 3,13 | 3,13 | 3,13 | 6,25 | 3,13 | 3,13 | 9,38 | 3,13 | 3,13 | 3,13 | 6,25 | 9,38 | 3,13 | 6,25 | 3,13 | 6,25 | 3,13 |
| Pos39 | 6,5 | 16 | 2,6 | 1,3 | 2,6 | 2,6 | 1,3 | 3,9 | 1,3 | 0 | 9,1 | 0 | 3,9 | 2,6 | 7,8 | 13 | 7,8 | 3,9 | 2,6 | 7,8 | 3,9 |
| Pos40 | | | 25 | | | 25 | 25 | 25 | | | | | | | | | | | | | |
| Pos40 | | | 18 | | | 21 | 17 | 44 | | | | | | | | | | | | | |
| Pos41 | | | | | | | | | | | 79 | 4,4 | | 8,8 | 3,6 | | | | | 4 | |
| Pos41 | | | | | | | | | | | 78 | 1,3 | | 14 | 2,6 | | | | | 3,9 | |

MGSSHHHHHHLQVD | ABD VARIANT |

FIGURE 8

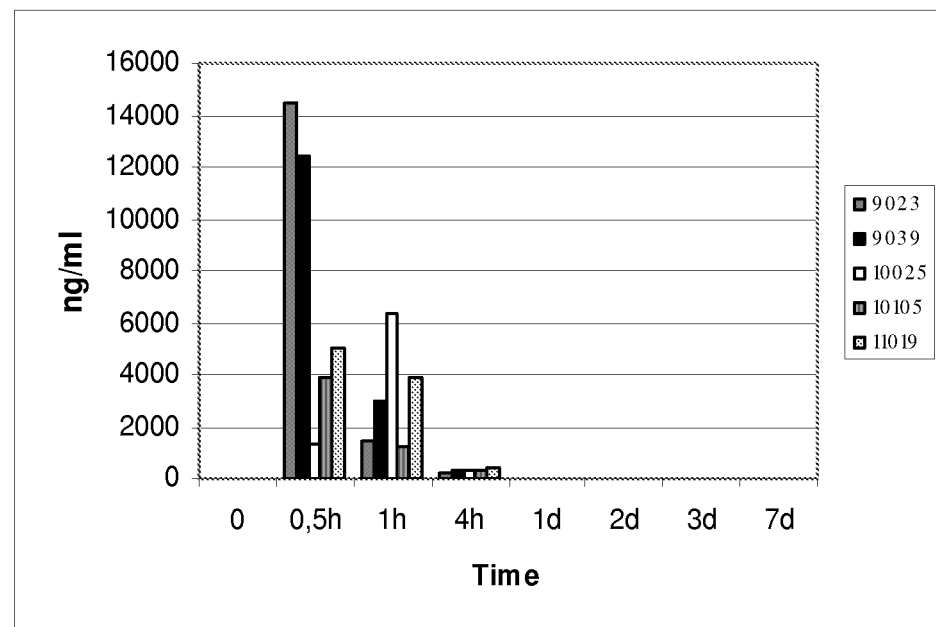
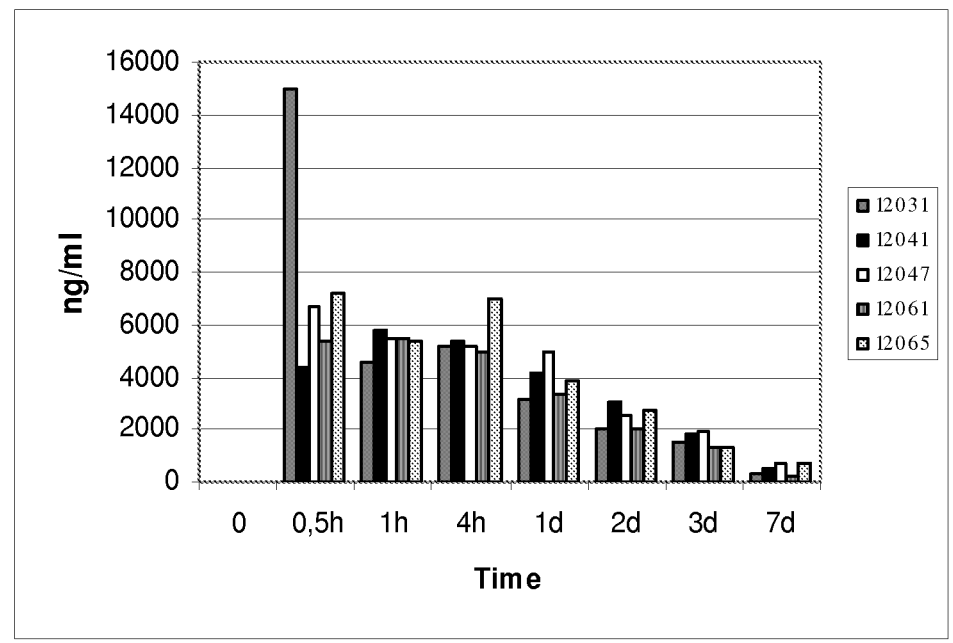
FIGURE 12

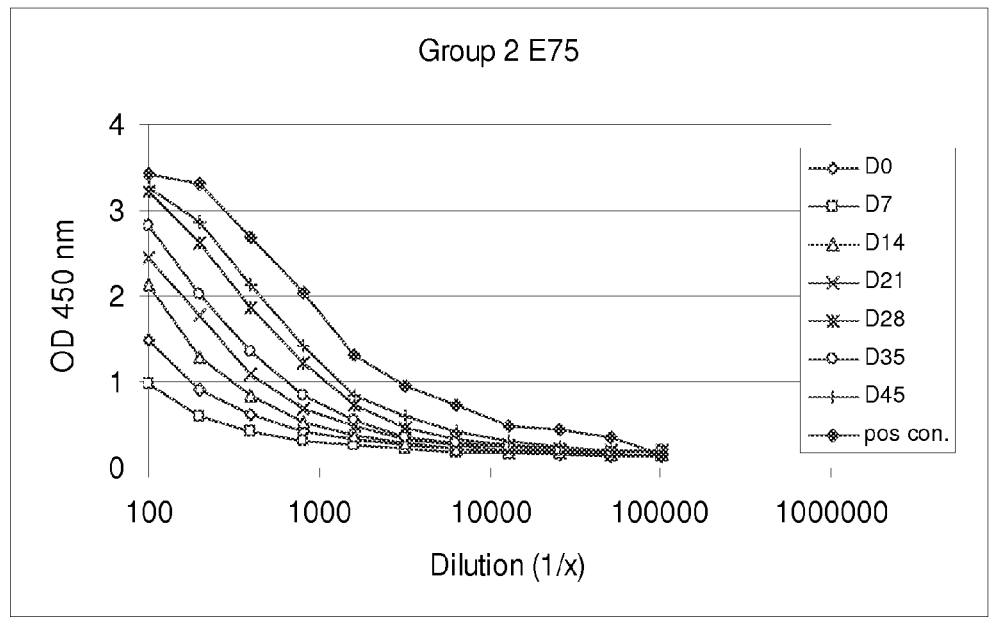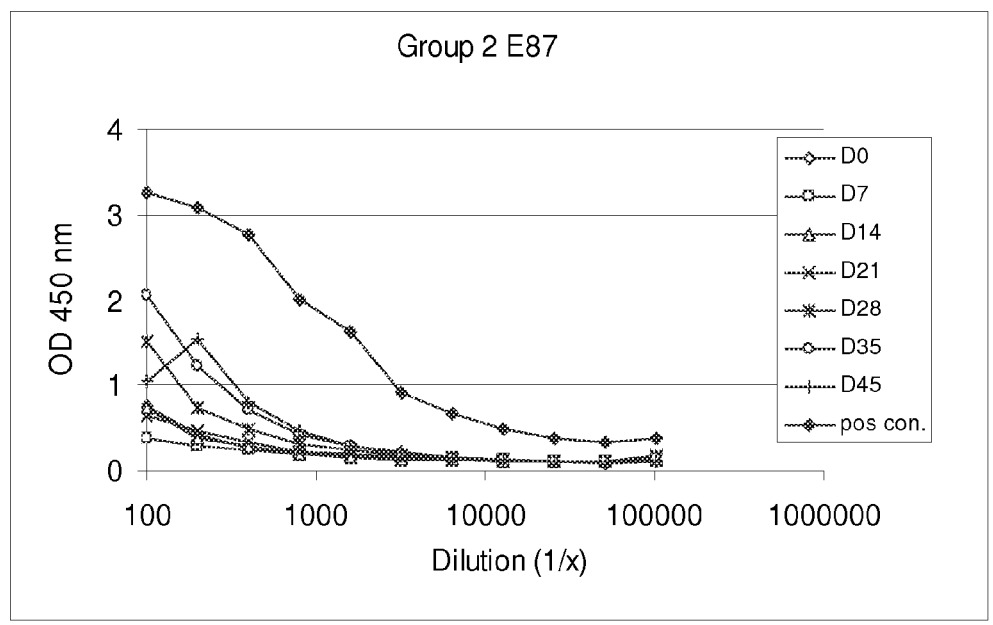
FIGURE 14A

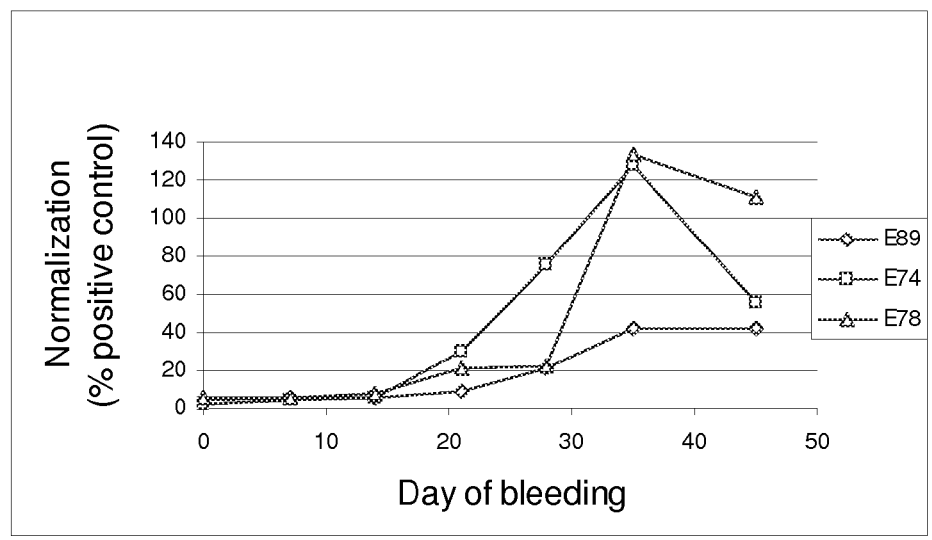
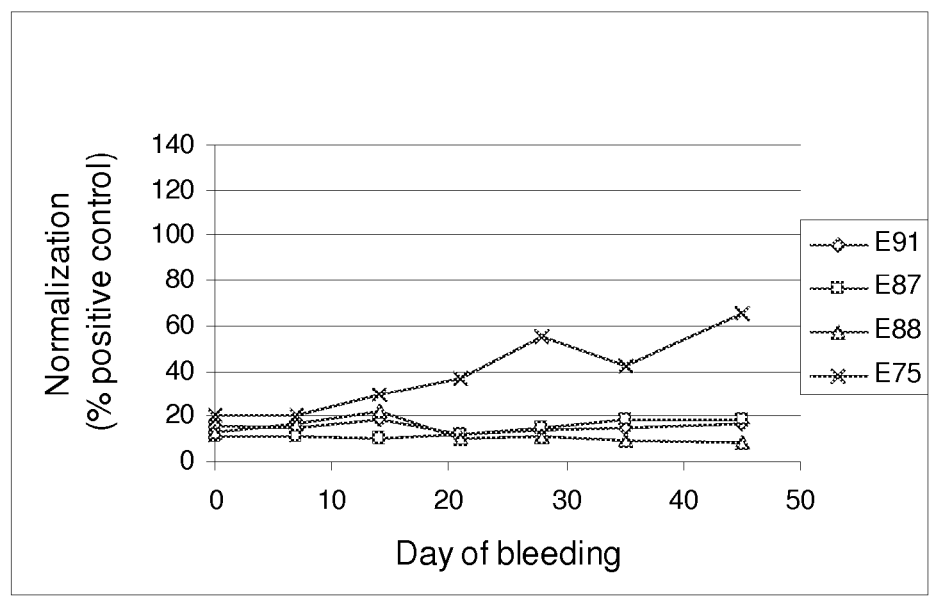
FIGURE 15

```
                        SEQUENCE LISTING

<160> NUMBER OF SEQ ID NOS: 541

<210> SEQ ID NO 1
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 1

Gly Val Ser Asp Phe Tyr Lys Asn Leu Ile Asn Arg Ala Lys Thr Val
1               5                   10                  15

Glu Gly Val His Ala Leu Ile Gly His Ile
            20                  25

<210> SEQ ID NO 2
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 2

Gly Val Ser Asp Phe Tyr Lys Asn Val Ile Asn Arg Ala Lys Thr Val
1               5                   10                  15

Glu Gly Val His Ala Leu Ile Asp His Ile
            20                  25

<210> SEQ ID NO 3
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 3

Gly Val Ser Asp Tyr Tyr Lys Asn Ile Ile Asn Arg Ala Lys Thr Val
1               5                   10                  15

Glu Gly Val Arg Ala Leu Lys Leu His Ile
            20                  25

<210> SEQ ID NO 4
<211> LENGTH: 26
```

```
<212> TYPE: PRT
<213> ORGANISM: Artificial Sequence
<220> FEATURE:
<223> OTHER INFORMATION: Engineered albumin binding polypeptide

<400> SEQUENCE: 4

Gly Val Ser Asp Phe Tyr Lys Asn Val Ile Asn Arg Ala Lys Thr Val
 1               5                  10                  15

Glu Gly Val Ser Ala Leu Ile His Glu Ile
            20                  25

<210> SEQ ID NO 5
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 5

Gly Val Ser Asp Phe Tyr Lys Arg Leu Ile Asn Arg Ala Lys Thr Val
 1               5                  10                  15

Glu Gly Val Asn Thr Leu Ile Ala Asp Ile
            20                  25

<210> SEQ ID NO 6
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 6

Gly Val Ser Asp Phe Tyr Lys Asn Leu Ile Asn Arg Ala Lys Thr Val
 1               5                  10                  15

Glu Gly Val Asn Thr Leu Ile Ala Asp Ile
            20                  25

<210> SEQ ID NO 7
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 7

Gly Val Ser Asp Tyr Tyr Lys Asn Leu Ile Asn Arg Ala Lys Thr Val
 1               5                  10                  15

Glu Gly Val Asn Ser Leu Ile Ser His Ile
            20                  25

<210> SEQ ID NO 8
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 8

Gly Val Ser Asp Phe Tyr Lys Arg Leu Ile Asn Arg Ala Lys Thr Val
 1               5                  10                  15

Gly Gly Val Gln Ser Leu Ile Ser Glu Ile
            20                  25

<210> SEQ ID NO 9
```

```
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 9

Gly Val Ser Asp Phe Tyr Lys Asn Leu Ile Asn Arg Ala Lys Thr Val
 1               5                  10                  15

Glu Gly Val Ser Ser Leu Lys Gly His Ile
            20                  25

<210> SEQ ID NO 10
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 10

Gly Val Ser Asp Phe Tyr Lys Asn Val Ile Asn Arg Ala Lys Thr Val
 1               5                  10                  15

Glu Gly Val Asp Ser Leu Ile Ala Glu Ile
            20                  25

<210> SEQ ID NO 11
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 11

Gly Val Ser Asp Phe Tyr Lys Asn Leu Ile Asn Arg Ala Arg Thr Val
 1               5                  10                  15

Glu Gly Val Gln Thr Leu Ile Ser Asp Ile
            20                  25

<210> SEQ ID NO 12
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 12

Gly Val Ser Asp Phe Tyr Lys Lys Phe Ile Asn Lys Ala Lys Thr Val
 1               5                  10                  15

Glu Gly Val Glu Thr Leu Ile Ser Glu Ile
            20                  25

<210> SEQ ID NO 13
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 13

Gly Val Ser Asp Phe Tyr Lys Ser Leu Ile Asn Arg Ala Lys Thr Val
 1               5                  10                  15

Glu Gly Val His Ser Leu Thr Asp Glu Ile
            20                  25
```

```
<210> SEQ ID NO 14
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 14

Gly Val Ser Asp Tyr Tyr Lys Asn Val Ile Asn Lys Ala Lys Thr Val
1               5                   10                  15

Glu Gly Val Ser Ser Leu Thr Ala Glu Ile
            20                  25

<210> SEQ ID NO 15
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 15

Gly Val Ser Asp Phe Tyr Lys Ser Leu Ile Asn Arg Ala Lys Thr Val
1               5                   10                  15

Glu Gly Val Asp Ala Leu Thr Ser His Ile
            20                  25

<210> SEQ ID NO 16
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 16

Gly Val Ser Asp Phe Tyr Lys Asn Leu Ile Asn Lys Ala Lys Thr Val
1               5                   10                  15

Glu Gly Val Ser Thr Leu Ile His Asp Ile
            20                  25

<210> SEQ ID NO 17
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 17

Gly Val Ser Asp Phe Tyr Lys Asn Leu Ile Asn Arg Ala Lys Thr Val
1               5                   10                  15

Glu Gly Val Ser Thr Leu Ile His Asp Ile
            20                  25

<210> SEQ ID NO 18
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 18

Gly Val Ser Asp Phe Tyr Lys Asn Leu Ile Asn Arg Ala Lys Thr Val
1               5                   10                  15

Glu Gly Val Gln Ala Leu Ile Ser Glu Ile
            20                  25
```

<210> SEQ ID NO 19
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 19

Gly Val Ser Asp Tyr Tyr Lys Ser Leu Ile Asn Lys Ala Lys Thr Val
1               5                   10                  15

Glu Gly Val Asp Ser Leu Ile Val His Ile
            20                  25

<210> SEQ ID NO 20
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 20

Gly Val Ser Asp Phe Tyr Lys Asn Leu Ile Asn Arg Ala Lys Thr Val
1               5                   10                  15

Glu Gly Val Gln Ser Leu Ile Thr Glu Ile
            20                  25

<210> SEQ ID NO 21
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 21

Gly Val Ser Asp Tyr Tyr Lys Asn Leu Ile Asn Arg Ala Lys Thr Val
1               5                   10                  15

Glu Gly Val Asp Ala Leu Ile Thr His Ile
            20                  25

<210> SEQ ID NO 22
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 22

Gly Val Ser Asp Phe Tyr Lys Ser Met Ile Asn Arg Ala Lys Thr Val
1               5                   10                  15

Glu Gly Val Asp Ser Leu Ile Thr His Ile
            20                  25

<210> SEQ ID NO 23
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 23

Gly Val Ser Asp Phe Tyr Lys Asn Leu Ile Asn Arg Ala Lys Thr Val
1               5                   10                  15

Glu Gly Val Thr Thr Leu Thr Thr Asp Ile
            20                  25

<210> SEQ ID NO 24
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 24

Gly Val Ser Asp Phe Tyr Lys Asn Leu Ile Asn Arg Ala Lys Thr Val
1               5                   10                  15

Glu Gly Val Glu Ser Leu Ile Asp His Ile
            20                  25

<210> SEQ ID NO 25
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 25

Gly Val Ser Asp Phe Tyr Lys Ser Tyr Ile Asn Arg Ala Lys Thr Val
1               5                   10                  15

Glu Gly Val His Thr Leu Ile Gly His Ile
            20                  25

<210> SEQ ID NO 26
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 26

Gly Val Ser Asp Phe Tyr Lys Asn Leu Ile Asn Arg Ala Lys Thr Val
1               5                   10                  15

Glu Gly Val Gln Thr Leu Ile Ser Asp Ile
            20                  25

<210> SEQ ID NO 27
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 27

Gly Val Ser Asp Phe Tyr Lys Asn Leu Ile Asn Arg Ala Lys Thr Val
1               5                   10                  15

Glu Gly Val Asn Ser Leu Thr Ser His Ile
            20                  25

<210> SEQ ID NO 28
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 28

Gly Val Ser Asp Phe Tyr Lys Asn Leu Ile Asn Arg Ala Lys Thr Val
1               5                   10                  15

Glu Gly Val Asn Thr Leu Ile His Asp Ile

```
<210> SEQ ID NO 29
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 29

Gly Val Ser Asp Phe Tyr Lys Asn Leu Ile Asn Arg Ala Lys Thr Val
 1               5                  10                  15
Glu Gly Val Glu Ser Leu Ile Gly Glu Ile
            20                  25

<210> SEQ ID NO 30
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 30

Gly Val Ser Asp Phe Tyr Lys Asn Leu Ile Asn Lys Ala Lys Thr Val
 1               5                  10                  15
Glu Gly Val His Thr Leu Ile His Asp Ile
            20                  25

<210> SEQ ID NO 31
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 31

Gly Val Ser Asp Tyr Tyr Lys Asn Leu Ile Asn Lys Ala Lys Thr Val
 1               5                  10                  15
Glu Gly Val Ser Ala Leu Lys Met His Ile
            20                  25

<210> SEQ ID NO 32
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 32

Gly Val Ser Asp Phe Tyr Lys Asn Leu Ile Asn Lys Ala Lys Thr Val
 1               5                  10                  15
Glu Gly Val Asp Ala Leu Ile Val His Ile
            20                  25

<210> SEQ ID NO 33
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 33

Gly Val Ser Asp Phe Tyr Lys Asn Leu Ile Asn Lys Ala Lys Thr Val
 1               5                  10                  15
```

-continued

Glu Gly Val Asp Ala Leu Ile Val His Ile
            20                  25

<210> SEQ ID NO 34
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 34

Gly Val Ser Asp Tyr Tyr Lys Asn Leu Ile Asn Arg Ala Arg Thr Val
1               5                   10                  15

Glu Gly Val Asp Thr Leu Ile His Asp Ile
            20                  25

<210> SEQ ID NO 35
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 35

Gly Val Ser Asp Phe Tyr Lys Lys Val Ile Asn Arg Ala Arg Thr Val
1               5                   10                  15

Glu Gly Val Gln Ala Leu Ile Ala Asp Ile
            20                  25

<210> SEQ ID NO 36
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 36

Gly Val Ser Asp Phe Tyr Lys Asn Leu Ile Asn Arg Ala Lys Thr Val
1               5                   10                  15

Glu Gly Val Glu Ser Leu Ile Ala Asp Ile
            20                  25

<210> SEQ ID NO 37
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 37

Gly Val Ser Asp Tyr Tyr Lys Asn Leu Ile Asn Lys Ala Lys Thr Val
1               5                   10                  15

Glu Gly Val Asp Ala Leu Ile Ala His Ile
            20                  25

<210> SEQ ID NO 38
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 38

Gly Val Ser Asp Tyr Tyr Lys Asn Leu Ile Asn Arg Ala Lys Thr Val
1               5                   10                  15

```
Glu Gly Val Glu Ser Leu Ile Thr His Ile
            20                  25

<210> SEQ ID NO 39
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 39

Gly Val Ser Asp Phe Tyr Lys Asn Leu Ile Asn Arg Ala Arg Thr Val
1               5                   10                  15

Glu Gly Val Asp Ser Leu Ile Val Glu Ile
            20                  25

<210> SEQ ID NO 40
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 40

Gly Val Ser Asp Phe Tyr Lys Asn Val Ile Asn Arg Ala Lys Thr Val
1               5                   10                  15

Glu Gly Val Ser Ala Leu Ile Arg Glu Ile
            20                  25

<210> SEQ ID NO 41
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 41

Gly Val Ser Asp Phe Tyr Lys Asn Leu Ile Asn Arg Ala Lys Thr Val
1               5                   10                  15

Glu Gly Val Asn Ala Leu Ile Ser Asp Ile
            20                  25

<210> SEQ ID NO 42
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 42

Gly Val Ser Asp Phe Tyr Lys Asn Leu Ile Asn Arg Ala Lys Thr Val
1               5                   10                  15

Glu Gly Val Ser Ala Leu Ile Gln Glu Ile
            20                  25

<210> SEQ ID NO 43
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 43

Gly Val Ser Asp Phe Tyr Lys Asn Leu Ile Asn Arg Ala Lys Thr Val
```

```
                1               5                  10                  15
Glu Gly Val Gln Ser Leu Ile Asp His Ile
            20                  25

<210> SEQ ID NO 44
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 44

Gly Val Ser Asp Phe Tyr Lys Asn Leu Ile Asn Arg Ala Lys Thr Val
 1               5                  10                  15
Glu Gly Val Asp Ala Leu Ile Cys His Ile
            20                  25

<210> SEQ ID NO 45
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 45

Gly Val Ser Asp Tyr Tyr Lys Arg Leu Ile Asn Lys Ala Lys Thr Val
 1               5                  10                  15
Glu Gly Val Asn Ala Leu Ile Thr His Ile
            20                  25

<210> SEQ ID NO 46
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 46

Gly Val Ser Asp Phe Tyr Lys Asn Val Ile Asn Lys Ala Lys Thr Val
 1               5                  10                  15
Glu Gly Val Glu Ala Leu Ile Ala Asp Ile
            20                  25

<210> SEQ ID NO 47
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 47

Gly Val Ser Asp Phe Tyr Lys Asn Leu Ile Asn Arg Ala Lys Thr Val
 1               5                  10                  15
Glu Gly Val Glu Thr Leu Ile Arg Asp Ile
            20                  25

<210> SEQ ID NO 48
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 48
```

```
Gly Val Ser Asp Phe Tyr Lys Asn Leu Ile Asn Arg Ala Arg Thr Val
1               5                   10                  15

Glu Gly Val Gln Thr Leu Ile Thr Asp Ile
            20                  25
```

<210> SEQ ID NO 49
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 49

```
Gly Val Ser Asp Phe Tyr Lys Arg Leu Ile Asn Lys Ala Lys Thr Val
1               5                   10                  15

Glu Gly Val Asn Ala Leu Thr His His Ile
            20                  25
```

<210> SEQ ID NO 50
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 50

```
Gly Val Ser Asp Tyr Tyr Lys Asn Leu Ile Asn Arg Ala Lys Thr Val
1               5                   10                  15

Glu Gly Val Gln Ala Leu Ile Ala His Ile
            20                  25
```

<210> SEQ ID NO 51
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 51

```
Gly Val Ser Asp Phe Tyr Lys Asn Val Ile Asn Arg Ala Lys Thr Val
1               5                   10                  15

Glu Gly Val Asn Ser Leu Ile Asn His Ile
            20                  25
```

<210> SEQ ID NO 52
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 52

```
Gly Val Ser Asp Phe Tyr Lys Ser Leu Ile Asn Arg Ala Arg Thr Val
1               5                   10                  15

Glu Gly Val Asp Ser Leu Ile Arg His Ile
            20                  25
```

<210> SEQ ID NO 53
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 53

```
Gly Val Ser Asp Tyr Tyr Lys Asn Leu Ile Asn Lys Ala Lys Thr Val
1               5                   10                  15

Glu Gly Val Glu Ala Leu Thr Leu His Ile
            20                  25
```

<210> SEQ ID NO 54
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 54

```
Gly Val Ser Asp Phe Tyr Lys Asn Leu Ile Asn Arg Ala Lys Thr Val
1               5                   10                  15

Glu Gly Val Asp Ala Leu Ile Ala His Ile
            20                  25
```

<210> SEQ ID NO 55
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 55

```
Gly Val Ser Asp Tyr Tyr Lys Asn Leu Ile Asn Lys Ala Lys Thr Val
1               5                   10                  15

Glu Gly Val Gln Ala Leu Ile Ala His Ile
            20                  25
```

<210> SEQ ID NO 56
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 56

```
Gly Val Ser Asp Phe Tyr Lys Arg Leu Ile Asn Arg Ala Lys Thr Val
1               5                   10                  15

Glu Gly Val His Ala Leu Ile Gly His Ile
            20                  25
```

<210> SEQ ID NO 57
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 57

```
Gly Val Ser Asp Phe Tyr Lys Arg Val Ile Asn Arg Ala Lys Thr Val
1               5                   10                  15

Glu Gly Val His Ala Leu Ile Asp His Ile
            20                  25
```

<210> SEQ ID NO 58
<211> LENGTH: 26
<212> TYPE: PRT
<213> ORGANISM: Artificial Sequence
<220> FEATURE:
<223> OTHER INFORMATION: Engineered albumin binding polypeptide

```
<400> SEQUENCE: 58

Gly Val Ser Asp Tyr Tyr Lys Arg Ile Ile Asn Arg Ala Lys Thr Val
1               5                   10                  15

Glu Gly Val Arg Ala Leu Lys Leu His Ile
            20                  25

<210> SEQ ID NO 59
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 59

Gly Val Ser Asp Phe Tyr Lys Arg Val Ile Asn Arg Ala Lys Thr Val
1               5                   10                  15

Glu Gly Val Ser Ala Leu Ile His Glu Ile
            20                  25

<210> SEQ ID NO 60
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 60

Gly Val Ser Asp Phe Tyr Lys Arg Leu Ile Asn Arg Ala Lys Thr Val
1               5                   10                  15

Glu Gly Val Asn Thr Leu Ile Ala Asp Ile
            20                  25

<210> SEQ ID NO 61
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 61

Gly Val Ser Asp Tyr Tyr Lys Arg Leu Ile Asn Arg Ala Lys Thr Val
1               5                   10                  15

Glu Gly Val Asn Ser Leu Ile Ser His Ile
            20                  25

<210> SEQ ID NO 62
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 62

Gly Val Ser Asp Phe Tyr Lys Arg Leu Ile Asn Arg Ala Lys Thr Val
1               5                   10                  15

Glu Gly Val Ser Ser Leu Lys Gly His Ile
            20                  25

<210> SEQ ID NO 63
<211> LENGTH: 26
<212> TYPE: PRT
<213> ORGANISM: Artificial Sequence
<220> FEATURE:
<223> OTHER INFORMATION: Engineered albumin binding polypeptide
```

-continued

```
<400> SEQUENCE: 63

Gly Val Ser Asp Phe Tyr Lys Arg Val Ile Asn Arg Ala Lys Thr Val
1               5                   10                  15

Glu Gly Val Asp Ser Leu Ile Ala Glu Ile
            20                  25

<210> SEQ ID NO 64
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 64

Gly Val Ser Asp Phe Tyr Lys Arg Leu Ile Asn Arg Ala Arg Thr Val
1               5                   10                  15

Glu Gly Val Gln Thr Leu Ile Ser Asp Ile
            20                  25

<210> SEQ ID NO 65
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 65

Gly Val Ser Asp Phe Tyr Lys Arg Phe Ile Asn Lys Ala Lys Thr Val
1               5                   10                  15

Glu Gly Val Glu Thr Leu Ile Ser Glu Ile
            20                  25

<210> SEQ ID NO 66
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 66

Gly Val Ser Asp Phe Tyr Lys Arg Leu Ile Asn Arg Ala Lys Thr Val
1               5                   10                  15

Glu Gly Val His Ser Leu Thr Asp Glu Ile
            20                  25

<210> SEQ ID NO 67
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 67

Gly Val Ser Asp Tyr Tyr Lys Arg Val Ile Asn Lys Ala Lys Thr Val
1               5                   10                  15

Glu Gly Val Ser Ser Leu Thr Ala Glu Ile
            20                  25

<210> SEQ ID NO 68
<211> LENGTH: 26
<212> TYPE: PRT
<213> ORGANISM: Artificial Sequence
<220> FEATURE:
```

<223> OTHER INFORMATION: Engineered albumin binding polypeptide

<400> SEQUENCE: 68

Gly Val Ser Asp Phe Tyr Lys Arg Leu Ile Asn Arg Ala Lys Thr Val
1               5                   10                  15

Glu Gly Val Asp Ala Leu Thr Ser His Ile
            20                  25

<210> SEQ ID NO 69
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 69

Gly Val Ser Asp Phe Tyr Lys Arg Leu Ile Asn Lys Ala Lys Thr Val
1               5                   10                  15

Glu Gly Val Ser Thr Leu Ile His Asp Ile
            20                  25

<210> SEQ ID NO 70
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 70

Gly Val Ser Asp Phe Tyr Lys Arg Leu Ile Asn Arg Ala Lys Thr Val
1               5                   10                  15

Glu Gly Val Ser Thr Leu Ile His Asp Ile
            20                  25

<210> SEQ ID NO 71
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 71

Gly Val Ser Asp Phe Tyr Lys Arg Leu Ile Asn Arg Ala Lys Thr Val
1               5                   10                  15

Glu Gly Val Gln Ala Leu Ile Ser Glu Ile
            20                  25

<210> SEQ ID NO 72
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 72

Gly Val Ser Asp Tyr Tyr Lys Arg Leu Ile Asn Lys Ala Lys Thr Val
1               5                   10                  15

Glu Gly Val Asp Ser Leu Ile Val His Ile
            20                  25

<210> SEQ ID NO 73
<211> LENGTH: 26
<212> TYPE: PRT
<213> ORGANISM: Artificial Sequence -continued

```
<220> FEATURE:
<223> OTHER INFORMATION: Engineered albumin binding polypeptide

<400> SEQUENCE: 73

Gly Val Ser Asp Phe Tyr Lys Arg Leu Ile Asn Arg Ala Lys Thr Val
1               5                   10                  15

Glu Gly Val Gln Ser Leu Ile Thr Glu Ile
            20                  25

<210> SEQ ID NO 74
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 74

Gly Val Ser Asp Tyr Tyr Lys Arg Leu Ile Asn Arg Ala Lys Thr Val
1               5                   10                  15

Glu Gly Val Asp Ala Leu Ile Thr His Ile
            20                  25

<210> SEQ ID NO 75
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 75

Gly Val Ser Asp Phe Tyr Lys Arg Met Ile Asn Arg Ala Lys Thr Val
1               5                   10                  15

Glu Gly Val Asp Ser Leu Ile Thr His Ile
            20                  25

<210> SEQ ID NO 76
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 76

Gly Val Ser Asp Phe Tyr Lys Arg Leu Ile Asn Arg Ala Lys Thr Val
1               5                   10                  15

Glu Gly Val Thr Thr Leu Thr Thr Asp Ile
            20                  25

<210> SEQ ID NO 77
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 77

Gly Val Ser Asp Phe Tyr Lys Arg Leu Ile Asn Arg Ala Lys Thr Val
1               5                   10                  15

Glu Gly Val Glu Ser Leu Ile Asp His Ile
            20                  25

<210> SEQ ID NO 78
<211> LENGTH: 26
<212> TYPE: PRT
```

<213> ORGANISM: Artificial Sequence
<220> FEATURE:
<223> OTHER INFORMATION: Engineered albumin binding polypeptide

<400> SEQUENCE: 78

Gly Val Ser Asp Phe Tyr Lys Arg Tyr Ile Asn Arg Ala Lys Thr Val
1               5                   10                  15
Glu Gly Val His Thr Leu Ile Gly His Ile
            20                  25

<210> SEQ ID NO 79
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 79

Gly Val Ser Asp Phe Tyr Lys Arg Leu Ile Asn Arg Ala Lys Thr Val
1               5                   10                  15
Glu Gly Val Gln Thr Leu Ile Ser Asp Ile
            20                  25

<210> SEQ ID NO 80
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 80

Gly Val Ser Asp Phe Tyr Lys Arg Leu Ile Asn Arg Ala Lys Thr Val
1               5                   10                  15
Glu Gly Val Asn Ser Leu Thr Ser His Ile
            20                  25

<210> SEQ ID NO 81
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 81

Gly Val Ser Asp Phe Tyr Lys Arg Leu Ile Asn Arg Ala Lys Thr Val
1               5                   10                  15
Glu Gly Val Asn Thr Leu Ile His Asp Ile
            20                  25

<210> SEQ ID NO 82
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 82

Gly Val Ser Asp Phe Tyr Lys Arg Leu Ile Asn Arg Ala Lys Thr Val
1               5                   10                  15
Glu Gly Val Glu Ser Leu Ile Gly Glu Ile
            20                  25

<210> SEQ ID NO 83
<211> LENGTH: 26

```
<212> TYPE: PRT
<213> ORGANISM: Artificial Sequence
<220> FEATURE:
<223> OTHER INFORMATION: Engineered albumin binding polypeptide

<400> SEQUENCE: 83

Gly Val Ser Asp Phe Tyr Lys Arg Leu Ile Asn Lys Ala Lys Thr Val
 1               5                  10                  15
Glu Gly Val His Thr Leu Ile His Asp Ile
             20                  25

<210> SEQ ID NO 84
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 84

Gly Val Ser Asp Tyr Tyr Lys Arg Leu Ile Asn Lys Ala Lys Thr Val
 1               5                  10                  15
Glu Gly Val Ser Ala Leu Lys Met His Ile
             20                  25

<210> SEQ ID NO 85
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 85

Gly Val Ser Asp Phe Tyr Lys Arg Leu Ile Asn Lys Ala Lys Thr Val
 1               5                  10                  15
Glu Gly Val Asp Ala Leu Ile Val His Ile
             20                  25

<210> SEQ ID NO 86
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 86

Gly Val Ser Asp Tyr Tyr Lys Arg Leu Ile Asn Arg Ala Arg Thr Val
 1               5                  10                  15
Glu Gly Val Asp Thr Leu Ile His Asp Ile
             20                  25

<210> SEQ ID NO 87
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 87

Gly Val Ser Asp Phe Tyr Lys Arg Val Ile Asn Arg Ala Arg Thr Val
 1               5                  10                  15
Glu Gly Val Gln Ala Leu Ile Ala Asp Ile
             20                  25

<210> SEQ ID NO 88
```

-continued

```
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 88

Gly Val Ser Asp Phe Tyr Lys Arg Leu Ile Asn Arg Ala Lys Thr Val
1               5                   10                  15

Glu Gly Val Glu Ser Leu Ile Ala Asp Ile
            20                  25

<210> SEQ ID NO 89
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 89

Gly Val Ser Asp Tyr Tyr Lys Arg Leu Ile Asn Lys Ala Lys Thr Val
1               5                   10                  15

Glu Gly Val Asp Ala Leu Ile Ala His Ile
            20                  25

<210> SEQ ID NO 90
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 90

Gly Val Ser Asp Tyr Tyr Lys Arg Leu Ile Asn Arg Ala Lys Thr Val
1               5                   10                  15

Glu Gly Val Glu Ser Leu Ile Thr His Ile
            20                  25

<210> SEQ ID NO 91
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 91

Gly Val Ser Asp Phe Tyr Lys Arg Leu Ile Asn Arg Ala Arg Thr Val
1               5                   10                  15

Glu Gly Val Asp Ser Leu Ile Val Glu Ile
            20                  25

<210> SEQ ID NO 92
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 92

Gly Val Ser Asp Phe Tyr Lys Arg Val Ile Asn Arg Ala Lys Thr Val
1               5                   10                  15

Glu Gly Val Ser Ala Leu Ile Arg Glu Ile
            20                  25
```

<210> SEQ ID NO 93
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 93

Gly Val Ser Asp Phe Tyr Lys Arg Leu Ile Asn Arg Ala Lys Thr Val
1               5                   10                  15

Glu Gly Val Asn Ala Leu Ile Ser Asp Ile
            20                  25

<210> SEQ ID NO 94
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 94

Gly Val Ser Asp Phe Tyr Lys Arg Leu Ile Asn Arg Ala Lys Thr Val
1               5                   10                  15

Glu Gly Val Ser Ala Leu Ile Gln Glu Ile
            20                  25

<210> SEQ ID NO 95
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 95

Gly Val Ser Asp Phe Tyr Lys Arg Leu Ile Asn Arg Ala Lys Thr Val
1               5                   10                  15

Glu Gly Val Gln Ser Leu Ile Asp His Ile
            20                  25

<210> SEQ ID NO 96
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 96

Gly Val Ser Asp Phe Tyr Lys Arg Leu Ile Asn Arg Ala Lys Thr Val
1               5                   10                  15

Glu Gly Val Asp Ala Leu Ile Cys His Ile
            20                  25

<210> SEQ ID NO 97
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 97

Gly Val Ser Asp Phe Tyr Lys Arg Val Ile Asn Lys Ala Lys Thr Val
1               5                   10                  15

Glu Gly Val Glu Ala Leu Ile Ala Asp Ile
            20                  25

<210> SEQ ID NO 98
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 98

Gly Val Ser Asp Phe Tyr Lys Arg Leu Ile Asn Arg Ala Lys Thr Val
1               5                   10                  15

Glu Gly Val Glu Thr Leu Ile Arg Asp Ile
            20                  25

<210> SEQ ID NO 99
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 99

Gly Val Ser Asp Phe Tyr Lys Arg Leu Ile Asn Arg Ala Arg Thr Val
1               5                   10                  15

Glu Gly Val Gln Thr Leu Ile Thr Asp Ile
            20                  25

<210> SEQ ID NO 100
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 100

Gly Val Ser Asp Tyr Tyr Lys Arg Leu Ile Asn Arg Ala Lys Thr Val
1               5                   10                  15

Glu Gly Val Gln Ala Leu Ile Ala His Ile
            20                  25

<210> SEQ ID NO 101
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 101

Gly Val Ser Asp Phe Tyr Lys Arg Val Ile Asn Arg Ala Lys Thr Val
1               5                   10                  15

Glu Gly Val Asn Ser Leu Ile Asn His Ile
            20                  25

<210> SEQ ID NO 102
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 102

Gly Val Ser Asp Phe Tyr Lys Arg Leu Ile Asn Arg Ala Arg Thr Val
1               5                   10                  15

Glu Gly Val Asp Ser Leu Ile Arg His Ile
            20                  25

```
<210> SEQ ID NO 103
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 103

Gly Val Ser Asp Tyr Tyr Lys Arg Leu Ile Asn Lys Ala Lys Thr Val
1               5                   10                  15

Glu Gly Val Glu Ala Leu Thr Leu His Ile
            20                  25

<210> SEQ ID NO 104
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 104

Gly Val Ser Asp Phe Tyr Lys Arg Leu Ile Asn Arg Ala Lys Thr Val
1               5                   10                  15

Glu Gly Val Asp Ala Leu Ile Ala His Ile
            20                  25

<210> SEQ ID NO 105
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 105

Gly Val Ser Asp Tyr Tyr Lys Arg Leu Ile Asn Lys Ala Lys Thr Val
1               5                   10                  15

Glu Gly Val Gln Ala Leu Ile Ala His Ile
            20                  25

<210> SEQ ID NO 106
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 106

Gly Val Ser Asp Phe Tyr Lys Asn Leu Ile Asn Arg Ala Lys Thr Val
1               5                   10                  15

Glu Gly Val His Ala Leu Lys Gly His Ile
            20                  25

<210> SEQ ID NO 107
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 107

Gly Val Ser Asp Phe Tyr Lys Asn Val Ile Asn Arg Ala Lys Thr Val
1               5                   10                  15

Glu Gly Val His Ala Leu Lys Asp His Ile
```

20                  25

<210> SEQ ID NO 108
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 108

Gly Val Ser Asp Phe Tyr Lys Asn Val Ile Asn Arg Ala Lys Thr Val
1               5                   10                  15

Glu Gly Val Ser Ala Leu Lys His Glu Ile
            20                  25

<210> SEQ ID NO 109
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 109

Gly Val Ser Asp Phe Tyr Lys Arg Leu Ile Asn Arg Ala Lys Thr Val
1               5                   10                  15

Glu Gly Val Asn Thr Leu Lys Ala Asp Ile
            20                  25

<210> SEQ ID NO 110
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 110

Gly Val Ser Asp Phe Tyr Lys Asn Leu Ile Asn Arg Ala Lys Thr Val
1               5                   10                  15

Glu Gly Val Asn Thr Leu Lys Ala Asp Ile
            20                  25

<210> SEQ ID NO 111
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 111

Gly Val Ser Asp Tyr Tyr Lys Asn Leu Ile Asn Arg Ala Lys Thr Val
1               5                   10                  15

Glu Gly Val Asn Ser Leu Lys Ser His Ile
            20                  25

<210> SEQ ID NO 112
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 112

Gly Val Ser Asp Phe Tyr Lys Arg Leu Ile Asn Arg Ala Lys Thr Val
1               5                   10                  15

Gly Gly Val Gln Ser Leu Lys Ser Glu Ile
            20                  25

<210> SEQ ID NO 113
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 113

Gly Val Ser Asp Phe Tyr Lys Asn Val Ile Asn Arg Ala Lys Thr Val
1               5                   10                  15

Glu Gly Val Asp Ser Leu Lys Ala Glu Ile
            20                  25

<210> SEQ ID NO 114
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 114

Gly Val Ser Asp Phe Tyr Lys Asn Leu Ile Asn Arg Ala Arg Thr Val
1               5                   10                  15

Glu Gly Val Gln Thr Leu Lys Ser Asp Ile
            20                  25

<210> SEQ ID NO 115
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 115

Gly Val Ser Asp Phe Tyr Lys Lys Phe Ile Asn Lys Ala Lys Thr Val
1               5                   10                  15

Glu Gly Val Glu Thr Leu Lys Ser Glu Ile
            20                  25

<210> SEQ ID NO 116
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 116

Gly Val Ser Asp Phe Tyr Lys Ser Leu Ile Asn Arg Ala Lys Thr Val
1               5                   10                  15

Glu Gly Val His Ser Leu Lys Asp Glu Ile
            20                  25

<210> SEQ ID NO 117
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 117

Gly Val Ser Asp Tyr Tyr Lys Asn Val Ile Asn Lys Ala Lys Thr Val
1               5                   10                  15

Glu Gly Val Ser Ser Leu Lys Ala Glu Ile
            20                  25

<210> SEQ ID NO 118
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 118

Gly Val Ser Asp Phe Tyr Lys Ser Leu Ile Asn Arg Ala Lys Thr Val
1               5                   10                  15

Glu Gly Val Asp Ala Leu Lys Ser His Ile
            20                  25

<210> SEQ ID NO 119
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 119

Gly Val Ser Asp Phe Tyr Lys Asn Leu Ile Asn Lys Ala Lys Thr Val
1               5                   10                  15

Glu Gly Val Ser Thr Leu Lys His Asp Ile
            20                  25

<210> SEQ ID NO 120
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 120

Gly Val Ser Asp Phe Tyr Lys Asn Leu Ile Asn Arg Ala Lys Thr Val
1               5                   10                  15

Glu Gly Val Ser Thr Leu Lys His Asp Ile
            20                  25

<210> SEQ ID NO 121
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 121

Gly Val Ser Asp Phe Tyr Lys Asn Leu Ile Asn Arg Ala Lys Thr Val
1               5                   10                  15

Glu Gly Val Gln Ala Leu Lys Ser Glu Ile
            20                  25

<210> SEQ ID NO 122
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 122

Gly Val Ser Asp Tyr Tyr Lys Ser Leu Ile Asn Lys Ala Lys Thr Val

```
                1               5                   10                  15
```

Glu Gly Val Asp Ser Leu Lys Val His Ile
            20              25

<210> SEQ ID NO 123
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 123

Gly Val Ser Asp Phe Tyr Lys Asn Leu Ile Asn Arg Ala Lys Thr Val
1               5                   10                  15

Glu Gly Val Gln Ser Leu Lys Thr Glu Ile
            20              25

<210> SEQ ID NO 124
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 124

Gly Val Ser Asp Tyr Tyr Lys Asn Leu Ile Asn Arg Ala Lys Thr Val
1               5                   10                  15

Glu Gly Val Asp Ala Leu Lys Thr His Ile
            20              25

<210> SEQ ID NO 125
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 125

Gly Val Ser Asp Phe Tyr Lys Ser Met Ile Asn Arg Ala Lys Thr Val
1               5                   10                  15

Glu Gly Val Asp Ser Leu Lys Thr His Ile
            20              25

<210> SEQ ID NO 126
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 126

Gly Val Ser Asp Phe Tyr Lys Asn Leu Ile Asn Arg Ala Lys Thr Val
1               5                   10                  15

Glu Gly Val Thr Thr Leu Lys Thr Asp Ile
            20              25

<210> SEQ ID NO 127
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 127

-continued

```
Gly Val Ser Asp Phe Tyr Lys Asn Leu Ile Asn Arg Ala Lys Thr Val
1               5                   10                  15

Glu Gly Val Glu Ser Leu Lys Asp His Ile
            20                  25

<210> SEQ ID NO 128
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 128

Gly Val Ser Asp Phe Tyr Lys Ser Tyr Ile Asn Arg Ala Lys Thr Val
1               5                   10                  15

Glu Gly Val His Thr Leu Lys Gly His Ile
            20                  25

<210> SEQ ID NO 129
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 129

Gly Val Ser Asp Phe Tyr Lys Asn Leu Ile Asn Arg Ala Lys Thr Val
1               5                   10                  15

Glu Gly Val Gln Thr Leu Lys Ser Asp Ile
            20                  25

<210> SEQ ID NO 130
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 130

Gly Val Ser Asp Phe Tyr Lys Asn Leu Ile Asn Arg Ala Lys Thr Val
1               5                   10                  15

Glu Gly Val Asn Ser Leu Lys Ser His Ile
            20                  25

<210> SEQ ID NO 131
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 131

Gly Val Ser Asp Phe Tyr Lys Asn Leu Ile Asn Arg Ala Lys Thr Val
1               5                   10                  15

Glu Gly Val Asn Thr Leu Lys His Asp Ile
            20                  25

<210> SEQ ID NO 132
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 132
```

-continued

Gly Val Ser Asp Phe Tyr Lys Asn Leu Ile Asn Arg Ala Lys Thr Val
1               5                   10                  15

Glu Gly Val Glu Ser Leu Lys Gly Glu Ile
            20                  25

<210> SEQ ID NO 133
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 133

Gly Val Ser Asp Phe Tyr Lys Asn Leu Ile Asn Lys Ala Lys Thr Val
1               5                   10                  15

Glu Gly Val His Thr Leu Lys His Asp Ile
            20                  25

<210> SEQ ID NO 134
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 134

Gly Val Ser Asp Phe Tyr Lys Asn Leu Ile Asn Lys Ala Lys Thr Val
1               5                   10                  15

Glu Gly Val Asp Ala Leu Lys Val His Ile
            20                  25

<210> SEQ ID NO 135
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 135

Gly Val Ser Asp Tyr Tyr Lys Arg Leu Ile Asn Arg Ala Lys Thr Val
1               5                   10                  15

Glu Gly Val His Ala Leu Lys Ala Glu Ile
            20                  25

<210> SEQ ID NO 136
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 136

Gly Val Ser Asp Tyr Tyr Lys Asn Leu Ile Asn Arg Ala Arg Thr Val
1               5                   10                  15

Glu Gly Val Asp Thr Leu Lys His Asp Ile
            20                  25

<210> SEQ ID NO 137
<211> LENGTH: 26
<212> TYPE: PRT
<213> ORGANISM: Artificial Sequence
<220> FEATURE:
<223> OTHER INFORMATION: Engineered albumin binding polypeptide

```
<400> SEQUENCE: 137

Gly Val Ser Asp Phe Tyr Lys Lys Val Ile Asn Arg Ala Arg Thr Val
1               5                   10                  15

Glu Gly Val Gln Ala Leu Lys Ala Asp Ile
            20                  25

<210> SEQ ID NO 138
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 138

Gly Val Ser Asp Phe Tyr Lys Asn Leu Ile Asn Arg Ala Lys Thr Val
1               5                   10                  15

Glu Gly Val Glu Ser Leu Lys Ala Asp Ile
            20                  25

<210> SEQ ID NO 139
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 139

Gly Val Ser Asp Tyr Tyr Lys Asn Leu Ile Asn Lys Ala Lys Thr Val
1               5                   10                  15

Glu Gly Val Asp Ala Leu Lys Ala His Ile
            20                  25

<210> SEQ ID NO 140
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 140

Gly Val Ser Asp Tyr Tyr Lys Asn Leu Ile Asn Arg Ala Lys Thr Val
1               5                   10                  15

Glu Gly Val Glu Ser Leu Lys Thr His Ile
            20                  25

<210> SEQ ID NO 141
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 141

Gly Val Ser Asp Phe Tyr Lys Asn Leu Ile Asn Arg Ala Arg Thr Val
1               5                   10                  15

Glu Gly Val Asp Ser Leu Lys Val Glu Ile
            20                  25

<210> SEQ ID NO 142
<211> LENGTH: 26
<212> TYPE: PRT
<213> ORGANISM: Artificial Sequence
<220> FEATURE:
<223> OTHER INFORMATION: Engineered albumin binding polypeptide
```

```
<400> SEQUENCE: 142

Gly Val Ser Asp Phe Tyr Lys Asn Val Ile Asn Arg Ala Lys Thr Val
1               5                   10                  15

Glu Gly Val Ser Ala Leu Lys Arg Glu Ile
            20                  25

<210> SEQ ID NO 143
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 143

Gly Val Ser Asp Phe Tyr Lys Asn Leu Ile Asn Arg Ala Lys Thr Val
1               5                   10                  15

Glu Gly Val Asn Ala Leu Lys Ser Asp Ile
            20                  25

<210> SEQ ID NO 144
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 144

Gly Val Ser Asp Phe Tyr Lys Asn Leu Ile Asn Arg Ala Lys Thr Val
1               5                   10                  15

Glu Gly Val Ser Ala Leu Lys Gln Glu Ile
            20                  25

<210> SEQ ID NO 145
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 145

Gly Val Ser Asp Phe Tyr Lys Asn Leu Ile Asn Arg Ala Lys Thr Val
1               5                   10                  15

Glu Gly Val Gln Ser Leu Lys Asp His Ile
            20                  25

<210> SEQ ID NO 146
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 146

Gly Val Ser Asp Phe Tyr Lys Asn Leu Ile Asn Arg Ala Lys Thr Val
1               5                   10                  15

Glu Gly Val Asp Ala Leu Lys Cys His Ile
            20                  25

<210> SEQ ID NO 147
<211> LENGTH: 26
<212> TYPE: PRT
<213> ORGANISM: Artificial Sequence
<220> FEATURE:
```

<223> OTHER INFORMATION: Engineered albumin binding polypeptide

<400> SEQUENCE: 147

Gly Val Ser Asp Tyr Tyr Lys Arg Leu Ile Asn Lys Ala Lys Thr Val
1               5                   10                  15

Glu Gly Val Asn Ala Leu Lys Thr His Ile
            20                  25

<210> SEQ ID NO 148
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 148

Gly Val Ser Asp Phe Tyr Lys Asn Val Ile Asn Lys Ala Lys Thr Val
1               5                   10                  15

Glu Gly Val Glu Ala Leu Lys Ala Asp Ile
            20                  25

<210> SEQ ID NO 149
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 149

Gly Val Ser Asp Phe Tyr Lys Asn Leu Ile Asn Arg Ala Lys Thr Val
1               5                   10                  15

Glu Gly Val Glu Thr Leu Lys Arg Asp Ile
            20                  25

<210> SEQ ID NO 150
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 150

Gly Val Ser Asp Phe Tyr Lys Asn Leu Ile Asn Arg Ala Arg Thr Val
1               5                   10                  15

Glu Gly Val Gln Thr Leu Lys Thr Asp Ile
            20                  25

<210> SEQ ID NO 151
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 151

Gly Val Ser Asp Phe Tyr Lys Arg Leu Ile Asn Lys Ala Lys Thr Val
1               5                   10                  15

Glu Gly Val Asn Ala Leu Lys His His Ile
            20                  25

<210> SEQ ID NO 152
<211> LENGTH: 26
<212> TYPE: PRT
<213> ORGANISM: Artificial Sequence

```
<220> FEATURE:
<223> OTHER INFORMATION: Engineered albumin binding polypeptide

<400> SEQUENCE: 152

Gly Val Ser Asp Tyr Tyr Lys Asn Leu Ile Asn Arg Ala Lys Thr Val
1               5                   10                  15

Glu Gly Val Gln Ala Leu Lys Ala His Ile
            20                  25

<210> SEQ ID NO 153
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 153

Gly Val Ser Asp Phe Tyr Lys Asn Val Ile Asn Arg Ala Lys Thr Val
1               5                   10                  15

Glu Gly Val Asn Ser Leu Lys Asn His Ile
            20                  25

<210> SEQ ID NO 154
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 154

Gly Val Ser Asp Phe Tyr Lys Ser Leu Ile Asn Arg Ala Arg Thr Val
1               5                   10                  15

Glu Gly Val Asp Ser Leu Lys Arg His Ile
            20                  25

<210> SEQ ID NO 155
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 155

Gly Val Ser Asp Tyr Tyr Lys Asn Leu Ile Asn Lys Ala Lys Thr Val
1               5                   10                  15

Glu Gly Val Glu Ala Leu Lys Leu His Ile
            20                  25

<210> SEQ ID NO 156
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 156

Gly Val Ser Asp Phe Tyr Lys Asn Leu Ile Asn Arg Ala Lys Thr Val
1               5                   10                  15

Glu Gly Val Asp Ala Leu Lys Ala His Ile
            20                  25

<210> SEQ ID NO 157
<211> LENGTH: 26
<212> TYPE: PRT
```

-continued

```
<213> ORGANISM: Artificial Sequence
<220> FEATURE:
<223> OTHER INFORMATION: Engineered albumin binding polypeptide

<400> SEQUENCE: 157

Gly Val Ser Asp Tyr Tyr Lys Asn Leu Ile Asn Lys Ala Lys Thr Val
1               5                   10                  15
Glu Gly Val Gln Ala Leu Lys Ala His Ile
            20                  25

<210> SEQ ID NO 158
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 158

Gly Val Ser Asp Phe Tyr Lys Arg Leu Ile Asn Arg Ala Lys Thr Val
1               5                   10                  15
Glu Gly Val His Ala Leu Lys Gly His Ile
            20                  25

<210> SEQ ID NO 159
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 159

Gly Val Ser Asp Phe Tyr Lys Arg Val Ile Asn Arg Ala Lys Thr Val
1               5                   10                  15
Glu Gly Val His Ala Leu Lys Asp His Ile
            20                  25

<210> SEQ ID NO 160
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 160

Gly Val Ser Asp Tyr Tyr Lys Arg Ile Ile Asn Arg Ala Lys Thr Val
1               5                   10                  15
Glu Gly Val Arg Ala Leu Lys Leu His Ile
            20                  25

<210> SEQ ID NO 161
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 161

Gly Val Ser Asp Phe Tyr Lys Arg Val Ile Asn Arg Ala Lys Thr Val
1               5                   10                  15
Glu Gly Val Ser Ala Leu Lys His Glu Ile
            20                  25

<210> SEQ ID NO 162
<211> LENGTH: 26
```

```
<212> TYPE: PRT
<213> ORGANISM: Artificial Sequence
<220> FEATURE:
<223> OTHER INFORMATION: Engineered albumin binding polypeptide

<400> SEQUENCE: 162

Gly Val Ser Asp Tyr Tyr Lys Arg Leu Ile Asn Arg Ala Lys Thr Val
1               5                   10                  15
Glu Gly Val Asn Ser Leu Lys Ser His Ile
            20                  25

<210> SEQ ID NO 163
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 163

Gly Val Ser Asp Phe Tyr Lys Arg Leu Ile Asn Arg Ala Lys Thr Val
1               5                   10                  15
Gly Gly Val Gln Ser Leu Lys Ser Glu Ile
            20                  25

<210> SEQ ID NO 164
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 164

Gly Val Ser Asp Phe Tyr Lys Arg Leu Ile Asn Arg Ala Lys Thr Val
1               5                   10                  15
Glu Gly Val Ser Ser Leu Lys Gly His Ile
            20                  25

<210> SEQ ID NO 165
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 165

Gly Val Ser Asp Phe Tyr Lys Arg Val Ile Asn Arg Ala Lys Thr Val
1               5                   10                  15
Glu Gly Val Asp Ser Leu Lys Ala Glu Ile
            20                  25

<210> SEQ ID NO 166
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 166

Gly Val Ser Asp Phe Tyr Lys Arg Leu Ile Asn Arg Ala Arg Thr Val
1               5                   10                  15
Glu Gly Val Gln Thr Leu Lys Ser Asp Ile
            20                  25

<210> SEQ ID NO 167
```

```
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 167

Gly Val Ser Asp Phe Tyr Lys Arg Phe Ile Asn Lys Ala Lys Thr Val
1               5                   10                  15

Glu Gly Val Glu Thr Leu Lys Ser Glu Ile
            20                  25

<210> SEQ ID NO 168
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 168

Gly Val Ser Asp Phe Tyr Lys Arg Leu Ile Asn Arg Ala Lys Thr Val
1               5                   10                  15

Glu Gly Val His Ser Leu Lys Asp Glu Ile
            20                  25

<210> SEQ ID NO 169
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 169

Gly Val Ser Asp Tyr Tyr Lys Arg Val Ile Asn Lys Ala Lys Thr Val
1               5                   10                  15

Glu Gly Val Ser Ser Leu Lys Ala Glu Ile
            20                  25

<210> SEQ ID NO 170
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 170

Gly Val Ser Asp Phe Tyr Lys Arg Leu Ile Asn Arg Ala Lys Thr Val
1               5                   10                  15

Glu Gly Val Asp Ala Leu Lys Ser His Ile
            20                  25

<210> SEQ ID NO 171
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 171

Gly Val Ser Asp Phe Tyr Lys Arg Leu Ile Asn Lys Ala Lys Thr Val
1               5                   10                  15

Glu Gly Val Ser Thr Leu Lys His Asp Ile
            20                  25
```

```
<210> SEQ ID NO 172
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 172

Gly Val Ser Asp Phe Tyr Lys Arg Leu Ile Asn Arg Ala Lys Thr Val
1               5                   10                  15

Glu Gly Val Ser Thr Leu Lys His Asp Ile
            20                  25

<210> SEQ ID NO 173
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 173

Gly Val Ser Asp Phe Tyr Lys Arg Leu Ile Asn Arg Ala Lys Thr Val
1               5                   10                  15

Glu Gly Val Gln Ala Leu Lys Ser Glu Ile
            20                  25

<210> SEQ ID NO 174
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 174

Gly Val Ser Asp Tyr Tyr Lys Arg Leu Ile Asn Lys Ala Lys Thr Val
1               5                   10                  15

Glu Gly Val Asp Ser Leu Lys Val His Ile
            20                  25

<210> SEQ ID NO 175
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 175

Gly Val Ser Asp Phe Tyr Lys Arg Leu Ile Asn Arg Ala Lys Thr Val
1               5                   10                  15

Glu Gly Val Gln Ser Leu Lys Thr Glu Ile
            20                  25

<210> SEQ ID NO 176
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 176

Gly Val Ser Asp Tyr Tyr Lys Arg Leu Ile Asn Arg Ala Lys Thr Val
1               5                   10                  15

Glu Gly Val Asp Ala Leu Lys Thr His Ile
            20                  25
```

<210> SEQ ID NO 177
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 177

Gly Val Ser Asp Phe Tyr Lys Arg Met Ile Asn Arg Ala Lys Thr Val
1               5                   10                  15

Glu Gly Val Asp Ser Leu Lys Thr His Ile
            20                  25

<210> SEQ ID NO 178
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 178

Gly Val Ser Asp Phe Tyr Lys Arg Leu Ile Asn Arg Ala Lys Thr Val
1               5                   10                  15

Glu Gly Val Thr Thr Leu Lys Thr Asp Ile
            20                  25

<210> SEQ ID NO 179
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 179

Gly Val Ser Asp Phe Tyr Lys Arg Leu Ile Asn Arg Ala Lys Thr Val
1               5                   10                  15

Glu Gly Val Glu Ser Leu Lys Asp His Ile
            20                  25

<210> SEQ ID NO 180
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 180

Gly Val Ser Asp Phe Tyr Lys Arg Tyr Ile Asn Arg Ala Lys Thr Val
1               5                   10                  15

Glu Gly Val His Thr Leu Lys Gly His Ile
            20                  25

<210> SEQ ID NO 181
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 181

Gly Val Ser Asp Phe Tyr Lys Arg Leu Ile Asn Arg Ala Lys Thr Val
1               5                   10                  15

Glu Gly Val Gln Thr Leu Lys Ser Asp Ile
            20                  25

<210> SEQ ID NO 182
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 182

Gly Val Ser Asp Phe Tyr Lys Arg Leu Ile Asn Arg Ala Lys Thr Val
 1               5                  10                  15

Glu Gly Val Asn Ser Leu Lys Ser His Ile
            20                  25

<210> SEQ ID NO 183
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 183

Gly Val Ser Asp Phe Tyr Lys Arg Leu Ile Asn Arg Ala Lys Thr Val
 1               5                  10                  15

Glu Gly Val Asn Thr Leu Lys His Asp Ile
            20                  25

<210> SEQ ID NO 184
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 184

Gly Val Ser Asp Phe Tyr Lys Arg Leu Ile Asn Arg Ala Lys Thr Val
 1               5                  10                  15

Glu Gly Val Glu Ser Leu Lys Gly Glu Ile
            20                  25

<210> SEQ ID NO 185
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 185

Gly Val Ser Asp Phe Tyr Lys Arg Leu Ile Asn Lys Ala Lys Thr Val
 1               5                  10                  15

Glu Gly Val His Thr Leu Lys His Asp Ile
            20                  25

<210> SEQ ID NO 186
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 186

Gly Val Ser Asp Tyr Tyr Lys Arg Leu Ile Asn Lys Ala Lys Thr Val
 1               5                  10                  15

Glu Gly Val Ser Ala Leu Lys Met His Ile

-continued 20              25

<210> SEQ ID NO 187
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 187

Gly Val Ser Asp Phe Tyr Lys Arg Leu Ile Asn Lys Ala Lys Thr Val
1               5                   10                  15

Glu Gly Val Asp Ala Leu Lys Val His Ile
            20              25

<210> SEQ ID NO 188
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 188

Gly Val Ser Asp Tyr Tyr Lys Arg Leu Ile Asn Arg Ala Lys Thr Val
1               5                   10                  15

Glu Gly Val His Ala Leu Lys Ala Glu Ile
            20              25

<210> SEQ ID NO 189
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 189

Gly Val Ser Asp Tyr Tyr Lys Arg Leu Ile Asn Arg Ala Arg Thr Val
1               5                   10                  15

Glu Gly Val Asp Thr Leu Lys His Asp Ile
            20              25

<210> SEQ ID NO 190
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 190

Gly Val Ser Asp Phe Tyr Lys Arg Val Ile Asn Arg Ala Arg Thr Val
1               5                   10                  15

Glu Gly Val Gln Ala Leu Lys Ala Asp Ile
            20              25

<210> SEQ ID NO 191
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 191

Gly Val Ser Asp Phe Tyr Lys Arg Leu Ile Asn Arg Ala Lys Thr Val
1               5                   10                  15

Glu Gly Val Glu Ser Leu Lys Ala Asp Ile
            20                  25

<210> SEQ ID NO 192
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 192

Gly Val Ser Asp Tyr Tyr Lys Arg Leu Ile Asn Lys Ala Lys Thr Val
1               5                   10                  15

Glu Gly Val Asp Ala Leu Lys Ala His Ile
            20                  25

<210> SEQ ID NO 193
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 193

Gly Val Ser Asp Tyr Tyr Lys Arg Leu Ile Asn Arg Ala Lys Thr Val
1               5                   10                  15

Glu Gly Val Glu Ser Leu Lys Thr His Ile
            20                  25

<210> SEQ ID NO 194
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 194

Gly Val Ser Asp Phe Tyr Lys Arg Leu Ile Asn Arg Ala Arg Thr Val
1               5                   10                  15

Glu Gly Val Asp Ser Leu Lys Val Glu Ile
            20                  25

<210> SEQ ID NO 195
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 195

Gly Val Ser Asp Phe Tyr Lys Arg Val Ile Asn Arg Ala Lys Thr Val
1               5                   10                  15

Glu Gly Val Ser Ala Leu Lys Arg Glu Ile
            20                  25

<210> SEQ ID NO 196
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 196

Gly Val Ser Asp Phe Tyr Lys Arg Leu Ile Asn Arg Ala Lys Thr Val
1               5                   10                  15

-continued

Glu Gly Val Asn Ala Leu Lys Ser Asp Ile
            20                  25

<210> SEQ ID NO 197
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 197

Gly Val Ser Asp Phe Tyr Lys Arg Leu Ile Asn Arg Ala Lys Thr Val
1               5                   10                  15

Glu Gly Val Ser Ala Leu Lys Gln Glu Ile
            20                  25

<210> SEQ ID NO 198
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 198

Gly Val Ser Asp Phe Tyr Lys Arg Leu Ile Asn Arg Ala Lys Thr Val
1               5                   10                  15

Glu Gly Val Gln Ser Leu Lys Asp His Ile
            20                  25

<210> SEQ ID NO 199
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 199

Gly Val Ser Asp Phe Tyr Lys Arg Leu Ile Asn Arg Ala Lys Thr Val
1               5                   10                  15

Glu Gly Val Asp Ala Leu Lys Cys His Ile
            20                  25

<210> SEQ ID NO 200
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 200

Gly Val Ser Asp Tyr Tyr Lys Arg Leu Ile Asn Lys Ala Lys Thr Val
1               5                   10                  15

Glu Gly Val Asn Ala Leu Lys Thr His Ile
            20                  25

<210> SEQ ID NO 201
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 201

Gly Val Ser Asp Phe Tyr Lys Arg Val Ile Asn Lys Ala Lys Thr Val

```
                1               5                   10                  15
Glu Gly Val Glu Ala Leu Lys Ala Asp Ile
            20                  25
```

<210> SEQ ID NO 202
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 202

```
Gly Val Ser Asp Phe Tyr Lys Arg Leu Ile Asn Arg Ala Lys Thr Val
 1               5                   10                  15
Glu Gly Val Glu Thr Leu Lys Arg Asp Ile
            20                  25
```

<210> SEQ ID NO 203
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 203

```
Gly Val Ser Asp Phe Tyr Lys Arg Leu Ile Asn Arg Ala Arg Thr Val
 1               5                   10                  15
Glu Gly Val Gln Thr Leu Lys Thr Asp Ile
            20                  25
```

<210> SEQ ID NO 204
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 204

```
Gly Val Ser Asp Phe Tyr Lys Arg Leu Ile Asn Lys Ala Lys Thr Val
 1               5                   10                  15
Glu Gly Val Asn Ala Leu Lys His His Ile
            20                  25
```

<210> SEQ ID NO 205
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 205

```
Gly Val Ser Asp Tyr Tyr Lys Arg Leu Ile Asn Arg Ala Lys Thr Val
 1               5                   10                  15
Glu Gly Val Gln Ala Leu Lys Ala His Ile
            20                  25
```

<210> SEQ ID NO 206
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 206

Gly Val Ser Asp Phe Tyr Lys Arg Val Ile Asn Arg Ala Lys Thr Val
1               5                   10                  15

Glu Gly Val Asn Ser Leu Lys Asn His Ile
            20                  25

<210> SEQ ID NO 207
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 207

Gly Val Ser Asp Phe Tyr Lys Arg Leu Ile Asn Arg Ala Arg Thr Val
1               5                   10                  15

Glu Gly Val Asp Ser Leu Lys Arg His Ile
            20                  25

<210> SEQ ID NO 208
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 208

Gly Val Ser Asp Tyr Tyr Lys Arg Leu Ile Asn Lys Ala Lys Thr Val
1               5                   10                  15

Glu Gly Val Glu Ala Leu Lys Leu His Ile
            20                  25

<210> SEQ ID NO 209
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 209

Gly Val Ser Asp Phe Tyr Lys Arg Leu Ile Asn Arg Ala Lys Thr Val
1               5                   10                  15

Glu Gly Val Asp Ala Leu Lys Ala His Ile
            20                  25

<210> SEQ ID NO 210
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 210

Gly Val Ser Asp Tyr Tyr Lys Arg Leu Ile Asn Lys Ala Lys Thr Val
1               5                   10                  15

Glu Gly Val Gln Ala Leu Lys Ala His Ile
            20                  25

<210> SEQ ID NO 211
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 211

Gly Val Ser Asp Phe Tyr Lys Arg Val Ile Asn Arg Ala Lys Thr Val
1               5                   10                  15

Glu Gly Val Ser Ala Leu Lys His His Ile
            20                  25

<210> SEQ ID NO 212
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 212

Gly Val Ser Asp Phe Tyr Lys Arg Leu Ile Asn Arg Ala Lys Thr Val
1               5                   10                  15

Glu Gly Val Asn Thr Leu Lys Ala His Ile
            20                  25

<210> SEQ ID NO 213
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 213

Gly Val Ser Asp Phe Tyr Lys Arg Leu Ile Asn Arg Ala Lys Thr Val
1               5                   10                  15

Gly Gly Val Gln Ser Leu Lys Ser His Ile
            20                  25

<210> SEQ ID NO 214
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 214

Gly Val Ser Asp Phe Tyr Lys Arg Val Ile Asn Arg Ala Lys Thr Val
1               5                   10                  15

Glu Gly Val Asp Ser Leu Lys Ala His Ile
            20                  25

<210> SEQ ID NO 215
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 215

Gly Val Ser Asp Phe Tyr Lys Arg Leu Ile Asn Arg Ala Arg Thr Val
1               5                   10                  15

Glu Gly Val Gln Thr Leu Lys Ser His Ile
            20                  25

<210> SEQ ID NO 216
<211> LENGTH: 26
<212> TYPE: PRT
<213> ORGANISM: Artificial Sequence
<220> FEATURE:
<223> OTHER INFORMATION: Engineered albumin binding polypeptide -continued

```
<400> SEQUENCE: 216

Gly Val Ser Asp Phe Tyr Lys Arg Phe Ile Asn Lys Ala Lys Thr Val
1               5                   10                  15

Glu Gly Val Glu Thr Leu Lys Ser His Ile
            20                  25

<210> SEQ ID NO 217
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 217

Gly Val Ser Asp Phe Tyr Lys Arg Leu Ile Asn Arg Ala Lys Thr Val
1               5                   10                  15

Glu Gly Val His Ser Leu Lys Asp His Ile
            20                  25

<210> SEQ ID NO 218
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 218

Gly Val Ser Asp Tyr Tyr Lys Arg Val Ile Asn Lys Ala Lys Thr Val
1               5                   10                  15

Glu Gly Val Ser Ser Leu Lys Ala His Ile
            20                  25

<210> SEQ ID NO 219
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 219

Gly Val Ser Asp Phe Tyr Lys Arg Leu Ile Asn Lys Ala Lys Thr Val
1               5                   10                  15

Glu Gly Val Ser Thr Leu Lys His His Ile
            20                  25

<210> SEQ ID NO 220
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 220

Gly Val Ser Asp Phe Tyr Lys Arg Leu Ile Asn Arg Ala Lys Thr Val
1               5                   10                  15

Glu Gly Val Ser Thr Leu Lys His His Ile
            20                  25

<210> SEQ ID NO 221
<211> LENGTH: 26
<212> TYPE: PRT
<213> ORGANISM: Artificial Sequence
<220> FEATURE:
<223> OTHER INFORMATION: Engineered albumin binding polypeptide
```

<400> SEQUENCE: 221

Gly Val Ser Asp Phe Tyr Lys Arg Leu Ile Asn Arg Ala Lys Thr Val
1               5                   10                  15
Glu Gly Val Gln Ala Leu Lys Ser His Ile
            20                  25

<210> SEQ ID NO 222
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 222

Gly Val Ser Asp Phe Tyr Lys Arg Leu Ile Asn Arg Ala Lys Thr Val
1               5                   10                  15
Glu Gly Val Gln Ser Leu Lys Thr His Ile
            20                  25

<210> SEQ ID NO 223
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 223

Gly Val Ser Asp Phe Tyr Lys Arg Leu Ile Asn Arg Ala Lys Thr Val
1               5                   10                  15
Glu Gly Val Thr Thr Leu Lys Thr His Ile
            20                  25

<210> SEQ ID NO 224
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 224

Gly Val Ser Asp Phe Tyr Lys Arg Leu Ile Asn Arg Ala Lys Thr Val
1               5                   10                  15
Glu Gly Val Gln Thr Leu Lys Ser His Ile
            20                  25

<210> SEQ ID NO 225
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 225

Gly Val Ser Asp Phe Tyr Lys Arg Leu Ile Asn Arg Ala Lys Thr Val
1               5                   10                  15
Glu Gly Val Asn Thr Leu Lys His His Ile
            20                  25

<210> SEQ ID NO 226
<211> LENGTH: 26
<212> TYPE: PRT
<213> ORGANISM: Artificial Sequence
<220> FEATURE:

<223> OTHER INFORMATION: Engineered albumin binding polypeptide

<400> SEQUENCE: 226

Gly Val Ser Asp Phe Tyr Lys Arg Leu Ile Asn Arg Ala Lys Thr Val
1               5                   10                  15

Glu Gly Val Glu Ser Leu Lys Gly His Ile
            20                  25

<210> SEQ ID NO 227
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 227

Gly Val Ser Asp Phe Tyr Lys Arg Leu Ile Asn Lys Ala Lys Thr Val
1               5                   10                  15

Glu Gly Val His Thr Leu Lys His His Ile
            20                  25

<210> SEQ ID NO 228
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 228

Gly Val Ser Asp Tyr Tyr Lys Arg Leu Ile Asn Arg Ala Lys Thr Val
1               5                   10                  15

Glu Gly Val His Ala Leu Lys Ala His Ile
            20                  25

<210> SEQ ID NO 229
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 229

Gly Val Ser Asp Tyr Tyr Lys Arg Leu Ile Asn Arg Ala Arg Thr Val
1               5                   10                  15

Glu Gly Val Asp Thr Leu Lys His His Ile
            20                  25

<210> SEQ ID NO 230
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 230

Gly Val Ser Asp Phe Tyr Lys Arg Val Ile Asn Arg Ala Arg Thr Val
1               5                   10                  15

Glu Gly Val Gln Ala Leu Lys Ala His Ile
            20                  25

<210> SEQ ID NO 231
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 231

Gly Val Ser Asp Phe Tyr Lys Arg Leu Ile Asn Arg Ala Lys Thr Val
1               5                   10                  15
Glu Gly Val Glu Ser Leu Lys Ala His Ile
            20                  25

<210> SEQ ID NO 232
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 232

Gly Val Ser Asp Phe Tyr Lys Arg Leu Ile Asn Arg Ala Arg Thr Val
1               5                   10                  15
Glu Gly Val Asp Ser Leu Lys Val His Ile
            20                  25

<210> SEQ ID NO 233
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 233

Gly Val Ser Asp Phe Tyr Lys Arg Val Ile Asn Arg Ala Lys Thr Val
1               5                   10                  15
Glu Gly Val Ser Ala Leu Lys Arg His Ile
            20                  25

<210> SEQ ID NO 234
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 234

Gly Val Ser Asp Phe Tyr Lys Arg Leu Ile Asn Arg Ala Lys Thr Val
1               5                   10                  15
Glu Gly Val Asn Ala Leu Lys Ser His Ile
            20                  25

<210> SEQ ID NO 235
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 235

Gly Val Ser Asp Phe Tyr Lys Arg Leu Ile Asn Arg Ala Lys Thr Val
1               5                   10                  15
Glu Gly Val Ser Ala Leu Lys Gln His Ile
            20                  25

<210> SEQ ID NO 236
<211> LENGTH: 26
<212> TYPE: PRT

<213> ORGANISM: Artificial Sequence
<220> FEATURE:
<223> OTHER INFORMATION: Engineered albumin binding polypeptide

<400> SEQUENCE: 236

Gly Val Ser Asp Phe Tyr Lys Arg Val Ile Asn Lys Ala Lys Thr Val
1               5                   10                  15

Glu Gly Val Glu Ala Leu Lys Ala His Ile
            20                  25

<210> SEQ ID NO 237
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 237

Gly Val Ser Asp Phe Tyr Lys Arg Leu Ile Asn Arg Ala Lys Thr Val
1               5                   10                  15

Glu Gly Val Glu Thr Leu Lys Arg His Ile
            20                  25

<210> SEQ ID NO 238
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 238

Gly Val Ser Asp Phe Tyr Lys Arg Leu Ile Asn Arg Ala Arg Thr Val
1               5                   10                  15

Glu Gly Val Gln Thr Leu Lys Thr His Ile
            20                  25

<210> SEQ ID NO 239
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 239

Gly Val Ser Asp Phe Tyr Lys Arg Leu Ile Asn Lys Ala Lys Thr Val
1               5                   10                  15

Glu Gly Val Glu Ala Leu Lys Leu His Ile
            20                  25

<210> SEQ ID NO 240
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 240

Gly Val Ser Asp Tyr Tyr Lys Asn Leu Ile Asn Arg Ala Arg Thr Val
1               5                   10                  15

Glu Gly Val Glu Ala Leu Lys Leu His Ile
            20                  25

<210> SEQ ID NO 241
<211> LENGTH: 26

```
<212> TYPE: PRT
<213> ORGANISM: Artificial Sequence
<220> FEATURE:
<223> OTHER INFORMATION: Engineered albumin binding polypeptide

<400> SEQUENCE: 241

Gly Val Ser Asp Tyr Tyr Lys Asn Ile Ile Asn Arg Ala Lys Thr Val
1               5                   10                  15
Glu Gly Val Glu Ala Leu Lys Leu His Ile
            20                  25

<210> SEQ ID NO 242
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 242

Gly Val Ser Asp Phe Tyr Lys Asn Leu Ile Asn Arg Ala Lys Thr Val
1               5                   10                  15
Glu Gly Val Glu Ala Leu Lys Leu His Ile
            20                  25

<210> SEQ ID NO 243
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 243

Gly Val Ser Asp Phe Tyr Lys Asn Val Ile Asn Lys Ala Lys Thr Val
1               5                   10                  15
Glu Gly Val Glu Ala Leu Lys Leu His Ile
            20                  25

<210> SEQ ID NO 244
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 244

Gly Val Ser Asp Tyr Tyr Lys Asn Leu Ile Asn Arg Ala Lys Thr Val
1               5                   10                  15
Glu Gly Val Glu Ala Leu Lys Leu His Ile
            20                  25

<210> SEQ ID NO 245
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 245

Gly Val Ser Asp Tyr Tyr Lys Asn Leu Ile Asn Arg Ala Arg Thr Val
1               5                   10                  15
Glu Gly Val His Ala Leu Ile Asp His Ile
            20                  25

<210> SEQ ID NO 246
```

```
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 246

Gly Val Ser Asp Phe Tyr Lys Arg Leu Ile Asn Lys Ala Lys Thr Val
1               5                   10                  15

Glu Gly Val Glu Ala Leu Lys Leu His Ile
            20                  25

<210> SEQ ID NO 247
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 247

Gly Val Ser Asp Tyr Tyr Lys Arg Leu Ile Ser Lys Ala Lys Thr Val
1               5                   10                  15

Glu Gly Val Lys Ala Leu Ile Ser Glu Ile
            20                  25

<210> SEQ ID NO 248
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 248

Gly Val Ser Asp Phe Tyr Lys Arg Leu Ile Asn Lys Ala Lys Thr Val
1               5                   10                  15

Glu Gly Val Glu Ala Leu Lys Leu His Ile
            20                  25

<210> SEQ ID NO 249
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 249

Gly Val Ser Asp Tyr Tyr Lys Arg Leu Ile Ser Lys Ala Lys Thr Val
1               5                   10                  15

Glu Gly Val Lys Ala Leu Ile Ser Glu Ile
            20                  25

<210> SEQ ID NO 250
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 250

Gly Val Ser Asp Tyr Tyr Lys Arg Leu Ile Ser Lys Ala Lys Thr Val
1               5                   10                  15

Glu Gly Val Lys Ala Leu Ile Ser Glu Ile
            20                  25
```

```
<210> SEQ ID NO 251
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 251

Gly Val Ser Asp Tyr Tyr Lys Arg Leu Ile Ser Lys Ala Lys Thr Val
1               5                   10                  15

Glu Gly Val Lys Ala Leu Ile Ser Glu Ile
            20                  25

<210> SEQ ID NO 252
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 252

Gly Val Ser Asp Tyr Tyr Lys Arg Leu Ile Ser Lys Ala Lys Thr Val
1               5                   10                  15

Glu Gly Val Lys Ala Leu Ile Ser Glu Ile
            20                  25

<210> SEQ ID NO 253
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 253

Gly Val Ser Asp Tyr Tyr Lys Arg Leu Ile Ser Lys Ala Lys Thr Val
1               5                   10                  15

Glu Gly Val Lys Ala Leu Ile Ser Glu Ile
            20                  25

<210> SEQ ID NO 254
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 254

Gly Val Ser Asp Tyr Tyr Lys Arg Leu Ile Ser Lys Ala Lys Thr Val
1               5                   10                  15

Glu Gly Val Lys Ala Leu Ile Ser Glu Ile
            20                  25

<210> SEQ ID NO 255
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 255

Gly Val Ser Asp Tyr Tyr Lys Arg Leu Ile Ser Lys Ala Lys Thr Val
1               5                   10                  15

Glu Gly Val Lys Ala Leu Ile Ser Glu Ile
            20                  25
```

<210> SEQ ID NO 256
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 256

Gly Val Ser Asp Tyr Tyr Lys Arg Leu Ile Ser Lys Ala Lys Thr Val
1               5                   10                  15

Glu Gly Val Lys Ala Leu Ile Ser Glu Ile
            20                  25

<210> SEQ ID NO 257
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 257

Gly Val Ser Asp Tyr Tyr Lys Arg Leu Ile Ser Lys Ala Lys Thr Val
1               5                   10                  15

Glu Gly Val Lys Ala Leu Ile Ser Glu Ile
            20                  25

<210> SEQ ID NO 258
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 258

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val His Ala Leu Ile Gly His Ile Leu Ala Ala Leu Pro
        35                  40                  45

<210> SEQ ID NO 259
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 259

Leu Ala Glu Ala Lys Val Leu Ala Asn Arg Glu Leu Asp Lys Tyr Gly
1               5                   10                  15

Val Ser Asp Phe Tyr Lys Asn Val Ile Asn Arg Ala Lys Thr Val Glu
            20                  25                  30

Gly Val His Ala Leu Ile Asp His Ile Leu Ala Ala Leu Pro
        35                  40                  45

<210> SEQ ID NO 260
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 260

```
Leu Ala Glu Ala Lys Val Leu Ala Asn Arg Glu Leu Asp Lys Tyr Gly
1               5                   10                  15

Val Ser Asp Tyr Tyr Lys Asn Ile Ile Asn Arg Ala Lys Thr Val Glu
            20                  25                  30

Gly Val Arg Ala Leu Lys Leu His Ile Leu Ala Ala Leu Pro
            35                  40                  45
```

<210> SEQ ID NO 261
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 261

```
Leu Ala Glu Ala Lys Val Leu Ala Asn Arg Glu Leu Asp Lys Tyr Gly
1               5                   10                  15

Val Ser Asp Phe Tyr Lys Asn Val Ile Asn Arg Ala Lys Thr Val Glu
            20                  25                  30

Gly Val Ser Ala Leu Ile His Glu Ile Leu Ala Ala Leu Pro
            35                  40                  45
```

<210> SEQ ID NO 262
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 262

```
Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Asn Thr Leu Ile Ala Asp Ile Leu Ala Ala Leu Pro
            35                  40                  45
```

<210> SEQ ID NO 263
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 263

```
Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Asn Thr Leu Ile Ala Asp Ile Leu Ala Ala Leu Pro
            35                  40                  45
```

<210> SEQ ID NO 264
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 264

```
Leu Ala Glu Ala Lys Val Leu Ala Asn Arg Glu Leu Asp Lys Tyr Gly
1               5                   10                  15
```

```
Val Ser Asp Tyr Tyr Lys Asn Leu Ile Asn Arg Ala Lys Thr Val Glu
            20                  25                  30

Gly Val Asn Ser Leu Ile Ser His Ile Leu Ala Ala Leu Pro
        35                  40                  45

<210> SEQ ID NO 265
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 265

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Gly
            20                  25                  30

Gly Val Gln Ser Leu Ile Ser Glu Ile Leu Ala Ala Leu Pro
        35                  40                  45

<210> SEQ ID NO 266
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 266

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Ser Ser Leu Lys Gly His Ile Leu Ala Ala Leu Pro
        35                  40                  45

<210> SEQ ID NO 267
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 267

Leu Ala Glu Ala Lys Val Leu Ala Asn Arg Glu Leu Asp Lys Tyr Gly
1               5                   10                  15

Val Ser Asp Phe Tyr Lys Asn Val Ile Asn Arg Ala Lys Thr Val Glu
            20                  25                  30

Gly Val Asp Ser Leu Ile Ala Glu Ile Leu Ala Ala Leu Pro
        35                  40                  45

<210> SEQ ID NO 268
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 268

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Arg Thr Val Glu
            20                  25                  30
```

-continued

```
Gly Val Gln Thr Leu Ile Ser Asp Ile Leu Ala Ala Leu Pro
        35                  40                  45

<210> SEQ ID NO 269
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 269

Leu Ala Glu Ala Lys Val Leu Ala Asn Arg Glu Leu Asp Lys Tyr Gly
  1               5                  10                  15

Val Ser Asp Phe Tyr Lys Lys Phe Ile Asn Lys Ala Lys Thr Val Glu
            20                  25                  30

Gly Val Glu Thr Leu Ile Ser Glu Ile Leu Ala Ala Leu Pro
        35                  40                  45

<210> SEQ ID NO 270
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 270

Leu Ala Glu Ala Lys Val Leu Ala Asn Arg Glu Leu Asp Lys Tyr Gly
  1               5                  10                  15

Val Ser Asp Phe Tyr Lys Ser Leu Ile Asn Arg Ala Lys Thr Val Glu
            20                  25                  30

Gly Val His Ser Leu Thr Asp Glu Ile Leu Ala Ala Leu Pro
        35                  40                  45

<210> SEQ ID NO 271
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 271

Leu Ala Glu Ala Lys Val Leu Ala Asn Arg Glu Leu Asp Lys Tyr Gly
  1               5                  10                  15

Val Ser Asp Tyr Tyr Lys Asn Val Ile Asn Lys Ala Lys Thr Val Glu
            20                  25                  30

Gly Val Ser Ser Leu Thr Ala Glu Ile Leu Ala Ala Leu Pro
        35                  40                  45

<210> SEQ ID NO 272
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 272

Leu Ala Glu Ala Lys Val Leu Ala Asn Arg Glu Leu Asp Lys Tyr Gly
  1               5                  10                  15

Val Ser Asp Phe Tyr Lys Ser Leu Ile Asn Arg Ala Lys Thr Val Glu
            20                  25                  30

Gly Val Asp Ala Leu Thr Ser His Ile Leu Ala Ala Leu Pro
        35                  40                  45
```

<210> SEQ ID NO 273
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 273

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Lys Ala Lys Thr Val Glu
            20                  25                  30

Gly Val Ser Thr Leu Ile His Asp Ile Leu Ala Ala Leu Pro
        35                  40                  45

<210> SEQ ID NO 274
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 274

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Ser Thr Leu Ile His Asp Ile Leu Ala Ala Leu Pro
        35                  40                  45

<210> SEQ ID NO 275
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 275

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Gln Ala Leu Ile Ser Glu Ile Leu Ala Ala Leu Pro
        35                  40                  45

<210> SEQ ID NO 276
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 276

Leu Ala Glu Ala Lys Val Leu Ala Asn Arg Glu Leu Asp Lys Tyr Gly
1               5                   10                  15

Val Ser Asp Tyr Tyr Lys Ser Leu Ile Asn Lys Ala Lys Thr Val Glu
            20                  25                  30

Gly Val Asp Ser Leu Ile Val His Ile Leu Ala Ala Leu Pro
        35                  40                  45

<210> SEQ ID NO 277

<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 277

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Gln Ser Leu Ile Thr Glu Ile Leu Ala Ala Leu Pro
        35                  40                  45

<210> SEQ ID NO 278
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 278

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Arg Ala Lys Thr Val Glu
            20                  25                  30

Gly Val Asp Ala Leu Ile Thr His Ile Leu Ala Ala Leu Pro
        35                  40                  45

<210> SEQ ID NO 279
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 279

Leu Ala Glu Ala Lys Val Leu Ala Asn Arg Glu Leu Asp Lys Tyr Gly
1               5                   10                  15

Val Ser Asp Phe Tyr Lys Ser Met Ile Asn Arg Ala Lys Thr Val Glu
            20                  25                  30

Gly Val Asp Ser Leu Ile Thr His Ile Leu Ala Ala Leu Pro
        35                  40                  45

<210> SEQ ID NO 280
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 280

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Thr Thr Leu Thr Thr Asp Ile Leu Ala Ala Leu Pro
        35                  40                  45

<210> SEQ ID NO 281
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 281

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Glu Ser Leu Ile Asp His Ile Leu Ala Ala Leu Pro
        35                  40                  45

<210> SEQ ID NO 282
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 282

Leu Ala Glu Ala Lys Val Leu Ala Asn Arg Glu Leu Asp Lys Tyr Gly
1               5                   10                  15

Val Ser Asp Phe Tyr Lys Ser Tyr Ile Asn Arg Ala Lys Thr Val Glu
            20                  25                  30

Gly Val His Thr Leu Ile Gly His Ile Leu Ala Ala Leu Pro
        35                  40                  45

<210> SEQ ID NO 283
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 283

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Gln Thr Leu Ile Ser Asp Ile Leu Ala Ala Leu Pro
        35                  40                  45

<210> SEQ ID NO 284
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 284

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Asn Ser Leu Thr Ser His Ile Leu Ala Ala Leu Pro
        35                  40                  45

<210> SEQ ID NO 285
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 285

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Asn Thr Leu Ile His Asp Ile Leu Ala Ala Leu Pro
        35                  40                  45

<210> SEQ ID NO 286
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 286

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Glu Ser Leu Ile Gly Glu Ile Leu Ala Ala Leu Pro
        35                  40                  45

<210> SEQ ID NO 287
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 287

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Lys Ala Lys Thr Val Glu
            20                  25                  30

Gly Val His Thr Leu Ile His Asp Ile Leu Ala Ala Leu Pro
        35                  40                  45

<210> SEQ ID NO 288
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 288

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Lys Ala Lys Thr Val Glu
            20                  25                  30

Gly Val Ser Ala Leu Lys Met His Ile Leu Ala Ala Leu Pro
        35                  40                  45

<210> SEQ ID NO 289
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 289

Leu Ala Glu Ala Lys Val Leu Ala Asn Arg Glu Leu Asp Lys Tyr Gly

```
                1               5                   10                  15
Val Ser Asp Phe Tyr Lys Asn Leu Ile Asn Lys Ala Lys Thr Val Glu
                20                  25                  30

Gly Val Asp Ala Leu Ile Val His Ile Leu Ala Ala Leu Pro
                35                  40              45

<210> SEQ ID NO 290
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 290

Leu Ala Glu Ala Lys Val Leu Ala Asn Arg Glu Leu Asp Lys Tyr Gly
1               5                   10                  15

Val Ser Asp Tyr Tyr Lys Arg Leu Ile Asn Arg Ala Lys Thr Val Glu
                20                  25                  30

Gly Val His Ala Leu Ile Ala Glu Ile Leu Ala Ala Leu Pro
                35                  40              45

<210> SEQ ID NO 291
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 291

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Arg Ala Arg Thr Val Glu
                20                  25                  30

Gly Val Asp Thr Leu Ile His Asp Ile Leu Ala Ala Leu Pro
                35                  40              45

<210> SEQ ID NO 292
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 292

Leu Ala Glu Ala Lys Val Leu Ala Asn Arg Glu Leu Asp Lys Tyr Gly
1               5                   10                  15

Val Ser Asp Phe Tyr Lys Lys Val Ile Asn Arg Ala Arg Thr Val Glu
                20                  25                  30

Gly Val Gln Ala Leu Ile Ala Asp Ile Leu Ala Ala Leu Pro
                35                  40              45

<210> SEQ ID NO 293
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 293

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
```

```
                20                  25                  30

Gly Val Glu Ser Leu Ile Ala Asp Ile Leu Ala Ala Leu Pro
            35                  40                  45

<210> SEQ ID NO 294
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 294

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Lys Ala Lys Thr Val Glu
            20                  25                  30

Gly Val Asp Ala Leu Ile Ala His Ile Leu Ala Ala Leu Pro
            35                  40                  45

<210> SEQ ID NO 295
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 295

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Arg Ala Lys Thr Val Glu
            20                  25                  30

Gly Val Glu Ser Leu Ile Thr His Ile Leu Ala Ala Leu Pro
            35                  40                  45

<210> SEQ ID NO 296
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 296

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Arg Thr Val Glu
            20                  25                  30

Gly Val Asp Ser Leu Ile Val Glu Ile Leu Ala Ala Leu Pro
            35                  40                  45

<210> SEQ ID NO 297
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 297

Leu Ala Glu Ala Lys Val Leu Ala Asn Arg Glu Leu Asp Lys Tyr Gly
1               5                   10                  15

Val Ser Asp Phe Tyr Lys Asn Val Ile Asn Arg Ala Lys Thr Val Glu
            20                  25                  30

Gly Val Ser Ala Leu Ile Arg Glu Ile Leu Ala Ala Leu Pro
```

-continued

```
                35                  40                  45
```

<210> SEQ ID NO 298
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 298

```
Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Asn Ala Leu Ile Ser Asp Ile Leu Ala Ala Leu Pro
        35                  40                  45
```

<210> SEQ ID NO 299
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 299

```
Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Ser Ala Leu Ile Gln Glu Ile Leu Ala Ala Leu Pro
        35                  40                  45
```

<210> SEQ ID NO 300
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 300

```
Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Gln Ser Leu Ile Asp His Ile Leu Ala Ala Leu Pro
        35                  40                  45
```

<210> SEQ ID NO 301
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 301

```
Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Asp Ala Leu Ile Cys His Ile Leu Ala Ala Leu Pro
        35                  40                  45
```

<210> SEQ ID NO 302
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 302

```
Leu Ala Glu Ala Lys Val Leu Ala Asn Arg Glu Leu Asp Lys Tyr Gly
 1               5                  10                  15
Val Ser Asp Tyr Tyr Lys Arg Leu Ile Asn Lys Ala Lys Thr Val Glu
            20                  25                  30
Gly Val Asn Ala Leu Ile Thr His Ile Leu Ala Ala Leu Pro
        35                  40                  45
```

<210> SEQ ID NO 303
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 303

```
Leu Ala Glu Ala Lys Val Leu Ala Asn Arg Glu Leu Asp Lys Tyr Gly
 1               5                  10                  15
Val Ser Asp Phe Tyr Lys Asn Val Ile Asn Lys Ala Lys Thr Val Glu
            20                  25                  30
Gly Val Glu Ala Leu Ile Ala Asp Ile Leu Ala Ala Leu Pro
        35                  40                  45
```

<210> SEQ ID NO 304
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 304

```
Leu Ala Glu Ala Lys Val Leu Ala Asn Arg Glu Leu Asp Lys Tyr Gly
 1               5                  10                  15
Val Ser Asp Phe Tyr Lys Asn Leu Ile Asn Arg Ala Lys Thr Val Glu
            20                  25                  30
Gly Val Glu Thr Leu Ile Arg Asp Ile Leu Ala Ala Leu Pro
        35                  40                  45
```

<210> SEQ ID NO 305
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 305

```
Leu Ala Glu Ala Lys Val Leu Ala Asn Arg Glu Leu Asp Lys Tyr Gly
 1               5                  10                  15
Val Ser Asp Phe Tyr Lys Asn Leu Ile Asn Arg Ala Arg Thr Val Glu
            20                  25                  30
Gly Val Gln Thr Leu Ile Thr Asp Ile Leu Ala Ala Leu Pro
        35                  40                  45
```

<210> SEQ ID NO 306
<211> LENGTH: 46
<212> TYPE: PRT

<210> SEQ ID NO 306
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 306

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

Gly Val Asn Ala Leu Thr His His Ile Leu Ala Ala Leu Pro
        35                  40                  45

<210> SEQ ID NO 307
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 307

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Arg Ala Lys Thr Val Glu
            20                  25                  30

Gly Val Gln Ala Leu Ile Ala His Ile Leu Ala Ala Leu Pro
        35                  40                  45

<210> SEQ ID NO 308
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 308

Leu Ala Glu Ala Lys Val Leu Ala Asn Arg Glu Leu Asp Lys Tyr Gly
1               5                   10                  15

Val Ser Asp Phe Tyr Lys Asn Val Ile Asn Arg Ala Lys Thr Val Glu
            20                  25                  30

Gly Val Asn Ser Leu Ile Asn His Ile Leu Ala Ala Leu Pro
        35                  40                  45

<210> SEQ ID NO 309
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 309

Leu Ala Glu Ala Lys Val Leu Ala Asn Arg Glu Leu Asp Lys Tyr Gly
1               5                   10                  15

Val Ser Asp Phe Tyr Lys Ser Leu Ile Asn Arg Ala Arg Thr Val Glu
            20                  25                  30

Gly Val Asp Ser Leu Ile Arg His Ile Leu Ala Ala Leu Pro
        35                  40                  45

<210> SEQ ID NO 310
<211> LENGTH: 46
<212> TYPE: PRT
<213> ORGANISM: Artificial Sequence
<220> FEATURE:
<223> OTHER INFORMATION: Engineered albumin binding polypeptide -continued

<400> SEQUENCE: 310

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Lys Ala Lys Thr Val Glu
            20                  25                  30

Gly Val Glu Ala Leu Thr Leu His Ile Leu Ala Ala Leu Pro
        35                  40                  45

<210> SEQ ID NO 311
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 311

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Asp Ala Leu Ile Ala His Ile Leu Ala Ala Leu Pro
        35                  40                  45

<210> SEQ ID NO 312
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 312

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Lys Ala Lys Thr Val Glu
            20                  25                  30

Gly Val Gln Ala Leu Ile Ala His Ile Leu Ala Ala Leu Pro
        35                  40                  45

<210> SEQ ID NO 313
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 313

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val His Ala Leu Ile Gly His Ile Leu Ala Ala Leu Pro
        35                  40                  45

<210> SEQ ID NO 314
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 314

Leu Ala Glu Ala Lys Val Leu Ala Asn Arg Glu Leu Asp Lys Tyr Gly
1               5                   10                  15

Val Ser Asp Phe Tyr Lys Arg Val Ile Asn Arg Ala Lys Thr Val Glu
            20                  25                  30

Gly Val His Ala Leu Ile Asp His Ile Leu Ala Ala Leu Pro
        35                  40                  45

<210> SEQ ID NO 315
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 315

Leu Ala Glu Ala Lys Val Leu Ala Asn Arg Glu Leu Asp Lys Tyr Gly
1               5                   10                  15

Val Ser Asp Tyr Tyr Lys Arg Ile Ile Asn Arg Ala Lys Thr Val Glu
            20                  25                  30

Gly Val Arg Ala Leu Lys Leu His Ile Leu Ala Ala Leu Pro
        35                  40                  45

<210> SEQ ID NO 316
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 316

Leu Ala Glu Ala Lys Val Leu Ala Asn Arg Glu Leu Asp Lys Tyr Gly
1               5                   10                  15

Val Ser Asp Phe Tyr Lys Arg Val Ile Asn Arg Ala Lys Thr Val Glu
            20                  25                  30

Gly Val Ser Ala Leu Ile His Glu Ile Leu Ala Ala Leu Pro
        35                  40                  45

<210> SEQ ID NO 317
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 317

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Asn Thr Leu Ile Ala Asp Ile Leu Ala Ala Leu Pro
        35                  40                  45

<210> SEQ ID NO 318
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 318

Leu Ala Glu Ala Lys Val Leu Ala Asn Arg Glu Leu Asp Lys Tyr Gly
1               5                   10                  15

Val Ser Asp Tyr Tyr Lys Arg Leu Ile Asn Arg Ala Lys Thr Val Glu
            20                  25                  30

Gly Val Asn Ser Leu Ile Ser His Ile Leu Ala Ala Leu Pro
        35                  40                  45

<210> SEQ ID NO 319
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 319

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Ser Ser Leu Lys Gly His Ile Leu Ala Ala Leu Pro
        35                  40                  45

<210> SEQ ID NO 320
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 320

Leu Ala Glu Ala Lys Val Leu Ala Asn Arg Glu Leu Asp Lys Tyr Gly
1               5                   10                  15

Val Ser Asp Phe Tyr Lys Arg Val Ile Asn Arg Ala Lys Thr Val Glu
            20                  25                  30

Gly Val Asp Ser Leu Ile Ala Glu Ile Leu Ala Ala Leu Pro
        35                  40                  45

<210> SEQ ID NO 321
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 321

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Arg Thr Val Glu
            20                  25                  30

Gly Val Gln Thr Leu Ile Ser Asp Ile Leu Ala Ala Leu Pro
        35                  40                  45

<210> SEQ ID NO 322
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 322

Leu Ala Glu Ala Lys Val Leu Ala Asn Arg Glu Leu Asp Lys Tyr Gly
1               5                   10                  15

Val Ser Asp Phe Tyr Lys Arg Phe Ile Asn Lys Ala Lys Thr Val Glu
            20                  25                  30

Gly Val Glu Thr Leu Ile Ser Glu Ile Leu Ala Ala Leu Pro
        35                  40                  45

<210> SEQ ID NO 323
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 323

Leu Ala Glu Ala Lys Val Leu Ala Asn Arg Glu Leu Asp Lys Tyr Gly
 1               5                  10                  15

Val Ser Asp Phe Tyr Lys Arg Leu Ile Asn Arg Ala Lys Thr Val Glu
            20                  25                  30

Gly Val His Ser Leu Thr Asp Glu Ile Leu Ala Ala Leu Pro
        35                  40                  45

<210> SEQ ID NO 324
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 324

Leu Ala Glu Ala Lys Val Leu Ala Asn Arg Glu Leu Asp Lys Tyr Gly
 1               5                  10                  15

Val Ser Asp Tyr Tyr Lys Arg Val Ile Asn Lys Ala Lys Thr Val Glu
            20                  25                  30

Gly Val Ser Ser Leu Thr Ala Glu Ile Leu Ala Ala Leu Pro
        35                  40                  45

<210> SEQ ID NO 325
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 325

Leu Ala Glu Ala Lys Val Leu Ala Asn Arg Glu Leu Asp Lys Tyr Gly
 1               5                  10                  15

Val Ser Asp Phe Tyr Lys Arg Leu Ile Asn Arg Ala Lys Thr Val Glu
            20                  25                  30

Gly Val Asp Ala Leu Thr Ser His Ile Leu Ala Ala Leu Pro
        35                  40                  45

<210> SEQ ID NO 326
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 326

Leu Ala Glu Ala Lys Val Leu Ala Asn Arg Glu Leu Asp Lys Tyr Gly
 1               5                  10                  15

Val Ser Asp Phe Tyr Lys Arg Leu Ile Asn Lys Ala Lys Thr Val Glu
            20                  25                  30

Gly Val Ser Thr Leu Ile His Asp Ile Leu Ala Ala Leu Pro
        35                  40                  45

<210> SEQ ID NO 327
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 327

Leu Ala Glu Ala Lys Val Leu Ala Asn Arg Glu Leu Asp Lys Tyr Gly
 1               5                  10                  15

Val Ser Asp Phe Tyr Lys Arg Leu Ile Asn Arg Ala Lys Thr Val Glu
            20                  25                  30

Gly Val Ser Thr Leu Ile His Asp Ile Leu Ala Ala Leu Pro
        35                  40                  45

<210> SEQ ID NO 328
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 328

Leu Ala Glu Ala Lys Val Leu Ala Asn Arg Glu Leu Asp Lys Tyr Gly
 1               5                  10                  15

Val Ser Asp Phe Tyr Lys Arg Leu Ile Asn Arg Ala Lys Thr Val Glu
            20                  25                  30

Gly Val Gln Ala Leu Ile Ser Glu Ile Leu Ala Ala Leu Pro
        35                  40                  45

<210> SEQ ID NO 329
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 329

Leu Ala Glu Ala Lys Val Leu Ala Asn Arg Glu Leu Asp Lys Tyr Gly
 1               5                  10                  15

Val Ser Asp Tyr Tyr Lys Arg Leu Ile Asn Lys Ala Lys Thr Val Glu
            20                  25                  30

Gly Val Asp Ser Leu Ile Val His Ile Leu Ala Ala Leu Pro
        35                  40                  45

<210> SEQ ID NO 330
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 330

Leu Ala Glu Ala Lys Val Leu Ala Asn Arg Glu Leu Asp Lys Tyr Gly
 1               5                  10                  15

Val Ser Asp Phe Tyr Lys Arg Leu Ile Asn Arg Ala Lys Thr Val Glu
            20                  25                  30

Gly Val Gln Ser Leu Ile Thr Glu Ile Leu Ala Ala Leu Pro
        35                  40                  45

<210> SEQ ID NO 331
<211> LENGTH: 46

```
<212> TYPE: PRT
<213> ORGANISM: Artificial Sequence
<220> FEATURE:
<223> OTHER INFORMATION: Engineered albumin binding polypeptide

<400> SEQUENCE: 331

Leu Ala Glu Ala Lys Val Leu Ala Asn Arg Glu Leu Asp Lys Tyr Gly
 1               5                  10                  15

Val Ser Asp Tyr Tyr Lys Arg Leu Ile Asn Arg Ala Lys Thr Val Glu
             20                  25                  30

Gly Val Asp Ala Leu Ile Thr His Ile Leu Ala Ala Leu Pro
         35                  40                  45

<210> SEQ ID NO 332
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 332

Leu Ala Glu Ala Lys Val Leu Ala Asn Arg Glu Leu Asp Lys Tyr Gly
 1               5                  10                  15

Val Ser Asp Phe Tyr Lys Arg Met Ile Asn Arg Ala Lys Thr Val Glu
             20                  25                  30

Gly Val Asp Ser Leu Ile Thr His Ile Leu Ala Ala Leu Pro
         35                  40                  45

<210> SEQ ID NO 333
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 333

Leu Ala Glu Ala Lys Val Leu Ala Asn Arg Glu Leu Asp Lys Tyr Gly
 1               5                  10                  15

Val Ser Asp Phe Tyr Lys Arg Leu Ile Asn Arg Ala Lys Thr Val Glu
             20                  25                  30

Gly Val Thr Thr Leu Thr Thr Asp Ile Leu Ala Ala Leu Pro
         35                  40                  45

<210> SEQ ID NO 334
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 334

Leu Ala Glu Ala Lys Val Leu Ala Asn Arg Glu Leu Asp Lys Tyr Gly
 1               5                  10                  15

Val Ser Asp Phe Tyr Lys Arg Leu Ile Asn Arg Ala Lys Thr Val Glu
             20                  25                  30

Gly Val Glu Ser Leu Ile Asp His Ile Leu Ala Ala Leu Pro
         35                  40                  45

<210> SEQ ID NO 335
<211> LENGTH: 46
<212> TYPE: PRT
<213> ORGANISM: Artificial Sequence
<220> FEATURE:
```

<223> OTHER INFORMATION: Engineered albumin binding polypeptide

<400> SEQUENCE: 335

Leu Ala Glu Ala Lys Val Leu Ala Asn Arg Glu Leu Asp Lys Tyr Gly
1               5                   10                  15

Val Ser Asp Phe Tyr Lys Arg Tyr Ile Asn Arg Ala Lys Thr Val Glu
            20                  25                  30

Gly Val His Thr Leu Ile Gly His Ile Leu Ala Ala Leu Pro
        35                  40                  45

<210> SEQ ID NO 336
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 336

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Gln Thr Leu Ile Ser Asp Ile Leu Ala Ala Leu Pro
        35                  40                  45

<210> SEQ ID NO 337
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 337

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Asn Ser Leu Thr Ser His Ile Leu Ala Ala Leu Pro
        35                  40                  45

<210> SEQ ID NO 338
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 338

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Asn Thr Leu Ile His Asp Ile Leu Ala Ala Leu Pro
        35                  40                  45

<210> SEQ ID NO 339
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 339

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Glu Ser Leu Ile Gly Glu Ile Leu Ala Ala Leu Pro
            35                  40                  45

<210> SEQ ID NO 340
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 340

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

Gly Val His Thr Leu Ile His Asp Ile Leu Ala Ala Leu Pro
            35                  40                  45

<210> SEQ ID NO 341
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 341

Leu Ala Glu Ala Lys Val Leu Ala Asn Arg Glu Leu Asp Lys Tyr Gly
1               5                   10                  15

Val Ser Asp Tyr Tyr Lys Arg Leu Ile Asn Lys Ala Lys Thr Val Glu
            20                  25                  30

Gly Val Ser Ala Leu Lys Met His Ile Leu Ala Ala Leu Pro
            35                  40                  45

<210> SEQ ID NO 342
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 342

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

Gly Val Asp Ala Leu Ile Val His Ile Leu Ala Ala Leu Pro
            35                  40                  45

<210> SEQ ID NO 343
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 343

Leu Ala Glu Ala Lys Val Leu Ala Asn Arg Glu Leu Asp Lys Tyr Gly
1               5                   10                  15

-continued

Val Ser Asp Tyr Tyr Lys Arg Leu Ile Asn Arg Ala Arg Thr Val Glu
            20                  25                  30

Gly Val Asp Thr Leu Ile His Asp Ile Leu Ala Ala Leu Pro
        35                  40                  45

<210> SEQ ID NO 344
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 344

Leu Ala Glu Ala Lys Val Leu Ala Asn Arg Glu Leu Asp Lys Tyr Gly
1               5                   10                  15

Val Ser Asp Phe Tyr Lys Arg Val Ile Asn Arg Ala Arg Thr Val Glu
            20                  25                  30

Gly Val Gln Ala Leu Ile Ala Asp Ile Leu Ala Ala Leu Pro
        35                  40                  45

<210> SEQ ID NO 345
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 345

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Glu Ser Leu Ile Ala Asp Ile Leu Ala Ala Leu Pro
        35                  40                  45

<210> SEQ ID NO 346
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 346

Leu Ala Glu Ala Lys Val Leu Ala Asn Arg Glu Leu Asp Lys Tyr Gly
1               5                   10                  15

Val Ser Asp Tyr Tyr Lys Arg Leu Ile Asn Lys Ala Lys Thr Val Glu
            20                  25                  30

Gly Val Asp Ala Leu Ile Ala His Ile Leu Ala Ala Leu Pro
        35                  40                  45

<210> SEQ ID NO 347
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 347

Leu Ala Glu Ala Lys Val Leu Ala Asn Arg Glu Leu Asp Lys Tyr Gly
1               5                   10                  15

Val Ser Asp Tyr Tyr Lys Arg Leu Ile Asn Arg Ala Lys Thr Val Glu
            20                  25                  30

```
Gly Val Glu Ser Leu Ile Thr His Ile Leu Ala Ala Leu Pro
        35                  40                  45

<210> SEQ ID NO 348
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 348

Leu Ala Glu Ala Lys Val Leu Ala Asn Arg Glu Leu Asp Lys Tyr Gly
 1               5                  10                  15

Val Ser Asp Phe Tyr Lys Arg Leu Ile Asn Arg Ala Arg Thr Val Glu
            20                  25                  30

Gly Val Asp Ser Leu Ile Val Glu Ile Leu Ala Ala Leu Pro
        35                  40                  45

<210> SEQ ID NO 349
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 349

Leu Ala Glu Ala Lys Val Leu Ala Asn Arg Glu Leu Asp Lys Tyr Gly
 1               5                  10                  15

Val Ser Asp Phe Tyr Lys Arg Val Ile Asn Arg Ala Lys Thr Val Glu
            20                  25                  30

Gly Val Ser Ala Leu Ile Arg Glu Ile Leu Ala Ala Leu Pro
        35                  40                  45

<210> SEQ ID NO 350
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 350

Leu Ala Glu Ala Lys Val Leu Ala Asn Arg Glu Leu Asp Lys Tyr Gly
 1               5                  10                  15

Val Ser Asp Phe Tyr Lys Arg Leu Ile Asn Arg Ala Lys Thr Val Glu
            20                  25                  30

Gly Val Asn Ala Leu Ile Ser Asp Ile Leu Ala Ala Leu Pro
        35                  40                  45

<210> SEQ ID NO 351
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 351

Leu Ala Glu Ala Lys Val Leu Ala Asn Arg Glu Leu Asp Lys Tyr Gly
 1               5                  10                  15

Val Ser Asp Phe Tyr Lys Arg Leu Ile Asn Arg Ala Lys Thr Val Glu
            20                  25                  30

Gly Val Ser Ala Leu Ile Gln Glu Ile Leu Ala Ala Leu Pro
        35                  40                  45
```

<210> SEQ ID NO 352
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 352

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Gln Ser Leu Ile Asp His Ile Leu Ala Ala Leu Pro
        35                  40                  45

<210> SEQ ID NO 353
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 353

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Asp Ala Leu Ile Cys His Ile Leu Ala Ala Leu Pro
        35                  40                  45

<210> SEQ ID NO 354
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 354

Leu Ala Glu Ala Lys Val Leu Ala Asn Arg Glu Leu Asp Lys Tyr Gly
1               5                   10                  15

Val Ser Asp Phe Tyr Lys Arg Val Ile Asn Lys Ala Lys Thr Val Glu
            20                  25                  30

Gly Val Glu Ala Leu Ile Ala Asp Ile Leu Ala Ala Leu Pro
        35                  40                  45

<210> SEQ ID NO 355
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 355

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Glu Thr Leu Ile Arg Asp Ile Leu Ala Ala Leu Pro
        35                  40                  45

<210> SEQ ID NO 356

```
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 356

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Arg Thr Val Glu
            20                  25                  30

Gly Val Gln Thr Leu Ile Thr Asp Ile Leu Ala Ala Leu Pro
        35                  40                  45

<210> SEQ ID NO 357
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 357

Leu Ala Glu Ala Lys Val Leu Ala Asn Arg Glu Leu Asp Lys Tyr Gly
1               5                   10                  15

Val Ser Asp Tyr Tyr Lys Arg Leu Ile Asn Arg Ala Lys Thr Val Glu
            20                  25                  30

Gly Val Gln Ala Leu Ile Ala His Ile Leu Ala Ala Leu Pro
        35                  40                  45

<210> SEQ ID NO 358
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 358

Leu Ala Glu Ala Lys Val Leu Ala Asn Arg Glu Leu Asp Lys Tyr Gly
1               5                   10                  15

Val Ser Asp Phe Tyr Lys Arg Val Ile Asn Arg Ala Lys Thr Val Glu
            20                  25                  30

Gly Val Asn Ser Leu Ile Asn His Ile Leu Ala Ala Leu Pro
        35                  40                  45

<210> SEQ ID NO 359
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 359

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Arg Thr Val Glu
            20                  25                  30

Gly Val Asp Ser Leu Ile Arg His Ile Leu Ala Ala Leu Pro
        35                  40                  45

<210> SEQ ID NO 360
<211> LENGTH: 46
<212> TYPE: PRT
<213> ORGANISM: Artificial Sequence
```

<220> FEATURE:
<223> OTHER INFORMATION: Engineered albumin binding polypeptide

<400> SEQUENCE: 360

Leu Ala Glu Ala Lys Val Leu Ala Asn Arg Glu Leu Asp Lys Tyr Gly
 1               5                  10                  15

Val Ser Asp Tyr Tyr Lys Arg Leu Ile Asn Lys Ala Lys Thr Val Glu
            20                  25                  30

Gly Val Glu Ala Leu Thr Leu His Ile Leu Ala Ala Leu Pro
        35                  40                  45

<210> SEQ ID NO 361
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 361

Leu Ala Glu Ala Lys Val Leu Ala Asn Arg Glu Leu Asp Lys Tyr Gly
 1               5                  10                  15

Val Ser Asp Phe Tyr Lys Arg Leu Ile Asn Arg Ala Lys Thr Val Glu
            20                  25                  30

Gly Val Asp Ala Leu Ile Ala His Ile Leu Ala Ala Leu Pro
        35                  40                  45

<210> SEQ ID NO 362
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 362

Leu Ala Glu Ala Lys Val Leu Ala Asn Arg Glu Leu Asp Lys Tyr Gly
 1               5                  10                  15

Val Ser Asp Tyr Tyr Lys Arg Leu Ile Asn Lys Ala Lys Thr Val Glu
            20                  25                  30

Gly Val Gln Ala Leu Ile Ala His Ile Leu Ala Ala Leu Pro
        35                  40                  45

<210> SEQ ID NO 363
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 363

Leu Ala Glu Ala Lys Val Leu Ala Asn Arg Glu Leu Asp Lys Tyr Gly
 1               5                  10                  15

Val Ser Asp Phe Tyr Lys Asn Leu Ile Asn Arg Ala Lys Thr Val Glu
            20                  25                  30

Gly Val His Ala Leu Lys Gly His Ile Leu Ala Ala Leu Pro
        35                  40                  45

<210> SEQ ID NO 364
<211> LENGTH: 46
<212> TYPE: PRT
<213> ORGANISM: Artificial Sequence
<220> FEATURE:
<223> OTHER INFORMATION: Engineered albumin binding polypeptide

```
<400> SEQUENCE: 364

Leu Ala Glu Ala Lys Val Leu Ala Asn Arg Glu Leu Asp Lys Tyr Gly
1               5                   10                  15

Val Ser Asp Phe Tyr Lys Asn Val Ile Asn Arg Ala Lys Thr Val Glu
            20                  25                  30

Gly Val His Ala Leu Lys Asp His Ile Leu Ala Ala Leu Pro
        35                  40                  45

<210> SEQ ID NO 365
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 365

Leu Ala Glu Ala Lys Val Leu Ala Asn Arg Glu Leu Asp Lys Tyr Gly
1               5                   10                  15

Val Ser Asp Phe Tyr Lys Asn Val Ile Asn Arg Ala Lys Thr Val Glu
            20                  25                  30

Gly Val Ser Ala Leu Lys His Glu Ile Leu Ala Ala Leu Pro
        35                  40                  45

<210> SEQ ID NO 366
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 366

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Asn Thr Leu Lys Ala Asp Ile Leu Ala Ala Leu Pro
        35                  40                  45

<210> SEQ ID NO 367
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 367

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Asn Thr Leu Lys Ala Asp Ile Leu Ala Ala Leu Pro
        35                  40                  45

<210> SEQ ID NO 368
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 368

Leu Ala Glu Ala Lys Val Leu Ala Asn Arg Glu Leu Asp Lys Tyr Gly
```

```
                1               5                   10                  15
Val Ser Asp Tyr Tyr Lys Asn Leu Ile Asn Arg Ala Lys Thr Val Glu
                20                  25                  30

Gly Val Asn Ser Leu Lys Ser His Ile Leu Ala Ala Leu Pro
            35                  40                  45

<210> SEQ ID NO 369
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 369

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Gly
                20                  25                  30

Gly Val Gln Ser Leu Lys Ser Glu Ile Leu Ala Ala Leu Pro
            35                  40                  45

<210> SEQ ID NO 370
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 370

Leu Ala Glu Ala Lys Val Leu Ala Asn Arg Glu Leu Asp Lys Tyr Gly
1               5                   10                  15

Val Ser Asp Phe Tyr Lys Asn Val Ile Asn Arg Ala Lys Thr Val Glu
                20                  25                  30

Gly Val Asp Ser Leu Lys Ala Glu Ile Leu Ala Ala Leu Pro
            35                  40                  45

<210> SEQ ID NO 371
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 371

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Arg Thr Val Glu
                20                  25                  30

Gly Val Gln Thr Leu Lys Ser Asp Ile Leu Ala Ala Leu Pro
            35                  40                  45

<210> SEQ ID NO 372
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 372

Leu Ala Glu Ala Lys Val Leu Ala Asn Arg Glu Leu Asp Lys Tyr Gly
1               5                   10                  15

Val Ser Asp Phe Tyr Lys Lys Phe Ile Asn Lys Ala Lys Thr Val Glu
```

```
                    20                  25                  30

Gly Val Glu Thr Leu Lys Ser Glu Ile Leu Ala Ala Leu Pro
        35                  40                  45

<210> SEQ ID NO 373
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 373

Leu Ala Glu Ala Lys Val Leu Ala Asn Arg Glu Leu Asp Lys Tyr Gly
 1               5                  10                  15

Val Ser Asp Phe Tyr Lys Ser Leu Ile Asn Arg Ala Lys Thr Val Glu
                20                  25                  30

Gly Val His Ser Leu Lys Asp Glu Ile Leu Ala Ala Leu Pro
        35                  40                  45

<210> SEQ ID NO 374
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 374

Leu Ala Glu Ala Lys Val Leu Ala Asn Arg Glu Leu Asp Lys Tyr Gly
 1               5                  10                  15

Val Ser Asp Tyr Tyr Lys Asn Val Ile Asn Lys Ala Lys Thr Val Glu
                20                  25                  30

Gly Val Ser Ser Leu Lys Ala Glu Ile Leu Ala Ala Leu Pro
        35                  40                  45

<210> SEQ ID NO 375
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 375

Leu Ala Glu Ala Lys Val Leu Ala Asn Arg Glu Leu Asp Lys Tyr Gly
 1               5                  10                  15

Val Ser Asp Phe Tyr Lys Ser Leu Ile Asn Arg Ala Lys Thr Val Glu
                20                  25                  30

Gly Val Asp Ala Leu Lys Ser His Ile Leu Ala Ala Leu Pro
        35                  40                  45

<210> SEQ ID NO 376
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 376

Leu Ala Glu Ala Lys Val Leu Ala Asn Arg Glu Leu Asp Lys Tyr Gly
 1               5                  10                  15

Val Ser Asp Phe Tyr Lys Asn Leu Ile Asn Lys Ala Lys Thr Val Glu
                20                  25                  30

Gly Val Ser Thr Leu Lys His Asp Ile Leu Ala Ala Leu Pro
```

35                  40                  45

<210> SEQ ID NO 377
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 377

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Ser Thr Leu Lys His Asp Ile Leu Ala Ala Leu Pro
        35                  40                  45

<210> SEQ ID NO 378
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 378

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Gln Ala Leu Lys Ser Glu Ile Leu Ala Ala Leu Pro
        35                  40                  45

<210> SEQ ID NO 379
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 379

Leu Ala Glu Ala Lys Val Leu Ala Asn Arg Glu Leu Asp Lys Tyr Gly
1               5                   10                  15

Val Ser Asp Tyr Tyr Lys Ser Leu Ile Asn Lys Ala Lys Thr Val Glu
            20                  25                  30

Gly Val Asp Ser Leu Lys Val His Ile Leu Ala Ala Leu Pro
        35                  40                  45

<210> SEQ ID NO 380
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 380

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Gln Ser Leu Lys Thr Glu Ile Leu Ala Ala Leu Pro
        35                  40                  45

<210> SEQ ID NO 381
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 381

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Arg Ala Lys Thr Val Glu
            20                  25                  30

Gly Val Asp Ala Leu Lys Thr His Ile Leu Ala Ala Leu Pro
        35                  40                  45

<210> SEQ ID NO 382
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 382

Leu Ala Glu Ala Lys Val Leu Ala Asn Arg Glu Leu Asp Lys Tyr Gly
1               5                   10                  15

Val Ser Asp Phe Tyr Lys Ser Met Ile Asn Arg Ala Lys Thr Val Glu
            20                  25                  30

Gly Val Asp Ser Leu Lys Thr His Ile Leu Ala Ala Leu Pro
        35                  40                  45

<210> SEQ ID NO 383
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 383

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Thr Thr Leu Lys Thr Asp Ile Leu Ala Ala Leu Pro
        35                  40                  45

<210> SEQ ID NO 384
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 384

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Glu Ser Leu Lys Asp His Ile Leu Ala Ala Leu Pro
        35                  40                  45

<210> SEQ ID NO 385
<211> LENGTH: 46
<212> TYPE: PRT

<213> ORGANISM: Artificial Sequence
<220> FEATURE:
<223> OTHER INFORMATION: Engineered albumin binding polypeptide

<400> SEQUENCE: 385

Leu Ala Glu Ala Lys Val Leu Ala Asn Arg Glu Leu Asp Lys Tyr Gly
1               5                   10                  15

Val Ser Asp Phe Tyr Lys Ser Tyr Ile Asn Arg Ala Lys Thr Val Glu
            20                  25                  30

Gly Val His Thr Leu Lys Gly His Ile Leu Ala Ala Leu Pro
        35                  40                  45

<210> SEQ ID NO 386
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 386

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Gln Thr Leu Lys Ser Asp Ile Leu Ala Ala Leu Pro
        35                  40                  45

<210> SEQ ID NO 387
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 387

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Asn Ser Leu Lys Ser His Ile Leu Ala Ala Leu Pro
        35                  40                  45

<210> SEQ ID NO 388
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 388

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Asn Thr Leu Lys His Asp Ile Leu Ala Ala Leu Pro
        35                  40                  45

<210> SEQ ID NO 389
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 389

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Glu Ser Leu Lys Gly Glu Ile Leu Ala Ala Leu Pro
        35                  40                  45

<210> SEQ ID NO 390
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 390

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Lys Ala Lys Thr Val Glu
            20                  25                  30

Gly Val His Thr Leu Lys His Asp Ile Leu Ala Ala Leu Pro
        35                  40                  45

<210> SEQ ID NO 391
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 391

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Lys Ala Lys Thr Val Glu
            20                  25                  30

Gly Val Asp Ala Leu Lys Val His Ile Leu Ala Ala Leu Pro
        35                  40                  45

<210> SEQ ID NO 392
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 392

Leu Ala Glu Ala Lys Val Leu Ala Asn Arg Glu Leu Asp Lys Tyr Gly
1               5                   10                  15

Val Ser Asp Tyr Tyr Lys Arg Leu Ile Asn Arg Ala Lys Thr Val Glu
            20                  25                  30

Gly Val His Ala Leu Lys Ala Glu Ile Leu Ala Ala Leu Pro
        35                  40                  45

<210> SEQ ID NO 393
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 393

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Arg Ala Thr Val Glu
            20                  25                  30

Gly Val Asp Thr Leu Lys His Asp Ile Leu Ala Ala Leu Pro
        35                  40                  45

<210> SEQ ID NO 394
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 394

Leu Ala Glu Ala Lys Val Leu Ala Asn Arg Glu Leu Asp Lys Tyr Gly
1               5                   10                  15

Val Ser Asp Phe Tyr Lys Lys Val Ile Asn Arg Ala Arg Thr Val Glu
            20                  25                  30

Gly Val Gln Ala Leu Lys Ala Asp Ile Leu Ala Ala Leu Pro
        35                  40                  45

<210> SEQ ID NO 395
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 395

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Glu Ser Leu Lys Ala Asp Ile Leu Ala Ala Leu Pro
        35                  40                  45

<210> SEQ ID NO 396
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 396

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Lys Ala Lys Thr Val Glu
            20                  25                  30

Gly Val Asp Ala Leu Lys Ala His Ile Leu Ala Ala Leu Pro
        35                  40                  45

<210> SEQ ID NO 397
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 397

Leu Ala Glu Ala Lys Val Leu Ala Asn Arg Glu Leu Asp Lys Tyr Gly
1               5                   10                  15

-continued

Val Ser Asp Tyr Tyr Lys Asn Leu Ile Asn Arg Ala Lys Thr Val Glu
            20                  25                  30

Gly Val Glu Ser Leu Lys Thr His Ile Leu Ala Ala Leu Pro
        35                  40                  45

<210> SEQ ID NO 398
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 398

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Arg Thr Val Glu
            20                  25                  30

Gly Val Asp Ser Leu Lys Val Glu Ile Leu Ala Ala Leu Pro
        35                  40                  45

<210> SEQ ID NO 399
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 399

Leu Ala Glu Ala Lys Val Leu Ala Asn Arg Glu Leu Asp Lys Tyr Gly
1               5                   10                  15

Val Ser Asp Phe Tyr Lys Asn Val Ile Asn Arg Ala Lys Thr Val Glu
            20                  25                  30

Gly Val Ser Ala Leu Lys Arg Glu Ile Leu Ala Ala Leu Pro
        35                  40                  45

<210> SEQ ID NO 400
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 400

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Asn Ala Leu Lys Ser Asp Ile Leu Ala Ala Leu Pro
        35                  40                  45

<210> SEQ ID NO 401
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 401

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Ser Ala Leu Lys Gln Glu Ile Leu Ala Ala Leu Pro
          35                  40                  45

<210> SEQ ID NO 402
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 402

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Gln Ser Leu Lys Asp His Ile Leu Ala Ala Leu Pro
          35                  40                  45

<210> SEQ ID NO 403
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 403

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Asp Ala Leu Lys Cys His Ile Leu Ala Ala Leu Pro
          35                  40                  45

<210> SEQ ID NO 404
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 404

Leu Ala Glu Ala Lys Val Leu Ala Asn Arg Glu Leu Asp Lys Tyr Gly
1               5                   10                  15

Val Ser Asp Tyr Tyr Lys Arg Leu Ile Asn Lys Ala Lys Thr Val Glu
            20                  25                  30

Gly Val Asn Ala Leu Lys Thr His Ile Leu Ala Ala Leu Pro
          35                  40                  45

<210> SEQ ID NO 405
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 405

Leu Ala Glu Ala Lys Val Leu Ala Asn Arg Glu Leu Asp Lys Tyr Gly
1               5                   10                  15

Val Ser Asp Phe Tyr Lys Asn Val Ile Asn Lys Ala Lys Thr Val Glu
            20                  25                  30

Gly Val Glu Ala Leu Lys Ala Asp Ile Leu Ala Ala Leu Pro
          35                  40                  45

<210> SEQ ID NO 406
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 406

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Glu Thr Leu Lys Arg Asp Ile Leu Ala Ala Leu Pro
        35                  40                  45

<210> SEQ ID NO 407
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 407

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Arg Thr Val Glu
            20                  25                  30

Gly Val Gln Thr Leu Lys Thr Asp Ile Leu Ala Ala Leu Pro
        35                  40                  45

<210> SEQ ID NO 408
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 408

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

Gly Val Asn Ala Leu Lys His His Ile Leu Ala Ala Leu Pro
        35                  40                  45

<210> SEQ ID NO 409
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 409

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Arg Ala Lys Thr Val Glu
            20                  25                  30

Gly Val Gln Ala Leu Lys Ala His Ile Leu Ala Ala Leu Pro
        35                  40                  45

<210> SEQ ID NO 410
<211> LENGTH: 46

```
<212> TYPE: PRT
<213> ORGANISM: Artificial Sequence
<220> FEATURE:
<223> OTHER INFORMATION: Engineered albumin binding polypeptide

<400> SEQUENCE: 410

Leu Ala Glu Ala Lys Val Leu Ala Asn Arg Glu Leu Asp Lys Tyr Gly
1               5                   10                  15

Val Ser Asp Phe Tyr Lys Asn Val Ile Asn Arg Ala Lys Thr Val Glu
            20                  25                  30

Gly Val Asn Ser Leu Lys Asn His Ile Leu Ala Ala Leu Pro
        35                  40                  45

<210> SEQ ID NO 411
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 411

Leu Ala Glu Ala Lys Val Leu Ala Asn Arg Glu Leu Asp Lys Tyr Gly
1               5                   10                  15

Val Ser Asp Phe Tyr Lys Ser Leu Ile Asn Arg Ala Arg Thr Val Glu
            20                  25                  30

Gly Val Asp Ser Leu Lys Arg His Ile Leu Ala Ala Leu Pro
        35                  40                  45

<210> SEQ ID NO 412
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 412

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Lys Ala Lys Thr Val Glu
            20                  25                  30

Gly Val Glu Ala Leu Lys Leu His Ile Leu Ala Ala Leu Pro
        35                  40                  45

<210> SEQ ID NO 413
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 413

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Asp Ala Leu Lys Ala His Ile Leu Ala Ala Leu Pro
        35                  40                  45

<210> SEQ ID NO 414
<211> LENGTH: 46
<212> TYPE: PRT
<213> ORGANISM: Artificial Sequence
<220> FEATURE:
```

<223> OTHER INFORMATION: Engineered albumin binding polypeptide

<400> SEQUENCE: 414

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Lys Ala Lys Thr Val Glu
            20                  25                  30

Gly Val Gln Ala Leu Lys Ala His Ile Leu Ala Ala Leu Pro
        35                  40                  45

<210> SEQ ID NO 415
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 415

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val His Ala Leu Lys Gly His Ile Leu Ala Ala Leu Pro
        35                  40                  45

<210> SEQ ID NO 416
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 416

Leu Ala Glu Ala Lys Val Leu Ala Asn Arg Glu Leu Asp Lys Tyr Gly
1               5                   10                  15

Val Ser Asp Phe Tyr Lys Arg Val Ile Asn Arg Ala Lys Thr Val Glu
            20                  25                  30

Gly Val His Ala Leu Lys Asp His Ile Leu Ala Ala Leu Pro
        35                  40                  45

<210> SEQ ID NO 417
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 417

Leu Ala Glu Ala Lys Val Leu Ala Asn Arg Glu Leu Asp Lys Tyr Gly
1               5                   10                  15

Val Ser Asp Tyr Tyr Lys Arg Ile Ile Asn Arg Ala Lys Thr Val Glu
            20                  25                  30

Gly Val Arg Ala Leu Lys Leu His Ile Leu Ala Ala Leu Pro
        35                  40                  45

<210> SEQ ID NO 418
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 418

-continued

```
Leu Ala Glu Ala Lys Val Leu Ala Asn Arg Glu Leu Asp Lys Tyr Gly
1               5                   10                  15

Val Ser Asp Phe Tyr Lys Arg Val Ile Asn Arg Ala Lys Thr Val Glu
            20                  25                  30

Gly Val Ser Ala Leu Lys His Glu Ile Leu Ala Ala Leu Pro
        35                  40                  45

<210> SEQ ID NO 419
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 419

Leu Ala Glu Ala Lys Val Leu Ala Asn Arg Glu Leu Asp Lys Tyr Gly
1               5                   10                  15

Val Ser Asp Tyr Tyr Lys Arg Leu Ile Asn Arg Ala Lys Thr Val Glu
            20                  25                  30

Gly Val Asn Ser Leu Lys Ser His Ile Leu Ala Ala Leu Pro
        35                  40                  45

<210> SEQ ID NO 420
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 420

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Gly
            20                  25                  30

Gly Val Gln Ser Leu Lys Ser Glu Ile Leu Ala Ala Leu Pro
        35                  40                  45

<210> SEQ ID NO 421
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 421

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Ser Ser Leu Lys Gly His Ile Leu Ala Ala Leu Pro
        35                  40                  45

<210> SEQ ID NO 422
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 422

Leu Ala Glu Ala Lys Val Leu Ala Asn Arg Glu Leu Asp Lys Tyr Gly
1               5                   10                  15
```

```
Val Ser Asp Phe Tyr Lys Arg Val Ile Asn Arg Ala Lys Thr Val Glu
            20                  25                  30

Gly Val Asp Ser Leu Lys Ala Glu Ile Leu Ala Ala Leu Pro
        35                  40                  45

<210> SEQ ID NO 423
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 423

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Arg Thr Val Glu
            20                  25                  30

Gly Val Gln Thr Leu Lys Ser Asp Ile Leu Ala Ala Leu Pro
        35                  40                  45

<210> SEQ ID NO 424
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 424

Leu Ala Glu Ala Lys Val Leu Ala Asn Arg Glu Leu Asp Lys Tyr Gly
1               5                   10                  15

Val Ser Asp Phe Tyr Lys Arg Phe Ile Asn Lys Ala Lys Thr Val Glu
            20                  25                  30

Gly Val Glu Thr Leu Lys Ser Glu Ile Leu Ala Ala Leu Pro
        35                  40                  45

<210> SEQ ID NO 425
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 425

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val His Ser Leu Lys Asp Glu Ile Leu Ala Ala Leu Pro
        35                  40                  45

<210> SEQ ID NO 426
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 426

Leu Ala Glu Ala Lys Val Leu Ala Asn Arg Glu Leu Asp Lys Tyr Gly
1               5                   10                  15

Val Ser Asp Tyr Tyr Lys Arg Val Ile Asn Lys Ala Lys Thr Val Glu
            20                  25                  30
```

```
Gly Val Ser Ser Leu Lys Ala Glu Ile Leu Ala Ala Leu Pro
        35                  40                  45

<210> SEQ ID NO 427
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 427

Leu Ala Glu Ala Lys Val Leu Ala Asn Arg Glu Leu Asp Lys Tyr Gly
  1               5                  10                  15

Val Ser Asp Phe Tyr Lys Arg Leu Ile Asn Arg Ala Lys Thr Val Glu
                 20                  25                  30

Gly Val Asp Ala Leu Lys Ser His Ile Leu Ala Ala Leu Pro
        35                  40                  45

<210> SEQ ID NO 428
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 428

Leu Ala Glu Ala Lys Val Leu Ala Asn Arg Glu Leu Asp Lys Tyr Gly
  1               5                  10                  15

Val Ser Asp Phe Tyr Lys Arg Leu Ile Asn Lys Ala Lys Thr Val Glu
                 20                  25                  30

Gly Val Ser Thr Leu Lys His Asp Ile Leu Ala Ala Leu Pro
        35                  40                  45

<210> SEQ ID NO 429
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 429

Leu Ala Glu Ala Lys Val Leu Ala Asn Arg Glu Leu Asp Lys Tyr Gly
  1               5                  10                  15

Val Ser Asp Phe Tyr Lys Arg Leu Ile Asn Arg Ala Lys Thr Val Glu
                 20                  25                  30

Gly Val Ser Thr Leu Lys His Asp Ile Leu Ala Ala Leu Pro
        35                  40                  45

<210> SEQ ID NO 430
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 430

Leu Ala Glu Ala Lys Val Leu Ala Asn Arg Glu Leu Asp Lys Tyr Gly
  1               5                  10                  15

Val Ser Asp Phe Tyr Lys Arg Leu Ile Asn Arg Ala Lys Thr Val Glu
                 20                  25                  30

Gly Val Gln Ala Leu Lys Ser Glu Ile Leu Ala Ala Leu Pro
        35                  40                  45
```

<210> SEQ ID NO 431
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 431

Leu Ala Glu Ala Lys Val Leu Ala Asn Arg Glu Leu Asp Lys Tyr Gly
1               5                   10                  15

Val Ser Asp Tyr Tyr Lys Arg Leu Ile Asn Lys Ala Lys Thr Val Glu
            20                  25                  30

Gly Val Asp Ser Leu Lys Val His Ile Leu Ala Ala Leu Pro
        35                  40                  45

<210> SEQ ID NO 432
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 432

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Gln Ser Leu Lys Thr Glu Ile Leu Ala Ala Leu Pro
        35                  40                  45

<210> SEQ ID NO 433
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 433

Leu Ala Glu Ala Lys Val Leu Ala Asn Arg Glu Leu Asp Lys Tyr Gly
1               5                   10                  15

Val Ser Asp Tyr Tyr Lys Arg Leu Ile Asn Arg Ala Lys Thr Val Glu
            20                  25                  30

Gly Val Asp Ala Leu Lys Thr His Ile Leu Ala Ala Leu Pro
        35                  40                  45

<210> SEQ ID NO 434
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 434

Leu Ala Glu Ala Lys Val Leu Ala Asn Arg Glu Leu Asp Lys Tyr Gly
1               5                   10                  15

Val Ser Asp Phe Tyr Lys Arg Met Ile Asn Arg Ala Lys Thr Val Glu
            20                  25                  30

Gly Val Asp Ser Leu Lys Thr His Ile Leu Ala Ala Leu Pro
        35                  40                  45

<210> SEQ ID NO 435

```
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 435

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Thr Thr Leu Lys Thr Asp Ile Leu Ala Ala Leu Pro
        35                  40                  45

<210> SEQ ID NO 436
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 436

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Glu Ser Leu Lys Asp His Ile Leu Ala Ala Leu Pro
        35                  40                  45

<210> SEQ ID NO 437
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 437

Leu Ala Glu Ala Lys Val Leu Ala Asn Arg Glu Leu Asp Lys Tyr Gly
1               5                   10                  15

Val Ser Asp Phe Tyr Lys Arg Tyr Ile Asn Arg Ala Lys Thr Val Glu
            20                  25                  30

Gly Val His Thr Leu Lys Gly His Ile Leu Ala Ala Leu Pro
        35                  40                  45

<210> SEQ ID NO 438
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 438

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Gln Thr Leu Lys Ser Asp Ile Leu Ala Ala Leu Pro
        35                  40                  45

<210> SEQ ID NO 439
<211> LENGTH: 46
<212> TYPE: PRT
<213> ORGANISM: Artificial Sequence
```

<220> FEATURE:
<223> OTHER INFORMATION: Engineered albumin binding polypeptide

<400> SEQUENCE: 439

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Asn Ser Leu Lys Ser His Ile Leu Ala Ala Leu Pro
        35                  40                  45

<210> SEQ ID NO 440
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 440

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Asn Thr Leu Lys His Asp Ile Leu Ala Ala Leu Pro
        35                  40                  45

<210> SEQ ID NO 441
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 441

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Glu Ser Leu Lys Gly Glu Ile Leu Ala Ala Leu Pro
        35                  40                  45

<210> SEQ ID NO 442
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 442

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

Gly Val His Thr Leu Lys His Asp Ile Leu Ala Ala Leu Pro
        35                  40                  45

<210> SEQ ID NO 443
<211> LENGTH: 46
<212> TYPE: PRT
<213> ORGANISM: Artificial Sequence
<220> FEATURE:
<223> OTHER INFORMATION: Engineered albumin binding polypeptide

```
<400> SEQUENCE: 443

Leu Ala Glu Ala Lys Val Leu Ala Asn Arg Glu Leu Asp Lys Tyr Gly
 1               5                  10                  15

Val Ser Asp Tyr Tyr Lys Arg Leu Ile Asn Lys Ala Lys Thr Val Glu
            20                  25                  30

Gly Val Ser Ala Leu Lys Met His Ile Leu Ala Ala Leu Pro
        35                  40                  45

<210> SEQ ID NO 444
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 444

Leu Ala Glu Ala Lys Val Leu Ala Asn Arg Glu Leu Asp Lys Tyr Gly
 1               5                  10                  15

Val Ser Asp Phe Tyr Lys Arg Leu Ile Asn Lys Ala Lys Thr Val Glu
            20                  25                  30

Gly Val Asp Ala Leu Lys Val His Ile Leu Ala Ala Leu Pro
        35                  40                  45

<210> SEQ ID NO 445
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 445

Leu Ala Glu Ala Lys Val Leu Ala Asn Arg Glu Leu Asp Lys Tyr Gly
 1               5                  10                  15

Val Ser Asp Tyr Tyr Lys Arg Leu Ile Asn Arg Ala Lys Thr Val Glu
            20                  25                  30

Gly Val His Ala Leu Lys Ala Glu Ile Leu Ala Ala Leu Pro
        35                  40                  45

<210> SEQ ID NO 446
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 446

Leu Ala Glu Ala Lys Val Leu Ala Asn Arg Glu Leu Asp Lys Tyr Gly
 1               5                  10                  15

Val Ser Asp Tyr Tyr Lys Arg Leu Ile Asn Arg Ala Arg Thr Val Glu
            20                  25                  30

Gly Val Asp Thr Leu Lys His Asp Ile Leu Ala Ala Leu Pro
        35                  40                  45

<210> SEQ ID NO 447
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 447

Leu Ala Glu Ala Lys Val Leu Ala Asn Arg Glu Leu Asp Lys Tyr Gly
```

```
                1               5                   10                  15
Val Ser Asp Phe Tyr Lys Arg Val Ile Asn Arg Ala Arg Thr Val Glu
                20                  25                  30
Gly Val Gln Ala Leu Lys Ala Asp Ile Leu Ala Ala Leu Pro
            35                  40                  45
```

<210> SEQ ID NO 448
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 448

```
Leu Ala Glu Ala Lys Val Leu Ala Asn Arg Glu Leu Asp Lys Tyr Gly
1               5                   10                  15
Val Ser Asp Phe Tyr Lys Arg Leu Ile Asn Arg Ala Lys Thr Val Glu
                20                  25                  30
Gly Val Glu Ser Leu Lys Ala Asp Ile Leu Ala Ala Leu Pro
            35                  40                  45
```

<210> SEQ ID NO 449
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 449

```
Leu Ala Glu Ala Lys Val Leu Ala Asn Arg Glu Leu Asp Lys Tyr Gly
1               5                   10                  15
Val Ser Asp Tyr Tyr Lys Arg Leu Ile Asn Lys Ala Lys Thr Val Glu
                20                  25                  30
Gly Val Asp Ala Leu Lys Ala His Ile Leu Ala Ala Leu Pro
            35                  40                  45
```

<210> SEQ ID NO 450
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 450

```
Leu Ala Glu Ala Lys Val Leu Ala Asn Arg Glu Leu Asp Lys Tyr Gly
1               5                   10                  15
Val Ser Asp Tyr Tyr Lys Arg Leu Ile Asn Arg Ala Lys Thr Val Glu
                20                  25                  30
Gly Val Glu Ser Leu Lys Thr His Ile Leu Ala Ala Leu Pro
            35                  40                  45
```

<210> SEQ ID NO 451
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 451

```
Leu Ala Glu Ala Lys Val Leu Ala Asn Arg Glu Leu Asp Lys Tyr Gly
1               5                   10                  15
Val Ser Asp Phe Tyr Lys Arg Leu Ile Asn Arg Ala Arg Thr Val Glu
```

```
                 20                  25                  30

Gly Val Asp Ser Leu Lys Val Glu Ile Leu Ala Ala Leu Pro
        35                  40                  45

<210> SEQ ID NO 452
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 452

Leu Ala Glu Ala Lys Val Leu Ala Asn Arg Glu Leu Asp Lys Tyr Gly
 1               5                  10                  15

Val Ser Asp Phe Tyr Lys Arg Val Ile Asn Arg Ala Lys Thr Val Glu
                20                  25                  30

Gly Val Ser Ala Leu Lys Arg Glu Ile Leu Ala Ala Leu Pro
        35                  40                  45

<210> SEQ ID NO 453
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 453

Leu Ala Glu Ala Lys Val Leu Ala Asn Arg Glu Leu Asp Lys Tyr Gly
 1               5                  10                  15

Val Ser Asp Phe Tyr Lys Arg Leu Ile Asn Arg Ala Lys Thr Val Glu
                20                  25                  30

Gly Val Asn Ala Leu Lys Ser Asp Ile Leu Ala Ala Leu Pro
        35                  40                  45

<210> SEQ ID NO 454
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 454

Leu Ala Glu Ala Lys Val Leu Ala Asn Arg Glu Leu Asp Lys Tyr Gly
 1               5                  10                  15

Val Ser Asp Phe Tyr Lys Arg Leu Ile Asn Arg Ala Lys Thr Val Glu
                20                  25                  30

Gly Val Ser Ala Leu Lys Gln Glu Ile Leu Ala Ala Leu Pro
        35                  40                  45

<210> SEQ ID NO 455
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 455

Leu Ala Glu Ala Lys Val Leu Ala Asn Arg Glu Leu Asp Lys Tyr Gly
 1               5                  10                  15

Val Ser Asp Phe Tyr Lys Arg Leu Ile Asn Arg Ala Lys Thr Val Glu
                20                  25                  30

Gly Val Gln Ser Leu Lys Asp His Ile Leu Ala Ala Leu Pro
```

<210> SEQ ID NO 456
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 456

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Asp Ala Leu Lys Cys His Ile Leu Ala Ala Leu Pro
        35                  40                  45

<210> SEQ ID NO 457
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 457

Leu Ala Glu Ala Lys Val Leu Ala Asn Arg Glu Leu Asp Lys Tyr Gly
1               5                   10                  15

Val Ser Asp Tyr Tyr Lys Arg Leu Ile Asn Lys Ala Lys Thr Val Glu
            20                  25                  30

Gly Val Asn Ala Leu Lys Thr His Ile Leu Ala Ala Leu Pro
        35                  40                  45

<210> SEQ ID NO 458
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 458

Leu Ala Glu Ala Lys Val Leu Ala Asn Arg Glu Leu Asp Lys Tyr Gly
1               5                   10                  15

Val Ser Asp Phe Tyr Lys Arg Val Ile Asn Lys Ala Lys Thr Val Glu
            20                  25                  30

Gly Val Glu Ala Leu Lys Ala Asp Ile Leu Ala Ala Leu Pro
        35                  40                  45

<210> SEQ ID NO 459
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 459

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Glu Thr Leu Lys Arg Asp Ile Leu Ala Ala Leu Pro
        35                  40                  45

```
<210> SEQ ID NO 460
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 460

Leu Ala Glu Ala Lys Val Leu Ala Asn Arg Glu Leu Asp Lys Tyr Gly
 1               5                  10                  15

Val Ser Asp Phe Tyr Lys Arg Leu Ile Asn Arg Ala Arg Thr Val Glu
            20                  25                  30

Gly Val Gln Thr Leu Lys Thr Asp Ile Leu Ala Ala Leu Pro
        35                  40                  45

<210> SEQ ID NO 461
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 461

Leu Ala Glu Ala Lys Val Leu Ala Asn Arg Glu Leu Asp Lys Tyr Gly
 1               5                  10                  15

Val Ser Asp Phe Tyr Lys Arg Leu Ile Asn Lys Ala Lys Thr Val Glu
            20                  25                  30

Gly Val Asn Ala Leu Lys His His Ile Leu Ala Ala Leu Pro
        35                  40                  45

<210> SEQ ID NO 462
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 462

Leu Ala Glu Ala Lys Val Leu Ala Asn Arg Glu Leu Asp Lys Tyr Gly
 1               5                  10                  15

Val Ser Asp Tyr Tyr Lys Arg Leu Ile Asn Arg Ala Lys Thr Val Glu
            20                  25                  30

Gly Val Gln Ala Leu Lys Ala His Ile Leu Ala Ala Leu Pro
        35                  40                  45

<210> SEQ ID NO 463
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 463

Leu Ala Glu Ala Lys Val Leu Ala Asn Arg Glu Leu Asp Lys Tyr Gly
 1               5                  10                  15

Val Ser Asp Phe Tyr Lys Arg Val Ile Asn Arg Ala Lys Thr Val Glu
            20                  25                  30

Gly Val Asn Ser Leu Lys Asn His Ile Leu Ala Ala Leu Pro
        35                  40                  45

<210> SEQ ID NO 464
<211> LENGTH: 46
<212> TYPE: PRT
```

<213> ORGANISM: Artificial Sequence
<220> FEATURE:
<223> OTHER INFORMATION: Engineered albumin binding polypeptide

<400> SEQUENCE: 464

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Arg Thr Val Glu
            20                  25                  30

Gly Val Asp Ser Leu Lys Arg His Ile Leu Ala Ala Leu Pro
        35                  40                  45

<210> SEQ ID NO 465
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 465

Leu Ala Glu Ala Lys Val Leu Ala Asn Arg Glu Leu Asp Lys Tyr Gly
1               5                   10                  15

Val Ser Asp Tyr Tyr Lys Arg Leu Ile Asn Lys Ala Lys Thr Val Glu
            20                  25                  30

Gly Val Glu Ala Leu Lys Leu His Ile Leu Ala Ala Leu Pro
        35                  40                  45

<210> SEQ ID NO 466
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 466

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Asp Ala Leu Lys Ala His Ile Leu Ala Ala Leu Pro
        35                  40                  45

<210> SEQ ID NO 467
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 467

Leu Ala Glu Ala Lys Val Leu Ala Asn Arg Glu Leu Asp Lys Tyr Gly
1               5                   10                  15

Val Ser Asp Tyr Tyr Lys Arg Leu Ile Asn Lys Ala Lys Thr Val Glu
            20                  25                  30

Gly Val Gln Ala Leu Lys Ala His Ile Leu Ala Ala Leu Pro
        35                  40                  45

<210> SEQ ID NO 468
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 468

Leu Ala Glu Ala Lys Val Leu Ala Asn Arg Glu Leu Asp Lys Tyr Gly
1               5                   10                  15

Val Ser Asp Phe Tyr Lys Arg Val Ile Asn Arg Ala Lys Thr Val Glu
            20                  25                  30

Gly Val Ser Ala Leu Lys His His Ile Leu Ala Ala Leu Pro
        35                  40                  45

<210> SEQ ID NO 469
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 469

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Asn Thr Leu Lys Ala His Ile Leu Ala Ala Leu Pro
        35                  40                  45

<210> SEQ ID NO 470
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 470

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Gly
            20                  25                  30

Gly Val Gln Ser Leu Lys Ser His Ile Leu Ala Ala Leu Pro
        35                  40                  45

<210> SEQ ID NO 471
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 471

Leu Ala Glu Ala Lys Val Leu Ala Asn Arg Glu Leu Asp Lys Tyr Gly
1               5                   10                  15

Val Ser Asp Phe Tyr Lys Arg Val Ile Asn Arg Ala Lys Thr Val Glu
            20                  25                  30

Gly Val Asp Ser Leu Lys Ala His Ile Leu Ala Ala Leu Pro
        35                  40                  45

<210> SEQ ID NO 472
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 472

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Thr Val Glu
            20                  25                  30

Gly Val Gln Thr Leu Lys Ser His Ile Leu Ala Ala Leu Pro
        35                  40                  45

<210> SEQ ID NO 473
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 473

Leu Ala Glu Ala Lys Val Leu Ala Asn Arg Glu Leu Asp Lys Tyr Gly
1               5                   10                  15

Val Ser Asp Phe Tyr Lys Arg Phe Ile Asn Lys Ala Lys Thr Val Glu
            20                  25                  30

Gly Val Glu Thr Leu Lys Ser His Ile Leu Ala Ala Leu Pro
        35                  40                  45

<210> SEQ ID NO 474
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 474

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val His Ser Leu Lys Asp His Ile Leu Ala Ala Leu Pro
        35                  40                  45

<210> SEQ ID NO 475
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 475

Leu Ala Glu Ala Lys Val Leu Ala Asn Arg Glu Leu Asp Lys Tyr Gly
1               5                   10                  15

Val Ser Asp Tyr Tyr Lys Arg Val Ile Asn Lys Ala Lys Thr Val Glu
            20                  25                  30

Gly Val Ser Ser Leu Lys Ala His Ile Leu Ala Ala Leu Pro
        35                  40                  45

<210> SEQ ID NO 476
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 476

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

Gly Val Ser Thr Leu Lys His His Ile Leu Ala Ala Leu Pro
        35                  40                  45

<210> SEQ ID NO 477
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 477

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Ser Thr Leu Lys His His Ile Leu Ala Ala Leu Pro
        35                  40                  45

<210> SEQ ID NO 478
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 478

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Gln Ala Leu Lys Ser His Ile Leu Ala Ala Leu Pro
        35                  40                  45

<210> SEQ ID NO 479
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 479

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Gln Ser Leu Lys Thr His Ile Leu Ala Ala Leu Pro
        35                  40                  45

<210> SEQ ID NO 480
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 480

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

```
Gly Val Thr Thr Leu Lys Thr His Ile Leu Ala Ala Leu Pro
            35                  40                  45
```

<210> SEQ ID NO 481
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 481

```
Leu Ala Glu Ala Lys Val Leu Ala Asn Arg Glu Leu Asp Lys Tyr Gly
 1               5                  10                  15

Val Ser Asp Phe Tyr Lys Arg Leu Ile Asn Arg Ala Lys Thr Val Glu
            20                  25                  30

Gly Val Gln Thr Leu Lys Ser His Ile Leu Ala Ala Leu Pro
            35                  40                  45
```

<210> SEQ ID NO 482
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 482

```
Leu Ala Glu Ala Lys Val Leu Ala Asn Arg Glu Leu Asp Lys Tyr Gly
 1               5                  10                  15

Val Ser Asp Phe Tyr Lys Arg Leu Ile Asn Arg Ala Lys Thr Val Glu
            20                  25                  30

Gly Val Asn Thr Leu Lys His His Ile Leu Ala Ala Leu Pro
            35                  40                  45
```

<210> SEQ ID NO 483
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 483

```
Leu Ala Glu Ala Lys Val Leu Ala Asn Arg Glu Leu Asp Lys Tyr Gly
 1               5                  10                  15

Val Ser Asp Phe Tyr Lys Arg Leu Ile Asn Arg Ala Lys Thr Val Glu
            20                  25                  30

Gly Val Glu Ser Leu Lys Gly His Ile Leu Ala Ala Leu Pro
            35                  40                  45
```

<210> SEQ ID NO 484
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 484

```
Leu Ala Glu Ala Lys Val Leu Ala Asn Arg Glu Leu Asp Lys Tyr Gly
 1               5                  10                  15

Val Ser Asp Phe Tyr Lys Arg Leu Ile Asn Lys Ala Lys Thr Val Glu
            20                  25                  30

Gly Val His Thr Leu Lys His His Ile Leu Ala Ala Leu Pro
            35                  40                  45
```

<210> SEQ ID NO 485
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 485

Leu Ala Glu Ala Lys Val Leu Ala Asn Arg Glu Leu Asp Lys Tyr Gly
1               5                   10                  15

Val Ser Asp Tyr Tyr Lys Arg Leu Ile Asn Arg Ala Lys Thr Val Glu
            20                  25                  30

Gly Val His Ala Leu Lys Ala His Ile Leu Ala Ala Leu Pro
        35                  40                  45

<210> SEQ ID NO 486
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 486

Leu Ala Glu Ala Lys Val Leu Ala Asn Arg Glu Leu Asp Lys Tyr Gly
1               5                   10                  15

Val Ser Asp Tyr Tyr Lys Arg Leu Ile Asn Arg Ala Arg Thr Val Glu
            20                  25                  30

Gly Val Asp Thr Leu Lys His His Ile Leu Ala Ala Leu Pro
        35                  40                  45

<210> SEQ ID NO 487
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 487

Leu Ala Glu Ala Lys Val Leu Ala Asn Arg Glu Leu Asp Lys Tyr Gly
1               5                   10                  15

Val Ser Asp Phe Tyr Lys Arg Val Ile Asn Arg Ala Arg Thr Val Glu
            20                  25                  30

Gly Val Gln Ala Leu Lys Ala His Ile Leu Ala Ala Leu Pro
        35                  40                  45

<210> SEQ ID NO 488
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 488

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Glu Ser Leu Lys Ala His Ile Leu Ala Ala Leu Pro
        35                  40                  45

<210> SEQ ID NO 489
<211> LENGTH: 46

```
<212> TYPE: PRT
<213> ORGANISM: Artificial Sequence
<220> FEATURE:
<223> OTHER INFORMATION: Engineered albumin binding polypeptide

<400> SEQUENCE: 489

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Arg Thr Val Glu
            20                  25                  30

Gly Val Asp Ser Leu Lys Val His Ile Leu Ala Ala Leu Pro
        35                  40                  45

<210> SEQ ID NO 490
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 490

Leu Ala Glu Ala Lys Val Leu Ala Asn Arg Glu Leu Asp Lys Tyr Gly
1               5                   10                  15

Val Ser Asp Phe Tyr Lys Arg Val Ile Asn Arg Ala Lys Thr Val Glu
            20                  25                  30

Gly Val Ser Ala Leu Lys Arg His Ile Leu Ala Ala Leu Pro
        35                  40                  45

<210> SEQ ID NO 491
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 491

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Asn Ala Leu Lys Ser His Ile Leu Ala Ala Leu Pro
        35                  40                  45

<210> SEQ ID NO 492
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 492

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Ser Ala Leu Lys Gln His Ile Leu Ala Ala Leu Pro
        35                  40                  45

<210> SEQ ID NO 493
<211> LENGTH: 46
<212> TYPE: PRT
<213> ORGANISM: Artificial Sequence
<220> FEATURE:
```

<223> OTHER INFORMATION: Engineered albumin binding polypeptide

<400> SEQUENCE: 493

Leu Ala Glu Ala Lys Val Leu Ala Asn Arg Glu Leu Asp Lys Tyr Gly
1               5                   10                  15

Val Ser Asp Phe Tyr Lys Arg Val Ile Asn Lys Ala Lys Thr Val Glu
            20                  25                  30

Gly Val Glu Ala Leu Lys Ala His Ile Leu Ala Ala Leu Pro
        35                  40                  45

<210> SEQ ID NO 494
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 494

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Lys Thr Val Glu
            20                  25                  30

Gly Val Glu Thr Leu Lys Arg His Ile Leu Ala Ala Leu Pro
        35                  40                  45

<210> SEQ ID NO 495
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 495

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Arg Ala Arg Thr Val Glu
            20                  25                  30

Gly Val Gln Thr Leu Lys Thr His Ile Leu Ala Ala Leu Pro
        35                  40                  45

<210> SEQ ID NO 496
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 496

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

Gly Val Glu Ala Leu Lys Leu His Ile Leu Ala Ala Leu Pro
        35                  40                  45

<210> SEQ ID NO 497
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 497

-continued

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Arg Ala Arg Thr Val Glu
            20                  25                  30

Gly Val Glu Ala Leu Lys Leu His Ile Leu Ala Ala Leu Pro
        35                  40                  45

<210> SEQ ID NO 498
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 498

Leu Ala Glu Ala Lys Val Leu Ala Asn Arg Glu Leu Asp Lys Tyr Gly
1               5                   10                  15

Val Ser Asp Tyr Tyr Lys Asn Ile Ile Asn Arg Ala Lys Thr Val Glu
            20                  25                  30

Gly Val Glu Ala Leu Lys Leu His Ile Leu Ala Ala Leu Pro
        35                  40                  45

<210> SEQ ID NO 499
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 499

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Glu Ala Leu Lys Leu His Ile Leu Ala Ala Leu Pro
        35                  40                  45

<210> SEQ ID NO 500
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 500

Leu Ala Glu Ala Lys Val Leu Ala Asn Arg Glu Leu Asp Lys Tyr Gly
1               5                   10                  15

Val Ser Asp Phe Tyr Lys Asn Val Ile Asn Lys Ala Lys Thr Val Glu
            20                  25                  30

Gly Val Glu Ala Leu Lys Leu His Ile Leu Ala Ala Leu Pro
        35                  40                  45

<210> SEQ ID NO 501
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 501

Leu Ala Glu Ala Lys Val Leu Ala Asn Arg Glu Leu Asp Lys Tyr Gly
1               5                   10                  15

-continued

Val Ser Asp Tyr Tyr Lys Asn Leu Ile Asn Arg Ala Lys Thr Val Glu
            20                  25                  30

Gly Val Glu Ala Leu Lys Leu His Ile Leu Ala Ala Leu Pro
        35                  40                  45

<210> SEQ ID NO 502
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 502

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Arg Ala Arg Thr Val Glu
            20                  25                  30

Gly Val His Ala Leu Ile Asp His Ile Leu Ala Ala Leu Pro
        35                  40                  45

<210> SEQ ID NO 503
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 503

Leu Ala Glu Ala Lys Val Leu Ala Leu Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

Gly Val Glu Ala Leu Lys Leu His Ile Leu Ala Ala Leu Pro
        35                  40                  45

<210> SEQ ID NO 504
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 504

Leu Ala Glu Ala Lys Val Leu Ala Leu Arg Glu Leu Asp Lys Tyr Gly
1               5                   10                  15

Val Ser Asp Tyr Tyr Lys Arg Leu Ile Ser Lys Ala Lys Thr Val Glu
            20                  25                  30

Gly Val Lys Ala Leu Ile Ser Glu Ile Leu Ala Ala Leu Pro
        35                  40                  45

<210> SEQ ID NO 505
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 505

Leu Ala Glu Ala Lys Val Leu Ala Ile Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

Gly Val Glu Ala Leu Lys Leu His Ile Leu Ala Ala Leu Pro
        35                  40                  45

<210> SEQ ID NO 506
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 506

Leu Ala Glu Ala Lys Val Leu Ala Ile Arg Glu Leu Asp Lys Tyr Gly
1               5                   10                  15

Val Ser Asp Tyr Tyr Lys Arg Leu Ile Ser Lys Ala Lys Thr Val Glu
            20                  25                  30

Gly Val Lys Ala Leu Ile Ser Glu Ile Leu Ala Ala Leu Pro
        35                  40                  45

<210> SEQ ID NO 507
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 507

Leu Ala Glu Ala Lys Val Leu Ala Ile Lys Glu Leu Asp Lys Tyr Gly
1               5                   10                  15

Val Ser Asp Tyr Tyr Lys Arg Leu Ile Ser Lys Ala Lys Thr Val Glu
            20                  25                  30

Gly Val Lys Ala Leu Ile Ser Glu Ile Leu Ala Ala Leu Pro
        35                  40                  45

<210> SEQ ID NO 508
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 508

Leu Ala Glu Ala Lys Glu Leu Ala Asn Arg Glu Leu Asp Lys Tyr Gly
1               5                   10                  15

Val Ser Asp Tyr Tyr Lys Arg Leu Ile Ser Lys Ala Lys Thr Val Glu
            20                  25                  30

Gly Val Lys Ala Leu Ile Ser Glu Ile Leu Ala Ala Leu Pro
        35                  40                  45

<210> SEQ ID NO 509
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 509

Leu Ala Glu Ala Lys Val Asp Ala Asn Arg Glu Leu Asp Lys Tyr Gly
1               5                   10                  15

Val Ser Asp Tyr Tyr Lys Arg Leu Ile Ser Lys Ala Lys Thr Val Glu
            20                  25                  30

Gly Val Lys Ala Leu Ile Ser Glu Ile Leu Ala Ala Leu Pro
        35                  40                  45

```
<210> SEQ ID NO 510
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 510

Leu Ala Glu Ala Lys Glu Asp Ala Asn Arg Glu Leu Asp Lys Tyr Gly
 1               5                  10                  15

Val Ser Asp Tyr Tyr Lys Arg Leu Ile Ser Lys Ala Lys Thr Val Glu
                20                  25                  30

Gly Val Lys Ala Leu Ile Ser Glu Ile Leu Ala Ala Leu Pro
            35                  40                  45

<210> SEQ ID NO 511
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 511

Leu Ala Glu Ala Lys Glu Asp Ala Ile Lys Glu Leu Asp Lys Tyr Gly
 1               5                  10                  15

Val Ser Asp Tyr Tyr Lys Arg Leu Ile Ser Lys Ala Lys Thr Val Glu
                20                  25                  30

Gly Val Lys Ala Leu Ile Ser Glu Ile Leu Ala Ala Leu Pro
            35                  40                  45

<210> SEQ ID NO 512
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 512

Leu Ala Glu Ala Lys Val Leu Ala Leu Lys Glu Leu Asp Lys Tyr Gly
 1               5                  10                  15

Val Ser Asp Tyr Tyr Lys Arg Leu Ile Ser Lys Ala Lys Thr Val Glu
                20                  25                  30

Gly Val Lys Ala Leu Ile Ser Glu Ile Leu Ala Ala Leu Pro
            35                  40                  45

<210> SEQ ID NO 513
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 513

Leu Ala Glu Ala Lys Glu Leu Ala Ile Lys Glu Leu Asp Lys Tyr Gly
 1               5                  10                  15

Val Ser Asp Tyr Tyr Lys Arg Leu Ile Ser Lys Ala Lys Thr Val Glu
                20                  25                  30

Gly Val Lys Ala Leu Ile Ser Glu Ile Leu Ala Ala Leu Pro
            35                  40                  45

<210> SEQ ID NO 514
```

-continued

```
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 514

Leu Ala Glu Ala Lys Val Asp Ala Ile Lys Glu Leu Asp Lys Tyr Gly
 1               5                  10                  15

Val Ser Asp Tyr Tyr Lys Arg Leu Ile Ser Lys Ala Lys Thr Val Glu
            20                  25                  30

Gly Val Lys Ala Leu Ile Ser Glu Ile Leu Ala Ala Leu Pro
        35                  40                  45

<210> SEQ ID NO 515
<211> LENGTH: 46
<212> TYPE: PRT
<213> ORGANISM: Streptococcus sp. G148

<400> SEQUENCE: 515

Leu Ala Glu Ala Lys Val Leu Ala Asn Arg Glu Leu Asp Lys Tyr Gly
 1               5                  10                  15

Val Ser Asp Tyr Tyr Lys Asn Leu Ile Asn Asn Ala Lys Thr Val Glu
            20                  25                  30

Gly Val Lys Ala Leu Ile Asp Glu Ile Leu Ala Ala Leu Pro
        35                  40                  45

<210> SEQ ID NO 516
<211> LENGTH: 26
<212> TYPE: PRT
<213> ORGANISM: Artificial Sequence
<220> FEATURE:
<223> OTHER INFORMATION: Engineered albumin binding polypeptide
<220> FEATURE:
<221> NAME/KEY: VARIANT
<222> LOCATION: 5, 8, 9, 11, 12, 14, 20, 23, 24, 25
<223> OTHER INFORMATION: Xaa = any amino acid

<400> SEQUENCE: 516

Gly Val Ser Asp Xaa Tyr Lys Xaa Xaa Ile Xaa Xaa Ala Xaa Thr Val
 1               5                  10                  15

Glu Gly Val Xaa Ala Leu Xaa Xaa Xaa Ile
            20                  25

<210> SEQ ID NO 517
<211> LENGTH: 26
<212> TYPE: PRT
<213> ORGANISM: Artificial Sequence
<220> FEATURE:
<223> OTHER INFORMATION: Engineered albumin binding polypeptide

<400> SEQUENCE: 517

Gly Val Ser Asp Tyr Tyr Lys Asn Leu Ile Asn Asn Ala Lys Thr Val
 1               5                  10                  15

Glu Gly Val Lys Ala Leu Ile Asp Glu Ile
            20                  25

<210> SEQ ID NO 518
<211> LENGTH: 20
<212> TYPE: PRT
<213> ORGANISM: Artificial Sequence
<220> FEATURE:
<223> OTHER INFORMATION: Engineered albumin binding polypeptide
<220> FEATURE:
<221> NAME/KEY: VARIANT
```

```
<222> LOCATION: 6
<223> OTHER INFORMATION: Xaa=V or E
<220> FEATURE:
<221> NAME/KEY: VARIANT
<222> LOCATION: 7
<223> OTHER INFORMATION: Xaa=L, E or D
<220> FEATURE:
<221> NAME/KEY: VARIANT
<222> LOCATION: 9
<223> OTHER INFORMATION: Xaa=N, L or I
<220> FEATURE:
<221> NAME/KEY: VARIANT
<222> LOCATION: 10
<223> OTHER INFORMATION: Xaa=R or K
<220> FEATURE:
<221> NAME/KEY: VARIANT
<222> LOCATION: 13
<223> OTHER INFORMATION: Xaa=D or K
<220> FEATURE:
<221> NAME/KEY: BINDING
<222> LOCATION: (15)...(16)
<223> OTHER INFORMATION: Albumin Binding Domain

<400> SEQUENCE: 518

Leu Ala Glu Ala Lys Xaa Xaa Ala Xaa Xaa Glu Leu Xaa Lys Tyr Leu
 1               5                  10                  15

Ala Ala Leu Pro
         20

<210> SEQ ID NO 519
<211> LENGTH: 11
<212> TYPE: PRT
<213> ORGANISM: Artificial Sequence
<220> FEATURE:
<223> OTHER INFORMATION: Engineered albumin binding polypeptide

<400> SEQUENCE: 519

Asp Ile Cys Leu Pro Arg Trp Gly Cys Leu Trp
 1               5                  10

<210> SEQ ID NO 520
<211> LENGTH: 11
<212> TYPE: PRT
<213> ORGANISM: Artificial Sequence
<220> FEATURE:
<223> OTHER INFORMATION: Engineered albumin binding polypeptide

<400> SEQUENCE: 520

Asp Leu Cys Leu Arg Asp Trp Gly Cys Leu Trp
 1               5                  10

<210> SEQ ID NO 521
<211> LENGTH: 11
<212> TYPE: PRT
<213> ORGANISM: Artificial Sequence
<220> FEATURE:
<223> OTHER INFORMATION: Engineered albumin binding polypeptide

<400> SEQUENCE: 521

Asp Ile Cys Leu Ala Arg Trp Gly Cys Leu Trp
 1               5                  10

<210> SEQ ID NO 522
<211> LENGTH: 24
<212> TYPE: DNA
<213> ORGANISM: Artificial Sequence
<220> FEATURE:
<223> OTHER INFORMATION: Primer

<400> SEQUENCE: 522
```

```
tgcttccggc tcgtatgttg tgtg                                              24
```

<210> SEQ ID NO 523
<211> LENGTH: 21
<212> TYPE: DNA
<213> ORGANISM: Artificial Sequence
<220> FEATURE:
<223> OTHER INFORMATION: Primer

<400> SEQUENCE: 523

```
cggaaccaga gccaccaccg g                                                 21
```

<210> SEQ ID NO 524
<211> LENGTH: 31
<212> TYPE: DNA
<213> ORGANISM: Artificial Sequence
<220> FEATURE:
<223> OTHER INFORMATION: Primer

<400> SEQUENCE: 524

```
tcccccgggg ttaagactcc ttattacgca g                                      31
```

<210> SEQ ID NO 525
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: protein_bind
<222> LOCATION: 1
<223> OTHER INFORMATION: 5'-biotin

<400> SEQUENCE: 525

```
cggaaccaga gccaccaccg g                                                 21
```

<210> SEQ ID NO 526
<211> LENGTH: 28
<212> TYPE: DNA
<213> ORGANISM: Artificial Sequence
<220> FEATURE:
<223> OTHER INFORMATION: Primer

<400> SEQUENCE: 526

```
gaagccctcg agttagctga agctaaag                                          28
```

<210> SEQ ID NO 527
<211> LENGTH: 55
<212> TYPE: DNA
<213> ORGANISM: Artificial Sequence
<220> FEATURE:
<223> OTHER INFORMATION: Primer

<400> SEQUENCE: 527

```
gttagctgaa gctaaagtct tagctaacag agagctctga aagcttggct tatgc            55
```

<210> SEQ ID NO 528
<211> LENGTH: 30
<212> TYPE: DNA
<213> ORGANISM: Artificial Sequence
<220> FEATURE:
<223> OTHER INFORMATION: Primer

<400> SEQUENCE: 528

```
cgcgcggaaa gctagccaaa cttcggatag                                        30
```

<210> SEQ ID NO 529
<211> LENGTH: 32
<212> TYPE: DNA
<213> ORGANISM: Artificial Sequence
<220> FEATURE:
<223> OTHER INFORMATION: Primer

<400> SEQUENCE: 529
ctagctttcc gcgcgtagac aacaaattca ac                          32

<210> SEQ ID NO 530
<211> LENGTH: 28
<212> TYPE: DNA
<213> ORGANISM: Artificial Sequence
<220> FEATURE:
<223> OTHER INFORMATION: Primer

<400> SEQUENCE: 530
ccggactata cgtattcggc gcctgagc                               28

<210> SEQ ID NO 531
<211> LENGTH: 27
<212> TYPE: DNA
<213> ORGANISM: Artificial Sequence
<220> FEATURE:
<223> OTHER INFORMATION: Primer

<400> SEQUENCE: 531
gaaatacgta tagtccggtg gtggctc                                27

<210> SEQ ID NO 532
<211> LENGTH: 24
<212> TYPE: DNA
<213> ORGANISM: Artificial Sequence
<220> FEATURE:
<223> OTHER INFORMATION: Primer

<400> SEQUENCE: 532
acagagagct cgacaaatat ggag                                   24

<210> SEQ ID NO 533
<211> LENGTH: 24
<212> TYPE: DNA
<213> ORGANISM: Artificial Sequence
<220> FEATURE:
<223> OTHER INFORMATION: Primer

<400> SEQUENCE: 533
cggaaagcta gcaggtaatg cagc                                   24

<210> SEQ ID NO 534
<211> LENGTH: 23
<212> TYPE: DNA
<213> ORGANISM: Artificial Sequence
<220> FEATURE:
<223> OTHER INFORMATION: Primer

<400> SEQUENCE: 534
gtgagcggat aacaattccc ctc                                    23

<210> SEQ ID NO 535
<211> LENGTH: 23
<212> TYPE: DNA
<213> ORGANISM: Artificial Sequence
<220> FEATURE:
<223> OTHER INFORMATION: Primer

```
<400> SEQUENCE: 535
cagcaaaaaa ccctcaaga ccc                                           23

<210> SEQ ID NO 536
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: protein_bind
<222> LOCATION: 1
<223> OTHER INFORMATION: 5'-biotin

<400> SEQUENCE: 536
gtgagcggat aacaattccc ctc                                          23

<210> SEQ ID NO 537
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: unsure
<222> LOCATION: 1
<223> OTHER INFORMATION: P

<400> SEQUENCE: 537
agacttagct gaagctaaag tcttagc                                      27

<210> SEQ ID NO 538
<211> LENGTH: 25
<212> TYPE: DNA
<213> ORGANISM: Artificial Sequence
<220> FEATURE:
<223> OTHER INFORMATION: Primer

<400> SEQUENCE: 538
acttagctga agctaaagtc ttagc                                        25

<210> SEQ ID NO 539
<211> LENGTH: 24
<212> TYPE: DNA
<213> ORGANISM: Artificial Sequence
<220> FEATURE:
<223> OTHER INFORMATION: Primer

<400> SEQUENCE: 539
gctttaaggt aatgcagcta aaat                                         24

<210> SEQ ID NO 540
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: unsure
<222> LOCATION: 1
<223> OTHER INFORMATION: P

<400> SEQUENCE: 540
ggccgcttta aggtaatgca gctaaaat                                     28

<210> SEQ ID NO 541
```

```
<211> LENGTH: 26
<212> TYPE: PRT
<213> ORGANISM: Artificial Sequence
<220> FEATURE:
<223> OTHER INFORMATION: Engineered Template Domain

<400> SEQUENCE: 541

Gly Val Ser Asp Tyr Tyr Lys Asn Leu Ile Asn Asn Ala Lys Thr Val
 1               5                  10                  15

Glu Gly Val Asn Ala Leu Lys Ala Glu Ile
             20                  25
```

COMPOSITIONS, METHODS AND USES

CROSS-REFERENCE TO RELATED APPLICATIONS

This application is a US National Stage application of PCT/EP2008/059389 filed 17 Jul. 2008, which claims the benefit of U.S. Provisional Patent Application No. 60/962,618 filed 31 Jul. 2007.

FIELD OF THE INVENTION

The present invention relates to a class of engineered polypeptides having a binding affinity for albumin. It also relates to new methods and uses that exploit binding by these and other compounds to albumin in different contexts, some of which have significance for the treatment of disease in mammals including humans.

BACKGROUND

Serum Albumin

Serum albumin is the most abundant protein in mammalian sera (40 g/l; approximately 0.7 mM in humans), and one of its functions is to bind molecules such as lipids and bilirubin (Peters T, Advances in Protein Chemistry 37:161, 1985). The half-life of serum albumin is directly proportional to the size of the animal, where for example human serum albumin (HSA) has a half-life of 19 days and rabbit serum albumin has a half-life of about 5 days (McCurdy T R et al, J Lab Clin Med 143:115, 2004). Human serum albumin is widely distributed throughout the body, in particular in the intestinal and blood compartments, where it is mainly involved in the maintenance of osmolarity. Structurally, albumins are single-chain proteins comprising three homologous domains and totaling 584 or 585 amino acids (Dugaiczyk L et al, Proc Natl Acad Sci USA 79:71, 1982). Albumins contain 17 disulfide bridges and a single reactive thiol, C34, but lack N-linked and O-linked carbohydrate moieties (Peters, 1985, supra; Nicholson J P et al, Br J Anaesth 85:599, 2000). The lack of glycosylation simplifies recombinant expression of albumin. This property of albumin, together with the fact that its three-dimensional structure is known (He X M and Carter D C, Nature 358:209 1992), has made it an attractive candidate for use in recombinant fusion proteins. Such fusion proteins generally combine a therapeutic protein (which would be rapidly cleared from the body upon administration of the protein per se) and a plasma protein (which exhibits a natural slow clearance) in a single polypeptide chain (Sheffield W P, Curr Drug Targets Cardiovacs Haematol Disord 1:1, 2001). Such fusion proteins may provide clinical benefits in requiring less frequent injection and higher levels of therapeutic protein in vivo.

Fusion or Association with HSA Results in Increased in vivo Half-Life of Proteins Serum albumin is devoid of any enzymatic or immunological function and, thus, should not exhibit undesired side effects upon coupling to a bioactive polypeptide. Furthermore, HSA is a natural carrier involved in the endogenous transport and delivery of numerous natural as well as therapeutic molecules (Sellers E M and Koch-Weser M D, Albumin Structure, Function and Uses, eds Rosenoer V M et al, Pergamon, Oxford, p 159, 1977). Several strategies have been reported to either covalently couple proteins directly to serum albumins or to a peptide or protein that will allow in vivo association to serum albumins. Examples of the latter approach have been described e.g. in WO91/01743, in WO01/45746 and in Dennis et al, J Biol Chem 277:35035-43 (2002). The first document describes inter alia the use of albumin binding peptides or proteins derived from streptococcal protein G (SpG) for increasing the half-life of other proteins. The idea is to fuse the bacterially derived, albumin binding peptide/protein to a therapeutically interesting peptide/protein, which has been shown to have a rapid clearance in blood. The thus generated fusion protein binds to serum albumin in vivo, and benefits from its longer half-life, which increases the net half-life of the fused therapeutically interesting peptide/protein. WO01/45746 and Dennis et al relate to the same concept, but here, the authors utilize relatively short peptides to bind serum albumin. The peptides were selected from a phage displayed peptide library. In Dennis et al, earlier work is mentioned in which the enhancement of an immunological response to a recombinant fusion of the albumin binding domain of streptococcal protein G to human complement receptor Type 1 was found. US patent application published as US2004/0001827 (Dennis) also discloses the use of constructs comprising peptide ligands, again identified by phage display technology, which bind to serum albumin and which are conjugated to bioactive compounds for tumor targeting.

Association with HSA Results in Decreased Immunogenicity

In addition to the effect on the in vivo half-life of a biologically active protein, it has been proposed that the non-covalent association with albumin of a fusion between a biologically active protein and an albumin binding protein acts to reduce the immune response to the biologically active protein. Thus, in WO2005/097202, there is described the use of this principle to reduce or eliminate the immune response to a biologically active protein.

Albumin Binding Domains of Bacterial Receptor Proteins

Streptococcal protein G (SpG) is a bi-functional receptor present on the surface of certain strains of streptococci and is capable of binding to both IgG and serum albumin (Björck et al, Mol Immunol 24:1113, 1987). The structure is highly repetitive with several structurally and functionally different domains (Guss et al, EMBO J 5:1567, 1986), more precisely three Ig-binding motifs and three serum albumin binding domains (Olsson et al, Eur J Biochem 168:319, 1987). The structure of one of the three serum albumin binding domains has been determined, showing a three-helix bundle domain (Kraulis et al, FEBS Lett 378:190, 1996). This motif was named ABD (albumin binding domain) and is 46 amino acid residues in size. In the literature, it has subsequently also been designated G148-GA3.

Other bacterial albumin binding proteins than protein G from Streptococcus have also been identified, which contain domains similar to the albumin binding three-helix domains of protein G. Examples of such proteins are the PAB, PPL, MAG and ZAG proteins. Studies of structure and function of such albumin binding proteins have been carried out and reported e.g. by Johansson and co-workers (Johansson et al, J Mol Biol 266:859-865, 1997; Johansson et al, J Biol Chem 277:8114-8120, 2002), who introduced the designation "GA module" (protein G-related albumin binding module) for the three-helix protein domain responsible for albumin binding. Furthermore, Rozak et al have reported on the creation of artificial variants of the GA module, which were selected and studied with regard to different species specificity and stability (Rozak et al, Biochemistry 45:3263-3271, 2006). In the present disclosure, the terminology with regard to GA modules from different bacterial species established in the articles by Johansson et al and by Rozak et al will be followed.

In addition to the three-helix containing proteins described above, other bacterial proteins exist that bind albumin. For example, the family of streptococcal proteins designated the "M proteins" comprises members that bind albumin (see e.g. Table 2 in Navarre & Schneewind, MMBR 63:174-229, 1999). Non-limiting examples are proteins M1/Emm1, M3/Emm3, M12/Emm12, EmmL55/Emm55, Emm49/EmmL49, and H.

Neonatal Fc Receptor (FcRn) Mediated Transcytosis of HSA

The MHC class I-related neonatal Fc receptor (FcRn) mediates cellular trafficking and recycling of albumin and IgG (Brambell et al, Nature 203:1352, 1964; Chaudhury et al, J Exp Med 197:315, 2003). The FcRn, also known as the Brambell receptor, specifically binds albumin and IgG at low endosomal pH and thus protect pinocytosed proteins from lysosomal degradation by transportation to the cell surface and release at neutral pH. The FcRn has a good affinity for both albumin and IgG at pH 5-6, while showing from poor to no affinity at neutral pH. In this manner, the concentrations and the half-lives of albumin and IgG are regulated. Furthermore, the FcRn is responsible for actively transporting albumin and IgG over cellular barriers, e.g. the epithelium of the airways and the endothelium covering the intestines and the placenta.

As evident from the different sections of this background description, the provision of a selection of polypeptide molecules with a high affinity for albumin is a key factor in the development of various biomedical, biotechnological and other applications, and there is therefore a need in the art of additional such polypeptide molecules.

DISCLOSURE OF THE INVENTION

The first aspect of the invention meets the need for novel polypeptides with a comparably high albumin affinity, through the provision of an albumin binding polypeptide comprising an albumin binding motif, which motif consists of the amino acid sequence:

```
GVSDX₅YKX₈X₉I X₁₁X₁₂AX₁₄TVEGVX₂₀    (SEQ ID NO: 516)
ALX₂₃X₂₄X₂₅I
``` wherein, independently of each other,
$X_5$ is selected from Y and F;
$X_8$ is selected from N, R and S;
$X_9$ is selected from V, I, L, M, F and Y;
$X_{11}$ is selected from N, S, E and D;
$X_{12}$ is selected from R, K and N;
$X_{14}$ is selected from K and R;
$X_{20}$ is selected from D, N, Q, E, H, S, R and K;
$X_{23}$ is selected from K, I and T;
$X_{24}$ is selected from A, S, T, G, H, L and D; and
$X_{25}$ is selected from H, E and D;
with the proviso that the amino acid sequence is not

```
GVSDYYKNLI NNAKTVEGVK ALIDEI;    (SEQ ID NO: 517)
``` the albumin binding polypeptide binding to albumin such that the $K_D$ value of the interaction is at most $1 \times 10^{-9}$ M.

The above definition of a class of sequence related, albumin binding polypeptides according to the invention is based on a statistical analysis of a large number of albumin binding polypeptides identified and characterized as detailed in the experimental section below. The variants were selected from a large pool of random variants of a parent polypeptide sequence or "scaffold", said selection being based on an interaction with albumin in e.g. phage display or other selection experiments. The identified albumin binding motif, or "ABM", corresponds to the albumin binding region of the parent scaffold, which region constitutes two alpha helices within a three-helical bundle protein domain. While the original amino acid residues of the two ABM helices in the parent scaffold already constitute a binding surface for interaction with albumin, that binding surface is modified by the substitutions according to the invention to provide an alternative albumin binding ability.

As the skilled person will realize, the function of any polypeptide, such as the albumin binding capacity of the polypeptides according to the invention, is dependent on the tertiary structure of the polypeptide. It is therefore possible to make minor changes to the sequence of amino acids in a polypeptide without affecting the function thereof. Thus, the invention encompasses modified variants of the ABM, which are such that the albumin binding characteristics are retained. For example, it is possible that an amino acid residue belonging to a certain functional grouping of amino acid residues (e.g. hydrophobic, hydrophilic, polar etc) could be exchanged for another amino acid residue from the same functional group.

In one embodiment of the polypeptide according to this aspect of the invention, $X_5$ is Y.

In one embodiment of the polypeptide according to this aspect of the invention, $X_8$ is selected from N and R, and may in particular be R.

In one embodiment of the polypeptide according to this aspect of the invention, $X_9$ is L.

In one embodiment of the polypeptide according to this aspect of the invention, $X_{11}$ is selected from N and S, and may in particular be N.

In one embodiment of the polypeptide according to this aspect of the invention, $X_{12}$ is selected from R and K, such as $X_{12}$ being R or $X_{12}$ being K.

In one embodiment of the polypeptide according to this aspect of the invention, $X_{14}$ is K.

In one embodiment of the polypeptide according to this aspect of the invention, $X_{20}$ is selected from D, N, Q, E, H, S and R, and may in particular be E.

In one embodiment of the polypeptide according to this aspect of the invention, $X_{23}$ is selected from K and I, and may in particular be K.

In one embodiment of the polypeptide according to this aspect of the invention, $X_{24}$ is selected from A, S, T, G, H and L.

In a more specific embodiment of the polypeptide according to this aspect of the invention, $X_{24}$ is L.

In an even more specific embodiment of the polypeptide according to this aspect of the invention, $X_{23}X_{24}$ is KL.

In another even more specific embodiment of the polypeptide according to this aspect of the invention, $X_{23}X_{24}$ is TL.

In one embodiment of the polypeptide according to this aspect of the invention, $X_{24}$ is selected from A, S, T, G and H.

In a more specific embodiment of the polypeptide according to this aspect of the invention, $X_{24}$ is selected from A, S, T, G and H and $X_{23}$ is I.

In one embodiment of the polypeptide according to this aspect of the invention, $X_{25}$ is H.

As described in detail in the experimental section to follow, the selection of albumin binding variants led to the identification of a substantial amount of individual albumin binding motif (ABM) sequences. These sequences constitute individual embodiments of the ABM sequence in the definition of albumin binding polypeptides according to this aspect of the present invention. The sequences of individual albumin binding motifs are presented in FIG. 1 and as SEQ ID NO:1-257. In certain embodiments of the albumin binding polypeptide according to the invention, the ABM consists of an amino acid sequence selected from SEQ ID NO:1-257. In a more specific embodiment of this aspect of the invention, the ABM sequence is selected from SEQ ID NO:2, SEQ ID NO:3, SEQ ID NO:9, SEQ ID NO:15, SEQ ID NO:25, SEQ ID NO:27, SEQ ID NO:46, SEQ ID NO:49, SEQ ID NO:53, SEQ ID NO:54, SEQ ID NO:55, SEQ ID NO:155, SEQ ID NO:239, SEQ ID NO:240, SEQ ID NO:241, SEQ ID NO:242, SEQ ID NO:243, SEQ ID NO:244 and SEQ ID NO:245. In yet more specific embodiments of this aspect of the invention, the ABM sequence is selected from SEQ ID NO:3, SEQ ID NO:53 and SEQ ID NO:239.

In embodiments of the present invention, the ABM may form part of a three-helix bundle protein domain. For example, the ABM may essentially constitute or form part of two alpha helices with an interconnecting loop, within said three-helix bundle protein domain.

In particular embodiments of the invention, such a three-helix bundle protein domain is selected from the group consisting of three-helix domains of bacterial receptor proteins. Non-limiting examples of such bacterial receptor proteins may be selected from the group consisting of albumin binding receptor proteins from species of *Streptococcus, Peptostreptococcus* and *Finegoldia*, such as for example selected from the group consisting of proteins G, MAG, ZAG, PPL and PAB. In a specific embodiment of the invention, the ABM forms part of protein G, such as for example protein G from *Streptococcus* strain G148. In different variants of this embodiment, the three-helix bundle protein domain of which the ABM forms a part is selected from the group consisting of domain GA1, domain GA2 and domain GA3 of protein G from *Streptococcus* strain G148, in particular domain GA3.

In alternative embodiments, the ABM forms part of one or more of the five three-helix domains of the bacterial receptor protein protein A from *Staphylococcus aureus*; i.e. the three-helix bundle protein domain is selected from the group consisting of protein A domains A, B, C, D and E. In other similar embodiments, the ABM forms part of protein Z, derived from domain B of protein A from *Staphylococcus aureus*.

In embodiments of the present invention wherein the ABM "forms part of" a three-helix bundle protein domain, this is understood to mean that the sequence of the ABM is "inserted" into or "grafted" onto the sequence of the naturally occurring (or otherwise original) three-helix bundle domain, such that the ABM replaces a similar structural motif in the original domain. For example, without wishing to be bound by theory, the ABM is thought to constitute two of the three helices of a three-helix bundle, and can therefore replace such a two-helix motif within any three-helix bundle. As the skilled person will realize, the replacement of two helices of the three-helix bundle domain by the two ABM helices has to be performed so as not to affect the basic structure of the polypeptide. That is, the overall folding of the Cα backbone of the polypeptide according to this embodiment of the invention will be substantially the same as that of the three-helix bundle protein domain of which it forms a part, e.g. having the same elements of secondary structure in the same order etc. Thus, an ABM according to the invention "forms part" of a three-helix bundle domain if the polypeptide according to this embodiment of the invention has the same fold as the original domain, implying that the basic structural properties are shared, those properties e.g. resulting in similar CD spectra. The skilled person is aware of other parameters that are relevant.

In one embodiment of the invention, the albumin binding polypeptide is a three-helix bundle protein domain, which comprises the albumin binding motif as defined above and additional sequences making up the remainder of the three-helix configuration. Thus, the invention provides an albumin binding polypeptide, which comprises the amino acid sequence:

LAEAKX$_a$X$_b$AX$_c$X$_d$ ELX$_e$KY-[ABM]-LAALP    (SEQ ID NO: 518)

wherein
[ABM] is an albumin binding motif as defined above, and, independently of each other,
X$_a$ is selected from V and E;
X$_b$ is selected from L, E and D;
X$_c$ is selected from N, L and I;
X$_d$ is selected from R and K; and
X$_e$ is selected from D and K.

In one embodiment of this polypeptide, X$_a$ is V.
In one embodiment of this polypeptide, X$_b$ is L.
In one embodiment of this polypeptide, X$_c$ is N.
In one embodiment of this polypeptide, X$_d$ is R.
In one embodiment of this polypeptide, X$_e$ is D.

Again, as described in detail in the experimental section to follow, the selection and sequencing of a number of albumin binding variants led to the identification of individual albumin binding polypeptide sequences. These sequences constitute individual embodiments of the albumin binding polypeptide according to the above embodiment of the first aspect of the present invention. The sequences of these individual albumin binding polypeptides are presented in FIG. 1 as SEQ ID NO:258-514. Also encompassed by the present invention is an albumin binding polypeptide having an amino acid sequence with 85% or greater identity to a sequence selected from SEQ ID NO: 258-514. In particular embodiments, the sequence of the albumin binding polypeptide is selected from SEQ ID NO:259, SEQ ID NO:260, SEQ ID NO:266, SEQ ID NO: 272, SEQ ID NO:282, SEQ ID NO:284, SEQ ID NO:303, SEQ ID NO:306, SEQ ID NO:310, SEQ ID NO:311, SEQ ID NO: 312, SEQ ID NO:412, SEQ ID NO:496, SEQ ID NO:497, SEQ ID NO:498, SEQ ID NO:499, SEQ ID NO:500, SEQ ID NO:501 and SEQ ID NO:502 and sequences having 85% or greater identity thereto. In more specific embodiments of this aspect of the invention, the sequence of the albumin binding polypeptide is selected from SEQ ID NO:260, SEQ ID NO:310 and SEQ ID NO:496 and sequences having 85% or greater identity thereto.

As is evident from the above, in addition to a polypeptide whose amino acid sequence is selected from SEQ ID NO:258-514 or a subset thereof, the present invention also encompasses variants thereof. The amino acid sequences of such encompassed variants exhibit small differences only in comparison with SEQ ID NO:258-514. One definition of such variants is given above, i.e. an albumin binding polypeptide with an amino acid sequence having at least 85% identity to a sequence selected from SEQ ID NO: 258-514. In some embodiments, the inventive polypeptide may have a sequence which is at least 86%, at least 87%, at least 88%, at least 89%, at least 90%, at least 91%, at least 92%, at least 93%, at least 94%, at least 95%, at least 96%, at least 97%, at least 98%, or at least 99% identical to the sequence selected from SEQ ID NO: 258-514. The comparison may be performed over a window corresponding to the shortest of the sequences being compared, or over a window corresponding to an albumin binding motif in at least one of the sequences being compared.

The terms "albumin binding" and "binding affinity for albumin" as used in this specification refer to a property of a polypeptide which may be tested for example by the use of surface plasmon resonance technology, such as in a Biacore instrument. For example as described in the examples below, albumin binding affinity may be tested in an experiment in which albumin, or a fragment thereof, is immobilized on a sensor chip of the instrument, and the sample containing the polypeptide to be tested is passed over the chip. Alternatively, the polypeptide to be tested is immobilized on a sensor chip of the instrument, and a sample containing albumin, or a fragment thereof, is passed over the chip. Albumin may, in this regard, be a serum albumin from a mammal, such as human serum albumin. The skilled person may then interpret the results obtained by such experiments to establish at least a qualitative measure of the binding affinity of the polypeptide for albumin. If a qualitative measure is desired, for example to determine a $K_D$ value for the interaction, surface plasmon resonance methods may also be used. Binding values may for example be defined in a Biacore2000 instrument (Biacore AB). Albumin is suitably immobilized on a sensor chip of the measurement, and samples of the polypeptide whose affinity is to be determined are prepared by serial dilution and injected in random order. $K_D$ values may then be calculated from the results using for example the 1:1 Langmuir binding model of the BIAevaluation 4.1 software provided by the instrument manufacturer (Biacore AB)

The albumin binding polypeptide according to this first aspect of the present invention binds to albumin such that the $K_D$ value of the interaction is at most $1\times10^{-9}$ M, i.e. 1 nM. In some embodiments, the $K_D$ value of the interaction is at most $1\times10^{-10}$ M, such as at most $1\times10^{-11}$ M, for example at most $1\times10^{-12}$ M.

In one embodiment of the invention, the albumin to which the albumin binding polypeptide binds is human serum albumin.

The invention also encompasses an albumin binding polypeptide as described above, which further comprises one or more additional amino acid(s) positioned on one or both sides of the albumin binding motif. These additional amino acid residues may play a role in enhancing the binding of albumin by the polypeptide, but may equally well serve other purposes, related for example to one or more of the production, purification, stabilization in vivo or in vitro, coupling or detection of the polypeptide, as well as any combination thereof. Such additional amino acid residues may comprise one or more amino acid residue(s) added for purposes of chemical coupling, e.g. to a chromatographic resin to obtain an affinity matrix or to a chelating moiety for complexing with a metal radionuclide. An example of this is the addition of a cysteine residue at the very first or very last position in the polypeptide chain, i.e. at the N or C terminus. Such additional amino acid residues may also comprise a "tag" for purification or detection of the polypeptide, such as a hexahistidyl ($His_6$) tag, or a "myc" ("c-Myc") tag or a "FLAG" tag for interaction with antibodies specific to the tag. The skilled person is aware of other alternatives.

The "additional amino acid residues" discussed above may also constitute one or more polypeptide domain(s) with any desired function, such as the same binding function as the first, albumin binding domain, or another binding function, or a therapeutic function, or an enzymatic function, or a fluorescent function, or mixtures thereof. Linked polypeptide "units" in a such a polypeptide according to the invention may be connected by covalent coupling using known organic chemistry methods, or expressed as one or more fusion polypeptides in a system for recombinant expression of polypeptides, or joined in any other fashion, directly or mediated by a linker comprising a number of amino acids.

Furthermore, this aspect of the invention also encompasses fragments of albumin binding polypeptides that retain albumin binding. The possibility of creating fragments of a wild-type three-helix domain with retained binding specificity was shown by Braisted A C et al in Proc Natl Acad Sci USA 93:5688-5692 (1996). In the experiments described in that paper, using a structure-based design and phage display methods, the binding domain of a three-helix bundle of 59 residues was reduced to a resulting two-helix derivative of 33 residues. This was achieved by stepwise selection of random mutations from different regions, which caused the stability and binding affinity to be iteratively improved. Following the same reasoning, with the polypeptides of the present invention, the skilled addressee will be able to obtain a "minimized" albumin binding polypeptide with the same binding properties as that of the "parent" albumin binding polypeptide. Thus, a polypeptide constituting a fragment of a polypeptide according to the invention and substantially retaining albumin binding is within the scope of the invention. As a non-limiting example, the fragment may correspond to an albumin binding polypeptide according to the description above which has been N-terminally truncated. Such a truncation may for example be by from 1 to 3 amino acids.

As outlined above, the invention also encompasses multimers of the polypeptide with affinity for albumin, i.e. polypeptide chains comprising at least two albumin binding polypeptides or fragments thereof as monomer units. It may be of interest, e.g. in a method of purification of albumin or in a therapeutic method exploiting the albumin binding function, to obtain even stronger binding of albumin than is possible with one polypeptide according to the invention. In this case, the provision of a multimer, such as a dimer, trimer or tetramer, of the polypeptide may provide the necessary avidity effects. The multimer may consist of a suitable number of polypeptides according to the invention. These polypeptide domains according to the invention, forming monomers in such a multimer, may all have the same amino acid sequence, but it is equally possible that they have different amino acid sequences. As described above, the linked polypeptide "units" in a multimer according to the invention may be connected by covalent coupling using known organic chemistry methods, or expressed as one or more fusion polypeptides in a system for recombinant expression of polypeptides, or joined in any other fashion, directly or mediated by a linker comprising a number of amino acids.

Additionally, "heterogenic" fusion polypeptides or proteins, or conjugates, in which an albumin binding polypeptide according to the invention, or fragment or multimer thereof, constitutes a first domain, or first moiety, and the second and further moieties have other functions than binding albumin, are also contemplated and fall within the ambit of the present invention. The second and further moiety/moieties of the fusion polypeptide or conjugate in such a protein suitably has a desired biological activity. Non-limiting examples of such a desired biological activity comprise a therapeutic activity, a binding activity, and an enzymatic activity. In some embodiments of this aspect of the invention, the second moiety and any further moieties are selected from the group consisting of GLP-1 (glucagon-like peptide 1); HGH (human growth hormone); G-CSF (granulocyte colony-stimulating factor); IL-1 receptor agonist (interleukin 1 receptor agonist); TNF-α (tumor necrosis factor alpha); and blood clotting factors VII, VIII, IX and X. In other embodiments, said second and any further moieties are selected from binding moieties capable of selective interaction (binding) with a target molecule, typically a target molecule other than albumin even though albumin is not excluded. Such a binding moiety is suitably selected from the group consisting of antibodies and fragments and domains thereof substantially retaining antibody binding activity; microbodies, maxybodies, avimers and other small disulfide-bonded proteins; and binding proteins derived from a scaffold selected from the group consisting of staphylococcal protein A and domains thereof, lipocalins, ankyrin repeat domains, cellulose binding domains, γ crystallines, green fluorescent protein, human cytotoxic T lymphocyte-associated antigen 4, protease inhibitors, PDZ domains, peptide aptamers, staphylococcal nuclease, tendamistats, fibronectin type III domain, zinc fingers, conotoxins, and Kunitz domains. In some embodiments of the invention, the target molecule for binding of said target binding moiety is selected from the group consisting of AR peptide; other disease-associated amyloid peptides; toxins, such as bacterial toxins and snake venoms; blood clotting factors, such as von Willebrand factor; interleukins, such as IL-13; myostatin; pro-inflammatory factors, such as TNF-α, TNF-α receptor and IL-8; complement factors, such as C3a and C5a; hypersensitivity mediators, such as histamine and IgE; tumor-related antigens, such as CD19, CD20, CD22, CD30, CD33, CD40, CD52, CD70, cMet, HER1, HER2, HER3, HER4, CA9, CEA, IL-2 receptor, MUC1, PSMA, TAG-72.

Other possibilities for the creation of fusion polypeptides or conjugates are also contemplated. Thus, an albumin binding polypeptide according to the first aspect of the invention may be covalently coupled to a second or further moiety or moieties, which in addition to or instead of target binding exhibit other functions. One example is a fusion between one or more albumin binding polypeptide(s) and an enzymatically active polypeptide serving as a reporter or effector moiety. Examples of reporter enzymes, which may be coupled to the albumin binding polypeptide to form a fusion protein, are known to the skilled person and include enzymes such as β-galactosidase, alkaline phosphatase, horseradish peroxidase, carboxypeptidase. Other options for the second and further moiety or moieties of a fusion polypeptide or conjugate according to the invention include, also without limitation, fluorescent polypeptides, such as green fluorescent protein, red fluorescent protein, luciferase and variants thereof.

With regard to the description above of fusion proteins or conjugates incorporating an albumin binding polypeptide according to the invention, it is to be noted that the designation of first, second and further moieties is made for clarity reasons to distinguish between albumin binding polypeptide or polypeptides according to the invention on the one hand, and moieties exhibiting other functions on the other hand. These designations are not intended to refer to the actual order of the different domains in the polypeptide chain of the fusion protein or conjugate. Thus, for example, said first moiety may without restriction appear at the N-terminal end, in the middle, or at the C-terminal end of the fusion protein or conjugate.

The invention also encompasses polypeptides in which an albumin binding polypeptide as described above has been provided with a label, such as selected from the group consisting of fluorescent dyes and metals, chromophoric dyes, chemiluminescent compounds and bioluminescent proteins, enzymes, radionuclides and particles, for example for purposes of detection of the polypeptide in vitro or in vivo.

Related aspects of the present invention provide a polynucleotide encoding a polypeptide as described above, as well as an expression vector comprising the polynucleotide and a host cell comprising the expression vector. The latter three aspects of the invention are tools for the production of a polypeptide according to the invention, and the skilled person will be able to obtain them and put them into practical use without undue burden, given the information herein concerning the polypeptide that is to be expressed and given the current level of skill in the art of recombinant expression of proteins. Thus, other related aspects of the invention are methods of producing a polypeptide according to the first aspect of the invention, comprising expressing a polynucleotide as herein described, for example via the culturing of a host cell as herein defined under conditions permitting expression of the polypeptide from the expression vector, and isolating the polypeptide.

As described in the background section and as is well known to the person skilled in the art, the possible applications of a polypeptide molecule with a binding affinity for albumin are several. The albumin binding polypeptide, as well as a fragment, multimer and fusion protein or conjugate thereof, of the invention may find use in any one or more of these applications.

As a non-limiting example of applications of the albumin binding polypeptides described above, the present invention provides, in another of its aspects, the use of a fusion protein or conjugate of an albumin binding polypeptide according to the first aspect of the invention with a polypeptide having a desired biological activity (as defined above) for the preparation of a medicament which exhibits a half-life in vivo which is longer than the half-life in vivo of the polypeptide having a desired biological activity per se. Alternatively speaking, the invention provides a method for prolonging the half-life in vivo of a polypeptide having a desired biological activity, through the fusion or conjugation of such a polypeptide to an albumin binding polypeptide according to the first aspect of the invention. For details of this application of albumin binding molecules, reference is made e.g. to the teachings of the PCT applications published as WO91/01743 and WO01/45746, which are incorporated herein by reference.

As another non-limiting example of applications, the present invention provides, in another of its aspects, the use of a fusion protein or conjugate of an albumin binding polypeptide according to the first aspect of the invention with a polypeptide having a desired biological activity (as defined above) for the preparation of a medicament which elicits no or a reduced immune response upon administration to the mammal, as compared to the immune response elicited upon administration to the mammal of the polypeptide having a desired biological activity per se. Alternatively speaking, the invention provides a method for decreasing the immunogenicity of a polypeptide having a desired biological activity, through the fusion or conjugation of such a polypeptide to an albumin binding polypeptide according to the first aspect of the invention. For details of this application of albumin binding molecules, reference is made to the teachings of the PCT application published as WO2005/097202, which is incorporated herein by reference.

Another set of aspects of the present invention concern the provision of new means to increase the solubility in water of a poorly soluble compound, through coupling thereof to an albumin binding polypeptide. The ensuing complex of poorly soluble compound and albumin binding polypeptide is able to associate with albumin in vivo or in vitro, which association increases the solubility in water. Examples of compounds whose solubility in water may be thus increased through use of the present invention may typically include poorly soluble cytotoxic agents useful for cancer chemotherapy. Using this approach, e.g. in the formulation of drug compositions, enables lyophilization of the resulting preparation, which may then subsequently be reconstituted in aqueous solution.

Also, the invention in these aspects provides preparations that have a reduced tendency for aggregation as compared to the compound per se.

Thus, yet another aspect of the present invention provides a composition comprising a compound which per se has a solubility in water of no more than 100 μg/ml; coupled to an albumin binding polypeptide, which has an affinity for albumin such that the $K_D$ of the interaction is no more than $1 \times 10^{-6}$ M.

In one embodiment, the compound per se has a solubility in water of no more than 10 μg/ml, such as no more than 1 μg/ml.

In one embodiment, the albumin binding polypeptide has an affinity for albumin such that the $K_D$ of the interaction is no more than $1 \times 10^{-7}$ M, such as no more than $1 \times 10^{-8}$ M, for example no more than $1 \times 10^{-9}$ M, such as no more than $1 \times 10^{-10}$ M, such as no more than $1 \times 10^{-11}$ M, for example no more than $1 \times 10^{-12}$ M.

In some embodiments, the compound may be a pharmaceutically active compound, for example a cytotoxic agent. Non-limiting examples of cytotoxic agents are those selected from calicheamycin, auristatin, doxorubicin, maytansinoid, taxol, ecteinascidin, geldanamycin and their derivatives, and combinations thereof. Alternatively, the cytotoxic agent may be a synthetic chemotoxin not derived from a naturally occurring compound.

The compound and albumin binding polypeptide may be non-covalently associated, but it is currently preferred that they be covalently coupled together.

The composition according to this aspect of the present invention comprises an albumin binding polypeptide. In one embodiment, the albumin binding polypeptide is a naturally occurring polypeptide or an albumin binding fragment or derivative thereof. The albumin binding polypeptide may, as non-limiting examples, be selected from the group consisting of albumin binding proteins M1/Emm1, M3/Emm3, M12/Emm12, EmmL55/Emm55, Emm49/EmmL49, H, G, MAG, ZAG, PPL and PAB. In a more specific embodiment, the albumin binding polypeptide is streptococcal protein G or an albumin binding fragment or derivative thereof. In an even more specific embodiment, the polypeptide capable of binding to albumin is selected from the group consisting of domain GA1, domain GA2 and domain GA3 of protein G from *Streptococcus* strain G148, and may thus, for example, be the GA3 domain.

In one embodiment, the albumin binding polypeptide comprises from about 5 to about 214 amino acid residues, such as from about 5 to about 46 amino acid residues, for example from about 10 to about 20 amino acid residues.

In another embodiment of this aspect of the present invention, the albumin binding polypeptide comprises an amino acid sequence selected from DICLPRWGCLW (SEQ ID NO: 519), DLCLRDWGCLW (SEQ ID NO: 520) and DICLARWGCLW (SEQ ID NO: 521).

In yet another embodiment of these aspects of the present invention, the albumin binding polypeptide comprises any albumin binding polypeptide according to the first aspect of the invention discussed extensively above, i.e. that aspect of the present invention which defines a class of novel albumin binding polypeptides via the sequence of the albumin binding motif thereof.

In another embodiment of these aspects of the present invention, the albumin binding polypeptide is capable of interacting with at least one of, and preferably all of, residues F228, A229, V325, F326 and M329 in human serum albumin so as to enhance binding of the molecule to albumin. For example, the albumin binding polypeptide includes an amino acid residue which forms an interaction with the M329 residue in human serum albumin so as to enhance binding of the molecule to albumin. In addition, or alternatively, the albumin binding polypeptide may include an amino acid residue which forms an interaction with helix 7 in the human serum albumin domain IIB so as to enhance binding of the molecule to albumin. In addition, or alternatively, the albumin binding polypeptide includes an amino acid residue which forms an interaction with residues in human serum albumin domain IIA so as to enhance binding of the molecule to albumin. In addition, or alternatively, the albumin binding polypeptide includes an amino acid residue which forms an interaction with residues between helices 2 and 3 of human serum albumin so as to enhance binding of the molecule to albumin.

In addition to the poorly soluble compound and albumin binding polypeptide, the composition according to this aspect of the invention may, in some embodiments, also comprise a binding polypeptide with an affinity for a clinically relevant target. This binding polypeptide is suitably different from the albumin binding polypeptide, and may be non-covalently or covalently coupled to the other components of the inventive composition. As non-limiting examples, the binding polypeptide with an affinity for a clinically relevant target may be selected from the group consisting of antibodies and fragments and domains thereof substantially retaining antibody binding activity; microbodies, maxybodies, avimers and other small disulfide-bonded proteins; and binding proteins derived from a scaffold selected from the group consisting of staphylococcal protein A and domains thereof, lipocalins, ankyrin repeat domains, cellulose binding domains, γ crystallines, green fluorescent protein, human cytotoxic T lymphocyte-associated antigen 4, protease inhibitors, PDZ domains, peptide aptamers, staphylococcal nuclease, tendamistats, fibronectin type III domain, zinc fingers, conotoxins, and Kunitz domains.

The composition according to the above aspect of the present invention has an ability to associate with albumin in vivo or in vitro, through the provision in the composition of an albumin binding polypeptide. In certain cases, it may be of benefit to form a complex of the composition with albumin outside of a living organism, i.e. to add exogenous albumin to the composition. Thus, the present invention also provides a composition as defined above which further comprises albumin, such as human serum albumin.

The present invention also provides the composition according to the above aspect for use as a medicament, in cases where the compound is a therapeutically active compound. Suitably, the provision of an albumin binding polypeptide and optionally albumin does not deleteriously affect the therapeutic efficacy of the active compound, so the inventive composition will be useful in those therapeutic or prophylactic settings where the compound per se is indicated.

A related aspect of the present invention provides a method of preparation of a composition as described immediately above. The method comprises providing a compound which per se has a solubility in water of no more than 100 μg/ml; and covalently coupling the compound to an albumin binding polypeptide, which has an affinity for albumin such that the $K_D$ of the interaction is no more than $1 \times 10^{-6}$ M, thus forming a covalent complex of compound and albumin binding polypeptide.

In embodiments of the invention where albumin is included into the composition, the method may beneficially comprise the additional step of mixing said complex of compound and albumin binding polypeptide with albumin, thus forming a composition comprising a non-covalent complex of i) the covalent complex of compound and albumin binding polypeptide and ii) albumin. The relative proportions of the two components of this non-covalent complex may for example be 1:1, so that one unit of the complex of poorly soluble compound and albumin binding polypeptide is associated with one molecule of albumin. In one embodiment, the method additionally comprises lyophilizing the non-covalent complex to obtain a lyophilized composition.

In another closely related aspect, the present invention provides a method of increasing the aqueous solubility of a compound, comprising providing a compound which per se has a solubility in water of no more than 100 μg/ml M;

covalently coupling the compound to an albumin binding polypeptide, which has an affinity for albumin such that the $K_D$ of the interaction is no more than $1 \times 10^{-6}$ M, thus forming a covalent complex of compound and albumin binding polypeptide; and mixing said complex of compound and albumin binding polypeptide with albumin under conditions that promote the non-covalent association of the albumin binding polypeptide with albumin;

whereby the solubility in water of the compound in said complex is greater than the solubility in water of the compound per se.

In these method aspects concerning the solubility of a poorly soluble compound, the optional features of the various components are as described in connection with the immediately preceding composition aspect.

As described above, embodiments of these aspects of the present invention relate inter alia to the combination of a targeting polypeptide with an albumin-binding polypeptide, conjugation of this molecule with e.g. a chemotoxin, and the formulation and administration of the resulting chemotoxin conjugate with albumin to avoid problems with low solubility.

Chemotoxins are generally hydrophobic compounds. Therefore, poor solubility is one of the challenges with handling and formulating chemotoxin conjugates, including antibodies conjugated with chemotoxins. The problem is accentuated when trying to couple clusters of toxin molecules to one carrier protein. In contrast, a chemotoxin conjugated albumin-binding fusion protein in complex with a molecule of albumin has a superior solubility stemming from the solubilizing properties of albumin, as reflected by its role as a carrier of many small molecules in plasma. One aspect of these embodiments of the invention is a strong association between the albumin-binding domain and albumin to prevent other interactions that could result in precipitation of the non-associated albumin-binding protein conjugate.

A slow extravasation of monoclonal antibodies from blood has been raised as one of the biological barriers that limit the efficacy of antibody mediated therapy (Wu and Senter, Nature Biotechnology 23:1137-46, 2005). Interestingly, at equilibrium, approximately 60% of the serum albumin in a human being is found in the interstitial space, whereas only 40% is found in the blood stream. Thus, the association with albumin as provided by the present invention is considered a superior means of obtaining a wide distribution outside of the blood stream. The affinity of the association with serum albumin is suitably characterized by an off-rate (decomposition of the complex) that is sufficiently slow, such that only a minute fraction of the complex dissociates during transition from the blood stream to the interstitium. However, the interaction does not have to be covalent, since some rebinding is possible during the transition.

One possible contributing mechanism for extravasation and wide distribution is active transport following binding of serum albumin to the FcRn receptor. Consequently, there are certain requirements on the albumin binding moiety in an albumin binding fusion protein to obtain a similar distribution. For example, the affinity may be very tight also in the acidic environment encountered during receptor transport in the cell, probably down to a pH below 6.

BRIEF DESCRIPTION OF THE FIGURES

FIG. 1A-1Q is a listing of the amino acid sequences of examples of albumin binding motifs comprised in albumin binding polypeptides of the invention (SEQ ID NO: 1-257), examples of albumin binding polypeptides according to the invention (SEQ ID NO: 258-514), and the GA3 domain from protein G of *Streptococcus* strain G148 (SEQ ID NO: 515).

FIG. 6 is a table showing the theoretical (shaded columns) and experimental (clear columns) values for the amino acid variation at each varied position in the ABD variant sub-library created using the AFFI-793 mixture of oligonucleotides, as described in Example 1.

FIG. 7 is a table showing the theoretical (shaded columns) and experimental (clear columns) values for the amino acid variation at each varied position in the ABD variant sub-library created using the AFFI-794 mixture of oligonucleotides, as described in Example 1.

FIG. 8 is a schematic illustration of the amino acid sequence of an ABD variant as expressed in the pAY442 vector according to the description in Example 2.

FIG. 12 shows the amount of A) Z00342 and B) Z00342-ABD00003 in blood circulation over time as analyzed by sandwich ELISA as described in Example 4.

FIGS. 14A-14B show ELISA titration curves for serum obtained at days 0-45 from primates injected with (Z01154)$_2$-ABD00239 as described in Example 5, when analyzed on ELISA plates coated with (Z01154)$_2$-ABD00239.

FIG. 15 shows normalized values of the A) (Z01154)$_2$ and B) (Z01154)$_2$-ABD00239 samples analyzed in FIGS. 13 and 14 respectively. The sample absorbances were normalized against the positive control at 1600× dilution.

The invention will now be illustrated further through the non-limiting description of experiments conducted in accordance therewith. Unless otherwise specified, conventional chemistry and molecular biology methods were used throughout.

EXAMPLES

Example 1

Construction of Phage Display Library of Variants of an Albumin Binding Polypeptide Summary In this example, a phage display library of polypeptide variants was created, through variation of 16 positions in helices 2 and 3 of the albumin binding domain GA3 of *Streptococcus* strain G148 (in the following referred to as "ABD").

Construction of Phagemide Vector pAY1075

Figure 2:
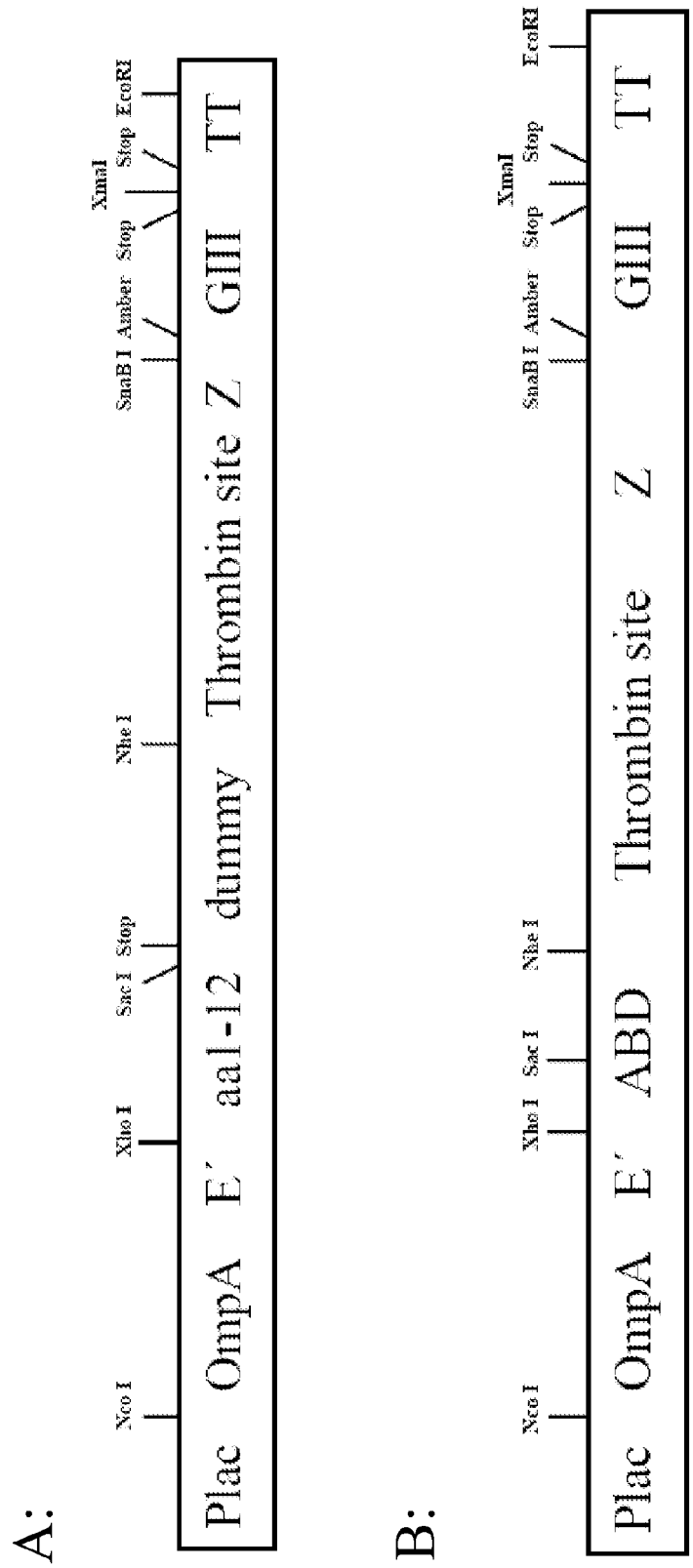
FIG. 2 is an illustration of the main features of the coding insert in expression vector pAY1075 without (A) and with (B) a cassette encoding helices 2 and 3 of variant ABD molecules.

A new phage display vector (pAY1075) was constructed for the new library. pAY1075 was based on the phagemid vector pAffi1 (Grönwall et al, supra). For creation of pAY1075, pAffi1 was digested with XhoI and XmaI (10 units/µl; New England Biolabs), and a new insert or cloning cassette was created and ligated into the vector. The new insert contained DNA encoding helix 1 of ABDwt, a dummy sequence, a thrombin site, Zwt (an engineered IgG binding domain based on domain B of staphylococcal protein A, see Nilsson et al, Prot Eng 1:107-113, 1987), truncated GIII (residues 249-406), the termination domain TT and some additional restriction enzyme sites. For a schematic representation of the elements encoded by this insert, see FIG. 2A. FIG. 2B shows the insert of the expression vector when the dummy sequence has been replaced by a sequence encoding the remaining ABD variant polypeptide (see below). The sequences of the various DNA oligonucleotides used as primers and templates in the cloning experiment and library construction are provided below in Table 1.

TABLE 1

| Oligo | Oligonucleotide primers and templates Sequence | |
|---|---|---|
| AFFI-21 | 5'-tgcttccggctcgtatgttgtgtg-3' | (SEQ ID NO: 522) |
| AFFI-22 | 5'-cggaaccagagccaccaccgg-3' | (SEQ ID NO: 523) |
| AFFI-40 | 5'-tccccccgggttaagactccttattacgcag-3' | (SEQ ID NO: 524) |
| AFFI-72 | 5'-*biotin*-cggaaccagagccaccaccgg-3' | (SEQ ID NO: 525) |
| AFFI-772 | 5'-gaagccctcgagttagctgaagctaaag-3' | (SEQ ID NO: 526) |
| AFFI-773 | 5'-gttagctgaagctaaagtcttagctaacagagagctctgaaagcttggcttatgc-3' | (SEQ ID NO: 527) |
| AFFI-774 | 5'-cgcgcggaaagctagccaaacttcggatag-3' | (SEQ ID NO: 528) |
| AFFI-775 | 5'-ctagctttccgcgcgtagacaacaaattcaac-3' | (SEQ ID NO: 529) |
| AFFI-776 | 5'-ccggactatacgtatttcggcgcctgagc-3' | (SEQ ID NO: 530) |
| AFFI-777 | 5'-gaaatacgtatagtccggtggtggctc-3' | (SEQ ID NO: 531) |
| AFFI-791 | 5'-acagagagctcgacaaatatggag-3' | (SEQ ID NO: 532) |
| AFFI-792 | 5'-cggaaagctagcaggtaatgcagc-3' | (SEQ ID NO: 533) |

The wildtype sequence of ABD ("ABDwt") is provided as SEQ ID NO:515 in FIG. 1 and in the appended sequence listing. A new phage display vector (pAY1075) based on the previously described pAffi1 vector (Gronwall et al, J Biotechnol 128:162-183, 2007) was constructed for this new library. The varied ABD fragment (helices 2-3) was cloned into pAY1075 with restriction enzymes SacI and NheI. Ligations were purified and electroporated to *E. coli* RR1ΔM15 cells (Rüther, Nucleic Acids Res 10:5765-5772, 1982). The newly constructed library was designated LibABDmat2005 and consisted of two sub-libraries, depending on which oligonucleotides had been used for creation of the varied sequence of helices 2 and 3. One was built on the ABD molecule and the other had an extra amino acid inserted between positions 17 and 18 of ABD, which some of the proteins homologous to ABD have (see e.g. Rozak et al, Biochemistry 45:3263-3271, 2006). The size of LibABDmat2005 was $1 \times 10^9$ members ($5 \times 10^8$ for each sub-library). The quality of the new library was satisfying, in that DNA sequencing showed that about 87% of the clones were functional and in that the measured values of relative frequencies of amino acids agreed well with the theoretical values.

Figure 3:
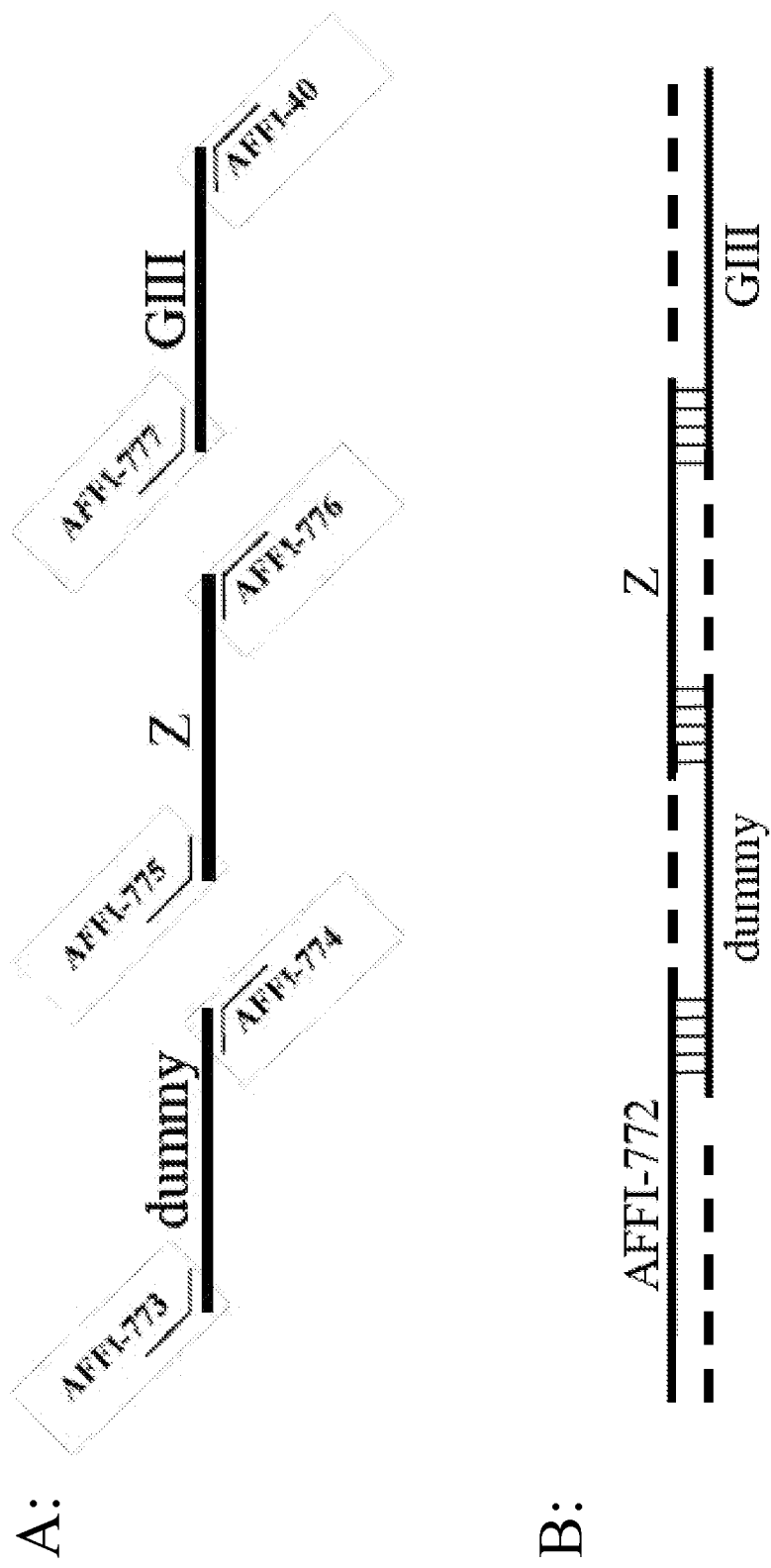
FIG. 3A shows the strategy for amplification of DNA fragments encoding dummy, Zwt and GIII in the preparation of the coding insert of expression vector pAY1075.
FIG. 3B shows the overlap of these fragments for the creation of the entire coding insert.

In order to create the new cloning cassette for pAY1075, the dummy fragment and GIII were PCR amplified from pAffi1, and Zwt was amplified from plasmid pEZZ18 (Lowenadler et al, Gene 58:87-97, 1987), using primers according to FIG. 3A. The newly generated fragments had overlapping segments to each other, as shown in FIG. 3B. The PCR fragments were gel purified with QIAquick gel extraction kit (Qiagen) according to the manufacturer's recommendations and thereafter assembled together with the oligonucleotide AFFI-772 (FIG. 3B) in an assembly PCR. A further PCR reaction using external primers AFFI-772 and AFFI-40 was performed to amplify the entire fragment. PCR products were purified using QIAquick PCR purification kit (Qiagen) according to the manufacturer's recommendations.

Figure 4:
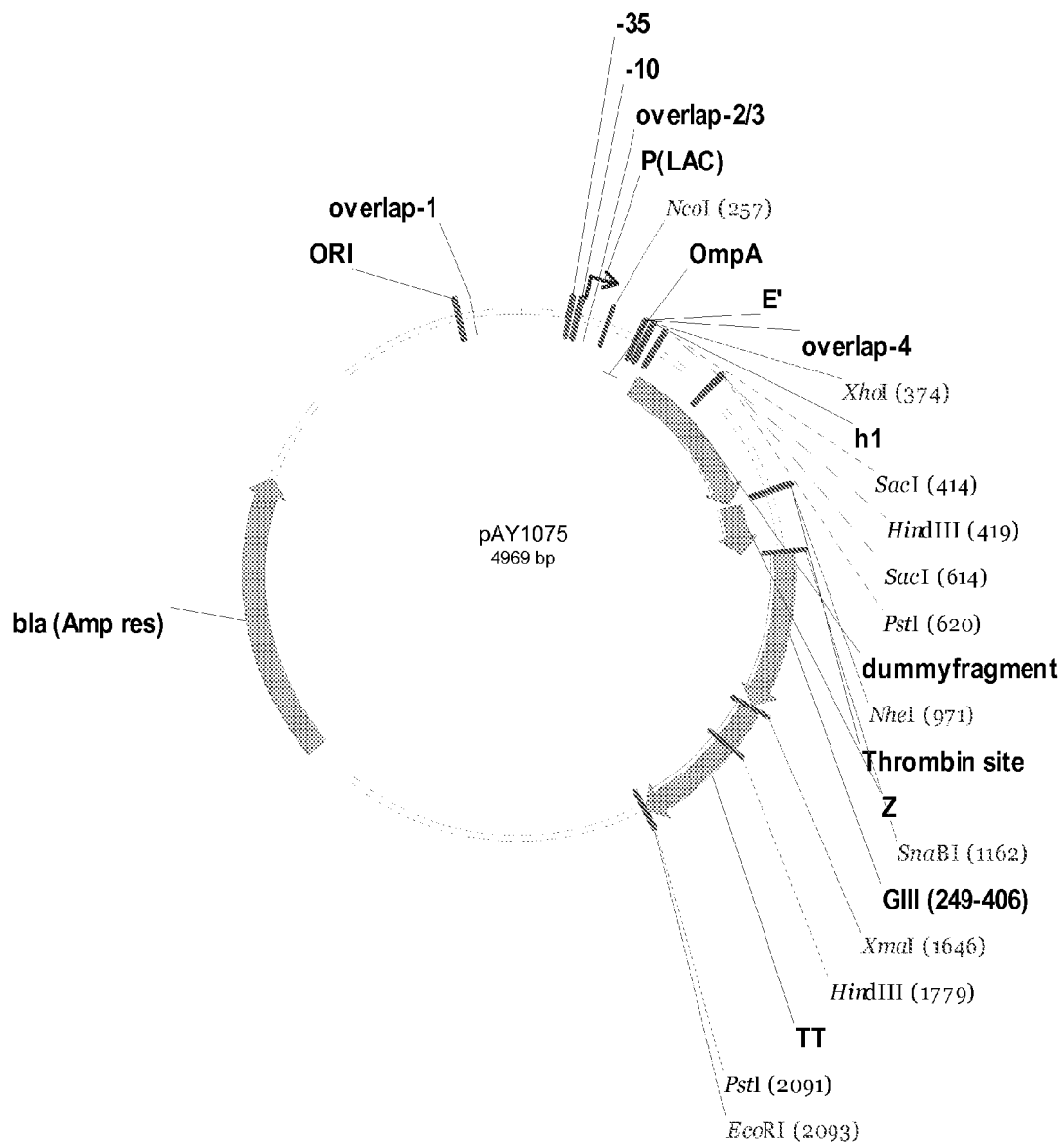
FIG. 4 is a vector map of the expression vector pAY1075, prepared as described in Example 1.
Figure 5:
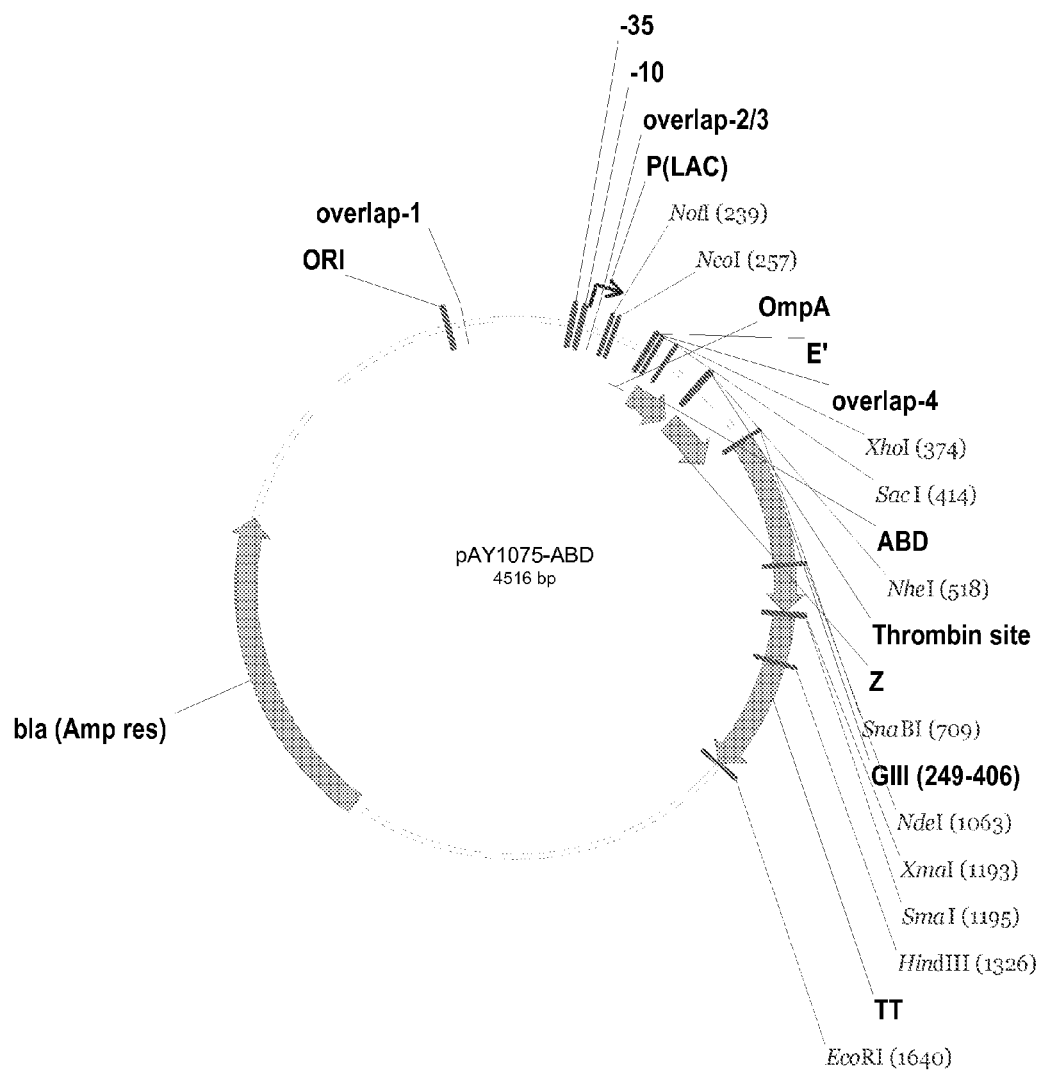
FIG. 5 is a vector map of the expression vector pAY1075-ABD, prepared as described in Example 1.

The plasmid pAffi1 was purified with QIAgen™ midi-prep kit (Qiagen), according to the manufacturer's recommendations. Thereafter, pAffi1 and the amplified PCR fragment for the cloning cassette were digested with XhoI and XmaI (10 units/µl; New England Biolabs) in NEB4 buffer (20 mM Tris acetate, 10 mM magnesium acetate, 50 mM potassium acetate, 1 mM dithiothreitol, pH 7.9; New England Biolabs) for 1 h at 37° C. and the vector was thereafter dephosphorylated using calf intestinal alkaline phosphatase (CIAP; Fermentas). The digestions were purified on a 1% agarose gel using QIAquick gel extraction kit according to the manufacturer's recommendations. The new fragment was ligated into XhoI and XmaI cleaved pAffi1 for 1 h at room temperature using T4 DNA ligase (5 units/µl; Fermentas). Part of the ligation mixture was electroporated into *E. coli* TG1 cells (Stratagene) using 1 mm cuvettes. The cells were plated on tryptose blood agar base plates (TBAB plates; 30 g/l TBAB) supplemented with 200 µg/ml ampicillin. Clones having a correct insert were identified by PCR, using the three different primer pairs AFFI-21/AFFI-42, AFFI-47/AFFI-40 and AFFI-21/AFFI-40. PCR fragments were analyzed on a 1% agarose gel, and positive clones were plasmid purified with QIAprep Miniprep kit (Qiagen), according to the manufacturer's recommendations. and thereafter sequenced with primers AFFI-38, 40, 71, 72, and 772 using ABI PRISM® BigDye™ Terminator Cycle Sequencing Ready Reaction kit 3.1 (Applied Biosystems). The sequence PCR reactions were purified on a Magnatrix 8000 instrument (Magnetic Biosolutions) and the nucleotide sequence was determined with an ABI PRISM® 3100 Genetic analyzer (Applied Biosystems). Sequencer™ v 4.0.5 (Gene Codes Corporation) was used to record and analyze the sequence data. Sequencing revealed that the new phagemid vector had been successfully created. Vector maps of the vector with dummy sequence (pAY1075) or with sequence encoding varied ABD helices 2 and 3 (pAY1075-ABD) are shown in FIGS. 4 and 5, respectively.

Design of a Library of Variant ABD Sequences

A set of oligonucleotides having a randomized sequence for helices 2 and 3 of the ABD molecule were prepared as described below. These oligonucleotides were subsequently used for replacement of the dummy sequence in pAY1075, to create pAY1075-ABD (FIGS. 2B and 5). The pAY1075-ABD vector was subsequently used for the expression of the library of ABD variants on the surface of phages The design was based on information from alanine mutations of ABD (Linhult et al, Protein Science 11:206-213, 2002), a study of the ALB8-HSA complex (Lejon et al, J Biol Chem 279:42924-42928, 2004), sequence homologies with other known albumin binding domains and ease of oligonucleotide preparation. 16 amino acid positions in the ABDwt sequence represented by SEQ ID NO:515 were selected for some degree of randomization, and were grouped in 4 different groups depending on characteristic: (I) the hydrophobic core, (II) conserved positions, (III) electrostatic interactions and (IV) others:

(I) Positions Y20, L24, L27 and I41 are involved in creating the central hydrophobic core in the interaction with serum albumin. These positions are highly conserved among domains homologous to ABD and randomization in these positions tested whether another hydrophobic amino acid residue could improve the hydrophobic interaction.

(II) Positions 18', S18, T30, E32 and G33 are very conserved among the albumin binding domains. Positions S18 and T30 are involved in two intermolecular H-bonds, and the rationale for randomization was that similar polar amino acids like threonine (T) and asparagine (N) could also work. E32 and G33 do not interact with the binding surface to any great extent. However, they are likely to be important for protein structure, and it was of interest to see if another amino acid could work. The sequence of ABDwt does not comprise position 18' (i.e. 18' represents an added amino acid residue between positions 17 and 18 in ABDwt), but homologous domains have threonine or serine at that position. It was of interest to see if binding could be improved with this additional amino acid.

(III) Positions N23, N27, K29 and E40 are involved or could be involved in electrostatic interactions. The randomization at these positions was based on an interest to see whether or not it would be possible to enhance or suppress some of the attractive or repulsive interactions of these amino acid residues with albumin.

(IV) Positions A36, K35 and D39 were randomized due to other similar considerations.

In order to create the desired mix of amino acid residues at each position, the ABDwt sequence was varied in accordance with Table 2. Variations were categorized as "randomized" or "doped". In "randomized" positions, all chosen amino acids were represented in equal proportions. In "doped" positions, the original amino acid was more frequent than the others, i.e. the position was biased towards the original amino acid.

TABLE 2

Design strategy for variant ABD sequences

Randomized positions

| Position | Desired variation | Codon combinations[1] | # codons | # amino acids |
|---|---|---|---|---|
| 20 | F, Y | T(T/A)T | 2 | 2 |
| 23 | N, S, K, R | A(G/A)(A/C) | 4 | 4 |
| 27 | N, S, K, R | A(G/A)(A/C) | 4 | 4 |
| 33 | All except aromatic | (C/A/G)N(G/T) | 24 | 16 |
| 35 | All | NN(G/T) | 32 | 20 |
| 36 | S, T, A | (T/A/G)CC | 3 | 3 |
| 39 | All | NN(G/T) | 32 | 20 |
| 40 | H, E, D, Q | (G/C)A(G/T) | 4 | 4 |

Doped positions

| Position | Desired variation[2] | Codon combinations[1] | # codons | # amino acids |
|---|---|---|---|---|
| 18' | -, S, T | no codon (50%) + A(C/G)C | 3 | 3 |
| 18 | S, T, N | AGT (80%) + A(A/G/C)C | 3 | 3 |
| 24 | F, L, I, M, V | CTG/T (70%) + NT(G/T) | 8 | 5 |

TABLE 2-continued

Design strategy for variant ABD sequences

| | | | | |
|---|---|---|---|---|
| 29 | R, K | AAG (90%) + A(G/A)A | 2 | 2 |
| 30 | T, S, N | ACT (80%) + A(A/G/C)C | 3 | 3 |
| 32 | All (E) | GAG (72%) + NN(G/T) | 32 | 20 |
| 37 | F, L, I, M, V | CTG/T (70%) + NT(G/T) | 8 | 5 |
| 41 | F, L, I, M, V | ATT (84%) + NT(G/T) | 8 | 5 |

[1] N = any nucleotide
[2] "doped" or biased towards the underlined amino acid residue Oligonucleotide mixtures AFFI-793 and AFFI-794 corresponding to DNA encoding residues 13-46 of the ABDwt sequence as modified according to Table 2 and including restriction sites were obtained from Scandinavian Gene Synthesis AB. AFFI-794 comprises the extra amino acid represented by position 18'.

```
AFFI-793:
                            41 40 39    37 36 35    33 32    30 29    27          24 23
5'-TTGCTAGCAGGTAATGCAGCTAAXXXXXXXXXTATXXXXXXXXXTACXXXXXXAACXXXXXXGGCXXXGTTGATXXXXXXCTT
    20 18
    GTAXXXGTCXXXTACTCCATATTTGTCGAG-3'      113 bp

AFFI-794:
                            41 40 39    37 36 35    33 32    30 29    27          24 23
5'-TTGCTAGCAGGTAATGCAGCTAAXXXXXXXXXTATXXXXXXXXXTACXXXXXXAACXXXXXXGGCXXXGTTGATXXXXXXCTT
    20   18 18'
    GTAXXXGTCXXXXXXTACTCCATATTTGTCGAG-3'   116 bp
```

Table 3 summarizes the required percentage distribution of nucleotides in the oligonucleotide mixtures necessary to achieve the library design described in Table 2.

TABLE 3

Distribution of nucleotides in AFFI-793 and AFFI-794 oligonucleotide mixtures

| | Position | | | | | | | | | | | | | | | | | |
|---|---|---|---|---|---|---|---|---|---|---|---|---|---|---|---|---|---|---|
| | 18" | | | 18 | | | 20 | | | 23 | | | 24 | | | 27 | | |
| Nucleotide | 1 | 2 | 3 | 1 | 2 | 3 | 1 | 2 | 3 | 1 | 2 | 3 | 1 | 2 | 3 | 1 | 2 | 3 |
| T | 0 | 0 | 100 | 0 | 10 | 100 | 0 | 50 | 0 | 50 | 50 | 100 | 0 | 0 | 10 | 50 | 50 | 100 |
| C | 0 | 50 | 0 | 0 | 80 | 0 | 0 | 0 | 0 | 0 | 50 | 0 | 50 | 0 | 10 | 0 | 50 | 0 |
| A | 0 | 0 | 0 | 0 | 0 | 0 | 100 | 50 | 100 | 0 | 0 | 0 | 50 | 100 | 10 | 0 | 0 | 0 |
| G | 100 | 50 | 0 | 100 | 10 | 0 | 0 | 0 | 0 | 50 | 0 | 0 | 0 | 0 | 70 | 50 | 0 | 0 |

| | Position | | | | | | | | | | | | | | | | | |
|---|---|---|---|---|---|---|---|---|---|---|---|---|---|---|---|---|---|---|
| | 29 | | | 30 | | | 32 | | | 33 | | | 35 | | | 36 | | |
| Nucleotide | 1 | 2 | 3 | 14 | 2 | 3 | 1 | 2 | 3 | 1 | 2 | 3 | 1 | 2 | 3 | 1 | 2 | 3 |
| T | 100 | 90 | 100 | 0 | 10 | 100 | 0 | 79 | 7 | 0 | 25 | 33 | 0 | 25 | 25 | 0 | 0 | 33 |
| C | 0 | 10 | 0 | 0 | 10 | 0 | 90 | 7 | 79 | 50 | 25 | 34 | 50 | 25 | 25 | 0 | 0 | 34 |
| A | 0 | 0 | 0 | 0 | 0 | 0 | 10 | 7 | 7 | 50 | 25 | 0 | 50 | 25 | 25 | 0 | 0 | 33 |
| G | 0 | 0 | 0 | 100 | 80 | 0 | 0 | 7 | 7 | 0 | 25 | 33 | 0 | 25 | 25 | 100 | 100 | 0 |

| | Position | | | | | | | | | | | | |
|---|---|---|---|---|---|---|---|---|---|---|---|---|---|
| | 37 | | | 39 | | | 40 | | | 41 | | | |
| Nucleotide | 1 | 2 | 3 | 1 | 2 | 3 | 1 | 2 | 3 | 1 | 2 | 3 | |
| T | 0 | 0 | 10 | 0 | 25 | 25 | 0 | 100 | 0 | 0 | 0 | 88 | |
| C | 50 | 0 | 10 | 50 | 25 | 25 | 50 | 0 | 50 | 10 | 0 | 4 | |
| A | 50 | 100 | 10 | 50 | 25 | 25 | 50 | 0 | 0 | 90 | 100 | 4 | |
| G | 0 | 0 | 70 | 0 | 25 | 25 | 0 | 0 | 50 | 0 | 0 | 4 | |

Library Construction

The following procedure was used to create the genetic library LibABDmat2005, encoding ABD variants. In an assembly reaction, the oligonucleotide AFFI-791 and oligonucleotide mixture AFFI-793 or AFFI-794 were annealed and extended with Taq DNA polymerase. A PCR reaction using the external primers AFFI-791 and AFFI-792 was performed to amplify the fragment. PCR products were purified using QIAquick PCR purification kit (Qiagen) according to the manufacturer's recommendations.

Phagemid pAY1075 was prepared from 250 ml overnight culture (tryptic soy broth, 2% glucose, 100 µg/ml ampicillin) using Qiagen plasmid midi kit (Qiagen) following the manufacturer's recommendations. The phagemid was digested with SacI and NheI (10 units/µl; New England Biolabs) in NEB4 buffer (20 mM Tris acetate, 10 mM magnesium acetate, 50 mM potassium acetate, 1 mM dithiothreitol, pH 7.9; New England Biolabs) for 3 h at 37° C. The solution was phenol/chloroform purified and EtOH precipitated, and the vector was then gel purified from a 1% agarose gel using QIAquick gel extraction kit (Qiagen) according to the manufacturer's recommendations.

The PCR amplified fragments from the assembly reactions between AFFI-791 and AFFI-793 or AFFI-794 were digested with SacI and NheI in NEB4 buffer for 3 h at 37° C. The DNA fragments were purified from a 1 agarose gel using QIAquick gel extraction kit according to the manufacturer's recommendations. The resulting gene fragments encoding two sub-libraries of variants of ABD were ligated into SacI and NheI cleaved pAY1075 for 1 h at room temperature using T4 DNA ligase (5 units/µl; Fermentas).

The ligations were then phenol/chloroform extracted, EtOH precipitated and resolved in a smaller volume of 10 mM Tris. Electrocompetent $E.$ $coli$ RR1ΔM15 cells (Rü ther, 1982, supra) were transformed with 60 aliquots of ligated material of each of the two sub-libraries using 0.2 cm gap size cuvettes in an ECM 630 set (BTX) using the parameters 2.5 kV, 125Ω and 50 µF. Cells were grown in SOC medium (47 ml TSB+YE (30 g/l tryptic soy broth, 5 g/l yeast extract) supplemented with 1% glucose, 10 mM MgCl$_2$, 10 mM MgSO$_4$, 10 mM NaCl and 2.5 mM KCl) for 50 minutes and transferred to ten Erlenmayer flasks, each containing 1 l of TSB+YE (30 g/l tryptic soy broth, 5 g/l yeast extract) supplemented with 2% glucose and 100 µg/ml ampicillin, and grown overnight at 37° C. The cells were then centrifuged at 6000 g and re-suspended in PBS/glycerol solution (PBS: 2.68 mM KCl, 1.47 mM KH$_2$PO$_4$, 137 mM NaCl, 8.1 mM Na$_2$HPO$_4$, pH 7.4) to a final approximate concentration of 20% glycerol. The cells were then aliquoted and stored at −80° C. The number of cells after electroporation, amplification and transfer to glycerol stocks was titrated on TBAB plates supplemented with 200 µg/ml ampicillin.

The size of each sub-library was $5 \times 10^8$, i.e. the total size of the library LibABDmat2005 was $1 \times 10^9$. The library was amplified about 50000 times and the glycerol stocks had a density of about $1 \times 10^{11}$ cells/ml. In this context, the "size" of the library means the total number of members comprised in the library, without any regard to the number of unique variants encoded by the library.

Ninety-six colonies from each of the two sub-libraries were picked for DNA sequencing in order to verify the design and the frequency of clones with a correct reading frame. These randomly picked colonies, cultured from glycerol stocks and originating from each pool of the library were PCR amplified using oligonucleotides AFFI-21 and AFFI-22. Sequencing of the amplified fragments was performed using ABI PRISM® dGTP, BigDye™ Terminator v3.0 Ready Reaction Cycle Sequencing Kit (Applied Biosystems) according to the manufacturer's recommendations and with the biotinylated oligonucleotide AFFI-72. The sequencing reactions were purified by binding to magnetic, streptavidin-coated beads using a Magnatrix 8000 (Magnetic Biosolutions), and analyzed on ABI PRISM® 3100 Genetic Analyser (Applied Biosystems).

In the sub-library created using AFFI-793, three clones were not readable, eleven were incorrect and seven clones were contaminations from the other sub-library. The amino acid distribution in this sub-library was deducted from the sequencing data, and compared to the theoretical values, and the results are presented in FIG. 6.

Regarding the sub-library created using AFFI-794, three clones were not readable and 16 were incorrect. The amino acid distribution in this sub-library was deducted from the sequencing data, and compared to the theoretical values, and the results are presented in FIG. 7.

The frequency of each amino acid agreed well with expected value, and about 87% of the clones had a correct reading frame.

Example 2

Phaqe Display Selection and Characterization of Albumin Binding Polypeptide Variants Summary Biotinylated human serum albumin (HSA) was used as target in phage display selections using the library constructed in Example 1. Selections were carried out using a variety of conditions in order to maximize the likelihood of obtaining ABD variants having a high affinity for albumin. After elution of selected phages, the corresponding expressed proteins were tested for affinity to albumin in an ELISA setup. Positive clones were identified and sequenced, and the predicted amino acid sequences of the corresponding polypeptides and their albumin binding motifs were deduced, which yielded a large number of sequences of albumin binding polypeptides according to the invention. The amino acid sequences of deduced albumin binding motifs are listed in FIG. 1 and in the sequence listing as SEQ ID NO:1-257, whereas the amino acid sequences of the corresponding full-length ABD variants are listed in FIG. 1 and in the sequence listing as SEQ ID NO:258-514.

Biotinylation of Human Serum Albumin

Lyophilized human serum albumin (Sigma, cat. no. A3782-5G) was dissolved in PBS (2.68 mM KCl, 1.47 mM KH$_2$PO$_4$, 137 mM NaCl, 8.1 mM Na$_2$HPO$_4$, pH 7.4) to a final concentration of 10 mg/ml. EZ-link Sulfo-NHS-LC-Biotin (Pierce, cat. no. 21335) was dissolved in water to a final concentration of 1 mg/ml and a 5 and 10 fold molar excess was added to 500 mg of albumin in a total volume of 0.5 ml. The mixtures were incubated at room temperature for 30 min. Unbound biotin was removed by dialyzing against PBS using a dialysis cassette (Slide-A-Lyser, 10 kDa; Pierce).

Phage Display Selection

In total, five rounds of selection were carried out, using increasingly stringent conditions. After three initial rounds performed chiefly with a view to establish a suitable selection protocol, the resulting phage stocks were prepared from glycerol stock prepared as in Example 1. Selection was then carried out for two more cycles using the combinations of selection buffer, target concentration and solid support that are listed in Table 4.

TABLE 4

Selection conditions for HSA selection

| | Sample name | Selection buffer | Target conc. (pM) | Beads (μg) |
|---|---|---|---|---|
| Cycle 4 | A | Gelatin | 1000 | 100 |
| | B | Gelatin | 200 | 100 |
| | C | BSA | 400 | 100 |
| | D | BSA | 100 | 100 |
| Cycle 5 | A | Gelatin | 500 | 50 |
| | B | Gelatin | 50 | 50 |
| | C | BSA | 100 | 50 |
| | D | BSA | 10 | 50 |

All tubes and beads used in the selection procedure were pre-blocked in TPBSB (5%) (0.05% Tween20, 5% bovine serum albumin (BSA), 0.02% Na azide in PBS) or gelatin (0.5%) for 30 min under gentle agitation at room temperature and subsequently left with no agitation over night at 4° C.

Selection solutions (1 ml) contained biotinylated human serum albumin, phages, Na azide (0.02%), Tween 20 (0.05%) and either BSA (3%) or gelatin (0.1%) according to Table 4, and were prepared in PBS. The phages were incubated with biotinylated human serum albumin target at 4° C. during three days for Cycle 4 and during one day for Cycle 5, followed by 1 h incubation under agitation at room temperature. The selection samples were transferred to blocked streptavidin beads for 15 min under agitation at room temperature. The beads were washed 10 times with 1 ml of selection buffer (i.e. TPBSB (3%) (0.05% Tween20, 3% bovine serum albumin (BSA), 0.02% Na azide in PBS) or GT (0.1%) (0.1% gelatin, 0.1% Tween 20 and 0.02% Na azide in PBS)), followed by 10 washes with PBS where the second to last wash lasted for 2 hours. Phages were either eluted with 1000 ml 0.05 M Glycine-HCl, pH 2.2, for 10 min at room temperature, followed by immediate neutralization with 900 ml PBS supplemented with 100 ml 1 M Tris-HCl, pH 8.0, or eluted with 1000 μl trypsin (2 mg/ml) for 30 min at room temperature followed by addition of 1000 μl aprotinin. The eluted phages (¾ of the volume) were used to infect 50 ml log phase *E. coli* RR1ΔM15 cells (Rü ther, 1982, supra) after each cycle of selection. After 30 min incubation with gentle agitation and 30 min with vigorous agitation at 37° C., the cells were centrifuged and the pellet was dissolved in a smaller volume and spread on TSB+YE plates (30 g/l tryptic soy broth, 5 g/l yeast extract) and finally incubated over night at 37° C.

The cycles of selection resulted in a satisfying number of eluted phages.

Phage Stock Preparation

Cells from plates were re-suspended in TSB medium (30 g/l tryptic soy broth) and the cell concentration was determined by measuring the optical density at 600 nm assuming that $OD_{600}=1$ corresponds to $5 \times 10^8$ cells/ml. Cells were inoculated (approximately 100 times excess of cells compared to eluted phages) in 100 ml TSB+YE medium supplemented with 2% glucose and 100 mg/ml ampicillin and grown at 37° C. to approximately $OD_{600}=0.5$-$0.7$. Thereafter, 10 ml were transferred to a new flask and infected by 25 times excess of M13K07 helper phage ($1 \times 10^{12}$ cfu/ml; New England Biolabs, cat. no. NO3155) and incubated for 30 min with low agitation. Cells were centrifuged at 2000 g for 10 min and re-suspended in 100 ml TSB+YE medium supplemented with 100 mM isopropyl β-D-1-thiogalactopyranoside (IPTG), 50 mg/ml kanamycin and 100 mg/ml ampicillin and grown over night at 100 rpm and 25° C. A portion of the re-suspended cells was stored at –80° C. as a glycerol stock.

The induced culture was centrifuged at 2500 g for 10 min and phages in the supernatant were precipitated by adding ¼ of the volume of precipitation buffer (PEG/NaCl) and incubated on ice for 1 hour. Precipitated phages were pelleted by centrifugation at 10000 g at 4° C. for 30 min, re-suspended in 20 ml PBS and thereafter the phage solution was filtered through a 0.45 μm filter. The precipitation procedure was repeated and the phages were finally re-suspended in 1 ml PBS.

Selection solution was titrated after the selection together with wash and elution solutions after each round of selection. Phage solutions were diluted in sterile water in a microtiter plate and 100 μl log phase *E. coli* RR1ΔM15 cells were added to each phage dilution. After 20 min incubation at room temperature, 5 μl from each titration were dropped on a TYE plate (15 g agar, 10 g tryptone, 5 g yeast extract, 3 g NaCl supplemented with 2 glucose and 100 μg/ml ampicillin) and incubated over night at 37° C. The resulting colonies were counted and the titers (cfu/ml) calculated.

ELISA Analysis of Albumin Binding

Clones from each selection plus ABDwt were expressed and screened for HSA binding activity using an ELISA setup enabling detection of binders having a $K_D$ value of from 10 nM down to low pM against serum albumin. Randomly picked colonies were expressed in 96 deep-well plates by inoculating each colony into 1 ml TSB+YE medium supplemented with 100 mg/ml ampicillin and 1 mM IPTG and grown over night at 37° C. Cells were pelleted by centrifugation at 3000 g for 15 min, re-suspended in 400 μl PBS-T (0.5% Tween 20 in PBS) and frozen at –80° C. Frozen samples were thawed in a water bath and cell debris was pelleted at 3700 g for 40 min. Supernatants containing ABD variant-Zwt fusion proteins were collected and stored at 4° C. until used in ELISA as follows.

Microtiter wells (Costar) were coated over night at 4° C. with 100 μl of HSA and with the controls rat serum albumin (RSA), human serum albumin (HSA) and mouse serum albumin (MSA) in one well each, at a concentration of 0.4 μg/ml in ELISA coating buffer (0.1 M sodium carbonate, pH 9.5). The wells were blocked with blocking buffer (2% milk in PBS) for 2 h at room temperature. A volume of 100 μl of the prepared ABD variant-Zwt fusion proteins was added to each well, and the plates were incubated for 1.5 h at room temperature. Biotinylated IgG at a concentration of 0.5 mg/ml in washing buffer (0.5% Tween 20 in PBS) was added to the wells and incubated for 1.5 h, so that the Zwt moiety of any albumin binding fusion proteins could bind to IgG. Bound complexes were detected with horse radish peroxidase conjugated streptavidin (Dako, cat. no. P0397) diluted 1:5000 in washing buffer, and incubated for 1 h at room temperature. Developing solution was prepared by mixing an equal volume of TMB substrates A and B (ImmunoPure TMB, Pierce), and 100 μl was added to each well. After 30 min incubation in darkness, 100 μl stop solution (2 M $H_2SO_4$) was added. The plates were read at $A_{450}$ in an ELISA spectrophotometer (Basic Sunrise, Tecan). Prior to addition of each new reagent, four washes were done with washing buffer.

In total, 372 clones (93 clones from each selection denoted Sample A-D in Table 4) were randomly picked for analysis of their HSA binding activity using the ELISA set-up described above. The majority of the analyzed clones gave a higher signal to HSA as compared to the ABDwt interaction with rat serum albumin, which is a low pico molar binding (70 pM; unpublished results). Based on the result of this experiment, clones were picked for sequencing as described next.

Sequencing of ELISA Positive Clones

PCR fragments from selected colonies were amplified using oligonucleotides AFFI-69 (5'-gtgagcggataacaattcccctc-3') (SEQ ID NO: 534) and AFFI-70 (5'-cagcaaaaaaccccctcaagaccc-3') (SEQ ID NO: 535). Sequencing of amplified fragments was performed using ABI PRISM® dGTP, BigDye™ Terminator v3.0 Ready Reaction Cycle Sequencing Kit (Applied Biosystems) according to the manufacturer's recommendations and with the biotinylated oligonucleotide AFFI-202 (5'-biotin-gtgagcggataacaattcccctc-3') (SEQ ID NO: 536). The sequencing reactions were purified by binding to magnetic streptavid in-coated beads using a Magnatrix 8000 instrument (Magnetic Biosolutions), and finally analyzed on ABI PRISM® 3100 Genetic Analyser (Applied Biosystems).

The clones exhibiting the highest $A_{450}$ value in the ELISA screening were subjected to sequencing of their ABD variant insert. 257 different identified ABD variants were given the designation ABD#####, wherein ##### is a five-digit unique label for the variant in question. The sequences of these identified ABD variants are listed in FIG. 1 as SEQ ID NO:257-514. Based on the existing knowledge of the albumin binding properties of the wild-type or "parent" ABD, the albumin binding motifs of the identified ABD variants were deduced to reside in the two helices 2 and 3, corresponding to the stretch from amino acid position G16 to 141. The albumin binding motifs of the identified ABD variants were given the designation ABM#####, where ##### is a five-digit unique label for the motif in question. The sequences of the identified albumin binding motifs are listed in FIG. 1 as SEQ ID NO:1-257. Interestingly, a subset of the sequences identified comprised a spontaneous mutation at the position corresponding to position 38 in ABDwt, despite the fact that this position had not been randomized in the creation of the library of variants.

Sub-Cloning of ABD Variants into Plasmid pAY442

DNA encoding ABDwt (SEQ ID NO:515) and twelve clones from the selection were selected for sub-cloning into the expression vector pAY442 (Grönwall et al, supra). With reference to FIG. 1, the selected ABD variant clones were ABD00002, ABD00003, ABD00009, ABD00015, ABD00025, ABD00027, ABD00046, ABD00049, ABD00053, ABD00054, ABD00055 and ABD00245. Plasmids containing inserts encoding these ABD variant molecules were purified from 2 ml over night cultures (tryptic soy broth medium (30 g/l) supplemented with 2% glucose and 100 μg/ml ampicillin) of E. coli RR1ΔM15 cells (Rü ther, 1982, supra) using Qiagen Mini Kit (Qiagen) according to the manufacturer's recommendations.

DNA for ABDwt and ABD variant molecules was subcloned into the expression vector pAY442 by AccI-NotI PCR sticky end cloning (10 units/μl of each enzyme; New England Biolabs) using the primer pairs AFFI-780, -898 and AFFI-782, -899 as listed in Table 5:

Two overlapping PCR products for each ABD variant molecule were generated from the library vector pAY1075, resulting in approximately 25% correct fragments with an AccI-NotI site. The expression vector pAY442 was digested in two steps at 37° C. for 4 h using AccI and NotI in NEB4 buffer (20 mM Tris acetate, 10 mM magnesium acetate, 50 mM potassium acetate, 1 mM dithiothreitol, pH 7.9; New England Biolabs) and NEB3 buffer (50 mM Tris-HCl, 10 mM MgCl$_2$, 100 mM NaCl, 1 mM dithiothreitol, pH 7.9; New England Biolabs), respectively, and dephosphorylated with calf intestinal alkaline phosphatase (CIAP; Fermentas) for 1 h at 37° C. The cleaved plasmid and fragments were purified by QIAquick PCR purification kit (Qiagen) according to the manufacturer's recommendations.

The PCR products were hybridized and ligated into AccI-NotI digested and dephosphorylated pAY442 for 1 h at room temperature using T4 DNA ligase (5 units/μl; Fermentas). Part of the ligations were electroporated into E. coli BL21 (DE3) cells (F$^-$ ompT hsdS$_B$(r$_B^-$ m$_b^-$) gal dcm (DE3)) using a 1 mm cuvette and an ECM 630 set (BTX) using the parameters 1700 V, 200Ω and 25 μF. The cells were plated on tryptose blood agar base (TBAB) plates supplemented with 50 μg/ml kanamycin and incubated over night at 37° C. Positive clones were first verified on agarose gel of bacterial PCR products and finally with DNA sequence analysis.

Figure 8:
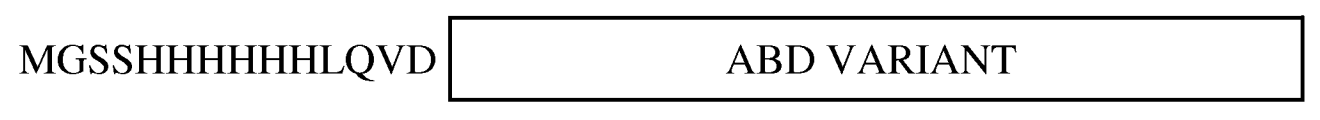

Clones of pAY442 containing a successfully sub-cloned ABD variant encode a construct that is schematically described in FIG. 8, i.e. essentially a His$_6$ tagged ABD variant.

Expression and Purification of His$_6$ Tagged ABD Variants

ABDwt and the twelve ABD variants, all sub-cloned in pAY442 as described above, were expressed in E. coli BL21 (DE3) as fusions to an N-terminal His$_6$-tag and purified by IMAC. A colony of each ABD variant was used to inoculate 5 ml TSB medium supplemented with 50 μg/ml kanamycin. The cultures were grown over night at 37° C. The following day, 50 μl of each culture were inoculated separately to 100 ml TSB+YE medium supplemented with 50 μg/ml kanamycin in a 1 liter flask. The cultures were grown at 100 rpm at 37° C. to an OD$_{600}$ of 0.7-1, after which IPTG was added to a final concentration of 0.5 mM and cells were incubated at room temperature over night at 100 rpm. Cultures were harvested by centrifugation at 8000 g for 5 minutes and pellets were stored in a freezer until protein preparation.

The His$_6$-tagged proteins were IMAC purified under denatured conditions using Ni-NTA Superflow columns and QIAsoft 4.1, protein/Ni-NTA Superflow 96 denaturing large scale 2 Vac4-24 samples, on a Biorobot 3000 (Qiagen). The buffer was exchanged to PBS using a dialysis cassette (Slide-A-Lyser, 3.5 kDa; Pierce cat. no. 66330) by dialyzing against 5 l PBS for 2 h followed by an additional dialysis over night.

Protein concentration was determined using $A_{280}$ and the BCA Protein Assay Reagent Kit (Pierce) as recommended by

TABLE 5

| Oligo | Oligonucleotide primers Sequence | |
|---|---|---|
| AFFI-780 | 5'-*P*-agacttagctgaagctaaagtcttagc-3' | (SEQ ID NO: 537) |
| AFFI-782 | 5'-acttagctgaagctaaagtcttagc-3' | (SEQ ID NO: 538) |
| AFFI-898 | 5'-gctttaaggtaatgcagctaaaat-3' | (SEQ ID NO: 539) |
| AFFI-899 | 5'-*P*-ggccgctttaaggtaatgcagctaaaat-3' | (SEQ ID NO: 540) | the manufacturer. The purity of the proteins was analyzed by SDS-PAGE on 4-12% Novex gels and stained with Coomassie Blue R, and this analysis showed that only small amounts of impurities were present.

Biosensor Analysis of ABD Variants' Affinity for HSA and MSA

Biosensor analysis on a Biacore2000 instrument (Biacore) was performed with MSA, HSA and RSA immobilized by amine coupling onto the carboxylated dextran layer on the surfaces of CM-5 chips (research grade; Biacore) according to the manufacturer's recommendations. Surface 1 on the chip was activated and deactivated and used as reference cell during injections, whereas surface 2 comprised MSA immobilized with 350 RU (resonance units), surface 3 comprised HSA immobilized with 360 RU and surface 4 comprised RSA immobilized with 340 RU. The ABD variants and ABDwt expressed and purified as described above were diluted in HBS-EP (Biacore) to 25 nM and injected at a constant flow-rate of 25 µl/min for 10 minutes, followed by injection of HBS-EP for 30 minutes. The surfaces were regenerated with two injections of 20 µl 15 mM HCl followed by 0.05% SDS and one more injection of 20 µl HCl.

The Biacore study was not carried out with a view to determine the exact parameters for the variants' affinity for human and mouse serum albumin, but the results provide a qualitative measure of the relative affinities of these molecules for albumin. Results for binding to MSA and HSA are presented in Table 6.

TABLE 6

Biosensor analysis of ABD variants' binding to serum albumin from mouse and human

|  | MSA $K_D$ (M) | HSA $K_D$ (M) |
| --- | --- | --- |
| ABDwt | $4.9 \times 10^{-9}$ | $1.5 \times 10^{-9}$ |
| ABD00025 | $2.2 \times 10^{-9}$ | $2.7 \times 10^{-11}$ |
| ABD00049 | $7.9 \times 10^{-10}$ | $2.2 \times 10^{-11}$ |
| ABD00245 | $6.5 \times 10^{-10}$ | $6.0 \times 10^{-11}$ |
| ABD00003 | $3.3 \times 10^{-9}$ | $1.6 \times 10^{-11}$ |
| ABD00009 | $1.9 \times 10^{-9}$ | $5.4 \times 10^{-11}$ |
| ABD00053 | $5.9 \times 10^{-9}$ | $1.1 \times 10^{-11}$ |
| ABD00054 | $1.3 \times 10^{-9}$ | $2.0 \times 10^{-11}$ |
| ABD00015 | $3.2 \times 10^{-9}$ | $4.5 \times 10^{-11}$ |
| ABD00027 | $1.5 \times 10^{-9}$ | $4.1 \times 10^{-11}$ |
| ABD00046 | $8.9 \times 10^{-9}$ | $1.2 \times 10^{-10}$ |
| ABD00055 | $1.1 \times 10^{-9}$ | $5.4 \times 10^{-11}$ |

As is evident from this table, all tested ABD variants had a substantially higher affinity for human serum albumin than the wild type ABD molecule, as evidenced by $K_D$ values at least one order of magnitude lower, frequently approaching two orders of magnitude lower. Furthermore, comparable and/or higher affinities towards mouse serum albumin was also exhibited by all variants.

Example 3

Additional Biosensor Characterization of Selected ABD Variants

Summary

In this example, selected ABD variants ABD00003, ABD00053 and ABD00239 plus ABDwt were all sub-cloned in pAY442 as described in Example 2 above, and expressed in a larger scale and purified with His Gravitrap™ kit. The expressed molecules were characterized for affinity to HSA using a Biacore instrument.

Protein Expression and Purification of His$_6$ Tagged ABD Variants

ABD00003, ABD00053, ABD00239 and ABDwt were expressed in E. coli BL21(DE3) cells as fusions to an N-terminal His$_6$-tag using constructs as described in Example 2, and purified by IMAC. A colony of each ABD variant was used to inoculate 10 ml TSB medium supplemented with 50 µg/ml kanamycin. The cultures were grown over night at 37° C. The following day, 500 µl of each culture were inoculated separately to 500 ml TSB+YE medium supplemented with 50 µg/ml kanamycin in a 5 liter flask. The cultures were grown at 100 rpm and 37° C. to an OD$_{600}$ of 0.7-1, which was followed by addition of IPTG to a final concentration of 0.5 mM and incubated at room temperature over night. Cultures were harvested by centrifugation at 8000 g for 5 minutes and pellets were stored at −20° C. until protein preparation.

The His$_6$-tagged proteins were IMAC purified under denaturing conditions using His-Gravitrap™ kit (GE Healthcare). The pellets were re-suspended (vortexed) in 20 ml of the denaturation buffer B-7M (100 mM NaH$_2$PO$_4$, 10 mM Tris-Cl, 7 M urea, pH 8) and 8 µl benzonase was added.

The solutions were incubated for 30 minutes at room temperature and 200 rpm. An additional 20 ml of buffer B-7M was added and the solutions were transferred to 50 ml Falcon tubes and sonicated on ice as follows: 3 s on/off during 3 min and with 40% amplitude. Cell debris was removed by centrifugation at 25000 g for 40 min. The Gravitrap™ columns were equilibrated with buffer B-7M and the samples were applied. The columns were then washed with 10 ml buffer B-7M, 20 ml binding buffer (20 mM NaPO$_4$, 500 mM NaCl, 20 mM imidazole) and finally with 10 ml wash buffer (20 mN NaPO$_4$, 500 mM NaCl, 60 mM imidazole). The ABD molecules were eluted with 3 ml elution buffer (20 mN NaPO$_4$, 500 mM NaCl, 500 mM imidazole).

A buffer exchange to PBS pH 7.2 using a Slide-A-Lyser dialysis cassette (3.5 kDa; Pierce, cat. no. 66330) was made by dialyzing against 5 l PBS pH 7.2 for 2 hours followed by an additional dialysis over night and finally a buffer exchange to PBS pH 5 using PD 10 columns (GE Healthcare) was performed according to manufacturers' recommendations. Protein concentration was determined using Abs$_{280}$. The purity of the proteins were analyzed by SDS-PAGE on 4-12% Novex gels and stained with Coomassie Blue R.

The proteins were successfully expressed and purified in an acceptable yield. The analysis with gel electrophoresis showed that no impurities were present (not shown).

Biosensor Analysis for Binding Kinetics to Human Serum Albumin

Biosensor analysis on a Biacore2000 instrument (Biacore) was performed with HSA (SIGMA, cat. no. A3782-5G) immobilized by amine coupling onto the carboxylated dextran layer on surfaces of a CM-5 chip (research grade; Biacore), according to the manufacturer's recommendations. The immobilization of HSA resulted in a signal of 450 resonance units. One cell surface on the chip was activated and deactivated and used as reference cell during injections. The purified His$_6$-ABD samples were diluted in HBS-EP (Biacore) to 4, 10, 40, 100 and 400 nM for ABDwt and to 0.2, 0.8, 2, 5 and 20 nM for the selected ABD variants. The samples were injected at a constant flow-rate of 25 µl/min for 10 min, followed by injection of HBS-EP for 3 hours. The surfaces were regenerated with two injections of 20 µl of 5 and 10 mM HCl. The $K_D$, $k_a$ and $k_d$ values were estimated and are given in Table 7, confirming the result of Example 2 that molecules exhibiting very high affinities to HSA had been obtained.

TABLE 7

Kinetic parameters ($k_a$, $k_d$ and $K_D$) to HSA of purified ABD molecules

| | $k_a$ (Ms$^{-1}$) | $k_d$ (s$^{-1}$) | $K_D$ (M) |
|---|---|---|---|
| ABDwt | $5.5 \times 10^5$ | $6.5 \times 10^{-4}$ | $1.2 \times 10^{-9}$ |
| ABD00003 | $8.0 \times 10^6$ | $3.0 \times 10^{-5}$ | $3.8 \times 10^{-12}$ |
| ABD00053 | $3.0 \times 10^6$ | $1.5 \times 10^{-5}$ | $5.0 \times 10^{-12}$ |
| ABD00239 | $3.0 \times 10^7$ | $1.5 \times 10^{-5}$ | $5.0 \times 10^{-13}$ |

Example 4

Primate Immunogenicity and Pharmacokinetics of a Z Variant Polypeptide Fused to a First ABD Variant Summary Previous studies in mouse and rat have shown that various Z variant molecules fused to ABDwt generate a lower antibody response compared to the Z variant alone. The aim of this study was 1) to confirm these results in primates and expand it to a mutated variant of ABD exhibiting a 10$^3$-fold higher binding affinity for albumin compared to ABDwt, and 2) to compare the serum half-lives of ABD-fused and naked Z variants. A Z variant with affinity for the HER2 receptor was administered to primates with or without the ABD variant as fusion partner. Repeated immunization and bleeding proceeded over a 45-day period. The specific antibody responses against, and the serum half-lives of, the Z variant molecules were analyzed by ELISA assays.

Molecules Studied

Z00342: a variant of protein Z, in turn derived from the B domain of staphylococcal protein A, with an affinity for the HER2 receptor. This variant was produced by recombinant DNA technology. Purification was performed using anion exchange and reverse phase chromatography methods followed by endotoxin removal on a Detoxi-Gel™ AffinityPak™ Pre-packed Column (Pierce, cat no 2034) according to the manufacturer's instructions. A detailed description of the Z00342 molecule is given in Orlova et al, Cancer Res 66:8, 4339-48 (2006), where it is denoted $Z_{Her2:342}$.

Z00342-ABD00003: a fusion protein between the Z variant Z00342 and the variant ABD molecule ABD00003 selected in Example 2. This fusion protein was produced by recombinant DNA technology. Purification was performed using affinity capture on HSA-sepharose and reverse phase chromatography followed by endotoxin removal as above.

Methods

Administration and sampling schemes: The animal study was performed at SMI (Smittskyddsinsitutet) in Solna, Sweden, with permission from the local ethical animal committee (N196/06). The primates were sedated before administration of the test molecules and blood sampling, by an intramuscular administration of ketamine (Ketalar®). 10 individual cynomolgus primates, *Macaca fascicularis*, divided into two groups were intravenously injected with the test molecules according to the scheme in Table 8.

TABLE 8

Administration of test molecules

| Group | Animal number | Molecule | Route of adm | mg/kg/ injection | ml/animal/ injection |
|---|---|---|---|---|---|
| 1 | 9023, 9039, 10025, 10105, 11019 | Z00342 | i.v. | 0.5 | 1 |

TABLE 8-continued

Administration of test molecules

| Group | Animal number | Molecule | Route of adm | mg/kg/ injection | ml/animal/ injection |
|---|---|---|---|---|---|
| 2 | 12031, 12041, 12047, 12061, 12065 | Z00342-ABD00003 | i.v. | 0.5 | 1 |

Time points for administration and bleeding are summarized in Table 9. PK refers to samples taken for the pharmacokinetic study. Blood was stored at 4° C. over night and sera were subsequently kept at −20° C.

TABLE 9

Time points for administration of test molecule and blood sampling

| Day | Action |
|---|---|
| 0 | Bleeding at 0, 30, 60 minutes, 4 hours (PK) & Injection 1 |
| 1 | Bleeding (PK) |
| 2 | Bleeding (PK) |
| 3 | Bleeding (PK) |
| 7 | Bleeding (PK) & Injection 2 |
| 14 | Bleeding & Injection 3 |
| 21 | Bleeding & Injection 4 |
| 28 | Bleeding & Injection 5 |
| 35 | Bleeding & Injection 6 |
| 45 | Bleeding |

General ELISA Method:

In general, a volume of 50 µl per well was used for all incubation steps except for blocking where a volume of 100 µl was used. Plates were coated over night at 4° C. in coating buffer (15 mM Na$_2$CO$_3$, 35 mM NaHCO$_3$, pH 9.6) and washed with tap water. Blocking and dilutions were done in PBS with 0.5% casein. Incubation times at room temperature were 1-2 hours for blocking and serum, 1 hour for secondary antibody and 10 min for substrate solution (ImmunoPure® TMB, Pierce, cat no 34021). Washing with 4×250 µl PBS-T (PBS with 0.05% Tween 20) per well was carried out between all steps, using an automated ELISA SkanWasher 300 (Skatron). The color reaction was stopped by addition of 50 µl 2 M H$_2$SO$_4$ and plates were read at 450 nm using an Ultra384 plate reader (Tecan) equipped with the Magellan software v3.11 (Tecan).

Anti-Z00342 IgG Specific ELISA:

Plates were coated with 0.3 µg/ml of Z00342 diluted in coating buffer and incubated over night at 4° C. After washing, plates were blocked as described above. Sera from primates were added in two-fold dilution series starting from 1/100. Purified serum from hyperimmunized primate was used as positive control and added in a two-fold dilution series starting from 8 µg/ml. Following incubation, plates were washed and a secondary, HRP conjugated anti-human IgG antibody (Southern Biotech cat. no. 2040-05) (diluted 1/10000) was added. After the final incubation, plates were washed and developed as described above.

Serum-Z Specific ELISA for PK Analysis:

Plates were coated with 2 µg/ml affinity purified goat anti-Z Ig (produced in-house and specific for an epitope common to all Z variants) and incubated over night at 4° C. After washing, plates were blocked as described above. Sera from primates injected with Z00342 or Z00342-ABD00003 were added in two-fold dilution series starting from 1/40 (for Z00342) or 1/80 (for Z00342-ABD00003). Standards of each molecule were added in a two-fold dilution series starting from 20 ng/ml. After incubation, plates were washed and the second step antibody was added (2 µg/ml of a rabbit IgG against Z (produced in-house) for Z00342; 1/5000 of a rabbit IgG against Z-ABD (produced in-house) for Z00342-ABD00003). Following incubation, plates were washed and HRP conjugated anti-rabbit Ig (Dako cat. no. 0448) diluted 1:5000 was added. After the final incubation, plates were washed and developed as described above.

Results

Figure 9A:
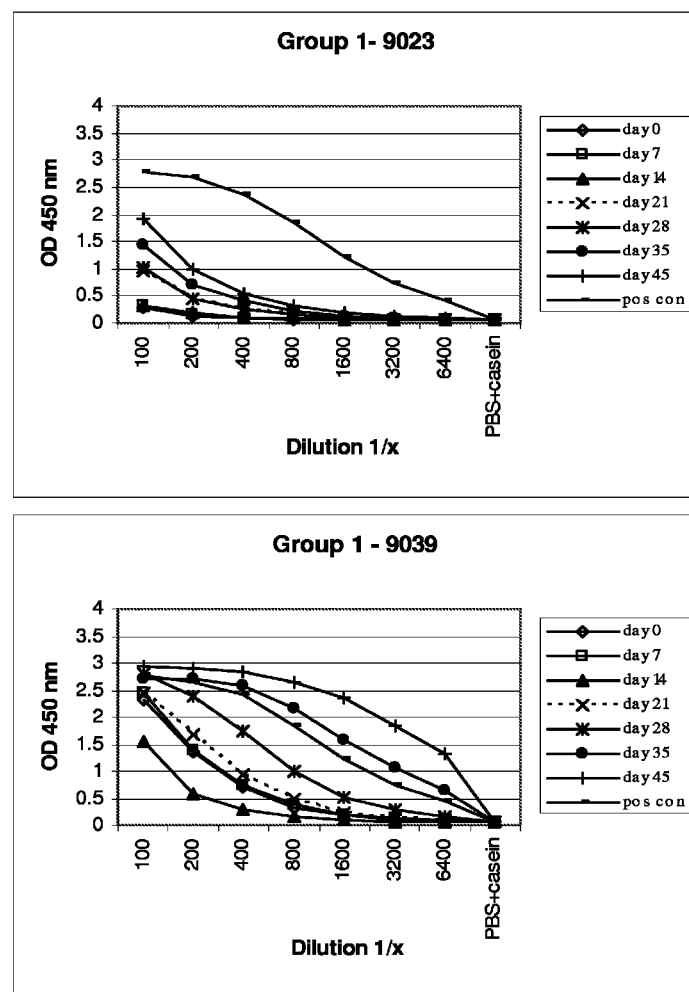
FIGS. 9A-9C show ELISA titration curves for serum obtained at days 0-45 from primates injected with Z00342 as described in Example 4, when analyzed on ELISA plates coated with Z00342.
Figure 9B:
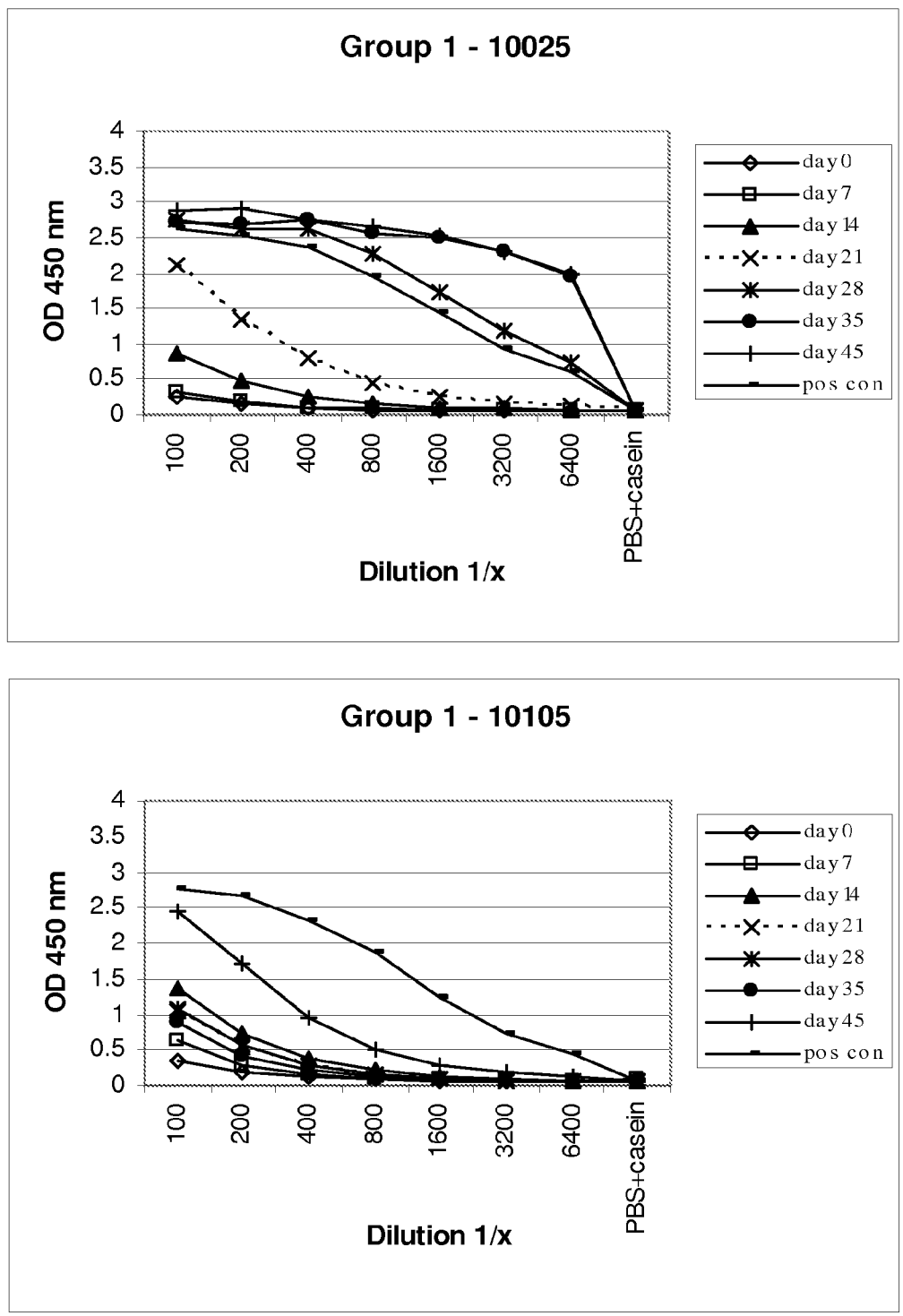
Figure 9C:
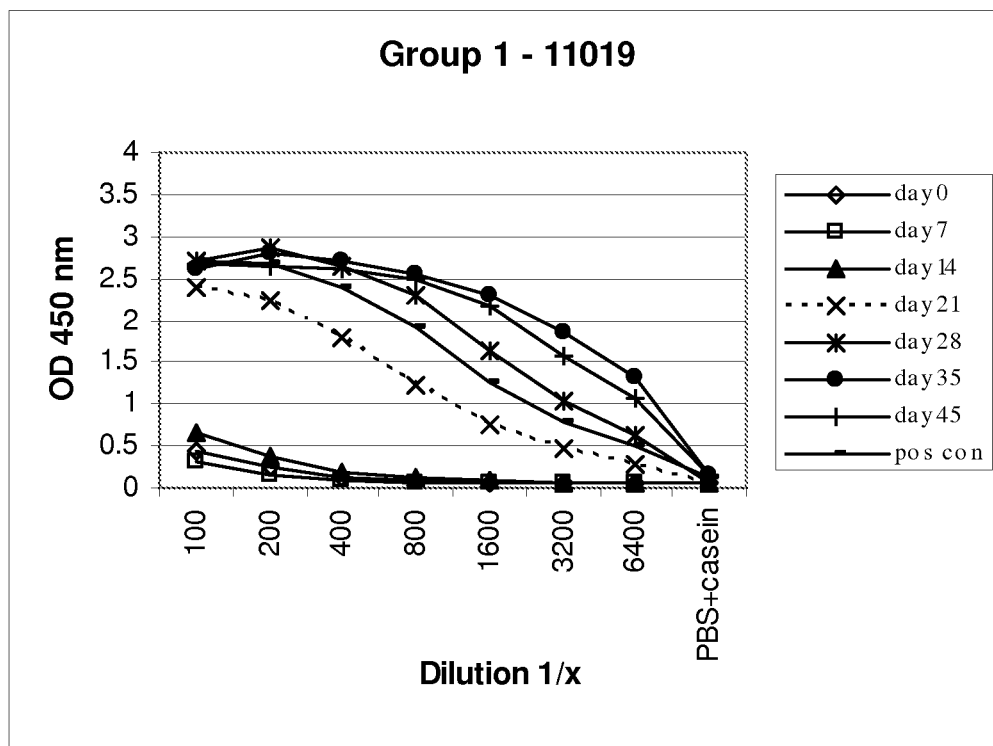

IgG Specific for Z in Primates Injected with Z00342:

The serum from each bleeding was analyzed by ELISA for the presence of IgG specific for Z variants (FIGS. 9A-9C). Low levels of IgG were detected at day 0 except for one primate (9039) that had moderate levels of pre-formed antibodies. After day 14, the antibody titer increased steadily and reached a maximum at day 28-35 in three of the animals (9039, 10025, 11019), whereas two showed a low antibody response (9023 and 10105) throughout the 45 day period.

Figure 10A:
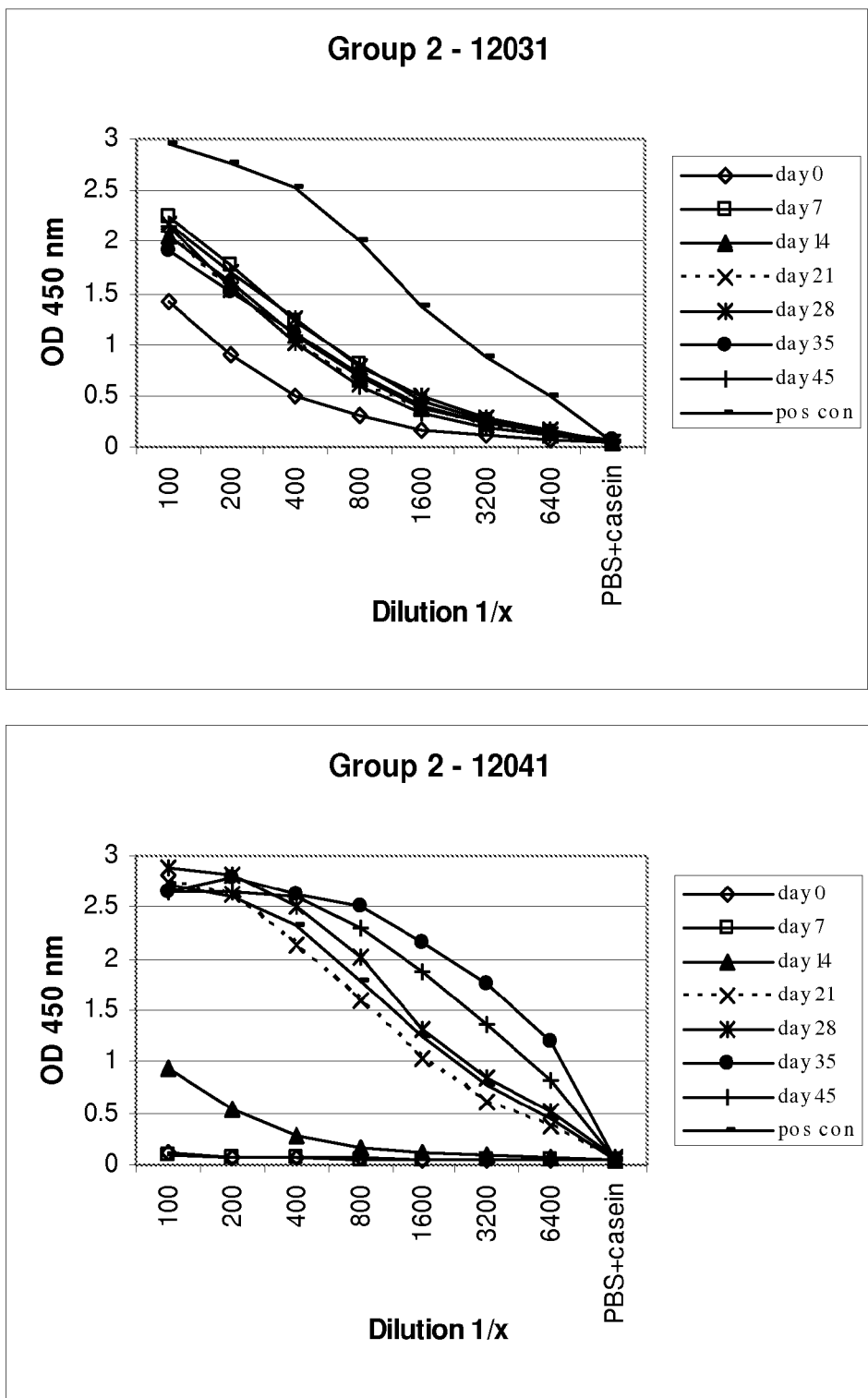
FIGS. 10A-10C show ELISA titration curves for serum obtained at days 0-45 from primates injected with Z00342-ABD00003 as described in Example 4, when analyzed on ELISA plates coated with Z00342-ABD00003.
Figure 10B:
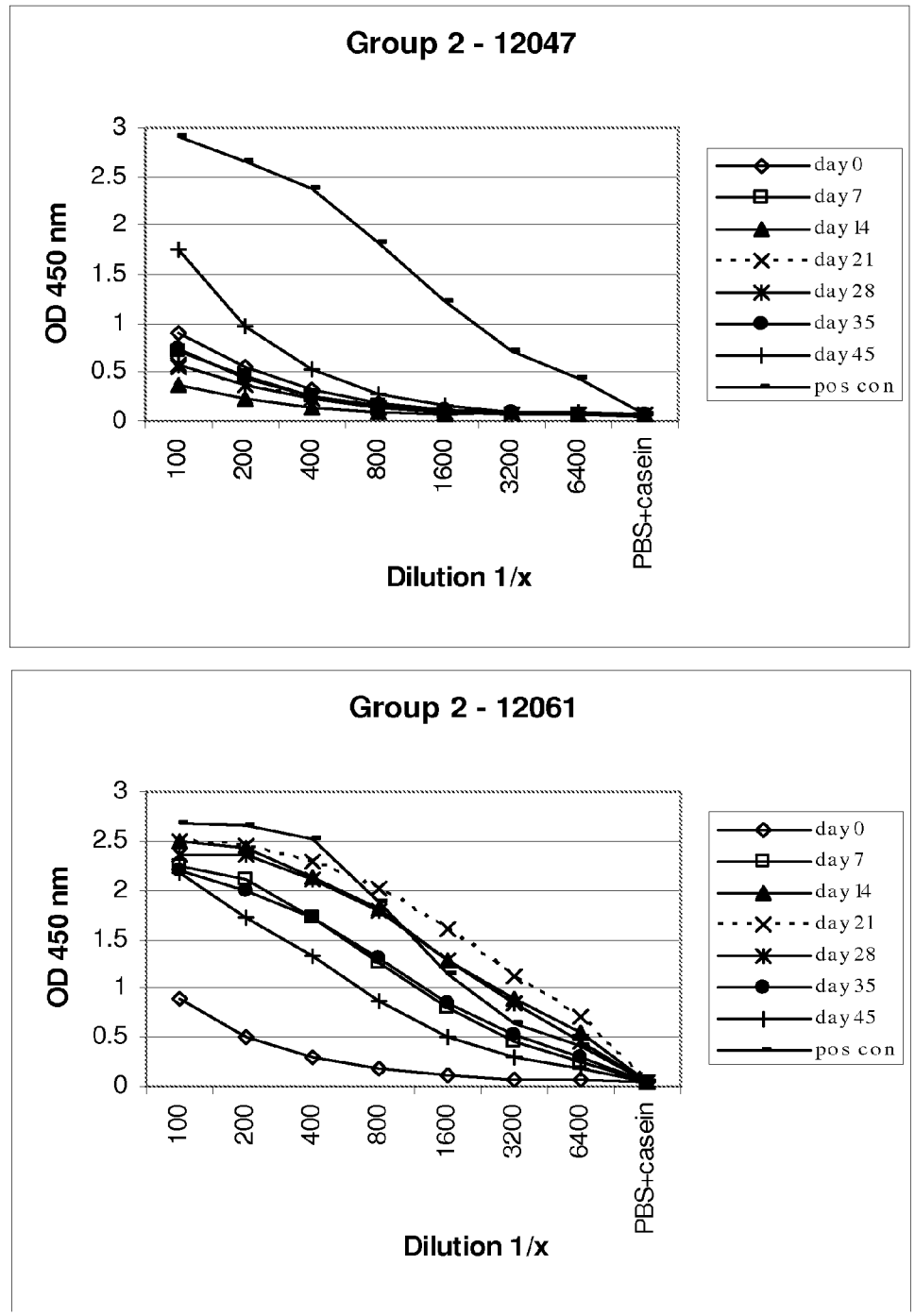
Figure 10C:
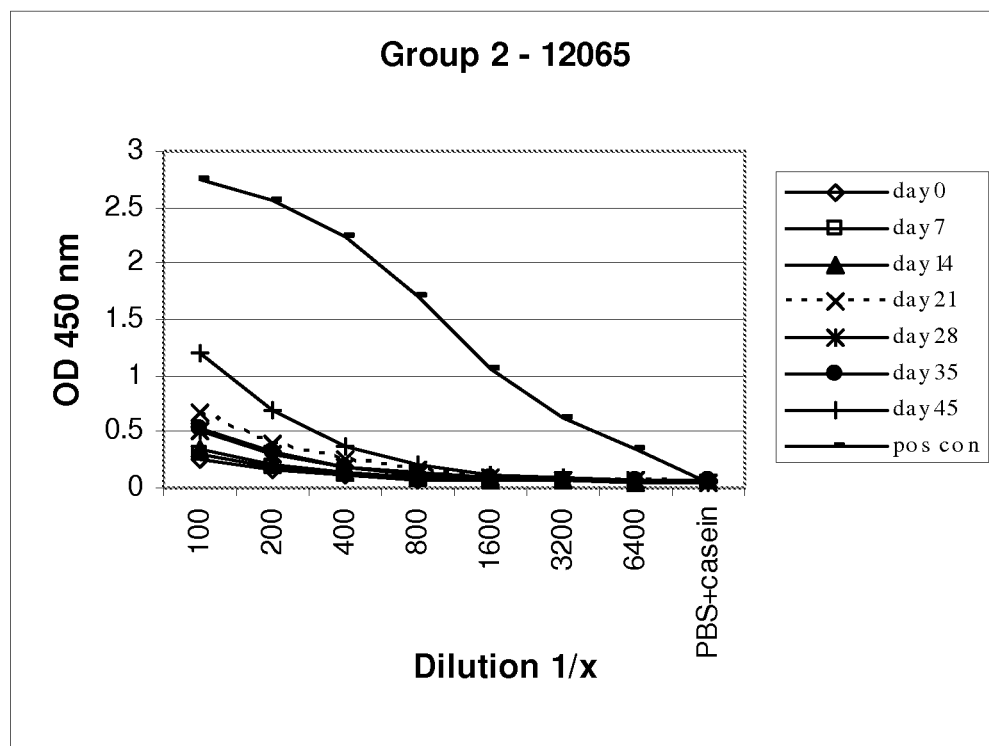

IgG Specific for Z in Primates Injected with Z00342-ABD00003:

The serum from each bleeding was analyzed by ELISA for the presence of IgG specific for the Z-ABD00003 molecule (FIGS. 10A-10C). No antibody response was observed in two of the primates (12047 and 12065), whereas two primates (12041 and 12061) showed a high response. The fifth primate (12031) had high pre-serum levels of antibodies that were barely altered during the 45-day period.

Figure 11:
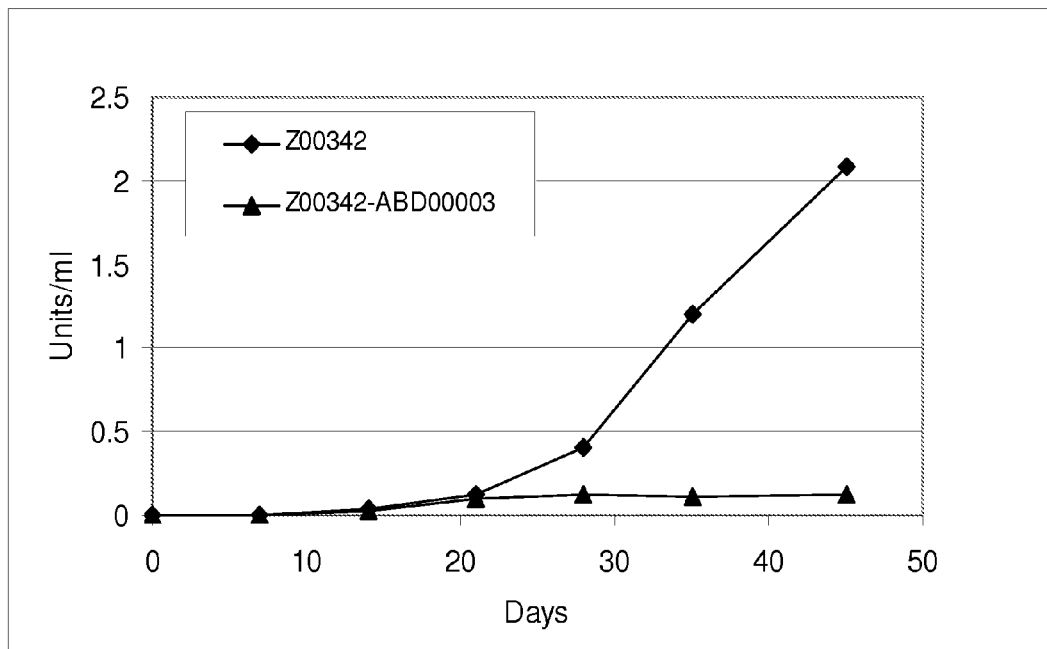
FIG. 11 shows the median concentration of IgG specific for Z variants in serum obtained at days 0-45 from primates injected with Z00342 and Z00342-ABD00003 as described in Example 4.
Figure 13A:
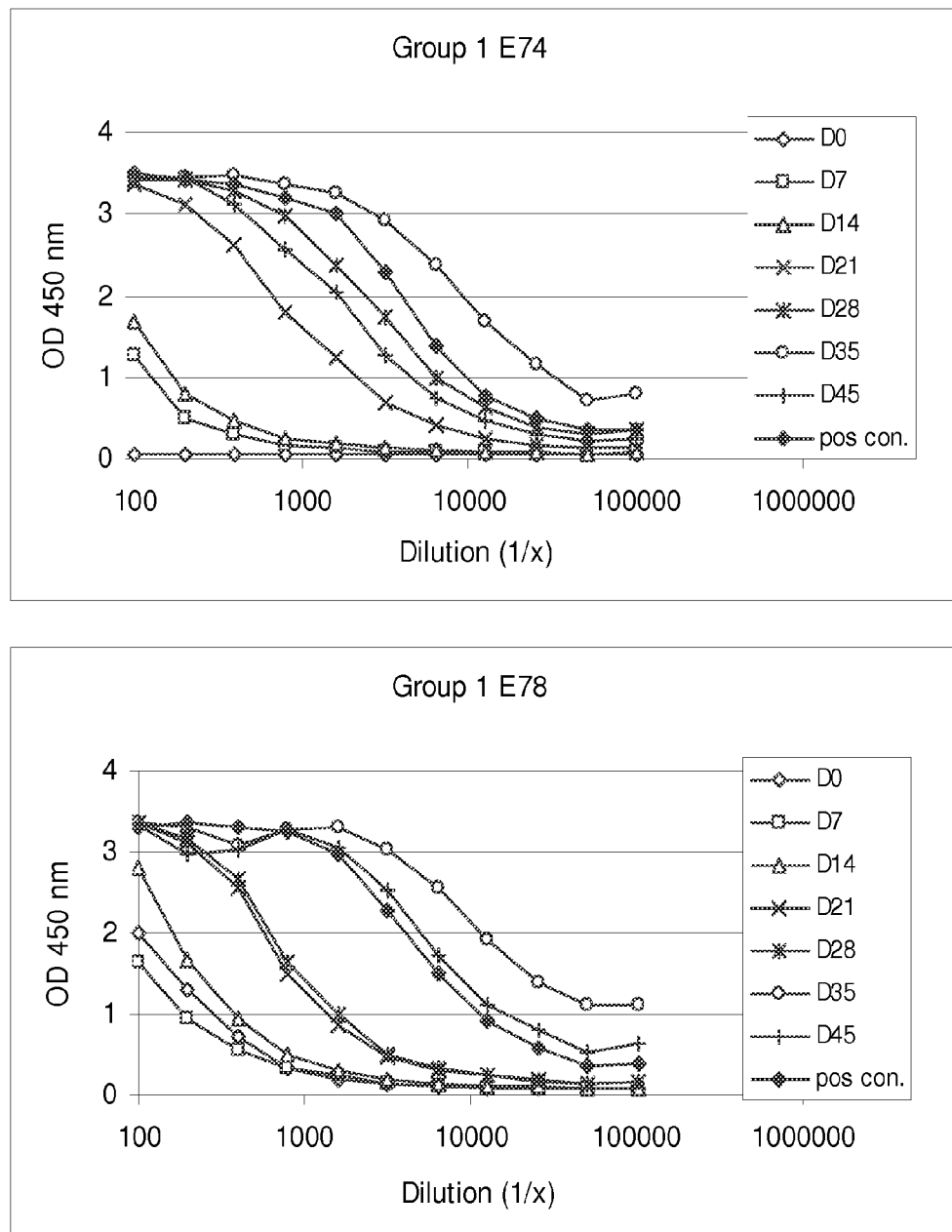
FIGS. 13A-13B show ELISA titration curves for serum obtained at days 0-45 from primates injected with (Z01154)$_2$ as described in Example 5, when analyzed on ELISA plates coated with (Z01154)$_2$.
Figure 13B:
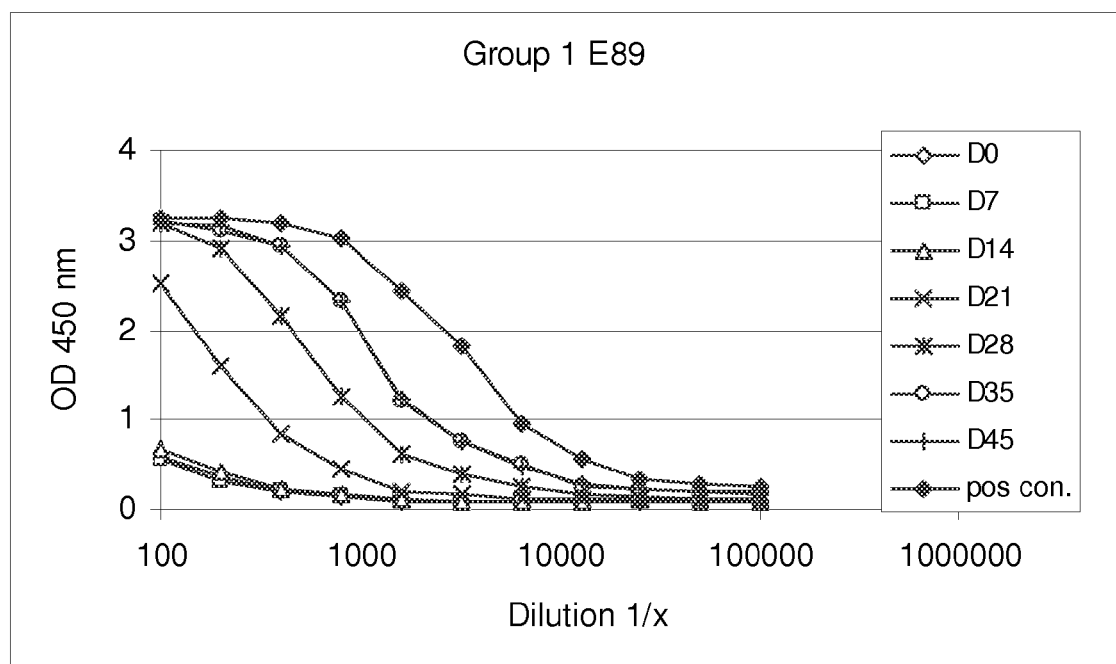
Figure 14B:
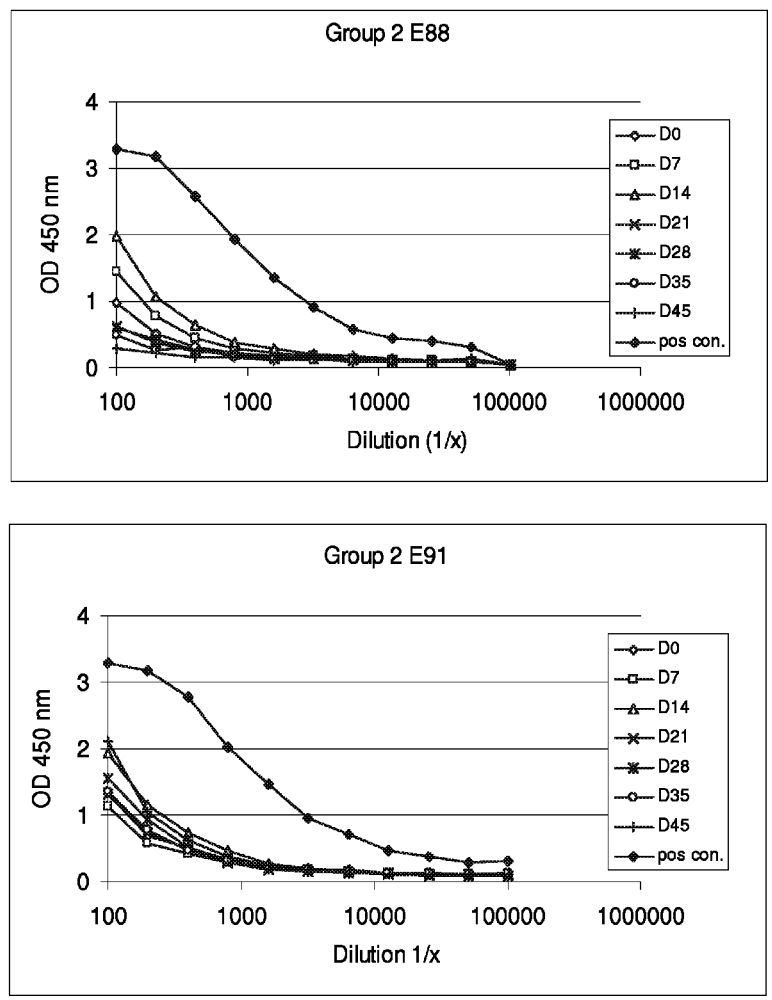

Concentration of Antibodies Specific for Z Variants:

The concentration of IgG specific for Z variants in the sera was calculated by linear regression using the positive control as standard (FIG. 11). Individual variations were seen within each group of primates. At day 45, the median concentration of specific IgG in groups 1 and 2 was 2 and 0.1 units/ml respectively, indicating that the fusion to ABD00003 decreases the antibody response against Z00342.

Pharmacokinetics of Z00342 in Serum:

The circulation times of Z00342 and Z00342-ABD00003 were compared in a pharmacokinetic analysis. The concentrations of the molecules over time were calculated from standard curves generated from dilution series of known amounts of Z00342 and Z00342-ABD00003, respectively. The results show that ABD-fused Z00342 fused to ABD00003 remains longer in the blood circulation compared to Z00342 alone (FIG. 12). Z00342 disappeared from the circulation within 4 hours whereas the ABD00003-fused molecules were still detectable after 7 days.

Summary

The results of this study indicate that the ABD-fused Z variant molecule generates a lower immune response as well as exhibiting an extended elimination half-life in comparison with the Z variant molecule without an albumin binding fusion partner.

Example 5

Primate Immunogenicity of a Z Variant Polypeptide Fused to a Second ABD Variant Molecules Studied In this extension of Example 4, a second variant of ABD with even higher affinity for albumin ($K_D=10^{-13}$ M), was fused to a dimeric Z variant and used for an immunogenicity study in primates.

$(Z01154)_2$: A dimeric variant of protein Z, in turn derived from the B domain of staphylococcal protein A. This dimer variant was produced by recombinant DNA technology. Purification was performed using anion exchange, reverse phase chromatography and cation exchange methods before endotoxin removal on a Detoxi-Gel™ AffinityPak™ Pre-packed Column (Pierce cat no 2034). A detailed description of the monomeric Z01154 molecule is given in Gunneriusson E et al, Protein Eng 12:10, 873-878 (1999), where it is denoted $Z^{Taq4:1}$.

$(Z01154)_2$-ABD00239: a fusion protein between the $(Z01154)_2$ dimer and the variant ABD molecule ABD00239 selected in Example 2. This fusion protein was produced by recombinant DNA technology. Purification was performed using affinity capture on HSA-sepharose and reverse phase chromatography followed by endotoxin removal as above.

Methods

Administration and Sampling Schemes:

The animal study was performed at SMI (Smittskyddsinsitutet) in Solna, Sweden, with permission from the local ethical animal committee (N196/06). The primates were sedated before administration of test molecule and blood sampling, by an intramuscular administration of ketamine (Ketalar®). 7 individual cynomolgus primates, *Macaca fascicularis*, divided into two groups of three and four respectively, were intravenously injected with the test molecules as outlined in Table 10.

TABLE 10

Administration of test molecules

| Group | Animal number | Molecule | Route of adm | mg/kg/ injection | ml/animal/ injection |
|---|---|---|---|---|---|
| 1 | E74, E78, E89 | $(Z01154)_2$ | i.v. | 0.5 | 1 |
| 2 | E75, E87, E88, E91 | $(Z01154)_2$-ABD00239 | i.v. | 0.5 | 1 |

Time points for administration and blood sampling are summarized in Table 11.

TABLE 11

Time points for administration of test molecule and blood sampling

| Day | Action |
|---|---|
| 0 | Bleeding 1 & Injection 1 |
| 7 | Bleeding 2 |
| 14 | Bleeding 3 & Injection 2 |
| 21 | Bleeding 4 |
| 28 | Bleeding 5 & Injection 3 |
| 35 | Bleeding 6 |
| 45 | Bleeding 7 |

Analysis of Plasma Samples by Specific ELISA:

Plates were coated with $(Z01154)_2$ or $(Z01154)_2$-ABD00239 diluted in coating buffer (15 mM $Na_2CO_3$, 35 mM $NaHCO_3$, pH 9.6) to a final concentration of 2 μg/ml. 50 μl solution was used per well and plates were incubated at 4° C. over night. Blocking with PBS+0.5% casein was performed at room temperature for 1-2 h. Serum was added in two-fold dilution series starting from a 1/100 dilution in blocking buffer. Purified serum from hyperimmunized primate was used as a positive control. Incubation was performed at room temperature for 1-2 hours and washing with 4×175 μl PBS-T (PBS with 0.05% Tween 20) per well was carried out using an automated ELISA SkanWasher 300 (Skatron). Incubation with secondary HRP-conjugated goat anti-human IgG F(ab)2 (Jackson cat. no. 109-035-097), diluted 1:5000 in blocking buffer, was performed at room temperature for 1-2 h. Automated washing was carried out as above. Detection was enabled using ImmunoPure® TMB (Pierce cat. no. 34021) where the reaction was quenched after 12 min by addition of 2 M $H_2SO_4$. Plates were read at 450 nm using an Ultra384 plate reader (Tecan) equipped with the Magellan software v3.11 (Tecan).

Results

Immunization with $(Z01154)_2$ and $(Z01154)_2$-ABD00239:

Sera from primates immunized with naked or ABD00239-fused $(Z01154)_2$ were titrated on $(Z01154)_2$ and $(Z01154)_2$-ABD00239 coated plates respectively, and the titration curves are shown in FIGS. 13A-13B and FIGS. 14A-14B. Serum from hyperimmunized monkey was included in the titration as positive control. The absorbance of the positive control at 1600× dilution was set to 100 and used for normalization. FIG. 15 shows normalized values of the individual responses. The results show that all three animals responded against $(Z01154)_2$, although the response in one primate (E89) was of a lower magnitude. In contrast, only one out of four animals responded against $(Z01154)_2$-ABD00239.

Example 6

Increased Solubility of Doxorubicin Conjugate After Complexation with Albumin

Summary

Conjugates were produced between the fusion protein ABDwt-$(Z00342)_2$-Cys (a recombinantly produced fusion protein comprising the wild-type ABD domain and a dimer of a Z variant, Z00342, with affinity for the HER2 receptor) and the non-polar molecule Maleimide-Spacelinker-Doxorubicin, the structural formula of which is given below.

Both the free linker and the conjugate have low solubility in aqueous solvents. For example, 30% organic solvent is needed to keep the conjugate in solution. However, the addition of human serum albumin to an aqueous solution greatly improves solubility.

Conjugation

Maleimide-Spacelinker-Doxorubicin (Syntarga B.V., Netherlands) was dissolved in N,N-dimethyl formamide (Sigma, cat. no. D-4551) to a final concentration of 4 μmol/ml, and stored at −80° C. before use. 4 ml of the fusion protein ABDwt-$(Z00342)_2$-Cys, 1.9 mg/ml in PBS, was reduced with 20 mM DTT (Acros Organics, cat. no. 165680250) at 40° C. for 30 minutes. Excess DTT was removed by buffer exchange on PD-10 columns to PBS (2.68 mM KCl, 1.47 mM $KH_2PO_4$, 137 mM NaCl, 8.1 mM $Na_2HPO_4$, pH 7.4). The protein sample was adjusted to 30% (v/v) organic solvent by addition of 3 ml acetonitrile (AcN, Merck, cat. no. 1.14291.2500). 198 μl, or a two-fold molar excess, of Maleimide-Spacelinker-Doxorubicin was added to the protein solution. After mixture for 30 minutes, the solution was incubated at 4° C. overnight. The reaction mixture was finally purified on a HiPrep 26/10 desalting column (GE, cat. no. 17-5087-01) equilibrated with deionized water/AcN (70:30, v/v). The protein concentration was determined to be 0.44 mg/ml by measuring the UV absorption at 280 nm.

Protein aliquots of 1.1 mg were lyophilized in an Alpha 2-4 LSC freeze dryer (Martin Christ GmbH, Germany). The vials were filled with nitrogen after finished lyophilization, capsulated and stored at 4° C.

Solubility Study

Three solutions were used for the solubility test:

1. DMEM, Dulbecco's modified Eagle's medium (Cambrex Bio Science, cat. no. BE12-917F),
2. DMEM as in 1, but supplemented with human serum albumin (HSA), 6 mg/ml (Sigma, cat. no. A1887-5G), and

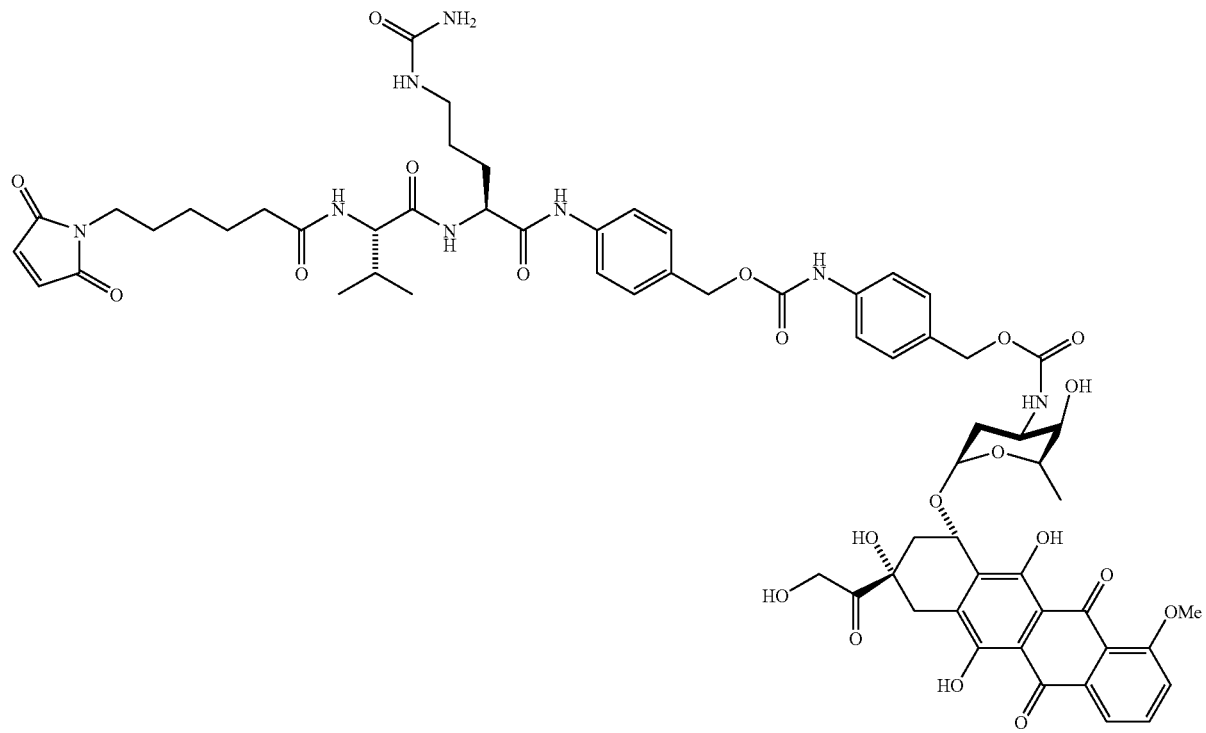

3. DMEM as in 1, but supplemented with 10% fetal calf serum (FCS).

Solutions 1 and 2 were filtered through a 0.22μ Millex-GV sterile filter (Millipore, cat. no. SLGV033RB).

Lyophilized conjugate was re-dissolved in vials containing 0.5 ml of each solution respectively. After 30 min incubation at 37° C., samples were evaluated by visual inspection. A large fraction of undissolved material was seen in the vials with solutions 1 and 3, while no visible precipitates were observed in the vial with solution 2.

LC-MS Analysis of Reconstituted Conjugate

30 μl from each vial (solutions 1-3) was centrifuged at 13000 rpm for 10 min in an eppendorf centrifuge. 20 μl of the resulting supernatant was analyzed by liquid chromatography with online mass-spectrometric detection (Agilent 1100, LC-MS). The column, Zorbax 300SB-C18 (4.6×150 mm, 3.5 u), was equilibrated with 65% solvent A (0.1% TFA in deionized water) and 35% solvent B (0.1% TFA in AcN) at a flow rate of 0.5 ml/min. The UV absorption at 220, 280, 254 and 495 nm were recorded. Sample components were eluted with a shallow linear gradient from 50-60% solvent B over 35 min. The peak area, corresponding to the amount of conjugate molecule in solution, was compared between the samples.

The results are shown in Table 12. Conjugate dissolved in DMEM supplemented with HSA (solution 2) showed a ten-fold larger area compared to the sample dissolved in DMEM only (solution 1), and a four-fold larger area compared to the sample dissolved in DMEM supplemented with 10% FCS (solution 3).

TABLE 12

| LC-MS analysis of reconstituted conjugate | | |
|---|---|---|
| Solvent | Peak area (mAU * s) | Ratio vs DMEM |
| DMEM | 2347.4 | 1.00 |
| DMEM + HSA | 22659.6 | 9.65 |
| DMEM + FCS | 5872.0 | 2.50 |

The invention claimed is:

1. An engineered albumin binding polypeptide comprising an albumin binding motif, which motif consists of the amino acid sequence:

GVSDX$_5$YKX$_8$X$_9$I X11X12AX14TVEGVX$_{20}$ ALX$_{23}$X$_{24}$X$_{25}$I (SEQ ID NO: 516)

wherein, independently of each other,
  X$_5$ is selected from Y and F;
  X$_8$ is selected from N, R and S;
  X$_9$ is selected from V, I, L, M, F and Y;
  X$_{11}$ is selected from N, S, E and D;
  X$_{12}$ is selected from R, K and N;
  X$_{14}$ is selected from K and R;
  X$_{20}$ is selected from D, N, Q, E, H, S, R and K;
  X$_{23}$ is selected from K, I and T;
  X$_{24}$ is selected from A, S, T, G, H, L and D; and
  X$_{25}$ is selected from H, E and D;
with the proviso that the amino acid sequence is not

```
GVSDYYKNLI NNAKTVEGVK ALIDEI; or    (SEQ ID NO: 517)
GVSDYYKNLI NNAKTVEGVN ALKAEI        (SEQ ID NO: 541)
``` the albumin binding polypeptide binding to albumin such that the K$_D$ value of the interaction is at most 1×10$^{-9}$ M.

2. The albumin binding polypeptide according to claim 1, wherein X$_5$ is Y.

3. The albumin binding polypeptide according to claim 1, wherein X$_8$ is selected from N and R.

4. The albumin binding polypeptide according to claim 3, wherein X$_8$ is R.

5. The albumin binding polypeptide according to claim 1, wherein X$_9$ is L.

6. The albumin binding polypeptide according to claim 1, wherein X$_{11}$ is selected from N and S.

7. The albumin binding polypeptide according to claim 6, wherein X$_{11}$ is N.

8. The albumin binding polypeptide according to claim 1, wherein X$_{12}$ is selected from R and K.

9. The albumin binding polypeptide according to claim 8, wherein X$_{12}$ is R.

10. The albumin binding polypeptide according to claim 8, wherein X$_{12}$ is K.

11. The albumin binding polypeptide according to claim 1, wherein X$_{14}$ is K.

12. The albumin binding polypeptide according to claim 1, wherein X$_{20}$ is selected from D, N, Q, E, H, R and S.

13. The albumin binding polypeptide according to claim 12, wherein X$_{20}$ is E.

14. The albumin binding polypeptide according to claim 1, wherein X$_{23}$ is selected from K and I.

15. The albumin binding polypeptide according to claim 14, wherein X$_{23}$ is K.

16. The albumin binding polypeptide according to claim 1, wherein X$_{24}$ is selected from A, S, T, G, H and L.

17. The albumin binding polypeptide according to claim 16, wherein X$_{24}$ is L.

18. The albumin binding polypeptide according to claim 17, wherein X$_{23}$X$_{24}$ is KL.

19. The albumin binding polypeptide according to claim 17, wherein X$_{23}$X$_{24}$ is TL.

20. The albumin binding polypeptide according to claim 16, wherein X$_{24}$ is selected from A, S, T, G and H.

21. The albumin binding polypeptide according to claim 20, wherein X$_{23}$ is I.

22. The albumin binding polypeptide according to claim 1, wherein X$_{25}$ is H.

23. The albumin binding polypeptide according to claim 1, in which said albumin binding motif consists of an amino acid sequence selected from SEQ ID NO:1-257.

24. The albumin binding polypeptide according to claim 23, in which said albumin binding motif consists of an amino acid sequence selected from SEQ ID NO:2, SEQ ID NO:3, SEQ ID NO:9, SEQ ID NO:15, SEQ ID NO:25, SEQ ID NO:27, SEQ ID NO:46, SEQ ID NO:49, SEQ ID NO:53, SEQ ID NO:54, SEQ ID NO:55, SEQ ID NO:155, SEQ ID NO:239, SEQ ID NO:240, SEQ ID NO:241, SEQ ID NO:242, SEQ ID NO:243, SEQ ID NO:244 and SEQ ID NO:245.

25. The albumin binding polypeptide according to claim 24, in which said albumin binding motif consists of an amino acid sequence selected from SEQ ID NO:3, SEQ ID NO:53 and SEQ ID NO:239.

26. The albumin binding polypeptide according to claim 1, in which said albumin binding motif forms part of a three-helix bundle protein domain.

27. The albumin binding polypeptide according to claim 26, in which said three-helix bundle protein domain is selected from the group consisting of three-helix domains of bacterial receptor proteins.

28. The albumin binding polypeptide according to claim 27, in which said bacterial receptor protein is selected from the group consisting of albumin binding receptor proteins from species of *Streptococcus, Peptostreptococcus* and *Finegoldia*.

29. The albumin binding polypeptide according to claim 28, in which said albumin binding receptor protein is selected from the group consisting of G; MAG; ZAG; PPL; and PAB.

30. The albumin binding polypeptide according to claim 29, in which said albumin binding receptor protein is protein G.

31. The albumin binding polypeptide according to claim 30, in which said albumin binding receptor protein is protein G from *Streptococcus* strain G148.

32. The albumin binding polypeptide according to claim 31, in which said three-helix bundle protein domain is selected from the group consisting of domain GA1, domain GA2 and domain GA3 of protein G from *Streptococcus* strain G148.

33. The albumin binding polypeptide according to claim 32, in which said three-helix bundle protein domain is domain GA3 of protein G from *Streptococcus* strain G148.

34. The albumin binding polypeptide according to claim 27, in which said bacterial receptor protein is protein A from *Staphylococcus aureus*.

35. The albumin binding polypeptide according to claim 34, in which said three-helix bundle protein domain is selected from the group consisting of protein A domains A, B, C, D and E.

36. The albumin binding polypeptide according to claim 34, in which said three-helix bundle protein domain is protein Z derived from domain B of protein A from *Staphylococcus aureus*.

37. The albumin binding polypeptide according to claim 26, which comprises the amino acid sequence:

LAEAKX$_a$X$_b$AX$_c$X$_d$ ELX$_e$KY-(ABM)-LAALP    (SEQ ID NO: 518)

wherein (ABM) is an albumin binding motif as defined in claim 1, and, independently of each other,
X$_a$ is selected from V and E;
X$_b$ is selected from L, E and D;
X$_c$ is selected from N, L and I;
X$_d$ is selected from R and K; and
X$_e$ is selected from D and K.

38. The albumin binding polypeptide according to claim 37, wherein X$_a$ is V.

39. The albumin binding polypeptide according to claim 37, wherein X$_b$ is L.

40. The albumin binding polypeptide according to claim 37, wherein X$_c$ is N.

41. The albumin binding polypeptide according to claim 37, wherein X$_d$ is R.

42. The albumin binding polypeptide according to claim 37, wherein X$_e$ is D.

43. The albumin binding polypeptide according to claim 1, whose amino acid sequence comprises a sequence selected from SEQ ID NO:258-514.

44. The albumin binding polypeptide according to claim 43, whose amino acid sequence comprises a sequence selected from SEQ ID NO:259, SEQ ID NO:260, SEQ ID; NO:266, SEQ ID NO:272, SEQ ID NO:282, SEQ ID NO:284, SEQ ID NO:303, SEQ ID NO:306, SEQ ID NO:310, SEQ ID NO:311, SEQ ID NO:312, SEQ ID NO:412, SEQ ID NO:496, SEQ ID NO:497, SEQ ID NO:498, SEQ ID NO:499, SEQ ID NO:500, SEQ ID NO:501 and SEQ ID NO:502.

45. The albumin binding polypeptide according to claim 44, whose amino acid sequence comprises a sequence selected from SEQ ID NO:260, SEQ ID NO:310 and SEQ ID NO:496.

46. The albumin binding polypeptide according to claim 1, which binds to albumin such that the K$_D$ value of the interaction is at most $1\times10^{-10}$ M.

47. The albumin binding polypeptide according to claim 46, which binds to albumin such that the K$_D$ value of the interaction is at most $1\times10^{41}$ M.

48. The albumin binding polypeptide according to claim 47, which binds to albumin such that the K$_D$ value of the interaction is at most $1\times10^{-12}$ M.

49. The albumin binding polypeptide according to claim 1, which binds to human serum albumin.

* * * * *